US012049493B2

(12) United States Patent
Ahn et al.

(10) Patent No.: US 12,049,493 B2
(45) Date of Patent: Jul. 30, 2024

(54) ANTI-ALPHA-SYNUCLEIN ANTIBODIES AND USES THEREOF

(71) Applicant: ABL Bio Inc., Seongnam-si (KR)

(72) Inventors: Jinhyung Ahn, Seongnam-si (KR); Sungwon An, Seongnam-si (KR); Dongin Kim, Seongnam-si (KR); Eunsil Sung, Seongnam-si (KR); Jaehyun Eom, Seongnam-si (KR); Sang Hoon Lee, Seongnam-si (KR); Seung-Jae Lee, Seoul (KR); Tae Kyung Kim, Seoul (KR); Min Sun Choi, Seoul (KR); Weonkyoo You, Yongin-si (KR); Jaeho Jung, Seongnam-si (KR); Juhee Kim, Seongnam-si (KR); Jinwon Jung, Seongnam-si (KR); Yeunju Kim, Seongnam-si (KR); Yonggyu Son, Seongnam-si (KR); Byungje Sung, Seongnam-si (KR)

(73) Assignee: ABL BIO INC., Seongnam-si (KR)

(*) Notice: Subject to any disclaimer, the term of this patent is extended or adjusted under 35 U.S.C. 154(b) by 1391 days.

(21) Appl. No.: 16/475,853

(22) PCT Filed: Jan. 5, 2018

(86) PCT No.: PCT/KR2018/000239
§ 371 (c)(1),
(2) Date: Jul. 3, 2019

(87) PCT Pub. No.: WO2018/128454
PCT Pub. Date: Jul. 12, 2018

(65) Prior Publication Data
US 2023/0227540 A1 Jul. 20, 2023

Related U.S. Application Data

(60) Provisional application No. 62/443,151, filed on Jan. 6, 2017.

(30) Foreign Application Priority Data

Jan. 5, 2018 (KR) .................. 10-2018-0001641

(51) Int. Cl.
*C07K 16/18* (2006.01)
*A61K 39/00* (2006.01)
(Continued)

(52) U.S. Cl.
CPC .............. *C07K 16/18* (2013.01); *A61P 25/14* (2018.01); *G01N 33/6896* (2013.01);
(Continued)

(58) Field of Classification Search
CPC ................ C07K 16/18; C07K 2317/56; C07K 2317/565; C07K 2317/622;
(Continued)

(56) References Cited

U.S. PATENT DOCUMENTS 3,773,919 A 11/1973 Boswell et al.
4,816,567 A 3/1989 Cabilly et al.
(Continued)

FOREIGN PATENT DOCUMENTS

EP 0058481 8/1982
EP 0088046 9/1983
(Continued)

OTHER PUBLICATIONS

Chen "Enhancement and destruction of antibody function by somatic mutation: unequal occurrence is controlled by V gene combinatorial associations" EMBO 14(12):2784-2794 (Year: 1995).*
(Continued)

*Primary Examiner* — Kimberly Ballard
(74) *Attorney, Agent, or Firm* — Steptoe LLP; Z. Ying Li; Wyan-Ching M. Lee

(57) ABSTRACT

The disclosure discloses anti α-Syn antibodies preferentially recognizing α-Syn aggregates. The antibodies of the present
(Continued)

M: monomers, A: aggregates
Antigen loaded from 50 ng, 2 fold dilution

| Clones | Selectivity |
|--------|-------------|
| AA9 | Aggregates |
| AD2 | Aggregates |
| AD7 | Aggregates |
| AC8 | Aggregates |
| DG8 | Aggregates |
| DG11 | Aggregates |
| DA9 | Aggregates |
| DG5 | Aggregates |
| AE8 | Both | invention bind to α-Syn aggregates with high affinity and specificity and inhibit accumulation or intercellular transfer of α-Syn aggregates, and thus can be used for detection, diagnosis and/or treatment or prevention of various diseases caused by the accumulation of α-Syn aggregates.

20 Claims, 18 Drawing Sheets

Specification includes a Sequence Listing.

(51) Int. Cl.
*A61P 25/14* (2006.01)
*G01N 33/68* (2006.01)

(52) U.S. Cl.
CPC .. *A61K 2039/505* (2013.01); *C07K 2317/565* (2013.01); *C07K 2317/622* (2013.01); *C07K 2317/92* (2013.01); *G01N 2800/2835* (2013.01)

(58) Field of Classification Search
CPC ............ C07K 2317/34; C07K 2317/92; A61K 2039/505; A61P 25/14; A61P 25/16; G01N 2800/2835; G01N 33/6896
See application file for complete search history.

(56) References Cited

U.S. PATENT DOCUMENTS

| | | |
|---|---|---|
| 4,946,778 A | 8/1990 | Ladner et al. |
| 4,965,195 A | 10/1990 | Namen et al. |
| 4,968,607 A | 11/1990 | Dower et al. |
| 5,011,912 A | 4/1991 | Hopp et al. |
| 5,260,203 A | 11/1993 | Ladner et al. |
| 5,260,503 A | 11/1993 | Dorman et al. |
| 5,262,522 A | 11/1993 | Gearing |
| 5,426,048 A | 6/1995 | Gearing |
| 5,457,035 A | 10/1995 | Baum et al. |
| 5,530,101 A | 6/1996 | Queen et al. |
| 5,545,806 A | 8/1996 | Lenberg et al. |
| 5,545,807 A | 8/1996 | Surani et al. |
| 5,585,089 A | 12/1996 | Queen et al. |
| 5,693,761 A | 12/1997 | Queen et al. |
| 5,693,762 A | 12/1997 | Queen et al. |
| 5,874,299 A | 2/1999 | Lenberg et al. |
| 5,877,397 A | 3/1999 | Lenberg et al. |
| 6,162,963 A | 12/2000 | Kucherlapati et al. |
| 6,180,370 B1 | 1/2001 | Queen et al. |
| 6,255,458 B1 | 7/2001 | Lonberg et al. |
| 6,270,964 B1 | 8/2001 | Michnick et al. |
| 6,300,129 B1 | 10/2001 | Lonberg et al. |
| 6,673,986 B1 | 1/2004 | Kucherlapati et al. |
| 6,713,610 B1 | 3/2004 | Kucherlapati et al. |
| 8,609,820 B2 | 12/2013 | Saldanha et al. |
| 8,940,276 B2 | 1/2015 | Weihofen et al. |
| 9,534,044 B2 | 1/2017 | El-Agnaf |
| 2009/0068110 A1 | 3/2009 | Shang et al. |
| 2010/0028370 A1 | 2/2010 | Zankel et al. |
| 2011/0014117 A1 | 1/2011 | Wang et al. |
| 2011/0300077 A1 | 12/2011 | Weihofen et al. |
| 2012/0308572 A1 | 12/2012 | Nordström et al. |
| 2014/0363447 A1 | 12/2014 | Nordstrom et al. |
| 2015/0093399 A1 | 4/2015 | Jefferies |
| 2015/0196663 A1* | 7/2015 | Shusta ............... C07K 16/28 435/254.11 |
| 2015/0266947 A1* | 9/2015 | Sierks ............... C07K 16/005 435/6.12 |
| 2016/0108113 A1 | 4/2016 | Ayalon et al. |
| 2017/0015748 A1 | 1/2017 | Stanimirovic et al. |
| 2017/0355756 A1* | 12/2017 | Julien ............... A61P 25/00 |
| 2022/0348665 A1 | 11/2022 | An et al. |
| 2022/0380446 A1 | 12/2022 | Ahn et al. |
| 2023/0227540 A1 | 7/2023 | Ahn et al. |
| 2023/0279085 A1 | 9/2023 | Lee et al. |
| 2023/0357412 A1 | 11/2023 | An et al. |

FOREIGN PATENT DOCUMENTS

| | | |
|---|---|---|
| EP | 0133988 | 3/1985 |
| EP | 0143949 | 6/1985 |
| EP | 0367566 | 5/1990 |
| EP | 0460846 | 12/1991 |
| EP | 0546073 | 6/1993 |
| EP | 2450056 | 5/2012 |
| EP | 3567054 A1 | 11/2019 |
| EP | 3567054 A4 | 3/2021 |
| EP | 3725802 A4 | 8/2021 |
| EP | 3725806 A4 | 3/2022 |
| JP | 2012-512634 | 6/2012 |
| JP | 2013-525266 | 6/2013 |
| JP | 2014-221835 | 11/2014 |
| JP | 2015-232002 | 12/2015 |
| JP | 2016-511254 | 4/2016 |
| JP | 2017-501848 | 1/2017 |
| JP | 2017-512464 | 5/2017 |
| JP | 2017-513461 | 6/2017 |
| JP | 2017-514456 | 6/2017 |
| JP | 2017-536102 | 12/2017 |
| KR | 10-2011-0110200 | 10/2011 |
| KR | 10-2011-0110220 | 10/2011 |
| KR | 10-2012-0047274 | 5/2012 |
| KR | 10-2013-0137654 | 12/2013 |
| KR | 10-2014-0053974 | 5/2014 |
| KR | 10-2014-0095074 | 7/2014 |
| KR | 10-2014-0125409 | 10/2014 |
| KR | 10-2014-0138533 | 12/2014 |
| KR | 10-1512853 | 4/2015 |
| KR | 10-2015-0063447 | 6/2015 |
| KR | 10-2016-0010402 | 1/2016 |
| KR | 10-2016-0127115 | 11/2016 |
| KR | 10-2016-0127815 | 11/2016 |
| KR | 10-2017-0041289 | 4/2017 |
| KR | 10-2019-0057004 | 5/2019 |
| WO | 1990/04036 | 4/1990 |
| WO | 1990-04036 | 4/1990 |
| WO | 1991-10741 | 7/1991 |
| WO | 1991/10741 | 7/1991 |
| WO | 1993-015722 | 8/1993 |
| WO | 1993/15722 | 8/1993 |
| WO | 1994/02602 | 2/1994 |
| WO | 1994-02602 | 2/1994 |
| WO | 1994/20069 | 9/1994 |
| WO | 1994-020069 | 9/1994 |
| WO | 1996-33735 | 10/1996 |
| WO | 1996/33735 | 10/1996 |
| WO | 1999/10494 | 3/1999 |
| WO | 1999-10494 | 3/1999 |
| WO | 2002/053596 | 7/2002 |
| WO | 2005/016967 | 2/2005 |
| WO | 2006/013472 | 2/2006 |
| WO | 2006/138729 | 12/2006 |
| WO | 2007/042289 | 4/2007 |
| WO | 2008/068048 A2 | 6/2008 |
| WO | WO2008068048 * | 6/2008 |
| WO | 2010/066868 | 6/2010 |
| WO | 2011/104696 | 9/2011 |
| WO | 2011/107544 | 9/2011 |
| WO | 2014/132210 | 9/2014 |
| WO | 2015/075011 | 5/2015 |
| WO | 2015-075011 | 5/2015 |
| WO | 2015/131257 | 9/2015 |
| WO | 2016-061389 | 4/2016 |
| WO | 2016/061389 | 4/2016 |
| WO | 2017/009312 | 1/2017 |
| WO | 2018/128454 | 7/2018 |
| WO | 2018/213316 | 11/2018 |
| WO | 2019/098763 A3 | 11/2018 |
| WO | 2019/023809 | 2/2019 |
| WO | 2019-098763 | 5/2019 |
| WO | 2019/098763 | 5/2019 |
| WO | 2019-117684 | 6/2019 |

(56) References Cited

FOREIGN PATENT DOCUMENTS

| WO | 2019/117684    | 6/2019  |
|----|----------------|---------|
| WO | 2019/117684 A1 | 6/2019  |
| WO | 2019-117685    | 6/2019  |
| WO | 2019/117685    | 6/2019  |
| WO | 2020/251316    | 12/2020 |
| WO | 2020/251316 A1 | 12/2020 |
| WO | 2022/238961    | 11/2022 |

OTHER PUBLICATIONS

Kussie "A Single Engineered Amino Acid Substitution Changes Antibody Fine Specificity" J immunol 152(1): 146-52 (Year: 1994).*

Brundin, P. et al., "Prion-like transmission of protein aggregates in neurodegenerative diseases" Nat Rev Mol Cell Biol., Apr. 2010, vol. 11, No. 4, pp. 301-307.

Wagner, J. et al., "Anle138b: a novel oligomer modulator for disease-modifying therapy of neurodegenerative diseases such as prion and Parkinson's disease", Acta Neuropathol, 2013, vol. 125, pp. 795-813.

Myohanen, T. T. et al., "A prolyl oligopeptidase inhibitor, KYP-2047, reduces a-synuclein protein levels and aggregates in cellular and animal models of Parkinson's disease", British Journal of Pharmacology, 2012, vol. 166, pp. 1097-1113.

Kokhan, V. S. et al., "Alpha-Synuclein knockout mice have cognitive impairments", Behavioural Brain Research, 2012, vol. 231, pp. 226-230.

Singleton, A.B., et al., "Alpha-Synuclein Locus Triplication Causes Parkinson's Disease", Science, Oct. 31, 2003, vol. 302, p. 841.

Kim, W. S. et al. "Alpha-synuclein biology in Lewy body diseases", Alzheimer's Research & Therapy, 2014, vol. 6, No. 73.

Murphy, D. D. et al., "Synucleins Are Developmentally Expressed, and a-Synuclein Regulates the Size of the Presynaptic Vesicular Pool in Primary Hippocampal Neurons", The Journal of Neuroscience, May 1, 2000, vol. 20, No. 9, pp. 3214-3220.

Ahn, J-.H. et al., "A Monoclonal Antibody against the Paraneoplastic Pemphigus (PNP) Antigen, Envoplakin: cDNA Sequences Encoding the Variable Regions of Heavy and Light Chains", Molecules and Cells, 2004, vol. 18, No. 2, pp. 237-241.

Bae, E-.J et al., "Antibody-Aided Clearance of Extracellular Alpha-Synuclein Prevents Cell-to-Cell Aggregate Transmission", The Journal of Neuroscience, Sep. 26, 2012, vol. 32, No. 39, pp. 13454-13469.

Lee, H-.J et al., "Clearance of Alpha-Synuclein Oligomeric Intermediates via the Lysosomal Degradation Pathway", The Journal of Neuroscience, Feb. 25, 2004, vol. 24, No. 8, pp. 1888-1896.

EPO, supplementary partial European Search Report of Application No. 18736765.1, dated Sep. 14, 2020.

Vaikath Nishant N et al., " Generation and characterization of novel conformation-specific monoclonal antibodies for [alpha]-synuclein patho", Neurobiology of Disease, vol. 79, Jul. 1, 2015, pp. 81-99, XP029174249.

Eun-Jin Bae et al., "Antibody-Aided Clearance of Extracellular [alpha]-Synuclein Prevents Cell-to-Cell Aggregate Transmission", Journal of Neuroscience, vol. 32, No. 39, Sep. 26, 2012 pp. 13454-13469, XP055107975.

Chen et al., "Enhancement and destruction of antibody function by somatic mutation: unequal occurrence is controlled by V gene combinatorial associations," EMBO (1995) 14(12):2784-94.

Kussie et al., "A Single Engineered Amino Acid Substitution Changes Antibody Fine Specificity," J Immunol. (1994) 152(1):146-52.

Galvin et al., "Synucleinopathies: Clinical and Pathological Implications," Arch. Neurol. (2001) 58:186-190.

Kokhan et al., "Alpha-synuclein knockout mice have cognitive impairments," Behav Brain Res. (2012) 231:226-30.

Lee et al., "Mechanisms of Anti-alpha-Synuclein Immunotherapy," J. Mov. Disord. (2016) 9(1):14-19.

Nimmo et al., "Novel antibodies detect additional alpha-synuclein pathology in synucleinopathies: potential development for immunotherapy," Alzheimer's Res. Ther. (2020) 12(1):159, 16 pages.

EPO, Extended European Search Report of EP 18736765.1, dated Feb. 8, 2021.

EPO, Supplementary Partial European Search Report of EP 18736765. 1, dated Sep. 14, 2020.

EPO, Search Report of EP 18879299.8, dated Jul. 8, 2021.

EPO, Search Report of EP 18889608.8, dated Sep. 27, 2021.

KIPO, PCT Search Report & Written Opinion of PCT/KR2018/014123, dated May 23, 2019.

KIPO, PCT Search Report & Written Opinion of PCT/KR2018/015953, dated Apr. 30, 2019.

KIPO, PCT Search Report & Written Opinion of PCT/KR2020/007704, dated Sep. 16, 2020.

Ahn et al., "A Monoclonal Antibody against the Paraneoplastic Pemphigus (PNP) Antigen, Envoplakin: cDNA Sequences Encoding the Variable Regions of Heavy and Light Chains," Molecules and Cells (2004) 18(2):237-41.

Anonymous, "Blood-brain barrier molecular carriers for Parkinson's disease," BIOPHARMADEALMAKERS, 2017.

Bae et al., "Antibody-Aided Clearance of Extracellular Alpha-Synuclein Prevents Cell-to-Cell Aggregate Transmission," The Journal of Neuroscience (2012) 32(39):13454-69.

Blakesley et al., "IGF-1 Receptor Function IGF-1 receptor function: transducing the IGF-1 signal into intracellular events," The IGF System, Humana Press, 1999, NJ: 143-63.

Blume-Jensen et al., "Oncogenic kinase signalling," Nature (2001) 411:355-65.

Brundin et al., "Prion-like transmission of protein aggregates in neurodegenerative diseases," Nat Rev Mol Cell Biol. (2010) 11(4):301-7.

Kim et al., "Alpha-synuclein biology in Lewy body diseases," Alzheimer's Research & Therapy (2014) 6(73):1-9.

Kostelny et al., "Formation of a Bispecific Antibody by the Use of Leucine Zippers," J. Immunol. (1992) 148:1547-53.

Lee et al., "Clearance of Alpha-Synuclein Oligomeric Intermediates via the Lysosomal Degradation Pathway," The Journal of Neuroscience (2004) 24(8):1888-96.

Li et al., "Two New Monoclonal Antibodies Against the Alpha Subunit of the Human Insulin-Like Growth Factor-I Receptor," Biochemical And Biophysical Research Communications (1993) 196(1):92-8.

Murphy et al., "Synucleins Are Developmentally Expressed, and a-Synuclein Regulates the Size of the Presynaptic Vesicular Pool in Primary Hippocampal Neurons," The Journal of Neuroscience (2000) 20(9):3214-20.

Myohanen et al., "A prolyl oligopeptidase inhibitor, KYP-2047, reduces a-synuclein protein levels and aggregates in cellular and animal models of Parkinson's disease," British Journal of Pharmacology (2012) 166:1097-113.

Paul, Fundamental Immunology, 5th edition, Aug. 2003, Lippincott Williams & Wilkins Publishers.

Singleton et al., "Alpha-Synuclein Locus Triplication Causes Parkinson's Disease," Science (2003) 302:841.

Songsivilai et al., "Bispecific antibody: a tool for diagnosis and treatment of disease," Clin. Exp. Immunol. (1990) 79:315-21.

Vaikath et al., "Generation and characterization of novel conformation-specific monoclonal antibodies for [alpha]- synuclein pathology," Neurobiology of Disease (2015) 79:81-99.

Wagner et al., "Anle138b: a novel oligomer modulator for disease-modifying therapy of neurodegenerative diseases such as prion and Parkinson's disease," Acta Neuropathol (2013) 125:795-813.

"*Homo sapiens* synuclein, alpha (non A4 component of amyloid precursor), partial [synthetic construct]," NCBI, Genbank Accession No. AAP36433.1.

\* cited by examiner

| Clones | EC50 (ng/ml) | | EC50 (nM) | |
|---|---|---|---|---|
| | Monomers | Fibrils | Monomers | Fibrils |
| 1E4 | - | 24.74 | - | 0.163 |
| 3A9 | - | 319.4 | - | 2.129 |
| 9B11 | - | 184.9 | - | 1.233 |
| 10F10 | 23.30 | 13.12 | 0.155 | 0.087 |
| 11F11 | - | 326.5 | - | 2.177 |
| 274 | 26.82 | 15.13 | 0.179 | 0.101 |

-: tested, but not available

| Clones | KD (M, $\times 10^{-9}$) | |
|---|---|---|
| | Monomers | Fibrils |
| 3A9 | - | 1.320 |
| 9B11 | - | 0.904 |
| 11F11 | - | 2.873 |

-: tested, but not available

FIG. 3B

| Clones | KD ($10^{-9}$ M) | Clones | KD ($10^{-9}$ M) |
|---|---|---|---|
| 1E4 | 0.18 | AA9 | 0.88 |
| 10F10 | 0.81 | DG5 | 1.26 |
| 11F4 | 0.14 | AD2 | 1.67 |
| 3A9 | 0.13 | AD7 | 0.17 |
| 9B11 | 0.018 | DG11 | 2.66 |
| 11F11 | 0.16 | DG8 | 3.80 |
| AC8 | 0.24 | DA9 | 4.31 |
| AE8 | 0.39 | | |

FIG. 6

ANTI-ALPHA-SYNUCLEIN ANTIBODIES AND USES THEREOF

SEQUENCE LISTING

The instant application contains a Sequence Listing that has been submitted electronically in ASCII format and is hereby incorporated by reference in its entirety. Said ASCII copy is entitled "122548.US011_ST25.txt", was created on Feb. 24, 2023, and is 304,882 bytes in size.

TECHNICAL FIELD

The present invention relates to an anti-α-syn antibody and its use.

BACKGROUND ART

Alpha-synuclein (α-syn) is a protein comprised of 140 amino acids that is expressed primarily in the presynaptic terminals of neurons. It is a naturally unfolded monomer in normal conditions. Alpha-synuclein has been known to maintain the supply of synaptic vesicles at the presynaptic terminals and to regulate the release of dopamine that is a neurotransmitter controlling voluntary or involuntary movements.

However, in pathological conditions, alpha-synuclein undergoes structural changes through binding and interaction with droplets, phospholipid bilayers, or lipid membranes, etc. so as to form aggregates including, for example, dimers, oligomers and/or fibrous molecules, by forming a folded or folded α-helical secondary structure of alpha-synuclein. These aggregates have been known to cause toxicity to cells and are the major component of an abnormal protein aggregate of Lewy bodies that are found in neurons of Parkinson's disease, dementia with Lewy bodies and various other diseases. In addition, post-translational modifications such as phosphorylation or ubiquitination of alpha-synuclein are also known to be involved in the aggregation and neurotoxicity of alpha-synuclein.

The alpha-synuclein aggregation is known to be associated with cause of Parkinson's disease (PD), Parkinson's disease dementia (PDD), dementia with Lewy bodies (DLB), multiple system atrophy (MSA) and various neurodegenerative diseases called as α-synucleinopathies including many neuro-axonal diseases (Kim et al. Alzheimer's Research & Therapy 2014, 6:73).

Furthermore, both oligomeric and monomeric forms of alpha-synuclein were found in cerebrospinal fluid and plasma samples of patients with Parkinson's disease, indicating that alpha-synuclein aggregates with small molecular weight can penetrate the cell membrane and access the extracellular space. It has also been shown that folded alpha-synuclein can be released from cells by exocytosis and then transferred from one region of the brain to another region by intercellular transfer like prion proteins (Brundin P. et al., Nat Rev Mol Cell Biol 2010, 11: 301-307).

Therefore, alpha-synuclein is a target for the development of therapeutic agents for α-synucleinopathy such as Parkinson's disease. The main development strategies include inhibition of aggregate formation, gene silencing, and removal of aggregates. In the former case, Epigallocatechin-3-gallate (EGCG) (Bieschke J. et al., Proc Natl Acad Sci USA 2010 107: 7710-7715), 3-(1,3-benzodioxol-1-bromophenyl)-1H-pyrazole (anle138b) (Wagner J. et al., Acta Neuropathol 2013, 125: 795-813), CLR0120 (Prabhudesai S. et al., Neurotherapeutics 2012, 9: 464-476) and KYP-20479 of prolyl oligopeptidase inhibitor (Myohanen T T et al., Brit J Pharmacol 2012, 166: 1097-1113) are included. Antibodies that bind to alpha-synuclein are disclosed in U.S. Pat. Nos. 8,609,820, 8,940,276 and the like.

The compounds with a low molecular weight should be administered at a high dose, due to low target specific binding capacity and short half-life. Compared to the compounds with low molecular weight, the antibody has a target specificity and long half-life. However, in order to increase the therapeutic potential of the disease, antibodies preferentially binding to the aggregates with high affinity are needed.

Therefore, for the treatment of diseases associated with the abnormal accumulation of α-syn aggregates, the development of antibodies being capable of preferentially binding to alpha-synuclein, particularly alpha-synuclein aggregates is needed.

DISCLOSURE

Technical Problem

The present invention is to provide an antibody specifically recognizing α-syn, especially α-syn aggregates, with high binding affinity.

Technical Solution

In one aspect, the present invention provides an isolated antibody specifically binding to α-syn aggregates, or an antigen-binding fragment thereof, where the antibody or antigen-binding fragment thereof according to the present invention comprises (i) heavy chain variable region comprising complementarity determining regions of CDRH1, CDRH2 and CDRH3, and/or (ii) light chain variable region comprising complementarity determining regions of CDRL1, CDRL2 and CDRL3, and the CDRH1 is any one selected from SEQ ID NOs: 1 to 14; and the CDRH2 is any one selected from SEQ ID NOs: 15 to 28; and the CDRH3 is any one selected from SEQ ID NOs: 29 to 42; and the CDRL1 is any one selected from SEQ ID NOs: 43 to 56; and the CDRL2 is any one selected from SEQ ID NOs: 57 to 70; and the CDRL3 is any one selected from SEQ ID NOs: 71 to 84.

In other embodiments, the antibody or antigen-binding fragment according to the present invention comprises (i) a heavy chain variable region comprising complementarity determining regions of CDRH1, CDRH2 and CDRH3, and/or (ii) a light chain variable region comprising complementarity determining regions of CDRL1, CDRL2 and CDRL3:
 (aa) CDRH1, CDRH2 and CDRH3 are SEQ ID NOs: 1, 15, and 29, respectively, and CDRL1, CDRL2, and CDRL3 are SEQ ID NOs: 43, 57 and 71, respectively;
 (ab) CDRH1, CDRH2 and CDRH3 are SEQ ID NOs: 2, 16, and 30, respectively, and CDRL1, CDRL2, and CDRL3 are SEQ ID NOs: 44, 58 and 72, respectively;
 (ac) CDRH1, CDRH2 and CDRH3 are SEQ ID NOs: 3, 17, and 31, respectively, and CDRL1, CDRL2, and CDRL3 are SEQ ID NOs: 45, 59 and 73, respectively;
 (ad) CDRH1, CDRH2 and CDRH3 are SEQ ID NOs: 4, 18, and 32, respectively, and CDRL1, CDRL2, and CDRL3 are SEQ ID NOs: 46, 60 and 74, respectively;
 (ae) CDRH1, CDRH2 and CDRH3 are SEQ ID NOs: 5, 19, and 33, respectively, and CDRL1, CDRL2, and CDRL3 are SEQ ID NOs: 47, 61 and 75, respectively;
 (af) CDRH1, CDRH2 and CDRH3 are SEQ ID NOs: 6, 20, and 34, respectively, and CDRL1, CDRL2, and CDRL3 are SEQ ID NOs: 48, 62 and 76, respectively;

(ag) CDRH1, CDRH2 and CDRH3 are SEQ ID NOs: 7, 21, and 35, respectively, and CDRL1, CDRL2, and CDRL3 are SEQ ID NOs: 49, 63 and 77, respectively;
(ah) CDRH1, CDRH2 and CDRH3 are SEQ ID NOs: 8, 22, and 36, respectively, and CDRL1, CDRL2, and CDRL3 are SEQ ID NOs: 50, 64 and 78, respectively;
(ai) CDRH1, CDRH2 and CDRH3 are SEQ ID NOs: 9, 23, and 37, respectively, and CDRL1, CDRL2, and CDRL3 are SEQ ID NOs: 51, 65 and 79, respectively;
(aj) CDRH1, CDRH2 and CDRH3 are SEQ ID NOs: 10, 24, and 38, respectively, and CDRL1, CDRL2, and CDRL3 are SEQ ID NOs: 52, 66 and 80, respectively;
(ak) CDRH1, CDRH2 and CDRH3 are SEQ ID NOs: 11, 25, and 39, respectively, and CDRL1, CDRL2, and CDRL3 are SEQ ID NOs: 53, 67 and 81, respectively;
(al) CDRH1, CDRH2 and CDRH3 are SEQ ID NOs: 12, 26, and 40, respectively, and CDRL1, CDRL2, and CDRL3 are SEQ ID NOs: 54, 68 and 82, respectively;
(am) CDRH1, CDRH2 and CDRH3 are SEQ ID NOs: 13, 27, and 41, respectively, and CDRL1, CDRL2, and CDRL3 are SEQ ID NOs: 55, 69 and 83, respectively; or
(an) CDRH1, CDRH2 and CDRH3 are SEQ ID NOs: 14, 28, and 42, respectively, and CDRL1, CDRL2, and CDRL3 are SEQ ID NOs: 56, 70 and 84.

In an embodiment, the heavy chain variable region of the isolated antibody specifically binding to α-syn aggregate or its antigen-binding fragment according to the present invention includes an amino acid sequence selected from SEQ ID NOs: 85 to 98, at least 90% or higher having sequence identity to an amino acid sequence selected from SEQ ID NOs: 85 to 98, or at least 95% or higher having sequence identity to an amino acid sequence selected from SEQ ID NOs: 85 to 98.

In an embodiment, the light chain variable region of the isolated antibody specifically binding to α-syn aggregate or its antigen-binding fragment according to the present invention includes an amino acid sequence selected from SEQ ID NOs: 99 to 112, at least 90% or higher having sequence identify to an amino acid sequence selected from SEQ ID NOs: 99 to 112, or at least 95% or higher having sequence identify to an amino acid sequence selected from SEQ ID NOs: 99 to 112.

In an embodiment, the isolated antibody specifically binding to α-syn aggregate or its antigen-binding fragment according to the present invention includes any one of the heavy chain variable region and the light chain variable region as follows. The heavy chain variable region and light chain variable region sequences can include SEQ ID NO: 85 and 99; SEQ ID NO: 86 and 100; SEQ ID NO: 87 and 101; SEQ ID NO: 88 and 102; SEQ ID NO: 89 and 103; SEQ ID NO: 90 and 104; SEQ ID NO: 91 and 105; SEQ ID NO: 92 and 106; SEQ ID NO: 93 and 107; SEQ ID NO: 94 and 108; SEQ ID NO: 95 and 109; SEQ ID NO: 96 and 110; SEQ ID NO: 97 and 111; or SEQ ID NO: 98 and 112.

Some antibodies or their antigen-binding fragments can be monoclonal antibody or scFv fragment, and the antibody or its antigen-binding fragment binding to α-syn aggregates.

The antibody of the present invention can be a human antibody, humanized antibody, or chimeric antibody.

The monoclonal antibody of the present invention can be IgG1, IgG2, IgG3 or IgG4 types.

The antibody or its antigen-binding fragment can be a monoclonal antibody, Fab fragment, Fab' fragment, F(ab') fragment, diabody or scFv.

In an embodiment, the isolated antibody specifically binding to α-syn aggregates or its antigen-binding fragment according to the present invention includes any one of the heavy chain and the light chains as follows. The heavy chain and light chain sequences are SEQ ID NO: 113 and SEQ ID NO: 141; SEQ ID NO: 114 and SEQ ID NO: 142; SEQ ID NO: 115 and SEQ ID NO: 143; SEQ ID NO: 116 and SEQ ID NO: 144; SEQ ID NO: 117 and SEQ ID NO: 145; SEQ ID NO: 118 and SEQ ID NO: 146; SEQ ID NO: 119 and SEQ ID NO: 147; SEQ ID NO: 120 and SEQ ID NO: 148; SEQ ID NO: 121 and SEQ ID NO: 149; SEQ ID NO: 122 and SEQ ID NO: 150; SEQ ID NO: 123 and SEQ ID NO: 151; SEQ ID NO:124 and SEQ ID NO: 152; SEQ ID NO: 125 and SEQ ID NO: 153; or SEQ ID NO: 126 and SEQ ID NO: 154. The antibody includes mouse IgG2a as constant region.

In an embodiment, the isolated antibody specifically binding to α-syn aggregates or its antigen-binding fragment according to the present invention includes any one of the heavy chain and the light chains as follows. The heavy chain and light chain sequences are SEQ ID NO: 127 and SEQ ID NO: 155; SEQ ID NO: 128 and SEQ ID NO: 156; SEQ ID NO: 129 and SEQ ID NO: 157; SEQ ID NO: 130 and SEQ ID NO: 158; SEQ ID NO: 131 and SEQ ID NO: 159; SEQ ID NO: 132 and SEQ ID NO: 160; SEQ ID NO: 133 and SEQ ID NO: 161; SEQ ID NO: 134 and SEQ ID NO: 162; SEQ ID NO: 135 and SEQ ID NO: 163; SEQ ID NO: 136 and SEQ ID NO: 164; SEQ ID NO: 137 and SEQ ID NO: 165; SEQ ID NO: 138 and SEQ ID NO: 166; SEQ ID NO: 139 and SEQ ID NO: 167; or SEQ ID NO: 140 and SEQ ID NO: 168. The antibody includes human IgG1 as constant region.

An antibody or antigen-binding fragment according to the present invention may be used for the inhibition of intercellular transfer of α-syn aggregates; degrade α-syn aggregates; or inhibit α-syn aggregate formation.

In another aspect, the present invention also provides an isolated polynucleotide encoding the antibody or antigen-binding fragment according to the present invention. Examples of such polynucleotides include the sequences represented by SEQ ID NOs: 169 to 224.

In another aspect, the present invention also provides an expression vector comprising the polynucleotide according to the present invention.

In another aspect, the present invention also provides a prokaryotic or eukaryotic cell or cell line transformed with the expression vector according to the present invention.

In another embodiments, the present invention further provides a method of producing a an isolated antibody specifically binding to α-syn, or antigen-binding fragment thereof, comprising culturing the cell of the present invention under the conditions sufficiently expressing the antibody or an antigen-binding fragment thereof, and isolating the antibody or antigen-binding fragment thereof from the cell line.

In another embodiment, the present invention also provides a kit or composition comprising an antibody or antigen-binding fragment thereof according to the present invention, wherein the composition may be provided as a pharmaceutical or diagnostic composition. The pharmaceutical composition may comprise a pharmaceutically acceptable carrier or an excipient, and the diagnostic composition may further comprise reagents required for diagnosis or detection.

The pharmaceutical composition or kit according to the present invention may be used for the treatment of α-synucleinopathy. For example, the α-synucleinopathy may be selected from the group consisting of Parkinson's disease (PD), Parkinson's disease dementia (PDD), dementia with Lewy bodies (DLB), Lewy body variant of Alzheimer's disease (LBV), combined Alzheimer's and Parkinson disease, or multiple system atrophy (MSA).

In another embodiment, the present invention provides a method of detecting α-syn aggregates in a biological sample, comprising providing an antibody or antigen-binding fragment according to the present invention, contacting the antibody or antigen-binding fragment thereof with a biological sample to be detected for α-syn aggregates. The biological samples include various samples that require detection of α-syn aggregates, including, for example, cerebrospinal fluid, blood including plasma, or urine, and cells, tissues or organs. The method may be performed in vitro or in vivo. The in vivo imaging can be performed using, for example, positron emission tomography (PET), single photon emission tomography (SPECT), near infrared (NIR) optical imaging or magnetic resonance imaging (MRI).

In another embodiment, the present invention provides a method of treating α-synucleinopathy of a subject or modulating a concentration of α-syn aggregates in the subject, administering an antibody or an antigen-binding fragment thereof according to the present invention, or a composition comprising the same, to the subject in need of a treatment of alpha-synucleinopathy and/or modulation of the concentration of α-syn aggregates.

In another embodiment, the present invention provides a method of diagnosing alpha-synucleinopathy in a subject in need of diagnosis of alpha-synucleinopathy, wherein the method comprises measuring/detecting a concentration or intercellular location of α-syn aggregates in the subject using any antibody or antigen binding fragment thereof of the present invention, and comparing the concentration or the intercellular location of α-syn aggregates measured in the subject with that of a control sample, and wherein the similarity or difference compared to the control sample result represents the subject with α-synucleinopathy. In the method, the control group can be normal sample or a sample of patient with α-synucleinopathy.

In another embodiment, the present invention provides a use of the antibody and antigen-binding fragment thereof or a composition comprising the same, in the treatment of α-synucleinopathy in a subject with an α-synucleinopathy, wherein the antibody and antigen-binding fragment thereof or a composition comprising the same inhibits the intercellular transfer of α-syn aggregates, degrades α-syn aggregates; or inhibits α-syn aggregate formation in the subject, or in the brain of the subject.

In another embodiment, the present invention provides a use of the antibody and antigen-binding fragment thereof or a composition comprising the same, in the modulation of concentration of α-syn aggregates in a brain cell, wherein the antibody and antigen-binding fragment thereof or a composition comprising the same inhibits the intercellular transfer of α-syn aggregates, degrades α-syn aggregates; or inhibits α-syn aggregates in the brain of the subject.

Advantageous Effects

The antibodies disclosed herein preferentially bind to α-syn, especially α-syn aggregates, with high binding affinity. The antibody and antigen-binding fragments with high affinity can reduce α-syn aggregate formation and reduce the concentration of aggregates in the brain. In addition, the antibody and antigen-binding fragments with high affinity to α-syn aggregates can reduce α-syn aggregate formation outside the central nervous system, resulting in reducing the concentration of aggregates in the central nervous system, by changing the equilibrium state of α-syn forms in boundary of brain blood barrier.

It also has the advantage of being administered at low dosage due to high affinity. This has great clinical advantages, since the antibody, for example, can be administered in the same manner as a simpler subcutaneous injection so as to achieve sufficient efficacy, but is not limited thereto.

The antibodies disclosed herein can effectively remove α-syn aggregates and promote degradation, and inhibit intercellular transfer of α-syn, thereby being useful for the treatment of diseases associated with the accumulation of α-syn aggregates.

BRIEF DESCRIPTION OF DRAWINGS

FIG. 3B is a table showing the results of FIG. 3A.

FIG. 6 is Octet analysis results for the preferential binding specificity of the monoclonal antibody used in FIG. 5 to α-syn aggregates. The results show that the antibody of the present invention preferentially binds to α-syn aggregates. This result indicates that it is possible to effectively remove or inhibit the activity of causative agents of neurodegenerative diseases with an alpha-synuclein pathogenesis such as Parkinson's disease.

MODE FOR INVENTION

Figures 1, 2:
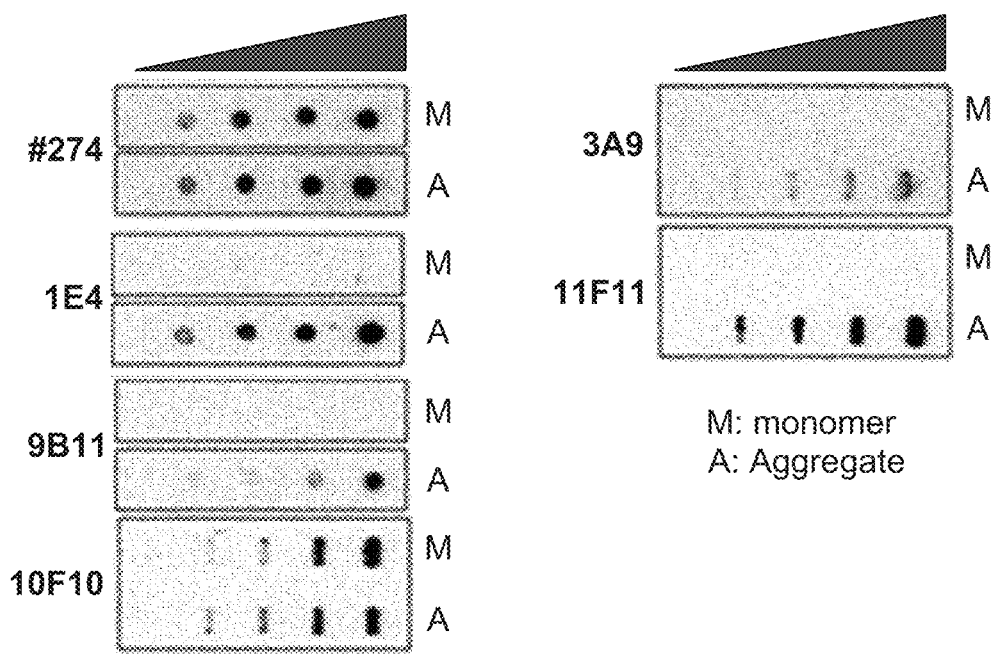
FIG. 1 is a dot-blot result showing that the produced monoclonal antibody preferentially binds to α-syn aggregates, as a result of measuring whether or not the monoclonal antibody specifically recognizes the native α-syn in the aggregated form.
FIG. 2 is a result of ELISA analysis of the affinity of monoclonal antibody produced in an embodiment of the present invention. The antibody of the present invention preferentially binds to α-syn aggregates with high affinity, but the affinity to a monomer cannot be obtained due to lower affinity than aggregates or no binding to monomer. These results indicate that it is possible to effectively remove or inhibit the activity of causative agents of neurodegenerative diseases with an alpha-synuclein pathogenesis such as Parkinson's disease.

The present invention relates to a method for detecting α-syn aggregates as well as reducing α-syn aggregates, inhibiting formation of α-syn aggregates and/or α-syn aggregates and/or inhibiting cell transfer of α-syn aggregates, based on the development of antibodies capable of binding to α-syn aggregates with high specificity.

The titles used in the present section are for convenience of specification only, and do not limit the present invention.

Unless otherwise defined herein, the scientific and technical terms used herein have the same meaning as commonly understood by those skilled in the art. Further, unless the context specifically requires, the singular includes the plural, and the plural includes the singular.

Definition

Herein, "polynucleotide" or "nucleic acid" includes a single or double strand nucleotide polymer. The nucleotide comprising such a polynucleotide may be a ribonucleotide or deoxyribonucleotide or their modified forms.

Unless otherwise stated herein, the left end of the polynucleotide stated herein is 5' end and its right end represents 3' end.

Herein, "isolated nucleic acid molecule" means DNA or RNA of genomic origin or mRNA, cDNA of synthetic origin or their combinations, which is linked to the polynucleotide that all or a portion of it is not associated with a polynucleotide present in nature, or it is not observed in nature. On the purpose of the present invention, the nucleic acid molecule comprising a specific nucleic acid sequence does not comprise an intact chromosome. Instead, the isolated nucleic acid molecule comprising a specific nucleic acid sequence may comprise at least several additional protein coding sequences, in addition to its specific sequence, or may further comprise a regulatory sequence and/or vector for expression of the specific nucleic acid sequence.

Herein, the term "regulatory sequence" means a polynucleotide sequence which can affect the expression and processing of a coding sequence by being operably connected thereto. This property of the regulatory sequence may be influenced by kinds of hosts. For example, the regulatory sequence applicable in a prokaryotic cell may include a promoter, occasionally an operator, a ribosome-binding site and a transcription termination sequence. In a eukaryotic cell, the regulatory sequence may comprise a promoter, comprising multiple recognition sites, a transcription enhancer, a polyadenylation sequence and a transcription termination sequence. The regulatory sequence may further comprise a reader sequence and/or a fusion partner sequence.

Herein, "vector" means any molecule used for delivering a nucleic acid molecule encoding a protein to a host cell, comprising for example, a nucleic acid, a plasmid, a bacteriophage or a virus.

Herein, "expression vector" means a vector which is suitable for transformation of a host cell and comprises a nucleic acid sequence that is operably connected to an expression vector and regulates the expression of heterologous sequences encoding a targeting protein. This expression vector may be also operably connected to the coding sequence, and in case of transcription, translation and that an intron is present, it may comprise a sequence regulating RNA splicing or affecting it.

Herein, "operably connected" means that nucleic acid sequences to be connected are positioned so as to perform a targeting function under an appropriate condition. For example, if the transcription of the coding sequence is affected by the regulatory sequence under an appropriate condition in a vector comprising a coding sequence and a regulatory sequence, it is operably connected.

Herein, "host cell" means a cell which can express a target gene that is transformed or to be transformed by a targeting nucleic acid sequence. The term includes progeny of the host cell, as long as expressing the targeting gene, regardless of identity of host cell and form and genetic makeup.

Herein, "transduction" commonly means movement of a nucleic acid from one bacterium to another bacterium by a bacteriophage. For example, it includes movement of a nucleic acid to a eukaryotic cell using a retrovirus which cannot replicate.

Herein, "transfection" means that a cell takes a foreign or exogenous DNA, and in this case, DNA is introduced in a cell through a cell membrane. This may refer methods known in the art, for example, Sambrook et al., Molecular Cloning: A Laboratory Manual, 4th ed., Cold Spring Harbor Laboratory Press, Cold Spring Harbor, N.Y. (2012), Ausubel et al., Current Protocols in Molecular Biology, Greene Publishing Associates.

Herein, "transformation" means a change of genetic properties of a cell, which are modified so that a cell comprises a new DNA or RNA. For example, a cell may be transformed as its genetic properties are changed, by introducing a new genetic material through transduction, transfection, or other techniques. The DNA transformed by methods including transduction or transfection, etc. may be present by being physically integrated in a chromosome of a cell, or may be temporarily present as an episome form without replication or a replicable plasmid. When the transformed DNA is replicated with division of a host cell, it is considered as stably transformed.

Herein, "amino acid" includes the common meaning understood in the art. Twenty natural-occurring amino acids and their abbreviations are as those commonly used in the art (*Immunology-A Synthesis*, 2nd Edition, E. S. Golub and D. R. Green, eds., Sinauer Associates: Sunderland, Mass. 1991). The amino acid includes typical amino acids, stereoisomers of typical 20 amino acids (D-amino acids), non-natural amino acids, for example, α-,α-disubstituted amino acids, N-alkyl amino acids, and other non-typical amino acids. As examples of non-typical amino acids, 4-hydroxyproline, γ-carboxyglutamate, F—N,N,N-trimethyllysine, F—N-acetyllysine, O-phosphoserine, N-acetylserine, N-formylmethionine, 3-methylhistidine, 5-hydroxylysine, σ-N-methylarginine and other similar amino acids and imino acids (for example, 4-hydroxyproline). In the mark of polypeptide used herein, as commonly used in the art, the left of a sequence is an amino terminal and the right represents a carboxy terminal.

Herein, "polypeptide" or "protein" means a polymer of an amino acid residue, and it is used interchangeably herein. This also includes not only polymers of naturally occurring amino acid residues but also polymers of their analogues or mimetics. In addition, the polypeptide or protein may comprise modification such as addition of carbohydrates for phosphorylation or glycosylation, etc. Moreover, the polypeptide or protein may be produced in a recombinant or naturally found cell. Furthermore, the polypeptide or protein may include those in which a portion of a wild type sequence or the amino acid sequence is deleted, added and/or substituted. In addition, the polypeptide or protein includes an antibody, for example, an anti-α-syn antibody (or named as α-syn antibody), α-syn binding protein, or an antigen-binding fragment, or a sequence in which one or more amino acids in the sequence are deleted, added and/or substituted. Moreover, "polypeptide fragment" means a polypeptide having an amino terminal deletion, a carboxyl terminal deletion and/or an internal deletion, compared to a full-length protein. This fragment may also include modified amino acids compared to a full-length protein. In one embodiment, the fragment may be about 5 to 500 amino acids in length, for example, at least 5, 6, 8, 10, 14, 20, 50, 70, 100, 110, 150, 200, 250, 300, 350, 400 or 450, or more amino acids in length. Considering the purpose of the present invention, the useful polypeptide fragment includes an immunological functional fragment of an antibody comprising an antigen-binding domain. In case of α-syn binding antibody, such a useful fragment includes a CDR sequence comprising 1, 2, or 3 of heavy chains or light chains, or all or a portion of antibody chain comprising a variable region or constant region of a heavy chain or light chain, but not limited thereto.

Herein, "isolated polypeptide, antibody or protein" is that there is not any other protein to be found together with them commonly and at least about 50% or more of lipids, carbohydrates and polynucleotides naturally connected to them are removed. Typically, the isolated protein, polypeptide or antibody comprises at least about 5%, at least about 10%, at least about 25% or at least about 50%, in a certain composition. This polypeptide may be encoded by genome DNA, cDNA, mRNA or other RNA of synthetic origins or any combinations thereof. In particular, the isolated protein, polypeptide or antibody is substantially free of contaminants of other proteins or other polypeptides, which interfere with its therapeutic, diagnostic and prophylactic researches or application for other uses.

Herein, "variant" of a polypeptide such as for example, an antigen-binding fragment, a protein or an antibody is a polypeptide in which one or more amino acid residues are inserted, deleted, added and/or substituted, as compared to another polypeptide sequence, and includes a fusion polypeptide. In addition, a protein variant includes one modified by protein enzyme cutting, phosphorylation or other post-translational modification, but maintaining biological activity of the antibody disclosed herein, for example, binding to α-syn and specificity. The variant may be about 99%, 98%, 97%, 96%, 95%, 94%, 93%, 92%, 91%, 90%, 89%, 88%, 87%, 86%, 85%, 84%, 83%, 82%, 81%, or 80% identical to the sequence of the antibody or its antigen-binding fragment disclosed herein.

The "derivative" of the polypeptide herein means a polypeptide chemically modified in one or more residues through conjugation with other chemical moiety, which is different from an insertion, deletion, addition or substitution variant.

Herein, the term "naturally found" used with regard to a polypeptide, nucleic acid, host cell, etc. means a naturally-occurring material.

As used herein, "α-syn" is native α-syn (NCBI ID: NP_000336) consisting of 140 amino acids encoded by the SNCA gene and includes processed various forms as well as unprocessed protein with full length. In addition, the α-syn includes naturally occurring variants of α-syn such as mutants, splice variants or allelic variants. The variants may include 126 and 112 residue protein forms (CAG3339.1), in addition to 140 residue proteins, in which exon 3 or exon 5 is deleted. Specific polymorphism or missense mutations of the SNCA gene are also known to be associated with the occurrence of Parkinson's disease (Singleton A B, et al., Science 2003, 302: 841), and such variants are also included in the variant of α-syn, beta-syn and gamma-syn are homologous to α-syn. In one embodiment, the antibody according to the present invention specifically recognizes α-syn. The amino acid sequence of α-syn is shown in SEQ ID NO: 225.

As used herein, the term "α-syn aggregate" forms due to a change in the conformation of α-syn, and refers to a structure or aggregate including at least one of an oligomer, a protofibril, and/or a fibril due to a change in the conformation of α-syn.

Herein "identity" means the sequence similarity of two or more polypeptides or two or more polynucleotides, which are determined by arranging and comparing two or more polypeptides or two or more polynucleotides. This identity between sequences is commonly represented by "identity percent", and this means the ratio of identical amino acids or nucleotides between molecules to be compared, and it is calculated on the basis of the smallest size of molecule, among molecules to be compared. The following documents may be referred for methods to be used for calculating the identity between many molecules by arranging nucleic acids or polypeptides: *Computational Molecular Biology*, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, *SIAM J. Applied Math.* 48:1073.

When the identity percent is calculated, sequences to be compared are arranged in the way of providing the maximum matching between sequences, and in the arranged sequences, gap, matching and mis-match may be present, and this is treated by a specific mathematical model or a computer algorithm. In one embodiment, this identity percent may be determined using a GCG program package including a GAP program which arranges two sequences in the way of maximizing the match between sequences to be compared and minimizing the number of gaps, using Needlman and Wunsch algorithm (Devereux et al., 1984, *Nucl. Acid Res.* 1984, 12:387; Genetics Computer Group, University of Wisconsin, Madison, WI, USA). The computer algorithm GAP determines "matching span" by arranging two sequences in the way of maximizing the match between them and minimizing the number of gaps in two polypeptide or polynucleotide sequences to be compared. The algorithm also uses a gap opening penalty [this is calculated as 3× average diagonal, wherein "average diagonal" is the average of diagonals of comparison matrix to be used; and "diagonal" is a score or number assigned for each complete amino acid match by a specific comparison matrix] and a gap extension penalty (this is commonly 1/10 fold of the gap opening penalty), and a comparison matrix, for example, PAM 250 or BLOSUM 62 together. In a specific embodiment, a standard comparison matrix (refer to Dayhoff et al., 1978, *Atlas of Protein Sequence and Structure* 1978, 5:345-352 for PAM 250 comparison matrix; refer to Henikoff et al., *Proc. Natl. Acad. Sci. U.S.A.* 1992, 89:10915-10919 for BLOSUM 62 comparison matrix) is used. In one embodiment, parameters recommended for determining the identity percent of polypeptides or polynucleotides in which the GAP program is used are as follows: algorithm: Needleman et al., *J. Mol. Biol.* 1970, 48:443-453; comparison matrix: BLOSUM 62 (Henikoff et al., 1992, supra); gap penalty: 12 (no penalty for a terminal gap); gap length penalty: 4; similarity threshold: 0.

When two sequences are arranged using specific parameters, although there is no significant relation between two sequences, the result that they are matched with high identity in a short sequence region may be derived. In this case, in order that two sequences are arranged through at least 50 sequential amino acids, parameters of the algorithm used as the GAP program can be corrected.

The term, "substantially pure" used herein is that a targeting molecule is present as a predominant species. In other words, it means that on the basis of mole, the concentration is higher than any other individual species in the same mixture. In one embodiment, a substantially pure molecule is comprised as at least about 50% (based on mole), at least about 80%, about 85%, at least about 90%, or at least about 99%, among all polymers comprised in a composition. In other embodiments, the targeting molecule is substantially homogeneously purified until any more contaminants are not detected by using a conventional method, and therefore the composition comprises one kind of homogeneous polymer material.

In one aspect, the present invention relates to a recombinant antibody specifically binding to α-syn protein or human α-syn protein, or its antigen-binding fragment. In this aspect, "recombinant protein" is a protein prepared using a recombination technique, namely, through the expression of the recombinant nucleic acid described in the present invention. The methods and techniques for production of a recombinant protein are widely known in the art.

Herein, "affinity", "affinity degree" or "binding affinity" is the strength of interaction between an antibody or its antigen-binding fragment and an antigen, and it is determined by properties of the antigen such as size, shape and/or charge of antigen, and CDR sequences of the antibody or antigen-binding fragment. The methods for determining the affinity are known in the art, and the followings can be referred.

The antibody or its antigen-binding fragment is called "specifically binding" to its target such as an antigen, when a dissociation constant ($K_D$) is $\leq 10^{-6}$ M. The antibody specifically binds to a target with "high affinity", when $K_D$ is Six $10^{-8}$ M. The antibody and antigen-binding fragment according to the present invention has a high affinity of Six $10^{-9}$ M, particularly Six $10^{-10}$ M, or more particularly Six $10^{-11}$ M to the aggregate.

As used herein, "preferentially binding" includes the binding to the α-syn aggregate only, or the binding to both of α-syn monomer and α-syn aggregate with higher affinity to the aggregate rather than the monomer. In an embodiment, the antibody or antigen-binding fragment thereof according to the present invention binds to the aggregate specifically with high affinity, but does not bind to α-syn monomer. In another embodiment, the antibody or antigen-binding fragment thereof according to the present invention can bind to both of the monomer and aggregate but binds to α-syn aggregate with higher affinity compared to the monomer. In one embodiment, the affinity for the α-syn aggregate is at least two times higher than the affinity for the α-syn monomer, or is at a low binding force that cannot be determined to specifically bind as an antibody or with a binding force that is not measurable at the experimental concentration range of antibody.

In one embodiment according to the present invention, the high affinity of the antibody or antigen-binding fragment of the present invention to α-syn aggregates is $K_D \leq 1.0 \times 10^{-8}$ M; $K_D \leq 1.0 \times 10^{-9}$ M in another embodiment; $K_D \leq 1.0 \times 10^{-10}$ in further embodiment; $K_D$ $1 \times 10^{-11}$ M; and $K_D \leq 1 \times 10^{-12}$ M in further embodiment. The antibodies and antigen-binding fragments with such high affinities may be administered at lower doses compared to antibodies having a lower affinity, for example greater than $K_D$ $10^{-7}$ M or $10^{-8}$ M, but not limited thereto. There is a great advantage in clinical practice, because the sufficient efficacy can be obtained by administering in the same manner as a simple subcutaneous injection. Furthermore, the antibodies and antigen-binding fragments with high affinity for α-syn aggregates can reduce α-syn aggregate formation, resulting in reduced concentration of aggregates in the brain. In addition, the antibody and antigen-binding fragments with high affinity for α-syn aggregates can reduce α-syn aggregate formation outside the central nervous system, and thus change the equilibrium state of α-syn forms in the boundary of brain blood barrier, thereby reducing the concentration of aggregates inside of the central nervous system.

Herein, "antigen-binding region or site" means a protein or a part of protein specifically binding to a specific antigen. For example, a part of an antibody comprising an amino acid residue providing the antibody with specificity and affinity to an antigen by interacting with the antigen. This antigen-binding region typically comprises one or more "complementary determining regions (CDR)". A specific antigen-binding region also comprises one or more "framework (FR)" regions. CDRs are amino acid sequences that contribute to the specificity and affinity of antigen binding. The framework region helps to maintain an appropriate conformation of these CDRs, thereby facilitating binding between the antigen-binding region and an antigen.

Herein, "antibody" means an antigen-binding fragment which can compete to an intact antibody for binding to any isotype of intact immunoglobulin, or a target antigen. For example, it includes chimeric, humanized, complete human and dual-specific antibodies or their antigen-binding fragments. The antibody is one kind of antigen binding protein by itself. The intact antibody commonly comprises at least 2 full-length heavy chains and 2 full-length light chains, but in some cases as naturally found in camelid animals, the antibody may comprise only heavy chains. The antibody or its antigen-binding fragment may be derived from only one source or chimeric. The chimeric antibody comprises a part derived from two kinds of different antibodies, and is described in more detail below. The antibody or its antigen-binding fragment can be produced by hybridoma, recombinant DNA technique or enzymatic or chemical cutting of an intact antibody. Unless otherwise stated, herein, the term "antibody" includes an antibody comprising 2 full-length heavy chains and 2 full-length light chains, and its derivatives, variants, fragments, and mutants, and their examples are as described below.

Herein, "light chain" includes a full-length light chain having a variable region sequence enough to provide binding specificity to an antigen or epitope and its fragment. The full-length light chain comprises a variable region domain VL and a constant region domain CL. The variable region domain of light chain is present in an amino terminal of a light chain polypeptide. The kinds of light chains include kappa and lambda chains.

Herein, "heavy chain" includes a full-length heavy chain having a variable region sequence enough to provide binding specificity to an antigen or epitope and its fragment. The full-length heavy chain comprises a variable region domain VH and 3 constant region domains CH1, CH2 and CH3. The VH domain is present in an amino terminal of a heavy chain polypeptide and the CH domain is present in a carboxy terminal, and the CH3 is positioned closest to a carboxy terminal. The heavy chain comprises IgG (comprising IgG1, IgG2a, IgG2b, IgG3 and IgG4 subtypes), IgA (comprising IgA1 and IgA2 subtypes), and isotypes of IgM and IgE.

The term "antigen-binding fragment" of a chain (heavy chain or light chain) of an antibody or immunoglobulin includes a part of an antibody which lacks some amino acids compared to a full-length chain, but can specifically bind to an antigen. This fragment can be considered as having biological activity, in an aspect that it can specifically bind to a target antigen, or can compete to other antibodies or an antigen-binding fragment to bind a specific epitope. In one aspect, this fragment comprises at least one CDR present in a full-length light chain or heavy chain, and in some embodiments, it comprises a short-chain heavy chain and/or light chain, or its part. This biological active fragment may be produced by a recombinant DNA technique or may be produced for example, by cutting an intact antibody enzymatically or chemically. An immunologically functional immunoglobulin fragment includes Fab, Fab', F(ab')2, Fv, domain antibody and single chain Ab, but is not limited thereto, and may be derived from any mammal including human, mouse, rat, camelid or rabbit, but is not limited thereto. The functional part of the antibody such as one or more CDRs described herein may be linked with a secondary protein or small molecular compound by a covalent bond, thereby being used as a target therapeutic agent to a specific target.

Herein, "Fab fragment" consists of 1 light chain and 1 heavy chain comprising a variable region and CH1 only. A Fab fragment cannot form a disulfide bond with other heavy chain.

Herein, "Fc" region comprises two heavy chain fragments comprising CH2 and CH3 domains of an antibody. These 2 heavy chain fragments are combined to each other by hydrophobic interaction of two or more of disulfide bonds and CH3 domain.

Herein, "Fab' fragment" comprises a region between CH1 and CH2 domains of a heavy chain, in addition to Fab fragment, and it can form a disulfide bond between two heavy chains of two molecules of Fab' fragment, to form a F(ab')2 molecule.

Herein, "F(ab')₂ fragment" comprises two light chains, and two heavy chains comprising a variable region, CH1 and a part of a constant region between CH1 and CH2 domains, as aforementioned, and thereby an intrachain disulfide bond between 2 heavy chains is formed. Thus, the F(ab')₂ fragment consists of two Fab' fragments, and the two Fab' fragments are meeting each other by the disulfide bond between them.

Herein, "Fv region" is a fragment of an antibody which comprises each variable region of a heavy chain and a light chain, but does not comprise a constant region. scFv can be one that a heavy chain and a light chain are linked by a disulfide bond. scFv can be one that Fv is linked by a flexible linker. scFv-Fc can be one that Fc is linked to scFv. The minibody can be one that CH3 is linked to scFv. The diabody comprises two molecules of scFv.

Herein, "single chain antibody (scAb)" is a single polypeptide chain comprising one variable region of a heavy chain or a light chain constant region in which a heavy chain and light chain variable region is linked by a flexible linker. The short-chain antibody may refer to for example, U.S. Pat. No. 5,260,203, and this is disclosed herein by reference.

Herein, "domain antibody (dAb)" is an immunologically functional immunoglobulin fragment comprising a variable region of heavy chain or a variable region of light chain only. In one embodiment, two or more of VH regions are linked by a covalent bond by a peptide linker, to form a bivalent domain antibody. Two VH regions of this bivalent domain antibody may target the same or different antigen.

Herein, "bivalent antigen-binding protein" or "bivalent antibody" comprises two antigen-binding sites. Two antigen-binding sites comprised in this bivalent antibody may have the same antigen specificity or may be a dual-specific antibody binding to different antigens separately.

Herein, "multi-specific antigen-binding protein" or "multi-specific antibody" is targeting two or more of antigens or epitopes.

Herein, "bispecific", "dual-specific" antigen-binding protein or antibody is a hybrid antigen-binding protein or antibody having 2 different antigen-binding sites. This bispecific antibody is one kind of multi-specific antigen-binding protein or multi-specific antibody, and it can be produced by known various methods, for example, methods such as fusion of hybridoma or linking of Fab' fragment. For example, Songsivilai and Lachmann, *Clin. Exp. Immunol.* 1990, 79:315-321; Kostelny et al., *J. Immunol.* 1992, 148: 1547-1553, etc. may be referred. The 2 epitopes different from each other to which 2 antigen-binding sites of the bispecific antigen-binding protein or antibody bind may be positioned on the same or different protein target. Herein, the term "antigen" or "immunogen" means a molecule or a part of molecule which for example, an antigen-binding protein (for example, antibody or its immunologically functional antigen-binding fragment) can bind to, and can be used for production of an antibody which can bind to an antigen in an animal. The antigen may comprise one or more epitopes which can interact with a different antibody or its fragment. In one embodiment according to the present invention, the antigen is a full-length α-syn protein or a partial α-syn protein 1 to 120 amino acid residues with deleted C-terminus.

Herein, "epitope" is a part of a molecule which is bound or recognized by an antigen-binding protein or antibody, and includes, for example, determinant molecules being capable of specifically binding to the antigen-binding protein, such as an antibody or a T-cell receptor. The epitope may be consecutive or inconsecutive, and for example, can be amino acid residues which are in separated locations and inconsecutive in polypeptide sequence and are bound by one antigen binding protein, like a conformational epitope. In one embodiment, the epitope includes a three-dimensional structure that is similar to an epitope used for antibody production, but may be a mimetic in an aspect that it does not include all residues or a part of residues in the epitope used for antibody production. Commonly, the epitope is a protein, but it may be other kinds of materials such as a nucleic acid. The epitope determining factor may be a chemically active group formed on a surface by a molecule such as an amino acid, a sugar side chain, a phosphoryl group or a sulfonyl group, or may have specific three-dimensional structural properties and/or specific charge properties. Generally, the antibody specific to a specific target antigen can recognize the epitope of the target antigen in protein and/or polymer complex. The antibody of the present invention can recognize C-terminus. In one embodiment, the antibody according to the present invention recognizes a C-terminus of α-syn protein, in particular 110-120 residues or 111-122 residues in other embodiments. Particularly, when the antibody recognizes 110 to 122 residues, the antibody shows the preferential binding property to the aggregates.

Herein, "conjugate" means a different molecule from the antibody or its antigen-binding fragment disclosed herein, particularly a chimeric molecule with particularly blood brain barrier transports described below or a therapeutic agent. In the conjugate, the antibody or its antigen-binding fragment according to the present invention is bound to other molecules by a covalent bond, van der Waals or hydrophobic interaction, capsulation, embedding or the combination method thereof. In the conjugate of one embodiment, the antibody or its antigen-binding fragment according to the present invention may be connected by a peptide linker. In addition, in the conjugate, the antibody or its antigen-binding fragment according to the present invention may be linked with a therapeutic agent by an alcohol group, acid group, carbonyl group, thiol group or amine group using the conventional chemical synthesis methods (see, for example, US2010/0028370). Herein, the antibody or its antigen-binding fragment according to the present invention forms a fusion protein, when it is linked to other peptide by a covalent bond or a peptide linker.

As used herein, the term "brain blood barrier" or BBB is a barrier formed by a tight junction in the capillary endothelial cell membrane of the brain, which exists between brain, vertebral column and its surrounding circulatory system. These barriers are very robust, and limit the passage of small molecules having about 60 Da of molecular weight into the brain. Brain blood barrier, vascular spinal cord barrier and vascular retinal barrier are continuous capillary barrier within the central nervous system, and are commonly referred to as BBB. The term "brain blood barrier transport" refers to proteins including peptides and polypeptides, nucleic acids, antibodies, or compounds with a low molecular weight that can pass through the brain blood barriers and deliver the antibody and antigen-binding fragment according to the present invention.

Herein, "therapeutic agent" means a molecule to be administered to a subject for a target therapeutic effect. The subject includes a non-human mammal, for example, primates or a human. The examples of the therapeutic agent include a protein comprising a peptide and a polypeptide, a nucleic acid, an antibody or a small molecular compound. In other aspects, the therapeutic agent can be used as a therapeutic agent of diseases related with α-syn aggregates by being bound to the antibody of the present invention.

Herein, the term "treating" means reduction, relief, alleviation or treatment of an injury, disease or symptom or condition of the disease; making a patient being able to withstand an injury, disease or symptom or morbid condition of the disease; delaying the deterioration rate of an injury, disease or symptom or morbid condition of the disease; or alleviation or treatment of an injury, disease or symptom or condition of the disease including objective or subjective parameters improving the quality of life of a patient mentally or physically. The alleviation or treatment of an injury, disease or symptom or condition of the disease may be determined on the basis of results of physical examination, examination of various indexes related to a disease and imaging examination. In one embodiment, the term includes the treatment of diseases related to α-syn, reduction of disease occurrence frequency, reduction of disease seriousness and/or alleviation of symptoms of a disease related to α-syn in the method of present invention.

As used herein, the term "disease related to α-syn aggregates" is a group of neurodegenerative diseases called as alpha-synucleinopathy, and has the characteristics that α-syn aggregates are found in lesions including neuron and glial populations, degeneration of dopamine system, change in movement performance, cognitive impairment, and formation of Lewy bodies and Lewy neurites (Kim et al., *Alzheimer's Research & Therapy* 2014, 6:73; McKeith et al., *Neurology* (1996) 47:1113-24). The diseases include Parkinson's disease (PD), Parkinson's disease dementia (PDD), dementia with Lewy bodies (DLB), Lewy body variant of Alzheimer's disease (LBV), combined Alzheimer's and Parkinson disease, multiple system atrophy (MSA) and other various diseases related to nerve axons, but are not limited thereto. In an embodiment, the antibody of present invention can be used for treatment of PD.

Herein, "effective dose" commonly means an amount enough to reduce seriousness and/or occurrence frequency of symptoms due to a disease, particularly, a disease related to α-syn, remove symptoms due to a disease, particularly, a disease related to α-syn and/or a root cause of disease occurrence, or prevent occurrence of symptoms due to a disease, particularly, a disease related to α-syn and/or a root cause, and/or improve or correct damages due to a disease, particularly, a disease related to α-syn. In some embodiments, the effective dose is a therapeutic effective dose or a prophylactic effective dose. The "therapeutic effective dose" is an amount enough to treat a disease, particularly symptoms or conditions related to α-syn, or prevent, delay a disease, particularly symptoms or conditions related to α-syn, or reverse its progress. The "prophylactic effective dose" is an amount for prevent or delay occurrence or reoccurrence of a disease, particularly, a disease related to α-syn or symptoms of the disease, particularly, a disease related to α-syn, and reduce its probability. The complete therapeutic or prophylactic effect can be caused by several times of administration of dose, rather than by a single administration of dose. Therefore, the therapeutic or prophylactic effective dose may be delivered by once or more of administration.

Antibody or Antigen-Binding Fragment

The present invention discloses an antibody or antigen-binding fragment specifically binding to α-syn protein including human α-syn. The antibody according to the present invention is a polypeptide comprising one or more of complementary determining regions or sites (CDR), as disclosed herein.

In an embodiment, a CDR is comprised in a "framework" region, and the framework orients a CDR(s) so that this CDR(s) can have appropriate antigen-binding properties.

The antibody according to the present invention specifically binds to α-syn protein found in brain derived from human, especially to α-syn aggregates at high affinity.

In one embodiment, an antibody according to the present invention may preferentially bind to α-syn aggregates with a high affinity and decrease their concentration. The reduction or degradation of α-syn aggregates by the antibody and its antigen-binding fragment according to the present invention involves the effective cleavage and degradation of the pathogen caused by antigen-antibody complex to facilitate the degradation of α-syn aggregates by lysosomes in the cell.

In yet another embodiment, the antibody or antigen-binding fragment thereof binds preferentially to α-syn aggregates with high affinity, and thus can prevent additional formation of α-syn aggregates, reduction of the concentration, inhibition of intercellular transport, and lower the effective dose in the drug development.

In another embodiment, the antibody or antigen-binding fragment thereof binds preferentially to α-syn aggregates with high affinity, thereby inhibiting or preventing α-syn aggregates from being transferred from one cell to another cell.

In one embodiment, the antibody includes a monoclonal antibody, dual-specific antibody, double antibody, multi-specific antibody, multiple antibody, minibody, domain antibody, antibody mimetic (or synthetic antibody), chimeric antibody, humanized antibody, human antibody, or antibody fusion (or antibody conjugate) and fragment thereof, but is not limited thereto, and includes various forms of antibodies disclosed herein. In one embodiment, the antibody fragment of the antibody disclosed herein includes Fab, Fab', F(ab')$_2$, Fv, diabody or single chain antibody molecule in which a heavy chain and a light chain are connected via a spacer. In other embodiments, the antibody disclosed herein may include a polypeptide of only light chains or only heavy chains including variable regions disclosed in Table 1a and Table 1b.

An antibody disclosed herein shares a specific region or sequence with another antibody disclosed herein. In one embodiment, it may share a constant region of the antibody or antigen-binding fragment. In another embodiment, it may share an Fc region. In another embodiment, it may share a framework of variable region.

It has been confirmed that the antibodies disclosed herein bind to human α-syn aggregates with high affinity. As additionally described in the Examples, multiple antibody clones were tested and found to have an epitope in the 110-120 or 111-122 residues at the C-terminus. Although it is not limited to this theory, the preferred binding and high affinity for the aggregates of the antibodies in the present invention may be due to the recognition of the 110-120 residues, as compared to conventional antibodies recognizing 121-130 residues at C-terminus.

In one embodiment, the antibody according to the present invention has a typical structure of an antibody found in nature. Camelid animals produce an antibody consisting of a single heavy chain, but the structural unit of this antibody commonly comprises a tetrameric polypeptide, and the tetramer comprises two of one pair of polypeptide chain bodies consisting of different 2 polypeptide chains. In a typical antibody, the one pair of polypeptide chain body comprises one full-length light chain (about 25 kDa) and one full-length heavy chain (about 50 to 70 kDa). Each chain shows a characteristic folding pattern, and consists of several immunoglobulin domains, consisting of about 90 to 110 amino acids. These domains are basic units consisting of an antibody polypeptide. The amino-terminal part of each chain typically comprises a part called a variable region or V region that is a part recognizing an antigen. The carboxy-terminal part is conserved evolutionarily more than the amino-terminal, and it comprises a part called a constant region or C region. The human light chain is commonly classified as kappa (κ) and lambda (λ) light chains, and these comprise one variable region and one constant region, respectively. The heavy chain is typically classified as mu (μ), delta (δ), gamma (γ), alpha (α) or epsilon (ε) chain, and these are defined as IgM, IgD, IgG, IgA and IgE isotypes, respectively. IgG includes IgG1, IgG2, IgG3 and IgG4, but has unlimited numerous subtypes. IgM subtype includes IgM and IgM2. IgA subtype includes IgA1 and IgA2. In human, IgA and IgD isotypes comprise 4 heavy chains and 4 light chains; IgG and IgE isotypes comprise 2 heavy chains and 2 light chains, and IgM isotype comprises 5 heavy chains and 5 light chains. The heavy chain constant region typically shows an effector function, but comprises one or more domains. The number of heavy chain constant region domains becomes different depending of isotypes. IgG heavy chain, for example, comprises 3 C region domains known as $C_H1$, $C_H2$ and $C_H3$, respectively. The antibody disclosed herein may be any one of these isotypes and subtypes. In one embodiment, the antibody according to the present invention is an IgG1, IgG2, IgG2a, IgG2b, IgG3 or IgG4 subtype.

The heavy chain variable region and light chain variable region according to the present invention may be linked to at least a part of a human constant region. The selection of a constant region may be determined by whether the antibody-dependent cell-mediated cytotoxicity, antibody-dependent cell phagocytosis, and/or complement-dependent cytotoxicity is required partially. For example, human isotype IgG1 and IgG3 have complement-dependent cytotoxicity and human isotype IgG2 and IgG4 do not have this cytotoxicity. In addition, human IgG1 and IgG3 induce a cell-mediated effector function stronger than human IgG2 and IgG4. The light chain constant region may be lambda or kappa.

In one embodiment, the anti-α-syn antibody according to the present invention may be a human antibody, and the heavy chain constant region may be an IgG1-, IgG2- IgG3- or IgG4-type. In a further embodiment, the antibody of the present invention is an IgG1- or IgG2-type.

In full-length light chain and heavy chain, a variable region and a constant region are linked by a "J" region that is about 12 or more amino acids in length, and the heavy chain also comprises a "D" region of about 10 or more amino acids. For example, Fundamental Immunology, 2nd ed., Ch. 7 (Paul, W., ed.) 1989, New York: Raven Press may be referred. Typically, a variable region of light chain/heavy chain pair of an antibody forms an antigen-binding site.

A variable region of an immunoglobulin chain has the same overall structure commonly, and comprises a comparatively conserved framework region (FR) connected by 3 hypervariable regions called "complementary determining site or region or domain" or CDR (Complementary Determining Region). The CDR of a variable region derived from each chain consisting of heavy chain/light chain pair is arranged by a framework region typically, thereby forming a structure specifically binding to a specific epitope of a target protein (α-syn). These factors of naturally occurring light chain and heavy chain regions are typically comprised from the N-terminal to the C-terminal in the following order: FR1, CDR1, FR2, CDR2, FR3, CDR3 and FR4. The position of amino acid sequences corresponding to each of them in the variable region may be determined by Kabat numbering system (Kabat, Sequences of Proteins of Immunological Interest (1987 and 1991, NIH, Bethesda, MD), or Chothia & Lesk, J. Mol. Biol. 1987, 196:901-917; Chothia et al., 1989, Nature 1989, 342:878-883).

The CDR sequences are composed of the heavy chain and light chain variable regions of the antibody or antigen-binding fragment according to one of the present invention disclosed in Table 1a to Table 1b, respectively. In each variable region, the CDR sequences are underlined and represent the CDR1, CDR2 and CDR3 sequences, respectively, in the order from front to back. The CDR sequences in the variable region are shown underlined. CDR1, CDR2 and CDR3 sequences are shown in the order from front to back, respectively.

TABLE 1a

| | VH CDR SEQ ID NOS | | | Heavy chain variable region VH amino acid sequences and SEQ ID Nos. | |
|---|---|---|---|---|---|
| clone | H1 | H2 | H3 | NO | amino acid sequence |
| 1E4 | 1 | 15 | 29 | 85 | EVQLQESGAELVRPGTSVKVSCKASGYAFTNYLIEWVKQRPGQ GLEWIGVINPGSGGTNYNEKFKGKATLTADKSSSTAYMQLSSLT SDDSAVYFCASGNYDTYWGQGTLVTVSA |
| 9B11 | 2 | 16 | 30 | 86 | EVQLQESGGGLVQPKGSLKLSCAASGFTFNTYAMNWVRQAPGK GLEWVARIRSKSNNYATYYADSVKDRFTISRDDSQSMLYLQMN NLKTEDTAMYYCVRQDFDYWGQGTTLTVSS |
| 3A9 | 3 | 17 | 31 | 87 | EVQLQESGGGLVKPGGSLKLSCAASGFTFSSYAMSWVRQTPEK RLEWVATISNGGGYTYYPDSVKGRFTISRDNAKNTLYLQMSSLR SEDTAMYYCARHITTVRPTKYFDYWGQGTTLTVSS |
| 10F10 | 4 | 18 | 32 | 88 | EVQLQESGPGLVKPSQSLSLTCSVTGYSITGGFYWNWIRQFPGN NLEWMGYINYDGSSDYSPSLKNRISITRDTSKNQFFLNLNSVTTE DTATYYCVRGDYDWGQGTTLTVSS |
| 11F11 | 5 | 19 | 33 | 89 | EVQLQESGGGLVQPGGSLRLSCATSGFTFSDFYMEWVRQPPGKR LEWIAASRNKANDYTTEYSASVKGRFIVSRDTSQSILYLQMNAL RAEDTAIYYCARDAHGKPFAYWGQGTLVTVSA |

TABLE 1a-continued

| clone | VH CDR SEQ ID NOS H1 | H2 | H3 | SEQ ID NO | Heavy chain variable region VH amino acid sequences and SEQ ID Nos. amino acid sequence |
|---|---|---|---|---|---|
| AC8 | 6 | 20 | 34 | 90 | EVQLLESGGGLVQPGGSLRLSCAASGFTFSDYSMSWVRQAPGK GLEWVSGISSGGSSKYYADSVKGRFTISRDNSKNTLYLQMNSLR AEDTAVYYCAKIFHNFDYWGQGTLVTVSS |
| AE8 | 7 | 21 | 35 | 91 | EVQLLESGGGLVQPGGSLRLSCAASGFTFSNYAMSWVRQAPGK GLEWVSAISSGGGNIYYADSVKGRFTISRDNSKNTLYLQMNSLR AEDTAVYYCARRPLYFDYWGQGTLVTVSS |
| AA9 | 8 | 22 | 36 | 92 | EVQLLESGGGLVQPGGSLRLSCAASGFTFSSYSMSWVRQAPGKG LEWVSAIYPGSSNKYYADSVKGRFTISRDNSKNTLYLQMNSLRA EDTAVYYCARHAATFDYWGQGTLVTVSS |
| DG5 | 9 | 23 | 37 | 93 | EVQLLESGGGLVQPGGSLRLSCAASGFTFSNYAMSWVRQAPGK GLEWVSVISPGSGNTYYADSVKGRFTISRDNSKNTLYLQMNSLR AEDTAVYYCARVTIACPTKRCSYSNGMDVWGQGTLVTVSS |
| AD2 | 10 | 24 | 38 | 94 | EVQLLESGGGLVQPGGSLRLSCAASGFTFSNYAMSWVRQAPGK GLEWVSAISHSGSSKYYADSVKGRFTISRDNSKNTLYLQMNSLR AEDTAVYYCARSGNNFDYWGQGTLVTVSS |
| AD7 | 11 | 25 | 39 | 95 | EVQLLESGGGLVQPGGSLRLSCAASGFTFSGYAMSWVRQAPGK GLEWVSAISPNGGNKYYADSVKGRFTISRDNSKNTLYLQMNSLR AEDTAVYYCARRPVYFDYWGQGTLVTVSS |
| DG11 | 12 | 26 | 40 | 96 | EVQLLESGGGLVQPGGSLRLSCAASGFTFSDYAMSWVRQAPGK GLEWVSVISPGSGSKYYADSVKGRFTISRDNSKNTLYLQMNSLR AEDTAVYYCAKVTISCARMRCSYADGMDVWGQGTLVTVSS |
| DG8 | 13 | 27 | 41 | 97 | EVQLLESGGGLVQPGGSLRLSCAASGFTFSDHAMSWVRQAPGK GLEWVSVISHGNGSKYYADSVKGRFTISRDNSKNTLYLQMNSLR AEDTAVYYCARVASRCRRGRCSYSDGMDVWGQGTLVTVSS |
| DA9 | 14 | 28 | 42 | 98 | EVQLLESGGGLVQPGGSLRLSCAASGFTFSNYAMSWVRQAPGK GLEWVSVISPSDSNTYYADSVKGRFTISRDNSKNTLYLQMNSLR AEDTAVYYCARVTLSCRASRCSYSNGMDVWGQGTLVTVSS |

TABLE 1b

| clone | VL CDR SEQ ID NOS L1 | L2 | L3 | SEQ ID NO | Light chain variable region VL amino acid sequences and SEQ ID Nos. amino acid sequence |
|---|---|---|---|---|---|
| 1E4 | 43 | 57 | 71 | 99 | DIVMTQSPLSLPVSLGDQASISCRSSQSLVHSNGNTYLHWYLQKP GQSPKLLIYKVSNRFSGVPDRFSGSGSGTDFTLKISRVEAEDLGV YFCSQSTHVPRTFGGGTKLEIK |
| 9B11 | 44 | 58 | 72 | 100 | DIVMTQSPLSLPVSLGDQASISCRSSQSLVHSNGNTYLHWYLQKP GQSPKLLIYKVSNRFSGVPDRFSGSGSGTDFTLKISRVEAEDLGV YFCSQSTHVPLTFGAGTKLEQK |
| 3A9 | 45 | 59 | 73 | 101 | DIVMTQSPKFMSTSVGDRVSITCKASQNVGTTVAWYQQKPGQS PKLLIYSASNRYTGVPDRFTGSGSGTDFTLTISNMQSEDLADYFC QQYSNYPLTFGAGTKLELR |
| 10F10 | 46 | 60 | 74 | 102 | DIVMTQSPLTLSVTIGQPASISCKSSQSLLDSDGETYLNWLLQRP GQSPKRLIYLVSKLDSGVPDRFSGSGSGTDFTLKISRVEAEDLGV YYCWQGTHFPQTFGGGTKLEIK |
| 11F11 | 47 | 61 | 75 | 103 | DIVMTQSPSSLAVSVGEKVTMSCKSSQSLLYSSNQKNYLAWYQ QKPGQSPKLLIYWASTRESGVPDRFTGSGSGTDFTLTISSVKAED LAVYYCQQYYSYPWTFGGGTKLEIK |
| AC8 | 48 | 62 | 76 | 104 | QSVLTQPPSASGTPGQRVTISCSGSSSNIGSNNVYWYQQLPGTAP KLLIYYDSQRPSGVPDRFSGSKSGTSASLAISGLRSEDEADYYCA SWDASLSAYVFGGGTKLTVLG |
| AE8 | 49 | 63 | 77 | 105 | QSVLTQPPSASGTPGQRVTISCSGSSSNIGNNSVNWYQQLPGTAP KLLIYANNNRPSGVPDRFSGSKSGTSASLAISGLRSEDEADYYCG SWDASLNGYVFGGGTKLTVLG |

TABLE 1b-continued

| | VL CDR SEQ ID NOS | | | Light chain variable region VL amino acid sequences and SEQ ID Nos. | |
|---|---|---|---|---|---|
| clone | L1 | L2 | L3 | NO | amino acid sequence |
| AA9 | 50 | 64 | 78 | 106 | QSVLTQPPSASGTPGQRVTISCSGSSSNIGSNYVSWYQQLPGTAP KLLIYGDNKRPSGVPDRFSGSKSGTSASLAISGLRSEDEADYYCG AWDDSLSGYVFGGGTKLTVLG |
| DG5 | 51 | 65 | 79 | 107 | QSVLTQPPSASGTPGQRVTISCSGSSSNIGSNAVSWYQQLPGTAP KLLIYSNSNRPSGVPDRFSGSKSGTSASLAISGLRSEDEADYYCA AWDASLSGYVFGGGTKLTVLG |
| AD2 | 52 | 66 | 80 | 108 | QSVLTQPPSASGTPGQRVTISCTGSSSNIGNNSVSWYQQLPGTAP KLLIYSDNNRPSGVPDRFSGSKSGTSASLAISGLRSEDEADYYCG SWDASLSGYVFGGGTKLTVLG |
| AD7 | 53 | 67 | 81 | 109 | QSVLTQPPSASGTPGQRVTISCTGSSSNIGSNAVNWYQQLPGTAP KLLIYSNNHRPSGVPDRFSGSKSGTSASLAISGLRSEDEADYYCG AWDSSLNGYVFGGGTKLTVLG |
| DG11 | 54 | 68 | 82 | 110 | QSVLTQPPSASGTPGQRVTISCTGSSSNIGSNSVSWYQQLPGTAP KLLIYANSNRPSGVPDRFSGSKSGTSASLAISGLRSEDEADYYCA AWDASLSAYVFGGGTKLTVLG |
| DG8 | 55 | 69 | 83 | 111 | QSVLTQPPSASGTPGQRVTISCSGSSSNIGSNSVSWYQQLPGTAP KLLIYANNNRPSGVPDRFSGSKSGTSASLAISGLRSEDEADYYCG AWDSSLSAYVFGGGTKLTVLG |
| DA9 | 56 | 70 | 84 | 112 | QSVLTQPPSASGTPGQRVTISCSGSPSNIGNNSVSWYQQLPGTAP KLLIYANSHRPSGVPDRFSGSKSGTSASLAISGLRSEDEADYYCG SWDASLNGYVFGGGTKLTVLG |

In one embodiment of the present invention, heavy chain and light chain variable regions of the antibody or antigen-binding fragment disclosed in the Table 1a and Table 1b can be combined in various manners to prepare the different antibodies. In addition, heavy chain and light chain variable regions of the antibody or antigen-binding fragment disclosed in the Table 1a and Table 1b can be combined freely without any limited method.

Each of the heavy chain and light chain variable regions disclosed herein may bind to targeting various heavy chain and light chain constant regions to form the heavy chain and light chain of an intact antibody, respectively. In addition, each of the heavy chain and light chain sequences bound to constant regions like this may be also combined to form an intact antibody structure.

Any variable region of a heavy chain and light chain of the antibody according to the present invention may be linked to at least a part of constant regions. The constant regions may be selected according to whether antibody-dependent cell-mediated cytotoxicity, antibody-dependent cell phagocytosis and/or complement-dependent cytotoxicity, etc. is required. For example, human isotype IgG1 and IgG3 have complement-dependent cytotoxicity, and human isotype IgG2 and IgG4 do not have the cytotoxicity. Human IgG1 and IgG3 also induce a cell-mediated effector function stronger than human IgG2 and IgG4. For example, the heavy chain variable region may bind to IgG constant regions including IgG1, IgG2, IgG2a, IgG2b, IgG3 and IgG4, and the light chain variable region may bind to a kappa or lambda constant region. For the constant region, one appropriate as desired can be used, and for example, a human or mouse-derived one can be used.

In one embodiment, the heavy chain variable region disclosed herein can be linked to a murine IgG2a constant region, or a human IgG1 constant region, which can be shown in SEQ ID NOs: 113 to 126 (including a murine IgG2a constant region) or SEQ ID NOs: 127 to 140 (including a human IgG1 constant region), respectively.

In another embodiment, the light chain variable regions disclosed herein may be linked to a mouse kappa constant region or human kappa constant region, which can be shown in SEQ ID NOs: 141 to 154 (mouse kappa constant region) and SEQ ID NOs: 155 to 168 (human kappa constant region).

In addition, such constant region sequences to be combined with the variable regions disclosed herein are exemplary, and those skilled in the art will know that other constant regions can be used, including modified constant regions which can be for stability, expression, manufacturability or other targeting properties.

The present invention comprises one or more amino acid sequences having substantial sequence identity with one or more amino acid sequences disclosed herein. The substantial identity means maintaining the effect disclosed herein in which the sequence variation is present.

In one embodiment, it has about 90%, 95%, or 99% identity to the heavy chain variable regions disclosed in Table 1a. In other embodiments, it has about 90%, 95%, or 99% identity to the light chain variable regions disclosed in Table 1b. For example, in case of variant showing 90%, 95%, or 99% identity to the antibody or antigen-binding fragment disclosed herein, any variation is occurred in a frame of variable regions than CDRs.

Herein, a nucleic acid encoding the antibody or a part or whole of its antigen binding fragment part disclosed herein is disclosed. The nucleic acid includes a PCR or sequence analysis primer used for amplification, investigation, analysis or mutant induction of a polynucleotide encoding each chain of antibody, or fragment of the antibody, its mutant, derivative, or variant, a polynucleotide encoding a light chain or heavy chain variable region or only CDR, a polynucleotide enough to be used as a hybridization probe, and a polynucleotide encoding a polypeptide. The nucleic acids can be of any length. These may be for example, 5, 10, 15, 20, 25, 30, 35, 40, 45, 50, 75, 100, 125, 150, 175, 200, 250, 300, 350, 400, 450, 500, 750, 1,000, or 1,500 or more of polynucleotides in length and/or may comprise one or more of additional sequences, for example, regulatory sequences, and/or may be a bigger nucleic acid, for example, a part of vector. The nucleic acid may be a single strand or double strand, and may comprise RNA and/or DNA polynucleotide, and its artificial variant (e.g. peptide nucleic acid).

In one embodiment, the nucleic acid encoding the antibody or its fragment disclosed herein is a nucleic acid encoding a CDR disclosed herein, a variable region comprising the CDR, a full-length antibody comprising the variable region and constant region. When the amino acid sequence is determined, the nucleic acid sequence may be usefully determined, considering a known reverse transcription program and codon usage, etc. The exemplary nucleic acid sequence can be SEQ ID NOs: 169-182 (heavy chain including mouse IgG2a constant region), SEQ ID NOs: 83-196 (heavy chain including human IgG1 constant region), SEQ ID NOs: 197-210 (light chain including mouse kappa constant region), and SEQ ID NOs: 211-224 (light chain including human kappa constant region).

The present invention also includes one or more nucleic acid sequences having the substantial sequence identity to one or more nucleic acid sequences disclosed herein. The substantial identity means that the antibody or antigen-binding fragment encoded by the nucleic acid maintains the effect disclosed herein, even in case of causing conservative substitution or amino acid variation in which the variation of nucleic acid does not accompany amino acid substitution.

Specificity and Affinity of Antibody to an Aggregate

The antibody or antigen-binding fragment according to the present invention particularly has specificity to α-syn aggregates and high affinity. In one embodiment, according to FIG. 6, the affinity to an aggregates is $K_D \leq 1.0 \times 10^{-9}$ M; in another embodiment, it is $K_D \leq 1.0 \times 10^{-10}$ M; and in another embodiment, it is $K_D \leq 1.0 \times 10^{-11}$ M. The antibody or antigen-binding fragment according to the present invention having the high affinity has an advantage in that it can be administered in a lower amount of administration, compared to an antibody having low affinity, for example, $10^{-7}$ M or $10^{-8}$ M of affinity. This does not limit the antibody, for example, but since enough efficacy can be obtained, despite of administration by simpler way such as subcutaneous injection, there is a big advantage clinically.

In addition, the antibody and antigen-binding fragments thereof having a high affinity to α-syn aggregates can inhibit and/or reduce α-syn aggregate formation and/or accumulation, and/or intercellular transport, thereby lowering the concentration of aggregates in brain.

Furthermore, the antibody and antigen-binding fragments having a high affinity to α-syn aggregates can reduce α-syn aggregate formation outside of the central nervous system, resulting in reducing the concentration of aggregates inside of the central nervous system, by changing the equilibrium state of α-syn forms in boundary of brain blood barrier. Although it is not limited to this theory, the antibody or antigen-binding fragment according to the present invention can inhibit the formation of aggregates by the removal of monomers, or remove both monomers and aggregates.

Variable Region of Antibody

The present invention relates to the antibody light chain variable region or antibody heavy chain variable region shown in Table 1a and Table 1b, and an antibody (and corresponding nucleic acid sequence) including an immunological functional fragment, a derivative, a mutant protein and a variant of the light chain and heavy chain variable regions.

Also, the nucleic acid sequences coding for the variable regions shown in Tables 1a and 1b are included. The nucleic acid sequences are not additionally disclosed, because they are included in the full length antibody shown in SEQ ID NOs: 169-182 (heavy chain comprising a murine IgG2a constant region), SEQ ID NOS: 183-196 (heavy chain comprising a human IgG1 constant region), SEQ ID NOs: 197-210 (light chain comprising a constant region of a mouse kappa) and a nucleic acid sequence encoding a full length antibody disclosed in SEQ ID NO: 211 to 224 (light chain comprising a human kappa constant region). Those skilled in the art can obtain easily the nucleic acid sequence encoding the protein sequence, on the basis of the amino acid sequence of the variable region set forth in Table 1.

The antibody in which the variable regions of heavy chain and light chain according to the present invention are combined variously may be represented by "VHx/VLy", wherein "x" corresponds to the heavy chain variable region SEQ ID NO, and "y" corresponds to the light chain variable region SEQ ID NO. In one embodiment, the variable region according to the present invention may include the following combinations, but not limited thereto: VH85/VL99, VH85/VL100, VH85/VL101, VH85/VL102, VH85/VL103, VH85/VL104, VH85/VL105, VH85/VL106, VH85/VL107, VH85/VL108, VH85/VL109, VH85/VL110, VH85/VL111, VH85/VL112; VH86/VL99, VH86/VL100, VH86/VL101, VH86/VL102, VH86/VL103, VH86/VL104, VH86/VL105, VH86/VL106, VH86/VL107, VH86/VL108, VH86/VL109, VH86/VL110, VH86/VL111, VH86/VL112; VH87/VL99, VH87/VL100, VH87/VL101, VH87/VL102, VH87/VL103, VH87/VL104, VH87/VL105, VH87/VL106, VH87/VL107, VH87/VL108, VH87/VL109, VH87/VL110, VH87/VL111, VH87/VL112; VH88/VL99, VH88/VL100, VH88/VL101, VH88/VL102, VH88/VL103, VH88/VL104, VH88/VL105, VH88/VL106, VH88/VL107, VH88/VL108, VH88/VL109, VH88/VL110, VH88/VL111, VH88/VL112; VH89/VL99, VH89/VL100, VH89/VL101, VH89/VL102, VH89/VL103, VH89/VL104, VH89/VL105, VH89/VL106, VH89/VL107, VH89/VL108, VH89/VL109, VH89/VL110, VH89/VL111, VH89/VL112; VH90/VL99, VH90/VL100, VH90/VL101, VH90/VL102, VH90/VL103, VH90/VL104, VH90/VL105, VH90/VL106, VH90/VL107, VH90/VL108, VH90/VL109, VH90/VL110, VH90/VL111, VH90/VL112; VH91/VL99, VH91/VL100, VH91/VL101, VH91/VL102, VH91/VL103, VH91/VL104, VH91/VL105, VH91/VL106, VH91/VL107, VH91/VL108, VH91/VL109, VH91/VL110, VH91/VL111, VH91/VL112; VH92/VL99, VH92/VL100, VH92/VL101, VH92/VL102, VH92/VL103, VH92/VL104, VH92/VL105, VH92/VL106, VH92/VL107, VH92/VL108, VH92/VL109, VH92/VL110, VH92/VL111, VH92/VL112; VH93/VL99, VH93/VL100, VH93/VL101, VH93/VL102, VH93/VL103, VH93/VL104, VH93/VL105, VH93/VL106, VH93/VL107, VH93/VL108, VH93/VL109, VH93/VL110, VH93/VL111, VH93/VL112; VH94/VL99, VH94/VL100, VH94/VL101, VH94/VL102, VH94/VL103, VH94/VL104, VH94/VL105, VH94/VL106, VH94/VL107, VH94/VL108, VH94/VL109, VH94/VL110, VH94/VL111, VH94/VL112; VH95/VL99, VH95/VL100, VH95/VL101, VH95/VL102, VH95/VL103, VH95/VL104, VH95/VL105, VH95/VL106, VH95/VL107, VH95/VL108, VH95/VL109, VH95/VL110, VH95/VL111, VH95/VL112; VH96/VL99, VH96/VL100, VH96/VL101, VH96/VL102, VH96/VL103, VH96/VL104, VH96/VL105, VH96/VL106, VH96/VL107, VH96/VL108, VH96/VL109, VH96/

VL110, VH96/VL111, VH96/VL112; VH97/VL99, VH97/ VL100, VH97/VL101, VH97/VL102, VH97/VL103, VH97/ VL104, VH97/VL105, VH97/VL106, VH97/VL107, VH97/ VL108, VH97/VL110, VH97/VL111, VH97/VL111, VH97/ VL112; VH98/VL99, VH98/VL100, VH98/VL101, VH98/ VL102, VH98/VL103, VH98/VL104, VH98/VL105, VH98/ VL106, VH98/VL107, VH98/VL108, VH98/VL109, VH98/ VL110, VH98/VL111, or VH98/VL112.

The various combinations of variable regions as aforementioned may be used as an intact antibody and various forms of antibodies comprising scFv, etc.

CDR

The antibody disclosed herein is a polypeptide in which one or more CDRs according to the present invention are grafted, inserted and/or linked. In one embodiment, the antibody may have 1, 2, 3, 4, 5 or 6 CDRs. Thus, the antibody may have for example, one heavy chain CDR1 ("CDRH1"), and/or one heavy chain CDR2 ("CDRH2"), and/or one heavy chain CDR3 ("CDRH3"), and/or one light chain CDR1 ("CDRL1"), and/or one light chain CDR2 ("CDRL2"), and/or one light chain CDR3 ("CDRL3").

The position of amino acid sequences corresponding to a complementarity determining region (CDR) and a framework region (FR) of an antibody in a variable region may be determined by Kabat (Kabat et al., Sequences of Proteins of Immunological Interest, 5th Ed., US Dept. of Health and Human Services, PHS, NIH, NIH Publication no. 91-3242, 1991) The CDRs to be comprised in the heavy chain and light chain of the antibody according to the present invention are disclosed in Tables 1a to 1b (or heavy chain CDR H1 is represented by SEQ ID NOs: 1 to 14, and heavy chain CDR H2 is represented by SEQ ID NOs: 15 to 28, and heavy chain CDR H3 is represented by SEQ ID NOs: 29 to 42, and light chain CDR L1 is represented by SEQ ID NOs: 43 to 56, and light chain CDR L2 is represented by SEQ ID NOs: 57 to 70, and light chain CDR L3 is represented by SEQ ID NOs: 71 to 84).

The present invention also comprises one or more amino acid sequences having substantial sequence identity with amino acid sequences of one or more CDRs disclosed in Tables 1a to 1b. The substantial identity means maintaining the effect disclosed herein in which the sequence variation is present.

The structure and properties of CDRs of a naturally occurring antibody are as aforementioned. Simply, in a typical antibody, the CDRs are comprised in a framework of heavy chain and light chain variable regions consisting of a region which is involved in antigen binding and recognition. The variable region comprises at least 3 heavy chain or light chain CDRs in a framework region (Kabat et al., 1991, Sequences of Proteins of Immunological Interest, Public Health Service N.I.H., Bethesda, MD; or Chothia and Lesk, J. Mol. Biol. 1987, 196:901-917; Chothia et al., 1989, Nature 1989, 342:877-883). However, the CDRs disclosed herein are used for defining a typical antibody structure of antigen-binding domain, and in addition, as disclosed herein, can be used as comprised in other various polypeptide structures.

Those skilled in the art will understand that each disclosed CDR can be selected and combined independently each other, when an antibody comprises one or more of CDRs disclosed herein. Thus, an antibody having 1, 2, 3, 4, 5 or 6 of independently selected CDRs. In addition, those skilled in the art may know that when the CDR is selected for combination, the same kind of CDR is not repeatedly used, and for example, the antibody is commonly not prepared as comprising two CDRH2 regions.

Monoclonal Antibody

The antibody disclosed herein comprises a monoclonal antibody binding to α-syn, specifically α-syn aggregates.

In addition, the monoclonal antibody may be prepared by using any technique known in the art. For example, it may be produced by immortalizing splenocytes collected from an immunized transformed animal. The splenocytes may be immortalized by using any technique known in the art, for example, by fusing them with myeloma cells to produce hybridoma. The myeloma cells to be used for the hybridoma-production fusion process are preferably non-antibody-productive, have high fusion efficiency, and are unable to grow in a specific selective medium that lacks certain enzymes and supports the growth of only the targeted fusion cells (hybridoma). Examples of appropriate cell lines to be used for mouse fusion include Sp-20, P3-X63/Ag8, P3-X63-Ag8.653, NS1/1.Ag4 1, Sp210-Ag14, FO, NSO/U, MPC-11, MPC11-X45-GTG 1.7 and S194/5XXO Bul, and examples of cell lines used for rat fusion include R210.RCY3, Y3-Ag 1.2.3, IR983F and 4B210. Other cell lines useful for cell fusion may be U-266, GM1500-GRG2, LICR-LON-HMy2 and UC729-6.

In some cases, hybridoma cell lines are produced by collecting splenocytes from an animal (for example, a transformed animal having a human immunoglobulin sequence, where the animal is immunized by α-syn immunogen); fusing collected splenocytes to myeloma cells to produce hybridoma cells; establishing hybridoma cell lines from hybridoma cells; and identifying hybridoma cell lines producing an antibody binding to α-syn.

The monoclonal antibody secreted by hybridoma cell lines may be purified by using a technique known in the art.

Chimeric and Humanized Antibody

The antibody can be also modified by various methods for various purposes. A chimeric antibody and humanized antibody can be provided. A chimeric antibody is an antibody forming an immunologically functional light chain, heavy chain or fragment thereof, by that polypeptide fragments derived from different antibodies are linked by covalent bonds. Commonly, a part of the light chain and/or heavy chain of the chimeric antibody is a sequence belonging to a certain species or certain class or subtype, and the rest of the sequence belongs to other species or other class or subtype. For a method of preparation of a chimeric antibody, for example, U.S. Pat. No. 4,816,567; and Morrison et al., 1985, *Proc. Natl. Acad. Sci. USA* 81:6851-6855 may be referred. For CDR grafting, for example, U.S. Pat. Nos. 6,180,370, 5,693,762, 5,693,761, 5,585,089 and 5,530,101 may be referred.

Commonly, a purpose for preparing a chimeric antibody is to maximize the number of amino acids found in an organism in which an antibody is used. One example is a "CDR-grafted" antibody, wherein the antibody comprises one or more of CDRs derived from a certain species, or certain class or subtype, and the rest is derived from other species, or another class or subtype of antibody. For example, to use it in humans, a naturally appearing variable region or CDR of human antibody by that a variable region or selected CDR of rodent antibody is grafted in the human antibody may be replaced or vice versa.

The most useful type of chimeric antibody is a "humanized" antibody. Generally, humanized antibodies are produced from monoclonal antibodies originally generated in non-human animals. In such a monoclonal antibody, a particular amino acid residue, which typically constitutes the non-antigen recognition portion of the antibody, is modified to be homologous to the corresponding residue of the corresponding isotype of the human antibody. Humanization can be performed with various known methods, for example, substituting at least a portion of the rodent variable region with the corresponding region of a human antibody (U.S. Pat. Nos. 5,585,089 and 5,693,762; Jones et al., Nature 1986, 321: 522-525; Riechmann et al., Nature 1988, 332: 323-27; Verhoeyen et al., Science 1988, 239: 1534-1536).

In one aspect, the CDRs of the light chain variable region and heavy chain variable region of the antibodies disclosed herein are implanted into framework regions (FRs) of antibodies derived from the same or different species phylogenetically. For example, the CDRs of the heavy chain variable region and light chain variable region disclosed herein may be transplanted into conserved human FRs. To generate conserved human FRs, the consensus amino acid sequence of an FR can be obtained by aligning several types of human heavy chain amino acid sequences or light chain amino acid sequences and extracting the conserved sequence from the aligned sequences. In other embodiments, the FRs of the heavy chain or light chain disclosed herein are replaced by FRs of a different heavy chain or light chain. In an aspect, while the specific amino acids found only in the FR of the heavy chain and light chain of the anti-α-syn antibody are not replaced, the remaining FR amino acids can be replaced. The specific amino acid is typically a specific amino acid present at a position that is not observed in the FR. Alternatively, a variable region grafted from one heavy chain or light chain can be used with a constant region that is different from the constant region of a particular heavy or light chain as disclosed herein. In other embodiments, the grafted variable region may be a part of a single chain Fv antibody. The CDRs of the light chain variable region and heavy chain variable region of the antibodies disclosed herein can be used in a transplanted form into any antibody.

In addition, in one embodiment, for a constant region derived from species other than human, a hybrid antibody combined with a variable region derived from human may be used.

Complete Human Antibody

Herein, a complete human antibody is also disclosed. A complete human antibody specific to a certain antigen ("complete human antibody") can be prepared without exposing a human to an antigen. One method producing a complete human antibody is "humanizing" a mouse humoral immune system. An endogenous Ig gene may introduce human immunoglobulin (Ig) genetic loci to a non-activated mouse, thereby producing a complete human monoclonal antibody (mAb) in the mouse. If using the complete human antibody, an immunogenic reaction and allergic reaction which may be caused by administering a mouse or mouse-derived mAb into humans may be minimized.

This complete human antibody may be produced by immunizing a transformed animal (commonly, mouse) which can produce a human antibody by lacking production of an endogenous immunoglobulin. An antigen for this purpose typically has 6 or more of sequential amino acids, and randomly, is conjugated to a carrier, for example, hapten. For example, the following may be referred: Jakobovits et al., 1993, Proc. Natl. Acad. Sci. USA 90:2551-2555; Jakobovits et al., 1993, Nature 362:255-258; and Bruggermann et al., 1993, Year in Immunol. 7:33. As one example, in this method, the transformed animal is produced by incapacitating endogenous mouse immunoglobulin gene loci encoding mouse heavy and light chain immunoglobulin chains and inserting a loci fragment comprising human genome DNA encoding human heavy chain and light chain proteins. By cross-mating a partially modified mouse partially comprising human immunoglobulin genetic loci, a mouse in which the complete human immunoglobulin gene loci are introduced is produced. When an immunogen is administered to the animal, an antibody which is immuno-specific to the immunogen, but comprises a variable region has a human amino acid sequence not murine. This method refers to for example, WO96/33735 and WO94/02602. A method related to a transformed mouse to prepare a human antibody may refer to U.S. Pat. Nos. 5,545,807; 6,713,610; 6,673,986; 6,162,963; 5,545,807; 6,300,129; 6,255,458; 5,877,397; 5,874,299 and 5,545,806; WO91/10741, WO90/04036, and EP 546073B1.

By using the hybridoma technique, antigen-specific human mAbs with the desired specificity can then be generated and selected from transgenic mice, e.g., those described above. Such antibodies may be cloned and expressed by using appropriate vectors and host cells, or the antibodies may be harvested from cultured hybridoma cells.

The complete human antibody may be also derived from a phage-display library (Hoogenboom et al., 1991, J. Mol. Biol. 227:381; and Marks et al., 1991, J. Mol. Biol. 222:581). The phage display technique is a method mimicking a kind of immune selection which displays an antibody repertory on a surface of filamentous bacteriophage and therefrom, sorts a phage binding to a target antigen. This one technique may refer to examples herein or WO 99/10494. In one embodiment, the complete human α-syn antibody of the present invention is sorted through the phage display method (Krebber et al., J. Immunol. Methods. 1997, 201:35).

Bi-Specific or Dual-Functional Antibody

The present invention also relates to an antibody specifically recognizing one or more antigens in addition to α-syn. In one embodiment, the antibody disclosed herein also comprises a bi-specific or dual-functional comprising one or more of CDRs or one or more of variable regions, as described above. In some cases, a dual-specific or dual-functional antibody is an artificial hybrid antibody having 2 different heavy chain/light chain pairs and two different binding sites, and the dual-specific antibody may be prepared by using various methods such as fusion of hybridoma or linking of Fab' fragment (Songsivilai and Lachmann, 1990, Clin. Exp. Immunol. 79:315-321; Kostelny et al., 1992, J. Immunol. 148:1547-1553.).

In one embodiment according to the present disclosure, an antibody of the present invention may take the form of a bispecific antibody, further comprising a binding to a carrier for delivery through the brain blood barrier. One way to deliver drugs through the brain blood barrier involves the use of inherent delivery systems such as glucose and amino acid transporters, and receptor-mediated transcytosis of receptors to insulin or transferrin. Examples of receptors in receptor-mediated transcytosis are as follows:

insulin receptor (e.g., human insulin receptor), transferrin receptor, LRP (e.g., LRP1, LRP6 and LRP8), melanocortin receptor, nicotinic acetylcholine receptor, VACM-1 receptor, IGFR, EPCR, EGFR, TNFR, Leptin receptor, M6PR, Lipoprotein receptor, NCAM, LIFR, LfR, MRP1, AchR, DTr, Glutathione transporter, SR-B1, MYOF, TFRC, ECE1, LDLR, PVR, CDC50A, SCARF1, MRCl, HLA-DRA, RAMP2, VLDLR, STAB1, TLR9, CXCL16, NTRK1, CD74, DPP4, endothelial growth factor receptors 1, 2 and 3, glucocorticoid receptor, ionotropic glutamate receptor, M3 receptor, aryl hydrocarbon receptor, GLUT-1, inositol-1,4,5-trisphosphate (IP3) receptor, N-methyl-D-aspartate receptor, SiPi, P2Y receptor, TMEM30A, and RAGE.

Various Variants of Antibodies

The antibody disclosed herein is also a variant of the antibody disclosed herein. For example, a part of antigen comprises conservative amino acid substitution in one or more of residues of the heavy chain or light chain, variable region or CDR sequence disclosed above. Naturally-occurring amino acids may be classified on the basis of common properties of side chain properties as follows: 1) hydrophobic: norleucine, Met, Ala, Val, Leu, Ile; 2) neutral, hydrophilic: Cys, Ser, Thr, Asn, Gln; 3) acidic: Asp, Glu; 4) basic: His, Lys, Arg; 5) residue affecting a chain direction: Gly, Pro; and 6) aromatic: Trp, Tyr, Phe.

The substitutions of conserved amino acids refer to the substitution into different residues belonging to the same class in the classification. The substitution of conservative amino acid may also comprise a non-naturally-occurring amino acid residue such as a peptide mimetic, and this residue is typically introduced by chemical synthesis, not a cell.

Non-conservative substitution includes substitution to a residue which belongs to other classification among the above classification. This substitution may be introduced in a region of an antibody which is homologous to a human antibody or a non-homologous region.

For introducing this substitution, in one embodiment, an index showing hydrophobicity or hydrophilicity of an amino acid (hydropathic index) may be considered. The index profile of a protein (hydropathic profile) is calculated by designating the index for each amino acid, and then repeatedly averaging these values. The indexes of each amino acid is designated on the basis of hydrophobicity and charge property as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

For giving an interactional biological function to a protein, the importance of index profile is known in the art (Kyte et al., 1982, J. Mol. Biol. 157:105-131). It is known that a specific amino acid may be substituted with other amino acid having a similar numerical value index or score, and the similar biological activity may be maintained. In one embodiment, in making a change based on the index, the substitution of amino acid with the index within the range of 2, in ±1, or in ±0.5 is included.

In addition, substitution between similar amino acids, in particular, when a protein produced by substitution is a protein having activity immunologically as described herein, may be performed on the basis of hydrophilicity. In one embodiment, the maximum local average hydrophilicity value of a protein, which is determined by hydrophilicity of a close amino acid, is related to biological properties of a protein such as immunogenicity and antigen-binding property.

The hydrophilicity values of amino acid residues are as follows: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5+1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In case of substitution based on similar hydrophilicity values, in one embodiment, substitution of amino acids of which hydrophilicity values are in +2, in +1, or in +0.5 is included. In addition, an epitope may be identified from the primary amino acid sequence on the basis of hydrophilicity. In addition, these regions are called "epitope core regions".

Exemplary conservative substitution of amino acids is shown in Table 2.

TABLE 2

| conservative substitution of amino acid | |
|---|---|
| original residue | Exemplary subsitutution |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Those skilled in the art will determine an appropriate variant of the polypeptide disclosed herein using a known technique. Those skilled in the art will find a site which can change a protein without destroying the activity, by targeting a region that is not considered important for activity in the polypeptide. Those skilled in the art will also identify a residue or part to be conserved between similar polypeptides. In addition, in other embodiments, for a part considered as important for biological activity or structure, conservative amino acid substitution may be performed, without destroying biological activity, or negatively affecting a polypeptide structure.

Moreover, those skilled in the art may perform a structural-functional analysis to identify a residue important for activity or structure in a similar polypeptide. Through this analysis, an important amino acid residue in a targeting protein may be predicted by finding a residue corresponding to an important amino acid residue for activity or structure of a protein similar to it, in one protein. Those skilled in the art may substitute the important amino acid residue predicted in this way to an amino acid chemically similar to it.

Those skilled in the art, in addition, may predict an amino acid residue related to a three-dimensional structure of an antibody based on the three-dimensional structure of a similar polypeptide and amino acid sequence analysis related to it. Those skilled in the art do not introduce a rapid change, since the amino acid residue predicted as present on a surface of a protein may be involved in an important interaction with another molecule. Moreover, those skilled in the art may produce test variants comprising substitution of a single amino acid in each targeting amino acid residue. These variants then are screened by using the binding capacity to an antigen, thereby collecting information as to which amino acid substitution matches the purpose. Using this information, those skilled in the art may easily determine a position to be substituted or a position to be avoided.

In addition, a position to be substituted may be determined on the basis of secondary structure of a protein. For example, one method of predicting the secondary structure is based on homology modeling. For example, 2 polypeptides or proteins having more than 30% of sequence identity or more than 40% of similarity may have similar structural phases (Holm et al., 1999, *Nucl. Acid. Res.* 27:244-247). For additional methods of predicting the secondary structure, "threading" (Jones, 1977, *Curr. Opin. Struct. Biol.* 7:377-387; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (Holm, 1999, ibid; and Brenner, 1997, ibid) are included.

In some embodiments, amino acid substitution performs (1) reducing sensitivity to protein decomposition, (2) reducing sensitivity to oxidation, (3) modifying binding affinity for forming a protein complex, (4) modifying antigen binding affinity and/or (5) modifying so as to provide a protein with other physiochemical or functional properties. For example, substitution of single or multiple amino acids including conservative substitution may perform substitution in not a domain which is involved in an intermolecular contact, but other parts. In this embodiment, the conservative amino acid substitution that does not substantially change structural properties of a parent sequence, for example, substitution to one or more of amino acids which does not change the secondary structure of the antibody, may be used. Examples of secondary and tertiary structures of polypeptides known in the art may refer to Proteins, Structures and Molecular Principles (Creighton, Ed.), 1984, W. H. New York: Freeman and Company; Introduction to Protein Structure (Branden and Tooze, eds.), 1991, New York: Garland Publishing; and Thornton et al., 1991, *Nature* 354:105).

In additional preferable antibody variants, a variant in which one or more of cysteine residues are deleted, or the cysteine residues are substituted to other amino acids such as serine, in a parent sequence is included. The cysteine variant is, in particular, a structure in which an antibody has biological activity, and it is useful when needed to be folded again. The cysteine variant may have a small number of cysteine residues compared to a parent antibody, and commonly, may be comprised in an even number in order to minimize interaction due to cysteines without a pair.

The heavy chain and light chains, variable region domains, and CDRs disclosed herein may be used for preparing a polypeptide comprising an antigen-binding region which can specifically bind to α-syn. For example, one or more of the CDRs disclosed in Table 1a to Table 1f may be non-covalently or covalently bound to a molecule like a polypeptide, and thereby they may be used as an immunogenic adhesion molecule. This immunogenic adhesion molecule may be that a CDR is integrated in a big polymer, or that a CDR is linked to another polypeptide. This immunogenic adhesion molecule allows specific binding to an antigen targeting a polypeptide linked thereto or other material, for example, α-syn or an epitope.

A peptide mimetic based on the variable region and CDR disclosed herein is also provided. This mimetic may be a peptide, non-peptide or combination of peptide and non-peptide, and the following may be referred: Fauchere, 1986, *Adv. Drug Res.* 15:29; Veber and Freidinger, 1985, TINS p. 392; and Evans et al., 1987, *J. Med. Chem.* 30:1229. A peptide mimetic structurally similar to one useful polypeptide has a similar effect to the original polypeptide. This compound may be developed by using computerized molecular modeling. Commonly, the peptide mimetic is structurally similar to an antibody showing specifically binding capacity to α-syn herein, but one or more peptide bonds may be replaced with bonds selected from —CH$_2$NH—, —CH$_2$S—, —CH$_2$—CH$_2$—, —CH═CH— (cis and trans), —COCH$_2$—, —CH(OH)CH$_2$— and CH$_2$SO—, by a method widely known in the art. For production of a more stable protein, one or more residues of a conservative sequence may be substituted to the same type of D-amino acid (for example, D-lysine instead of L-lysine). In addition, the molecule which can cyclize a peptide may introduce a crosslink forming cysteine residue on the inside, thereby producing a peptide structurally imposing restrictions to a conservative sequence (Rizo and Gierasch, 1992, *Ann. Rev. Biochem.* 61:387).

The present invention also provides a derivative of the antibody disclosed herein. The derivatized antibody may comprise any molecule or material providing targeting properties, for example, an increased half-life in certain uses to the antibody or its fragment. The derivatized antibody may comprise a detectable (or labeling) residue (e.g.: molecule binding to a radioactive, colorimetric, antigenic, or enzyme molecule, detectable bead (e.g.: magnetic or electron-dense (e.g.: gold) bead), or other molecules (e.g.: biotin or streptavidin)), a therapeutic or diagnostic residue (e.g.: radioactive, cytotoxic, or pharmaceutically active residue), or a molecule increasing suitability of the antibody for special uses (for example, administration to a subject, for example, a human subject, or other in vivo or in vitro uses). For examples of a molecule to be used for derivatizing an antibody, albumin (e.g.: human serum albumin) and polyethylene glycol (PEG) are included. The albumin-linked and pegylated derivatives of the antibody may be prepared by using techniques widely known in the art. In one embodiment, a pegylated single chain polypeptide is comprised. In another embodiment, the antibody may be conjugated or linked to transthyretin (TTR) or a TTR variant. The TTR or TTR variant may be chemically modified by chemical materials selected from the group consisting of for example, dextran, poly(n-vinyl pyrrolidone), polyethylene glycol, propropylene glycol homopolymer, polypropylene oxide/ethylene oxide copolymer, polyoxyethylated polyol and polyvinyl alcohol.

Other derivatives include a covalent or agglomerating conjugate of α-syn binding protein and another protein or polypeptide, which can be prepared for example, by expression of a recombinant fusion protein comprising a heterogeneous polypeptide fused in N-terminal or C-terminal of the α-syn protein. For example, the conjugated peptide may be a heterogeneous signal (or reader) polypeptide, for example, a yeast alpha-factor reader, or a peptide, for example, an epitope tag. The α-syn antibody-containing fusion protein may comprise a peptide added to make purification or identification of α-syn binding protein (e.g.: poly-His) easy. The α-syn binding protein may be also linked to FLAG peptide as described in Hopp et al., 1988, *Bio/Technology* 6:1204; and U.S. Pat. No. 5,011,912. The FLAG peptide has excellent antigenicity, and therefore acts as an epitope to be reversibly bound by a specific monoclonal antibody (mAb), thereby allowing rapid confirmation and easy purification of a recombinant protein.

In one embodiment, it relates to an oligomer comprising multiple α-syn-binding polypeptides to be bound through covalent or non-covalent interaction between peptide residues fused to the α-syn binding protein. This peptide to be bound may be a peptide such as a peptide linker (spacer) or a leucine zipper having a property of facilitating oligomerization. In one embodiment, the oligomer comprises 2 or 4 of α-syn binding proteins. The α-syn binding protein residue of the oligomer may be any aforementioned form, for example, a variant or fragment. Preferably, the oligomer comprises an α-syn binding protein having α-syn binding activity.

In one embodiment, the oligomer is prepared by using a polypeptide derived from an immunoglobulin. The preparation of a fusion protein comprising heterogeneous polypeptides fused to various sites (including an Fc domain) of an antibody-derived polypeptide may refer to for example, Ashkenazi et al., 1991, *Proc. Natl. Acad. Sci. USA* 88: 10535; Byrn et al., 1990, *Nature* 344:677; and Hollenbaugh et al., 1992 "Construction of Immunoglobulin Fusion Proteins", in Current Protocols in Immunology, Suppl. 4, pages 10.19.1-10.19.11.

Other embodiments relate to a dimer comprising 2 fusion proteins in which the α-syn binding protein is fused to a Fc region of an antibody. The dimer may be prepared by inserting a gene fusion encoding a fusion protein into an appropriate expression vector, expressing the gene fusion in a host cell transformed by a recombinant expression vector, and allowing the expressed fusion protein to combine similarly to an antibody molecule, and in this regard, a disulfide bond between chains is formed between Fc residues to collect the dimer.

The term "Fc polypeptide" used herein is a polypeptide derived from an Fc region of an antibody, and includes a wildtype or mutant form. A cut form of polypeptide comprising a hinge region which facilitates dimerization is also included. The fusion protein comprising Fc or oligomer formed therefrom has an advantage of being separated easily with an affinity chromatography using a protein A or protein G column.

For examples of appropriate Fc polypeptides, there are those described in U.S. Pat. Nos. 5,426,048 and 5,262,522, 5,457,035 and Baum et al., 1994, *EMBO J.* 13:3992-4001. In the amino acid sequence of this mutant protein, the wildtype amino acid $19^{th}$ residue is substituted from Leu to Ala, and the amino acid $20^{th}$ residue is substituted from Leu to Glu, and the amino acid $22^{nd}$ residue is substituted from Gly to Ala. In the mutant protein, the affinity to an Fc receptor is reduced.

In other embodiments, the variable region of heavy chain and/or light chain of α-syn binding protein disclosed herein may be substituted and enter a variable region of heavy chain and/or light chain of another antibody.

Label and Effector Groups

In some embodiments, the antibody or antigen-binding fragment according to the present invention may comprise one or more labels. "Label" means any detectable material. For examples of appropriate label groups, a radioactive isotope or radioactive nuclide (e.g.: $^3H$, $^{14}C$, $^{15}N$, $^{35}S$, $^{90}Y$ $^{99}Tc$, $^{111}In$, $^{125}I$, $^{131}I$), a fluorescent group (e.g.: FITC, rhodamine, lanthanoid fluorescent substance), an enzyme group (e.g.: horseradish peroxidase, β-galactosidase, luciferase, alkaline phosphatase), a chemiluminescent group, a biotinyl group, or certain polypeptide epitopes recognized by a secondary reporter (for example, leucine zipper pair sequence, secondary antibody binding site, metal binding domain, epitope tag) is included, but not limited thereto. In some embodiments, the labeling group is coupled to an antibody through various lengths of spacer arms to reduce potential steric hindrance. Various methods to label a protein are known in the art, and those skilled in the art will select an appropriate label and a proper method for a specific purpose.

The term "effector group" is a material to be coupled or conjugated to an antibody or material to function as cytotoxic agent. Examples of appropriate materials for treatment include radioactive materials for treatment such as a radioactive isotope or radioactive nuclide (e.g.: $^3H$, 14C, $^{15}N$, $^{35}S$, 9 $^{99}Tc$, $^{111}In$, $^{125}I$, $^{131}I$). In some embodiments, the effector group is coupled to an antibody through various lengths of spacer arms to reduce potential steric hindrance. Commonly, labels may be classified according to detection methods: a) radioactive or isotope label; b) magnetic label (e.g.: magnetic particle); c) oxidation-reduction active residue; d) optical dye; enzyme group (for example, horse radish peroxidase, β-galactosidase, luciferase, alkaline phosphatase); e) biotinyl group; and f) certain polypeptide epitope recognized by a secondary reporter (e.g.: leucine zipper pair sequence, binding site for a secondary antibody, metal binding domain, epitope tag, etc.). In some embodiments, the labeling group is coupled to an antibody through various length of spacer arms to reduce potential steric hindrance. Various methods for labeling a protein are known in the art.

In one embodiment, the label comprises an optical dye comprising a chromophore, a phosphor and a fluorescent substance, but not limited thereto. The fluorescent substance may be a small-molecular fluorescent material or protein fluorescent material.

"Fluorescent label" means any molecule to be detected by fluorescent properties which a material has. For examples of fluorescent labels, fluorescein, rhodamine, tetramethylrhodamine, eosin, erythrosine, coumarin, methyl-coumarin, pyrene, malachite green, stilbene, lucifer yellow, cascade blue J, texas red, IAEDANS, EDANS, BODIPY FL, LC red 640, Cy 5, Cy 5.5, LC red 705, oregon green, alexa-fluor dye (alexa-fluor 350, alexa-fluor 430, alexa-fluor 488, alexa-fluor 546, alexa-fluor 568, alexa-fluor 594, alexa-fluor 633, alexa-fluor 647, alexa-fluor 660, alexa-fluor 680), cascade blue, cascade yellow and R-phycoerythrin (PE), FITC,), Cy5, Cy5.5, and Cy7 etc. are included, but not limited thereto. Various optical dyes may refer to Molecular Probes Handbook, Richard P. Haugland.

The protein fluorescent label substances include green fluorescent proteins including Renilla, Ptilosarcus or Aequorea species of GFP (Chalfie et al., 1994, *Science* 263:802-805), EGFP(Clontech Labs., Inc., Genbank Accession Number U55762), blue fluorescent proteins (BFP, Quantum Biotechnologies, Inc., Quebec, Canada; Stauber, 1998 Biotechniques 24:462-471; Heim et al., 1996, *Curr. Biol.* 6:178-182), enhanced yellow fluorescent proteins (EYFP, Clontech Labs., Inc.), luciferase (Ichiki et al., 1993, *J. Immunol.* 150:5408-5417), R galactosidase (Nolan et al., 1988, *Proc. Natl. Acad. Sci. U.S.A.* 85:2603-2607), but not limited thereto.

Nucleic Acid

In one aspect, the present invention relates to a nucleic acid confused to the nucleic acid disclosed herein under a specific hybridization condition. The hybridization method of the nucleic acid is widely known in the art. For example, Current Protocols in Molecular Biology, John Wiley & Sons, N.Y. (1989), 6.3.1-6.3.6 may be referred. Herein, a strict hybridization condition uses pre-washing solution comprising 5× sodium chloride/sodium citrate (SSC), 0.5% SDS, 1.0 mM EDTA(pH 8.0); a hybridization buffer of about 50% formamide, 6×SSC, and a hybridization temperature of 55° C. (or other similar hybridization solution, for example, a solution comprising about 50% formamide, a hybridization temperature of 42° C.), and a washing condition of 60° C. in 0.5×SSC, 0.1% SDS. The strict hybridization condition is hybridization by 6×SSC at 45° C., and then 0.1×SSC at 68° C., and one or more of washing in 0.2% SDS. Further, those skilled in the art will select proper hybridization conditions required so that a nucleic acid comprising at least 65%, 70%, 75%, 80%, 85%, 90%, 95%, 98% or 99% identical nucleotide sequences between sequences typically maintains a state hybridized to each other.

Basic parameters affecting selection of hybridization conditions and appropriate conditions may refer to, for example, Sambrook, Fritsch, and Maniatis, (2001, Molecular Cloning: A Laboratory Manual, Cold Spring Harbor Laboratory Press, Cold Spring Harbor, N.Y., above; and Current Protocols in Molecular Biology, 1995, Ausubel et al., eds., John Wiley & Sons, Inc., section 2.10 and 6.3-6.4. These conditions may be easily determined by those skilled in the art, based on for example, the length and/or base composition (configuration of A, G, C and T (U)) of the nucleic acid, etc.

The nucleic acid disclosed herein also includes a mutant variant. A change in an amino acid sequence of a polypeptide (antibody or antibody derivative) which the nucleic acid encodes may be induced by mutation in the nucleic acid. The mutant may be introduced by using any technique known in the art. For example, a site-directed mutagenesis method or a random mutagenesis method may be used. The nucleic acid mutant prepared likewise is sorted for a polypeptide having targeting properties.

Without significantly changing biological activity of a polypeptide encoded by the nucleic acid, the mutant may be introduced in the nucleic acid. For example, nucleotide substitution which causes amino acid substitution in a non-essential amino acid residue may be performed. Alternatively, one or more mutants which selectively change biological activity of a polypeptide encoded by the nucleic acid may be introduced in the nucleic acid. For example, the mutant may change biological activity quantitatively or qualitatively. Examples of quantitative changes include increase, decrease or removal of activity. Examples of qualitative changes include a change of specificity to an antigen of an antibody. In an embodiment, the nucleic acid encoding any antibody or its fragment disclosed herein may be mutated so that the amino acid sequence is modified, by using a molecular biology technique widely known in the art.

In other aspects, in addition, the present invention relates to a nucleic acid molecule proper to be used as a primer or hybridization probe for detection of the nucleic acid sequence disclosed herein. This nucleic acid may comprise a part of a full-length nucleic acid sequence, for example, a fragment of a nucleic acid encoding a full-length polypeptide, or a fragment nucleic acid encoding an active part (α-syn binding part) of a polypeptide, to be used as a probe or a primer.

The primer and probe prepared based on the nucleic acid sequence may be used for detecting a transcriptome encoding the nucleic acid disclosed herein or similar nucleic acid, or polypeptide. In one embodiment, this probe may be used for identifying a cell expressing the polypeptide according to the present invention. The primer or probe may be labeled by a label material such as a radioactive isotope, fluorescent compound, enzyme or enzyme cofactor.

In other aspects, in addition, the present invention provides a vector comprising a nucleic acid encoding the polypeptide or its part (for example, a fragment comprising one or more of CDRs or one or more of variable region domains) according to the present invention. The examples of the vector include a plasmid, virus vector, non-episome mammal vector and (recombinant) expression vector, etc., but not limited thereto. The recombinant expression vector may comprise a suitable form of nucleic acid for expression of nucleic acid in a host cell. The recombinant expression vector comprises one or more regulatory sequences based on a host cell to be used for expression, and these regulatory sequences are operably connected to a nucleic acid sequence to be expressed. In the regulatory sequence, for example, SV40 initial gene enhancer, promoter such as Rous sarcoma virus promoter and cytomegalovirus promoter, which can control expression of a nucleotide sequence in various kinds of host cells; or for example, tissue-specific regulatory sequence, which controls expression of a nucleotide sequence only in a specific host cell (Voss et al., 1986, *Trends Biochem. Sci.* 11:287, Maniatis et al., 1987, *Science* 236:1237), and metallothionein promoter working in a mammal cell, and tet-reactive and/or streptomycin reactive promoter working in both prokaryote and eukaryote systems, which instructs inductive expression of a nucleotide sequence by responding to special treatment or conditions, are included. Those skilled in the art will select an appropriate vector and a regulatory sequence, considering factors such as the kind of host cell to be transformed, and expression degree of a targeting protein. The selected expression vector may be delivered in a host cell and may be used for production of a protein encoded by the nucleic acid disclosed herein.

In other aspects, the present invention provides a host cell in which a recombinant expression vector is introduced. The host cell may be any prokaryote (for example, *E. coli*) or eukaryote (for example, yeast, insect, or mammal cell). The vector DNA may be introduced in a prokaryotic or eukaryotic cell through a known transformation or transfection technique. It is known that in case of stable transfection in a mammal cell, depending on kinds of expression vector used and transformation techniques, only a small number of cells can integrate DNA delivered by transfection in its genome. Thus, to identify and select a transfected cell, commonly a gene encoding a selectable marker such as an antibiotic resistant marker is introduced into a host cell together with a targeting gene. For preferable selectable markers, drugs, for example, those providing resistance to, for example, G418, hygromycin and methotrexate are included. The sorting of a cell in which a targeting nucleic acid is stably introduced may be achieved by selecting a survived cell only through drug treatment.

Preparation of Antibody

Herein, a non-human antibody may be derived from, for example, any antibody-producing animal, for example, mouse, rat, rabbit, goat, donkey or non-human primates (for example, monkeys such as a cynomolgus or rhesus monkey) or anthropoid (for example, chimpanzee). The non-human antibody may be produced by immunizing an animal by using a method known in the art. The antibody may be polyclonal, monoclonal, or may be synthesized in a host cell by expressing a recombinant DNA. A complete human antibody may be prepared by administering an antigen to a transformed animal comprising human immunoglobulin gene loci, or treating a phage display library expressing a human antibody repertory with an antigen, and then selecting an antibody of interest.

A monoclonal antibody (mAb) may be produced by various techniques including the conventional monoclonal antibody method, for example, a standard somatic cell hybridization technique of documents (see: Kohler and Milstein, 1975, *Nature* 256:495). Alternatively, for example, a method of transforming a B-lymphocyte into a virus or tumor gene may be used. A murine system is a widely used animal system for production of a hybridoma cell. An immunization protocol and a separation technique of splenocytes of an immunized mouse for fusion are widely known in the art. In this method, a B cell derived from an immunized mouse is fused with, for example, an immortalized fusion partner cell such as a murine myeloma cell line. If necessary, instead of the mouse, a rat or other mammals may be immunized, and a B cell derived from these animals may be fused with a murine myeloma cell line, to produce hybridoma. Alternatively, as a myeloma cell line used for fusion, those derived from animals other than mouse may be used. The fusion process for preparing this hybridoma is also widely known.

The single antibody disclosed herein may be produced by linking heavy chain and light chain variable domain (Fv region) fragments, using an amino acid crosslinker (short peptide linker). This single chain Fv (scFv) may be prepared by fusing DNA encoding a peptide linker between DNAs encoding 2 variable domain polypeptides (VL and VH). The prepared polypeptide may form an antigen-binding multimer by folding, or may form a polymer (for example, dimer, trimer or tetramer), according to the length of a flexible linker between 2 variable domains (Kortt et al., 1997, *Prot. Eng.* 10:423; Kortt et al., 2001, *Biomol. Eng.* 18:95-108). By combining different $V_L$ and $V_H$-comprising polypeptides, a polymeric scFv binding to different epitopes may be formed (Kriangkum et al., 2001, *Biomol. Eng.* 18:31-40). Further, a technique for production of an additional single chain antibody may refer to, for example, the following: U.S. Pat. No. 4,946,778; Bird, 1988, *Science* 242:423; Huston et al., 1988, *Proc. Natl. Acad. Sci. U.S.A.* 85:5879; Ward et al., 1989, *Nature* 334:544, de Graaf et al., 2002, *Methods Mol Biol.* 178:379-387. The single chain antibody disclosed herein includes scFv comprising a combination of domains of heavy chain and light chain variable regions described in Tables 1a and 1b, or a combination of light chain and heavy chain variable domains comprising a CDR described in Table 1, but not limited thereto.

The antibody disclosed herein may also be modified into a different subtype antibody, through subtype switching. Thus, an IgG antibody may be derived from, for example, an IgM antibody, and the reverse is also possible. Through this technique, preparation of a new antibody having the same antigen-binding property as a parent antibody, but having a characteristic biological property to the changed subtype that is different from the parent antibody. For this switching, a recombinant DNA technique may be used. For example, a DNA encoding a constant domain of a targeting isotype antibody may be used for preparation of this antibody. For example, Lantto et al., 2002, *Methods Mol. Biol.* 178:303-316 may be referred. In addition, in case of switching of IgG4, to reduce a tendency of forming a disulfide bond in a heavy chain which can cause heterogeneity in an IgG4 antibody, it may be preferable to introduce point mutation (CPSCP→CPPCP) in a hinge region as described in the document, Bloom et al., 1997, *Protein Science* 6:407.

Thus, the antibody disclosed herein, comprises the variable domain combination antibody which is switched, for example, with a targeting isotype (for example, IgA, IgG1, IgG2, IgG3, IgG4, IgE, and IgD) disclosed herein.

In addition, a technique of preparing an antibody having different properties like an antibody having various affinities to an antigen is also known. This technique is, for example, chain shuffling performed by displaying an immunoglobulin variable domain gene repertory on a surface of filament bacteriophage called a phage display. An additional technique can be referred to the disclosure in Marks et al., 1992, *BioTechnology* 10:779.

To produce an α-syn binding protein having targeting preferable functional and biochemical properties, conservative modification (and modification corresponding to a coding nucleic acid) may be performed to heavy chain and light chain variable regions described in Table 1a and Table 1b, or CDRs described in Table 1b. The method for performing this modification is as aforementioned.

The α-syn antibody may be further modified in various methods. For example, when used for a therapeutic purpose, to increase a serum half-life, or improve protein delivery, it may be conjugated with polyethylene glycol, namely, pegylated. Alternatively, the variable region of the antibody or its fragment of the present invention may be fused with an Fc region of a different antibody molecule. The Fc region used for this purpose does not bind to a complement, and therefore when a fusion protein is used as a therapeutic agent, it is modified in the direction of reducing occurrence of cell lysis in a patient. In addition, the antibody or its functional fragment of the present invention may be conjugated with a human serum albumin to improve a serum half-life of the antibody or its antigen-binding fragment. Another useful fusion partner of the antibody or its antigen-binding fragment is transthyretin (TTR). TTR has an ability to form a tetramer, and thus an antibody-TTR fusion protein may form a multivalent antibody in which the binding avidity of a protein is increased.

Alternatively, substantial modification for functional and/or biochemical properties of the antibody disclosed herein may be achieved through substitution in the amino acid sequence of heavy chain and light chain, which significantly affects for example, (a) a structure of molecular framework in the substitution site like a sheet or spiral form, (b) a degree of charge or hydrophobicity of the molecule in a target site, or (c) bulkiness of a side chain.

The amino acid substitution (conservative or non-conservative) of the antibody disclosed herein may be performed by those skilled in the art by applying a common technique. The amino acid substitution may be used for identifying an important residue of the antibody disclosed herein, or increasing or reducing affinity of the antibody to human α-syn, or modifying binding affinity of another antibody disclosed herein.

Method for Expressing Antibody

The present invention also relates to an expression system and construct in a form of plasmid, expression vector, transcription or expression cassette comprising at least one polynucleotide as aforementioned, and a host cell comprising the expression system or construct, and a production method of an antibody using the expression system or host cell.

The antibody disclosed herein may be prepared by using the aforementioned technique. For example, α-syn antibody can be prepared using a recombinant expression system according to the technique known in the art by referring to Monoclonal Antibodies, Hybridomas: A New Dimension in Biological Analyses, Kennet et al. (eds.) Plenum Press, New York (1980); and Antibodies: A Laboratory Manual, Harlow and Lane (eds.), Cold Spring Harbor Laboratory Press, Cold Spring Harbor, N.Y. (1988)

The antibody may be expressed in a hybridoma cell line or expression cell line other than hybridoma. The expression construct encoding an antibody may be used for transforming a mammal, insect or microorganism host cell. The construct, like a plasmid, may be performed by using any of various known methods for introducing a polynucleotide into a host cell as aforementioned. Detailed methods may be different according to kinds of host celsl. The method of introducing a heterogeneous polynucleotide in a mammal cell is widely known in the art, and for example, it may be performed by for example, dextran-mediated transfection, calcium phosphate precipitation, polybrene-mediated transfection, protoplast fusion, electroporation, capsulation of a polynucleotide delivered using a liposome, mixing of a nucleic acid and a positively charged lipid, and direct microinjection of DNA into a nucleus, but not limited thereto.

The recombinant expression structure typically comprises a nucleic acid molecule encoding a polypeptide comprising one or more of the following: one or more of CDRs disclosed herein; light chain constant region; light chain variable region; heavy chain variable region; heavy chain constant region (for example, CH1, CH2 and/or CH3); and/or the other scaffold part of α-syn antibody. The nucleic acid sequence is inserted into a proper expression vector by using a standard ligation technique. In one embodiment, the heavy chain or light chain constant region is linked to the C-terminal of the anti-α-syn-specific heavy chain or light chain variable region, and is ligated into the expression vector. The vector is selected so as to function in a specific host cell in which the vector is used. In other words, the vector should amplify and/or express a gene comprised in the vector using a device of the host cell to be used. In one embodiment, a vector using a protein-fragment complementation analysis using a protein reporter, for example, dihydrofolate reductase disclosed in U.S. Pat. No. 6,270,964 is used. The proper expression vector may be purchased commercially, for example, from a company such as Life Technologies or BD Biosciences. Examples of other vectors useful for cloning and expressing an antibody and a fragment may refer to those disclosed in Bianchi and McGrew, 2003, *Biotech. Biotechnol. Bioeng.* 84:439-44; *Methods Enzymol.*, vol. 185 (D. V. Goeddel, ed.), 1990, New York: Academic Press.

Typically, an expression vector used in any host cell may comprise a basic sequence required for plasmid maintenance and cloning and expressing of an exogeneous nucleotide sequence. In a specific embodiment, such a basic sequence typically comprises one or more of the following nucleotide sequences: a promoter, one or more of enhancer sequences, a replication origin, a transcription termination sequence, a complete intron sequence comprising donor and receptor splicing sites, a sequence encoding a reader sequence for polypeptide secretion, a ribosome binding site, a polyadenylated sequence, a polylinker region for inserting a nucleic acid encoding a polypeptide to be expressed, and a selectable marker sequence.

Selectively, the vector may comprise a "tag"-encoding sequence, in other words, an oligonucleotide molecule positioned in 5' or 3' end of α-syn binding protein coding sequence; the oligonucleotide sequence may encode polyHis (e.g.: hexaHis), or other "tag" present in a commercially available antibody, for example, FLAG®, HA (hemagglutinin influenza virus), or myc. Typically, these tags may be fused to a polypeptide and expressed, and function as means of affinity purification or detection during separation of α-syn binding protein in a host cell. The affinity purification may be achieved, for example, by column chromatography using an antibody for a tag as an affinity matrix. Selectively, these tags may be removed from the α-syn binding protein purified by various means including use of a specific peptidase.

The aforementioned basic sequence may be homogeneous, heterogeneous, or hybrid, synthetic or intrinsic. On this wise, the basic sequence derived from any prokaryote or eukaryote, any vertebrate or invertebrate, or any plant, if it can be activated and function in a host cell device.

The useful basic sequence comprised in a vector may be collected by various methods widely known in the art. Typically, the basic sequence used herein is confirmed in advance by mapping and/or restriction enzyme cutting, and therefore, it can be separated from an appropriate tissue source of supply using a proper restriction enzyme. In some cases, the total nucleotide sequence of basic sequence may be known, and the basic sequence may be synthesized by using the nucleic acid synthesis or cloning method disclosed herein.

Regardless of whether the total or a part of sequence of the basic sequence is known, the basic sequence may be collected by using polymerase chain reaction (PCR), and/or screening a genome library with an appropriate probe, for example, an oligonucleotide and/or basic sequence fragment from the same or different species. If the basic sequence is not known, a fragment of DNA comprising the basic sequence may be separated from, for example, a coding sequence or even from a bigger fragment of DNA which can comprise (an) other gene(s). A targeting fragment may be separated by using restriction enzyme treatment, agarose gel purification and column chromatography or other methods known to those skilled in the art. It is obvious that those skilled in the art can select a proper enzyme to achieve such a purpose.

The replication origin is required for amplification of a vector in a host cell, and typically, it is comprised in a commercially available prokaryotic expression vector. If a selected vector does not comprise the replication origin, it may be chemically synthesized on the basis of the known sequence, and ligated into the vector. For example, the replication origin of plasmid pBR322 (New England Biolabs, Beverly, MA, USA) is suitable for most of gram-negative bacteria, and various virus origins (for example, SV40, polyoma, adenovirus, vesicular stomatitis virus (VSV), or papilloma virus, for example, HPV or BPV) is useful for cloning a vector in a mammal cell. Typically, the replication origin is not needed for a mammal expression vector (for example, SV40 origin is also used, since it comprises a virus initial promoter).

Typically, the transcription termination sequence is positioned at the 3' end of a polypeptide coding region and functions to terminate transcription. Commonly, the transcription termination sequence in a prokaryote is a fragment rich in G-C followed by a poly-T sequence. Such a sequence may be easily cloned from a library, or purchased commercially, or collected by using the nucleic acid synthesis method disclosed herein.

The selectable marker gene encodes a protein required for survival and growth in a selectable culture medium of a host cell. The typical selectable marker gene encodes a protein (a) providing resistance to antibiotics or other toxins, for example, in case of a prokaryotic host cell, ampicillin, tetracycline, or kanamycin; (b) complementing auxotrophic deficiency of a cell; or (c) supplying important nutrients that cannot be obtained from a complex medium or defined medium. In one embodiment, the selectable marker is a kanamycin-resistant gene, an ampicillin-resistant gene and a tetracycline-resistant gene. A neomycin-resistant gene may be also used for selection in both prokaryotic and eukaryotic host cells.

Other selectable gene may be used for amplification of a gene to be expressed. The amplification is a process that a gene required for production of a protein important for growth or survival of a cell is serially repeated in a chromosome of a recombinant cell of the subsequent generation. Examples of a selectable marker suitable for a mammal cell include dihydrofolate reductase (DHFR) and thymidine kinase gene without a promoter. To a mammal cell transformant, a selection pressure which allows only the transformant to be survivable by a selectable gene present in a vector is applied. The selection pressure may be applied by gradually increasing the concentration of a selector comprised in a medium, and culturing a cell under the condition to amplify all the genes encoding an antibody binding to α-syn. Thus, the amount of a polypeptide expressed by the amplified DNA, for example, an antibody, may be increased.

The ribosome-binding site is commonly required for translation initiation of mRNA and characterized by Shine-Dalgarno sequence (prokaryote) or Kozak sequence (eukaryote). This is typically positioned in 3' of a promoter and 5' of a coding sequence of a polypeptide to be expressed.

When glycosylation is required in a eukaryotic host cell expression system, to improve glycosylation or yield, various pre- or pro-sequences may be fabricated. For example, a peptidase cutting site of a specific signal peptide may be modified, or a prosequence which can affect glycosylation may be added. The final protein product may have one or more of additional amino acids in −1 position (for the first amino acid of mature protein), as these amino acids are not completely removed. For example, the final protein product may have 1 or 2 of amino acid residues found in the peptide cutting site added to an amino-terminal. Alternatively, if using a protein cutting enzyme, in case that the cutting site is comprised in a targeting protein, a cut form of protein may be produced.

The expression and cloning may typically comprise use of a promoter operably connected to a molecule encoding an α-syn binding protein which is recognized by a host organism. The promoter is the upper class of initiation codon of a structural gene regulating transcription of the structural gene (commonly, within about 100 to 1000 bp), namely, a nontranscriptional sequence positioned in 5'. The promoter is classified to an inducible promoter and a constant promoter. The inducible promoter responds to changes of culturing conditions, for example, presence or absence of a specific ingredient of a medium, or temperature change, and initiates or controls transcription from DNA connected thereto. On the other hand, the constant promoter does not control transcription of a gene operably connected thereto, and expresses constantly. Numerous promoters recognized by various host cells are widely known. An appropriate promoter is operable connected to DNA encoding a heavy chain or light chain comprising an α-syn binding protein, by inserting it in a vector, after removing a promoter from template DNA using a restriction enzyme.

A promoter suitable for using together with a yeast host is also widely known in the art. In addition to the yeast promoter, a yeast enhancer may be also used. A promoter suitable to be used in a mammal host cell includes those collected from genome of virus, for example, polyoma virus, pharynx virus, adenovirus (e.g., adenovirus 2), bovine papilloma virus, avian sarcoma virus, cytomegalovirus, retrovirus, hepatitis B virus and anthropoid virus 40 (SV40), but not limited thereto. The examples of other proper mammal promoters include a heterogeneous mammal promoter, for example, a heat-shock promoter and an actin promoter.

For an additional promoter, SV40 initial promoter (Benoist and Chambon, 1981, *Nature* 290:304-310); CMV promoter (Thomsen et al., 1984, *Proc. Natl. Acad U.S.A.* 81:659-663); promoter comprised in 3' long terminal repeat of Rous sarcoma virus (Yamamoto et al., 1980, *Cell* 22:787-797); herpes thymidine kinase promoter (Wagner et al., 1981, *Proc. Natl. Acad Sci. U.S.A.* 78:1444-1445); promoter and regulatory sequence of metallothionine gene (Prinster et al., 1982, *Nature* 296:39-42); and prokaryotic promoter, for example, beta-lactamase promoter (Villa-Kamaroff et al., 1978, *Proc. Natl. Acad Sci. U.S.A.* 75:3727-3731); or tac promoter(DeBoer et al., 1983, *Proc. Natl. Acad Sci. U.S.A.* 80:21-25) is included, but not limited thereto. In addition, a transcription regulatory region of an animal as follows, which is used for a transformed animal showing tissue specificity, may be used: elastase I gene regulatory region which is active in a pancreatic acinar cell (Swift et al., 1984, *Cell* 38:639-646; Ornitz et al., 1986, *Cold Spring Harbor Symp. Quant. Biol.* 50:399-409; MacDonald, 1987, *Hepatology* 7:425-515); insulin gene regulatory region which is active in a pancreatic beta cell (Hanahan, 1985, *Nature* 315:115-122); immunoglobulin gene regulatory region which is active in a lymphoid cell (Grosschedl et al., 1984, *Cell* 38:647-658; Adames et al., 1985, *Nature* 318:533-538; Alexander et al., 1987, *Mol. Cell. Biol.* 7:1436-1444); mouse mammary gland tumor virus regulatory region which is active in a testis, breast, lymphoid and mast cell (Leder et al., 1986, *Cell* 45:485-495); albumin gene regulatory region which is active in liver (Pinkert et al., 1987, *Genes and Devel.* 1:268-276); alpha-feto-protein gene regulatory region which is active in liver (Krumlauf et al., 1985, *Mol. Cell. Biol.* 5:1639-1648; Hammer et al., 1987, *Science* 253:53-58); alpha 1-antitrypsin gene regulatory region which is active in liver (Kelsey et al., 1987, *Genes and Devel.* 1:161-171); beta-globin gene regulatory region which is active in a marrow cell (Mogram et al., 1985, *Nature* 315:338-340; Kollias et al., 1986, *Cell* 46:89-94); myelin basic protein gene regulatory region which is active in an oligodendrocyte in brain (Readhead et al., 1987, *Cell* 48:703-712); myosin light chain-2 gene regulatory region which is active in skeletal muscle (Sani, 1985, *Nature* 314:283-286); and gonadotropin releasing hormone gene regulatory region which is active in hypothalamus (Mason et al., 1986, *Science* 234:1372-1378).

The enhancer sequence may be inserted into a vector in order to increase transcription of DNA encoding a light chain or heavy chain comprising a human α-syn binding protein in a higher eukaryote. The enhancer is a cis-acting factor of DNA having commonly about 10-300 bp length, which acts on a promoter and increases transcription. The enhancer is observed in 5' and 3' positions of a transcription unit, and relatively, is not affected by position and direction. Various enhancer sequences are known in a mammal gene (for example, globin, elastase, albumin, alpha-feto-protein and insulin). However, typically, an enhancer derived from a virus is used. The exemplary enhancers for activation of a promoter known in the art include an SV40 enhancer, cytomegalovirus initial promoter enhancer, polyoma enhancer and adenovirus enhancer. The enhancer for activation of a eukaryotic promoter may be arranged in 5' or 3' of a coding sequence in a vector, but typically, is positioned in a 5' site of a promoter. The sequence encoding a proper intrinsic or heterogeneous signal sequence (reader sequence or signal peptide) may be integrated into an expression vector to facilitate extracellular secretion of an antibody. The selection of the signal peptide or reader sequence is determined according to kinds of a host cell in which an antibody is produced, and the intrinsic signal sequence may be replaced with the heterogeneous signal sequence. The examples of functional signal peptides in a mammal host cell include the signal sequence for interleukin-7 (IL-7) described in U.S. Pat. No. 4,965,195; the signal sequence for interleukin-2 receptor described in the document Cosman et al., 1984, *Nature* 312:768; the signal sequence for interleukin-4 receptor described in EP patent No. 0367 566; type I interleukin-1 receptor signal peptide described in U.S. Pat. No. 4,968,607; type II interleukin-1 receptor signal peptide described in EP patent No. 0 460 846.

Herein, the expression vector may be fabricated by using a commercially available vector. This expression vector may comprise the whole or a part of a targeting basic sequence or not comprise it at all. When one or more of basic sequences described herein are not present in a vector in advance, they may be individually collected and ligated into a vector. The method of collecting each sequence comprised in basic sequences is widely known to those skilled in the art.

After preparing a vector and inserting a nucleic acid molecule encoding a light chain and a heavy chain comprising a light chain, heavy chain, or α-syn antigen-binding sequence into an appropriate site of the vector, this recombinant vector may be introduced into a proper host cell, for amplification and/or polypeptide expression. The method of introducing an antibody expression vector into a selected host cell may be achieved by transfection, infection, calcium phosphate co-precipitation, electroporation, microinjection, lipofection, DEAE-dextran-mediated transfection, or other widely known methods. The introduction method is determined according to kinds of a host cell to be used mainly. This method is widely known to those skilled in the art, and for example, the aforementioned document, Sambrook et al., 2001 may be referred.

Subsequently, after culturing the host cell under proper conditions, an antibody is collected from a culture medium (in case that a cell secrets an antibody to the medium), or directly from the host cell producing it (in case that an antibody is not secreted). The selection of a proper host cell may be affected by various factors, for example, targeting expression level, polypeptide modification which is preferable or necessary for activity (for example, glycosylation or phosphorylation) and easiness of folding for production of a biological active molecule, etc.

The mammal cell lines available for expression are widely known in the art, and for example, an immortalized cell purchasable from ATCC (American Type Culture Collection), for example, Chinese hamster ovary (CHO) cell, HeLa cell, baby hamster kidney (BHK) cell, monkey kidney cell (COS), human liver cell carcinoma cell (e.g., Hep G2) and numerous other cell lines are included, but not limited thereto. In one embodiment, the cell line may be determined in accordance with expressing an antibody having an α-syn binding property with high expression level. In other embodiments, a cell line can be selected from a B cell system that has an ability to prepare and secret a heterogeneous antibody, although it cannot prepare its own antibody.

Role of α-Syn in Disease

α-Syn is a protein consisting of 140 amino acids that is mainly expressed in presynaptic sites of the neuron. It exists as a monomer that is naturally unfolded form in cytoplasm under normal conditions. The precise function of α-syn has not been elucidated, and seems to play an important role in maintaining the supply of synaptic vesicle at mature presynaptic terminals on the basis that it is only detected after the development of synapses (Murphy D D et al., J Neurosci 2000, 20: 3214-3220). α-Syn may modulate the release of dopamine regulating involuntary or voluntary exercise, or may affect memory and cognitive function (Kokhan V S et al., Behav Brain Res 2012, 231: 226230). In particular, the function of α-syn is important as synapse activity increases and ages, and is an important factor in neurodegeneration.

In a pathological state, α-syn undergoes structural changes by binding and interacting with lipid droplets, phospholipid bilayers or lipid membranes to form a folded α-helical secondary structure, resulting in forming aggregates including dimers, oligomers and the fibrous form.

In particular, α-syn aggregation is related to the pathogenesis of a group of neurodegenerative diseases called α-synucleinopathy, including Parkinson's disease (PD), Parkinson's disease dementia (PDD), dementia with Lewy bodies (DLB), multiple system atrophy (MSA) and many neuro-axonal diseases, and is secondarily found in Alzheimer's disease (Kim et al., Alzheimer's Research & Therapy 2014, 6:73).

Furthermore, both oligomeric and monomeric forms of alpha-synuclein are found in cerebrospinal fluid and serum samples of patients with Parkinson's disease, indicating that alpha-synuclein aggregates with small molecular weight permeate the cell membrane to access the extracellular space. It has also been shown that misfolded alpha-synuclein can be released from cells by exocytosis and then transferred from one region of the brain to another region by intercellular transport, like prion proteins (Brundin P et al., Nat Rev Mol Cell Biol 2010, 11: 301-307).

α-Synucleinopathy is a group of neurodegenerative diseases characterized by the presence of entities or bodies containing α-syn aggregates inside a cell. These bodies are somewhat different in appearance depending on the disease, and are called as Lewy bodies in Parkinson's disease (PD) and dementia with Lewy bodies (DLB), ganglia cytoplasmic bodies in multiple system atrophy (MSA), and axon spheroids in neuro-axonal diseases. Antibodies according to the present invention recognize α-syn aggregates preferentially and specifically, and thus recognizing these bodies.

Lewy Body Disease (LBD) or alpha-synuclein neuronal disease is characterized by degeneration of the dopaminergic system, motor impairment, cognitive impairment and formation of Lewy bodies (LB) (McKeith et al., Neurology 1996, 47: 1113-24). Lewy bodies are spherical protein deposits found in nerve cells. The Lewy body blocks the normal function of the brain by interfering with the action of chemical messengers including acetylcholine and dopamine in the brain. Lewy body diseases include Parkinson's disease (including idiopathic Parkinson's disease (PD)), Diffuse Lewy Body Disease (DLBD) also referred to as Dementia with Lewy Body, the combined disease of Alzheimer's disease and Parkinson's disease, and multiple system atrophy (MSA). DLBD has the same symptoms as Alzheimer's disease and Parkinson's disease, but the position of the Lewy bodiesy is different from that of Parkinson's disease. In DLBD, leucocytes are mainly present in the cortex, and are predominantly in the substantia nigra in Parkinson's disease.

Other Lewy body diseases include Pure Autonomic Failure, Lewy body disorder (dysphagia), Incidental LBD, Inherited LBD (e.g., mutants of α-syn gene, and PARK3 and PARK4 genes) and Multiple System Atrophy (MSA, e.g., Olivopontocerebellar Atrophy, Striatonigral Degeneration and Shy-Drager Syndrome).

The anti α-syn antibody of the present invention specifically recognizing α-syn aggregates with a high affinity can be useful for the diagnosis or detection of such diseases. Further, the α-syn antibody specifically recognizing α-syn aggregates according to the present invention inhibits the formation of α-syn aggregates or degrades aggregates, and inhibits the intercellular transfer of aggregates, thereby inhibiting α-synucleinopathy, particularly Lewy body diseases and Parkinson's disease.

Use of Human α-Syn Antibody for Diagnostic and Therapeutic Purposes

The antibodies disclosed herein are useful for the detection of α-syn, particularly α-syn aggregates such as Lewy bodies, and the identification of cells or tissues containing α-syn aggregates in a biological sample. For example, an anti α-syn antibody can be used for diagnosis, for example, the detection and/or quantitative analysis of α-sSyn aggregates in a biological sample such as blood containing serum, cerebrospinal fluid (CSF), or urine, or α-syn aggregates expressed inside of tissue or cells, and/or the diagnosis of α-synucleinopathy based thereon.

In particular, the antibodies specifically binding to aggregates according to the present invention can be used for the treatment of α-syn aggregate-related diseases in subjects in need of treatment, diagnosis, and/or detection of diseases related to α-syn aggregates. The antibody or antigen-binding fragment according to the present invention can be effectively used for the treatment of diseases related to α-syn aggregates as described above by inhibiting the production, promoting degradation, and inhibiting intercellular transfer of α-syn aggregates.

Diagnosis Method

The antibody disclosed herein may be usefully used for detection, diagnosis, or monitoring of α-syn related diseases or symptoms.

In one embodiment, the method of the present invention is a method of diagnosing α-synucleinopathy in a subject in need of diagnosis of α-synucleinopathy, wherein the method comprises determining the concentration or intercellular location of α-syn aggregates in the subject using the antibody and antigen-binding fragments according to the present invention; and comparing the concentration or the intercellular location of the α-syn aggregates measured in the subject with the result of the control sample, and the similarity or difference to the result of the control indicates that the subject suffers alpha-synucleinopathy.

In the method, the subject includes patients who have no symptoms or are before occurrence of symptoms. In one embodiment, the control may be a patient with α-synucleinopathy including PD, DLB, or MSA, wherein the similarity to the control group in the comparison step provides the diagnosis the subject is a patient with α-synucleinopathy. In another embodiment, when the control is a sample derived from a normal person, the difference from the control group in the comparison step, for example, an increase in the aggregate concentration, provides the diagnosis that the subject has α-synucleinopathy. In another embodiment, the age of the subject and the control can be matched. The method may be performed in vivo or in a biological sample separated from subject, such as blood, cerebrospinal fluid (CSF), or urine samples.

The method can be performed with in vivo imaging. In vivo imaging can be performed using, for example, positron emission tomography (PET), single photon emission tomography (SPECT), near infrared (NIR) optical imaging or magnetic resonance imaging (MRI).

The method can be performed in vitro. The methods can be performed using Western blot, immunoprecipitation, ELISA, radioimmunoassay (RIA), or immunohistochemical methods which are well known to those skilled in the art, for example, Tijssen, 1993, Practice and Theory of Enzyme Immunoassays, Vol. 15 (Eds R. H. Burdon and P. H. van Knippenberg, Elsevier, Amsterdam); Zola, 1987, Monoclonal Antibodies: A Manual of Techniques, pp. 147-158 (CRC Press, Inc.); Jalkanen et al., 1985, J. Cell. Biol. 101:976-985; Jalkanen et al., 1987, J. Cell Biol. 105:3087-3096). The detection of α-syn may be performed in vivo or in vitro In addition, ELISA (Enzyme Linked Immuno Sorbent Assay) and Radio Immuno Assay (RIA) are included.

For detection or diagnosis use, typically, the antibody may be labeled with a detectable labeling substance. The appropriate labeling substances include a radioisotope or radioactive nuclide (for example, $^3$H, $^{14}$C, $^{15}$N, 35, $^{90}$Y $^{99}$Tc, $^{111}$In, $^{125}$I, $^{131}$I), fluorescent material (for example, FITC, rhodamine, lanthanoid fluorescent substance), enzyme (for example, horse radish peroxidase, β-galactosidase, luciferase, alkaline phosphatase), a chemiluminescent group, a biotinyl group, or polypeptide epitope recognized by a secondary reporter (for example, leucine zipper pair sequence, secondary antibody binding site, metal binding domain, epitope tag), but not limited thereto. In some embodiments, the labeling substance may be coupled to an antibody through various spacer arms in length to reduce potential steric hindrance. Various methods for labeling a protein are known in the art and may be applied herein.

In other aspects, the antibody of the present invention may be used for identification of a tissue including α-syn aggregates. In a specific embodiment, the antibody is labeled by a labeling substance, and the binding to α-syn aggregates of the labeled antibody is detected. In one embodiment, the binding of the antibody to α-syn aggregates is detected in vivo.

In other aspects, the present invention discloses detecting or sorting test materials competing to the antibody disclosed herein for binding to α-syn aggregates. For example, in the presence or absence of test materials, a step of detecting the amount of free antibodies in a solution comprising α-syn aggregates is comprised. The increase of the concentration of the free antibody, that is, the antibody which is not bound to α-syn aggregates may instruct that the test molecule can compete to the antibody for α-syn binding. In one embodiment, the antibody is labeled by a labeling group. Alternatively, the test materials are labeled and the amount of free test materials is monitored by the presence or absence of the antibody.

In addition to that, the antibody or antigen-binding fragment disclosed herein has various usefulness. For example, it may be used for specific binding analysis, α-syn purification based on affinity, or screening method for α-syn antagonist investigation, etc.

Treatment Method: Pharmaceutical Formulation, Administration Route

The antibody or antigen-binding fragment according to the present invention is useful for the treatment of diseases associated with α-syn aggregates as described above, by inhibiting the production, promoting degradation, and inhibiting intercellular transport of α-syn aggregates.

Accordingly, the treatment methods using the antibody and antigen-binding fragment according to the present invention are also provided. In one embodiment, the antibody is provided to the patient. The diseases and the patients that can be effectively treated by the antibody and antigen-binding fragment according to the present invention are described above.

In one embodiment, an antibody according to the present disclosure may be used in a connected form to a delivery vehicle for passage through the brain blood barrier. Many methods for delivering medication through the brain blood barrier are disclosed. For example, there is a method of breaking down the osmotic pressure of the BBB by using a method such as Brad quinine or HIFU (high density focused ultrasound). They also involve the use of cellular delivery systems, for example, glucose and amino acid transport and receptor-mediated transcytosis of insulin or transferrin, or the blocking of efflux transporter of glycoproteins. The examples of the receptor in the receptor-mediated transcytosis system are described below: insulin receptor (e.g., human insulin receptor), transferrin receptor, LRP (e.g., LRP1, LRP6 and LRP8), melanocortin receptor, nicotinic acetylcholine receptor, VACM-1 receptor, IGFR, EPCR, EGFR, TNFR, Leptin receptor, M6PR, Lipoprotein receptor, NCAM, LIFR, LfR, MRP1, AchR, DTr, Glutathione transporter, SR-B1, MYOF, TFRC, ECE1, LDLR, PVR, CDC50A, SCARF1, MRCl, HLA-DRA, RAMP2, VLDLR, STAB1, TLR9, CXCL16, NTRK1, CD74, DPP4, endothelial growth factor receptors 1, 2 and 3, glucocorticoid receptor, ionotropic glutamate receptor, M3 receptor, aryl hydrocarbon receptor, GLUT-1, inositol-1,4,5-trisphosphate (IP3) receptor, N-methyl-D-aspartate receptor, S1P1, P2Y receptor, TMEM30A, and RAGE.

In yet another embodiment, an antibody according to the present invention may be used in connected form to other therapeutic agents for the treatment of diseases associated with α-syn aggregates.

A pharmaceutical composition comprising a therapeutically effective dose of the antibody and a pharmaceutically acceptable diluent, carrier, solubilizer, emulsifier, preservative and/or supplement is also provided. In addition, for example, a method for treating a cancer patient by administering such a pharmaceutical composition is included. The term "patient" includes a human patient related with α-syn.

An acceptable formulation material is non-toxic to a recipient, in used capacity and concentration. In a specific embodiment, a pharmaceutical composition comprising a therapeutically effective dose of human α-syn antibody is provided.

In a specific embodiment, the acceptable formulation material is preferably non-toxic in used capacity and concentration. In one embodiment, for example, the pharmaceutical composition may comprise a specific formulation material for pH, osmolality, viscosity, transparency, color, isotonicity, scent, sterility, stability, rate of dissolution or release, modification, maintenance or conservation of absorption or penetration, of the composition. In this embodiment, the appropriate formulation material includes amino acid (e.g.: glycine, glutamine, asparagine, arginine or lysine); antimicrobial agent; antioxidant (e.g.: ascorbic acid, sodium sulfite or sodium bisulfite); buffer (e.g.: borate, bicarbonate, Tris-HCl, citrate, phosphate or other organic acids); bulking agent (e.g.: mannitol or glycine); chelating agent (e.g.: ethylenediamine tetraacetic acid (EDTA)); complexing agent (e.g.: caffeine, polyvinylpyrrolidone, beta-cyclodextrin or hydroxypropyl-beta-cyclodextrin); filler; monosaccharide; disaccharide; and other carbohydrates (e.g.: glucose, mannose or dextrin); protein (e.g.: serum albumin, gelatin or immunoglobulin); coloring agent, flavoring agent and diluent; emulsifier; hydrophilic polymer (e.g.: polyvinylpyrrolidone); low molecular polypeptide; salt-forming counterion (e.g.: sodium); preservative (e.g.: benzalkonium chloride, benzoic acid, salicylic acid, thimerosal, phenylethyl alcohol, methylparaben, propylparaben, chlorohexidine, sorbic acid, or peroxide); solvent (e.g.: glycerin, propylene glycol or polyethylene glycol); sugar alcohol (e.g.: mannitol or sorbitol); suspension; supernatant or wetting agent (e.g.: Pluronics, PEG, sorbitan ester, polysorbate, for example, polysorbate 20, polysorbate, triton, tromethamine, lecithin, cholesterol, tyloxapol); stability enhancer (e.g.: sucrose or sorbitol); robustness enhancer (e.g.: alkaline metal halide, preferably sodium chloride or potassium chloride, mannitol, sorbitol); delivery vehicle; diluent; excipient and/or pharmaceutical supplement, but not limited thereto. For example, REMINGTON'S PHARMACEUTICAL SCIENCES, 18" Edition, (A.R. Genrmo, ed.), 1990, Mack Publishing Company may be referred.

In a specific embodiment, the optimum pharmaceutical composition may be determined by those skilled in the art according to for example, a targeting administration route, delivery method and a targeting capacity (see, the above REMINGTON'S PHARMACEUTICAL SCIENCES). In a specific embodiment, this composition may affect the physical condition, stability, release rate in vivo and rate of clearance in vivo of the antibody disclosed herein. In a specific embodiment, the major vehicle or carrier in the pharmaceutical composition may be aqueous or non-aqueous. For example, an appropriate vehicle or carrier may be possibly injection water, physiological saline solution supplemented by common other materials in a composition for parenteral administration. In addition, neutral buffer saline solution or saline solution mixed with serum albumin may be used as a vehicle. In a specific embodiment, the pharmaceutical composition may comprise about pH 7.0-8.5 Tris buffer, or about pH 4.0-5.5 acetate buffer, and may further comprise sorbitol or proper substitutes. In a specific embodiment, the human α-syn antibody composition may be prepared by mixing a selected composition having a targeting level of purity in a form of lyophilized cake or aqueous solution with any formulating agent (see, REMINGTON'S PHARMACEUTICAL SCIENCES) for storage. Further, in a specific embodiment, the human α-syn antibody may be formulated as a lyophilizing using a proper excipient, for example, sucrose.

The pharmaceutical composition may be delivered parenterally. Alternatively, the composition may be inhaled or delivered through a digestive tract, for example, orally. The preparation of this pharmaceutically acceptable composition is within the technical level in the art.

The components required for formulations are present preferably at the concentration acceptable for administration sites. In a specific embodiment, the buffer is used to maintain the composition at a physiological pH or slightly low pH or typically in the pH range of about 5 to about 8.

In case of parenteral administration, the therapeutic composition comprises a targeting human α-syn binding protein in a pharmaceutically acceptable vehicle, and it may be provided in a form of aqueous solution acceptable for the parenteral administration, which does not comprise a pyrogen. The vehicle which is particularly appropriate for parenteral injection is sterile distilled water, and here, the human α-syn antibody is formulated with a properly conserved sterile isotonic solution. In a specific embodiment, this formulation may accompany formulation using an agent providing controlled release or sustained release of a composition, which can be delivered through depot injection, for example, an injectable microsphere, biodegradable particle, polymeric compound (e.g.: polylactic acid or polyglycolic acid), bead or liposome. In a specific embodiment, a hyaluronic acid having an effect of increasing duration time in blood may be also used. In a specific embodiment, to deliver a targeting antibody, implantable drug delivery device may be also used.

In addition, the pharmaceutical composition is formulated for inhalation. In some embodiments, the human α-syn antibody is formulated as a dry inhalable powder. In a specific embodiment, the human α-syn antibody inhaling solution may be also formulated as a propellant for aerosol delivery. In a specific embodiment, the solution may be sprayed. These lung administration and formulation methods are further described in PCT application No. PCT/US94/001875. Some formulations may be administered orally. The human α-syn antibody administered in this way may be formulated with a solid dose form, for example, a carrier commonly used for purification and preparation of capsules or without such a carrier. In a specific embodiment, the capsule may be designed so as to release the active part of the formulation at the point in the gastrointestinal tract where the bioavailability is maximized and pre-systemic degradation is minimized. To facilitate the absorption of the human α-syn antibody, an additional agent may be comprised. A diluent, flavoring agent, low melting point wax, vegetable oil, lubricant, suspension, tablet disintegrating agent and binding agent may be also used.

Some pharmaceutical compositions comprise the effective dose of human α-syn antibody mixed with a non-toxic excipient proper for preparation of tablet. By dissolving the tablet in sterile water or other proper vehicles, the solution may be prepared as a unit-dose form. The proper excipients include an inactive diluent, for example, calcium carbonate, sodium carbonate, sodium bicarbonate, lactose or calcium phosphate; or binding agent, for example, starch, gelatin or acacia; or lubricant, for example, magnesium stearate, stearic acid or talc, but not limited thereto.

The additional pharmaceutical composition including a formulation comprising other human α-syn antibody comprising a sustained- or controlled-delivery formulation is obvious to those skilled in the art. Various other sustained- or controlled-delivery means, for example, a technique for formulating a liposome carrier, bioerosive particulate or porous bead and depot injection material are also known to those skilled in the art. For example, PCT/US93/00829 in which the controlled release of porous polymeric particulate is described may be referred. The sustained-release agent may comprise a molded product, for example, a film or microcapsule form of semipermeable polymer matrix. The sustained-release matrix may comprise a polyester, hydrogel, polylactide (described in U.S. Pat. No. 3,773,919 and EP 058481), copolymer of L-glutamic acid and gamma ethyl-L-glutamate (Sidman et al., 1983, Biopolymers 2:547-556), poly(2-hydroxyethyl-methacrylate (Langer et al., 1981, J. Biomed. Mater. Res. 15:167-277; and Langer, 1982, Chem. Tech. 12:98-105), ethylene vinyl acetate (Langer et al., 1981, the above) or poly-D(−)-3-hydroxybutyric acid (EP 133,988). The sustained-release composition may also comprise a liposome to be prepared by one of various methods known in the art. For example, Eppstein et al., 1985, Proc. Natl. Acad. Sci. U.S.A. 82:3688-3692; EP 036,676; EP 088,046 and EP 143,949 may be referred.

The pharmaceutical composition to be used for administration in vivo may be provided typically as a sterile agent. The sterileness may be achieved by filtration through a sterile filtering membrane. When the composition is lyophilized, a process of dissolving it in a solution, as well as freeze-drying should be sterilely performed. The composition for parenteral administration may be stored in a lyophilized form or solution. For example, the parenteral composition is commonly comprised in a container having a sterile access port such as a vial with a lid which a hypodermic needle can enter or solution bag for intravenous administration.

In a specific embodiment, a cell expressing the recombinant antibody described herein may be capsulated for delivery (Invest. Ophthalmol Vis Sci 43:3292-3298, 2002; and Proc. Natl. Acad. Sciences 103:3896-3901, 2006).

In a specific formulation, the antibody has the concentration of, for example, at least 10 mg/mL, 20 mg/mL, 30 mg/mL, 40 mg/mL, 50 mg/mL, 60 mg/mL, 70 mg/mL, 80 mg/mL, 90 mg/mL, 100 mg/mL or 150 mg/mL. Some formulations comprise buffer, sucrose and polysorbate. One example of formulations is comprising 50-100 mg/mL antibody, 5-20 mM sodium acetate, 5-10% w/v sucrose, and 0.002-0.008% w/v polysorbate. A specific tablet comprises for example, 65-75 mg/mL antibody in 9-11 mM sodium acetate buffer, 8-10% w/v sucrose, and 0.005-0.006% w/v polysorbate. The pH of this specific formulation is within the range of 4.5-6. Other formulation has pH of 5.0-5.5 (for example, pH of 5.0, 5.2 or 5.4).

Once the pharmaceutical composition is formulated, this may be stored in a sterile vial as a solution, suspension, gel, emulsion, solid, crystal or dehydrated or lyophilized powder. This formulation may be stored in an immediately usable form or a form restructured just before administration (for example, lyophilized). A kit for producing a single-dose administration unit is also provided. This kit comprises a primary container having a dried protein and a secondary container having an aqueous formulation. In a specific embodiment, a kit comprising a pre-filled syringe having a single chamber and multiple chamber are provided. The therapeutically effective dose of the human α-syn antibody-comprising pharmaceutical composition to be used may be affected by for example, a therapeutic situation and purpose. Those skilled in the art may understand that the dose proper for treatment may be different at least partially according to a disease in which the human α-syn antibody is used, administration route, and body condition of a patient (weight, body surface or organ size) and/or condition (age and overall health). In a specific embodiment, a clinician may determine the optimum dose and change the administration route to collect the optimum therapeutic effect.

The typical dose may be in a range of about 1 μg/kg to about 30 mg/kg or more, considering the aforementioned factors. In a specific embodiment, the dose may be in a range of 10 μg/kg to about 30 mg/kg, selectively, 0.1 mg/kg to about 30 mg/kg, or alternatively, 0.3 mg/kg to about 20 mg/kg. In some cases, the dose is 0.5 mg/kg to 20 mg/kg. In some cases, the antibody is administered at 0.3 mg/kg, 0.5 mg/kg, 1 mg/kg, 3 mg/kg, 10 mg/kg, or 20 mg/kg.

The administration frequency may be affected by pharmacokinetics parameters of the used formulation of human α-syn antibody. Typically, a clinician administers a composition until the dose achieving a targeting effect is reached. Thus, the composition may be administered over time, as a single dose, or 2 times or more of doses, or be administered as continuous injection through an implantable device or catheter. The appropriate dose may be confirmed through the use of proper dose-reaction data. In a specific embodiment, the antibody may be administered to a patient over a long time. The chronic administration of an antibody may minimize a harmful immunoreaction or allergic reaction, which is generally accompanied by the antibody not a complete human, for example, the antibody produced for a human antigen in a non-human animal, for example, a non-complete human antibody or non-human antibody produced in a non-human animal.

The administration route of the pharmaceutical composition may use known methods, for example, injection through oral; intravenous, intraperitoneal, intracerebral (interstitial), intraventricular, intramuscular, intraocular, intra-arterial, intraportal or intralesional route; sustained-release system or implant device. In a specific embodiment, the composition may be continuously administered by bolus injection, or injection or implant device.

In addition, the composition may be locally administered by implanting a membrane, sponge or other proper materials in which a targeting molecule is absorbed or capsulated. In a specific embodiment, in case of using the implant device, the device may be implanted to any appropriate tissue or organ, and the delivery of a targeting molecule may be achieved through diffusion, timed bolus or continuous administration.

In addition, it may be preferable to use the human α-syn antibody pharmaceutical composition in vitro. In this case, a cell, tissue or organ removed from a patient may be exposed for the human α-syn antibody pharmaceutical composition, and then the cell, tissue and/or organ is subsequently implanted into the patient.

In particular, the human α-syn antibody may be delivered by implanting a specific cell which is genetically engineered using methods described herein, to express and secret a polypeptide. In a specific embodiment, this cell may be an animal or human cell, and may be derived autologously, non-autologously or heterogeneously. In a specific embodiment, the cell may be immortalized. In other embodiment, to reduce an immunoreaction, the cell may be capsulated to avoid penetration into a surrounding tissue. In an additional embodiment, the capsulated material typically allows the release of protein products, but it is a biocompatible semipermeable polymeric enclosure or membrane preventing cell disruption by other harmful factors from an immune system or surrounding tissue of a patient.

Hereinafter, desirable examples are presented to facilitate understanding of the present invention. However, the following examples are provided for a better understanding of the present invention, and the scope of the present invention is not limited by the following examples.

The terms and techniques used herein related with cell and tissue culture, molecular biology, immunology, microbiology, genetics, protein and nucleic acid chemistry, and hybridization are widely used and known in the art. Otherwise, the methods and techniques disclosed herein may be practiced using conventional techniques that are within the skill of those skilled in the art of cell biology, cell culture, molecular biology, genetic transformation technology, microbiology, DNA recombinant technology, immunology, and the like. A more detailed description of common techniques can be found in the following books and literature. For general methods of molecular biology and biochemistry, Molecular Cloning: A Laboratory Manual, 3rd Ed. (Sambrook et al., Harbor Laboratory Press 2001); Short Protocols in Molecular Biology, 4th Ed. (Ausubel et al., eds., John Wiley &Sons 1999); DNA Cloning, Volumes I and II (Glover, ed., 1985); Oligonucleotide Synthesis (Gait, ed., 1984); Nucleic Acid Hybridization (Hames and Higgins, eds. 1984); Transcription And Translation (Hames and Higgins, eds. 1984); Culture Of Animal Cells (Freshney and Alan, Liss, Inc., 1987); Gene Transfer Vectors for Mammalian Cells (Miller and Calos, eds.); *Current Protocols in Molecular Biology* and Short Protocols in Molecular Biology, 3rd Edition (Ausubel et al., eds.); and Recombinant DNA Methodology (Wu, ed., Academic Press); Harlow and Lane *Antibodies: A Laboratory Manual* Cold Spring Harbor Laboratory Press, Cold Spring Harbor, N.Y. (1990) can be referred.

Protein reaction and purification techniques are performed routinely in the art or according to the manufacturer's method as described herein. In the present invention, the terms used related with analytical chemistry, synthetic organic chemistry, and medicinal and pharmaceutical chemistry laboratory techniques and methods are well known and commonly used in the art. Standard techniques can be used for chemical synthesis, chemical analysis, pharmaceutical preparation, pharmaceutical formulation and administration, patient treatment, and the like.

Example 1: Preparation of α-Syn Antibody

Example 1-1: Mouse Monoclonal Antibody

Immunization

α-syn monomer with a full length (140 residues) or cleaved with C-terminal 21 residues (119 residues) were placed in a thermomixer at 37° C., aggregated with shaking at 1050 rpm for 14 days, and sonicated. Each of 140 residues and 119 residues of the α-syn fibril at 1 mg/ml was mixed with the adjuvant at a ratio of 1:1 (vol: vol).

Then, 200 μL of the prepared mixture was injected subcutaneously into 5 to 7 week old BALB/c female mice. After 2 weeks, 200 μL of the prepared mixture was further injected subcutaneously for antibody boosting. After one week of boosting, blood was collected and immunization titration was performed by the ELISA method using the administered antigen. Subsequently, third boosting was performed by subcutaneous injection of antigen alone.

Hybridoma Production

The spleen of the immunized mouse was removed, and the spleen cells were obtained from the spleen. The spleen cells were suspended in Hybridoma-SFM medium (Thermo Fisher Scientific, USA) supplemented with 10% FBS. To prepare the hybridoma, the spleen cells and SP2/0-Ag14 of a murine myeloma cell were mixed in a Hybridoma-SFM medium without serum, and followed by centrifugation to remove the medium. Then, PEG was added to the obtained cell pellet and incubated at 37° C. for 1 minute to induce cell fusion.

Single Cell Cloning

After 2 weeks in the fusion, the fusion with mouse B cells producing antibodies was confirmed with an ELISA method using the antigen administered to the mouse and a cell culture medium. Then, single-cell cloning was carried out using a hybridoma to select 16 hybridomas producing monoclonal antibodies. Clones of 1E4 and 9B11 (IgG1 kappa, IgG3 kappa and IgG3 kappa, respectively) were obtained using the aggregate of full length (140 residues) α-syn as an antigen, and Clones of 3A9, 10F10 and 11F11 (IgG2b kappa, IgG2a kappa, IgG2b kappa, respectively) were obtained using α-syn aggregates with cleaved C-terminal 21 residues as antigens.

Purification of Antibodies

Each hybridoma was cultured in RPMI1640 medium containing 10% FBS. For antibody production, the culture medium was replaced with serum-free SFM medium and cultured for about 4 days. The cell culture supernatant was separated, centrifuged, filtered with a 0.22 m filter, and purified with a protein G column for IgG1 type and the protein A column for the remaining antibodies.

Determination of Variable Region Sequence

The variable region and CDR sequences were determined by referring to the disclosure Ahn et al., Mol. Cells 2004, 18 (2): 237-241. Hybridomas were cultured and centrifuged to isolate only the cells. The RNA was isolated from the isolated hybridoma by the addition of a triazole and was used for synthesize cDNA as a template. The variable region and CDR sequence were confirmed by sequencing.

The amino acid sequences are shown in Table 1, and the nucleotide sequences are shown in Table 2.

Example 1-2: Phage Library Screening

Preparation of Library Phage $1 \times 10^{10}$ of the competent cells of single-chain variable fragment (scFv) with diversity derived from human (obtained from EHWA WOMANS UNIVERSITY) were inoculated in 2×YT medium [17 g of Tripton (CONDA, 1612.00), 10 g of yeast extract (CONDA, 1702.00) and 5 g of NaCl (Sigma, S7653)] containing 34 μg/ml of chloramphenicol (Sigma, C0857), 2% glucose (Sigma, G5400) and 5 mM $MgCl_2$ (Sigma, C0857) at 30° C. for 3 hours to be OD600 of 0.5 to 0.7. Then, the cells were infected with a helper phage, and cultured in 2×YT medium containing 34 μg/ml of chloramphenicol, 5 mM $MgCl_2$, 70 μg/ml of kanamycin (Sigma, K1876) and 1 mM IPTG (ELPISBIO, IPTG025) at 30° C. for 6 hours to induce the phage packing. The culture solution was centrifuged at 4500 rpm at 4° C. for 15 minutes. The supernatant was added with 4% PEG 6000 (Fluka, 81253) and 3% NaCl (Sigma, S7653) and incubated for 1 hour on ice. The product was centrifuged at 8000 rpm for 20 minutes at 4° C., and then, the pellet was suspended in PBS and centrifuged again at 4° C. and 12,000 rpm for 10 minutes to obtain a supernatant containing the phage library. The obtained supernatant was stored at 4° C. until subsequent use.

Phage Display Panning

In order to select antibodies that preferentially bind to alpha-synuclein aggregates to the monomers, the panning was performed using the full-length alpha-synuclein aggregates prepared in Example 1, and total three panning were performed as follows.

Bovine serum albumin (BSA) was added to the cells at a concentration of 3% in a test tube at 4° C. overnight, adding 10 μg/ml of recombinant α-syn aggregates and monomers to the PBS in an immunotube (maxisorp 444202) solution was added to the test tube and the surface of which α-syn aggregates and monomers were not adsorbed was protected. After emptying the test tube, the antibody phage library of $10^{12}$ CFU dispersed in BSA 3% solution was put into the immunotube in which the α-syn aggregates and monomers were absorbed and reacted for 1 hour (negative selection). Then, the phages were not bound to α-syn aggregates and monomers were recovered and reacted for 2 hours at room temperature in the α-syn aggregates and monomers were adsorbed. Phosphate buffered saline (0.05% Tween 20) solution was used to recover 100 M triethylamine solution, which was recovered by using a PBS-T solution. *E. coli* at 37° C. for 1 hour, and the infected *E. coli* was painted out on a 2×YT agar medium and cultured at 37° C. overnight (pH 7.4), they were infected by ER2537. Next day, the cultured *E. coli* was suspended in a 4 ml of 2×YT carbenicillin culture solution and 15% glycerol was added, and a part was stored at −80° C. and the rest was used for preparing phages for next experiments. By repeating this process at 3 rounds in total, an α-syn antigen-specific phage pool was amplified and concentrated. As the panning round progressed, the number of washing using PBS-T was increased to amplify and concentrate the antigen-specific phage.

Single Clone Screening

To sort monoclonal antibodies specifically binding to synuclein aggregate from the phage pool obtained through the panning, the experiment as follows was performed.

To isolate monoclones from the concentrated pool, after painting out the phage pool on a LB-tetracycline/carbenicillin agar medium and culturing, a single colony was secured. Then, after inoculating monoclones on a 96-deep well plate in which 400 μL of 2×YT-tetracycline/carbenicillin medium was put per well and growing overnight, 10 μL culture solution was put on a new 96-deep well plate in which 390 μL of 2×YT-tetracycline/carbenicillin medium was put and it was cultured at 37° C. for 4 hours. 1 mM IPTG was put into the culture solution and it was cultured at 30° C. overnight. The culture solution cultured overnight was centrifuged to take a supernatant.

Then, clones expressing a monoclone-soluble scFv which binds to synuclein aggregate were selected by using the ELISA method as follows (Steinberger. Rader and Barbas III. 2000. Phage display vectors. In: Phage Display Laboratory Manual. 1sted. Cold Spring Harbor Laboratory Press. NY. USA. pp. 11.9-11.12). specifically, the selected 7B7 antibody in Example 1-1 was put on a 96-well plate (Nunc-Immuno Plates, NUNC, USA) and it was coated at 4° C. overnight. 3% BSA was added to each well in an amount of 200 μL, followed by blocking at 37° C. for 2 hours. Then, the synuclein aggregates and the monomer were loaded at a concentration of 100 ng/well, reacted at 37° C. for 2 hours and washed five times with 300 μL of PBS-T. The prepared single clone supernatant was mixed with 3% BSA in a volume ratio of 1:1 (vol: vol), and 100 μL of the solution was loaded on the plate bound to the aggregate and the monomer, followed by reaction at 37° C. for 2 hours. The cells were washed five times with 300 L of PBS-T, and incubated at 37° C. for 1 hour with an anti-HA HRP-conjugated antibody, followed by washing with PBS-T five times. After adding 100 μL of TMB (Tetramethylbenzidine, Sigma, T0440), the reaction was stopped by adding 50 μL of 1 N $H_2SO_4$ to measure the absorbance at 450 nm. Clones with an absorbance of 0.5 or greater were regarded as positive reaction by binding and clones bind to BSA nonspecifically were excluded.

Accordingly, AC8, AE8, AA9, DG5, AD2, AD7, DG11, DG8 and DA9 antibody clones which specifically bound to the synuclein aggregates were selected and performed by sequencing the protein and nucleotide sequences. The nucleic acid sequences of the clones are disclosed in of SEQ ID NOs: 169-224.

Example 2 Analysis of Antigen Binding Specificity and Binding Affinity Using α-Syn Antibody Example 2-1: Dot Blot Analysis Using Mouse Monoclonal Anti α-Syn Antibody Dot blot experiments were performed to analyze whether the antibody according to the present invention bound to monomers or aggregates in the native state. For the experiment, 50 ng or 100 ng of α-syn monomer or fibrin protein (manufactured by Professor Lee Seung-jae of Seoul National University; Bae et al., *J. Neurosci* 32: 13454, 2012) were spot-loaded on the nitrocellulose membrane. Twice-fold diluted monomer or fibril proteins were loaded sequentially from the right side of the membrane to the left (12.5, 25, 50, 100 ng). The membrane was blocked with 5% non-fat dry milk of TBST composition for 1 hour at room temperature. 1 mg/ml of the α-syn antibody prepared in Example 1 was added to TBST containing 1% bovine serum albumin and were incubated at room temperature for 1 hour. After washing with TBST, signals were analyzed using a chemiluminscence substrate (NEN) as substrate and secondary antibody conjugated with HRP (horse radish peroxidase) according to the manufacturer's manual. The results were imaged using a LAS-3000 Luminescent Image Analysis System (FUJIFILM Life Science). The results are shown in FIG. 1. As shown therein, the α-syn antibody according to the present invention was found to preferentially bind only to aggregates as compared to α-syn monomers. Particularly, 1E4, 9B11, 3A9 and 11F11 bound only to the aggregate and 10F10 bound to both aggregates and monomers. 274 antibody (Bae et al., J Neurosci. 2012 Sep. 26; 32 (39): 13454-13469) was used as a comparative antibody that binds both to monomers and aggregates.

Example 2-2: ELISA Analysis Using Mouse Monoclonal Anti α-Syn Antibody

ELISA analysis was performed to quantitatively analyze the binding affinity of the antibody of the present invention to the antigen. For this, alpha-synuclein antibody of the present invention was coated on a 96-well plate at a concentration of 1 mg/ml and treated with alpha, synuclein fibril aggregates at 10, 100, 1000 and 10,000 ng/ml. After washing with PBS, streptavidin conjugated with HRP and secondary antibody conjugate with biotin was treated and then reacted with TMB as a substrate. The absorbance was measured. The results are shown in FIG. 2. As shown therein, the antibodies of the present invention were found to preferentially bind to aggregates with high binding affinity. The ELISA results showed that antibodies binding to aggregates preferentially hasd the affinity of $0.1\sim2\times10^{-9}$ M, while antibodies binding to both monomers and aggregates showed higher values of $\sim1\times10^{-10}$ M.

Examples 2-3. BIAcore Analysis Using Mouse Monoclonal Anti α-Syn Antibody

Quantitative analysis of the binding of alpha-synuclein antibody prepared in Example 1 to monomer and aggregate antigen was performed using BIAcore analysis.

Figure 3A:
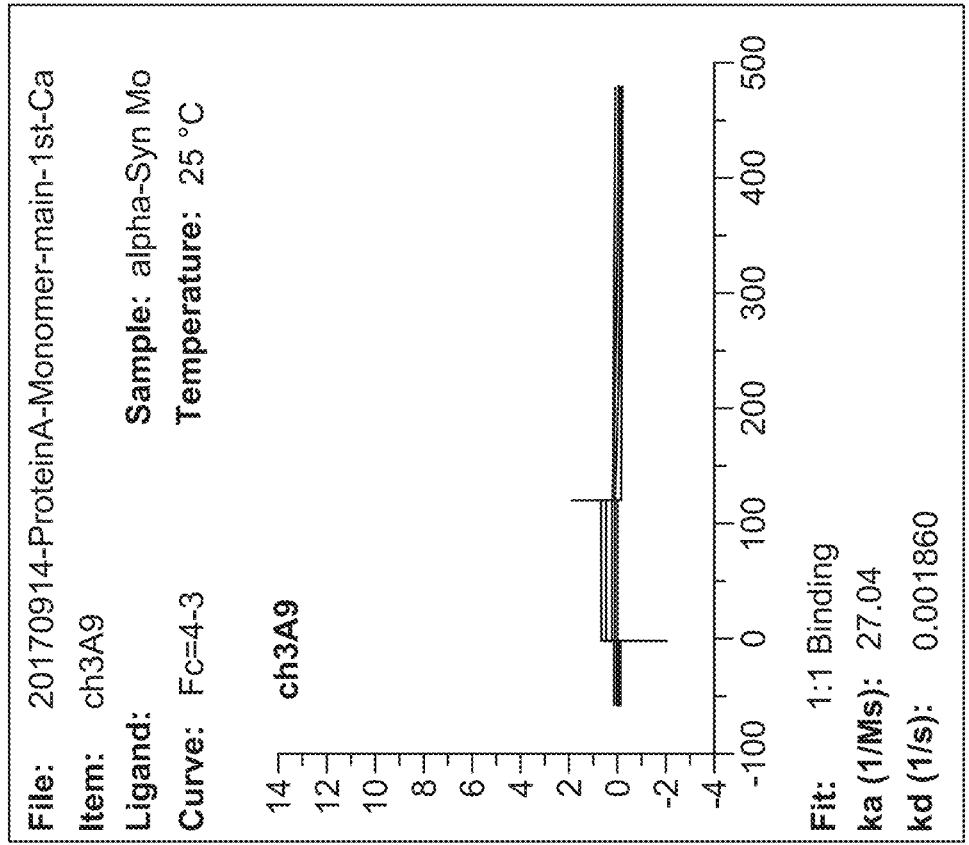
FIG. 3A is BIAcore analysis results for the preferential binding specificity and affinity of the monoclonal antibody produced in in an embodiment of the present invention to α-syn aggregates. The result indicates that the antibody of present invention preferentially binds to α-syn aggregates with high affinity. These results indicate that it is possible to effectively remove or inhibit the activity of causative agents of neurodegenerative diseases with an alpha-synuclein pathogenesis such as Parkinson's disease.
Figure 3A:
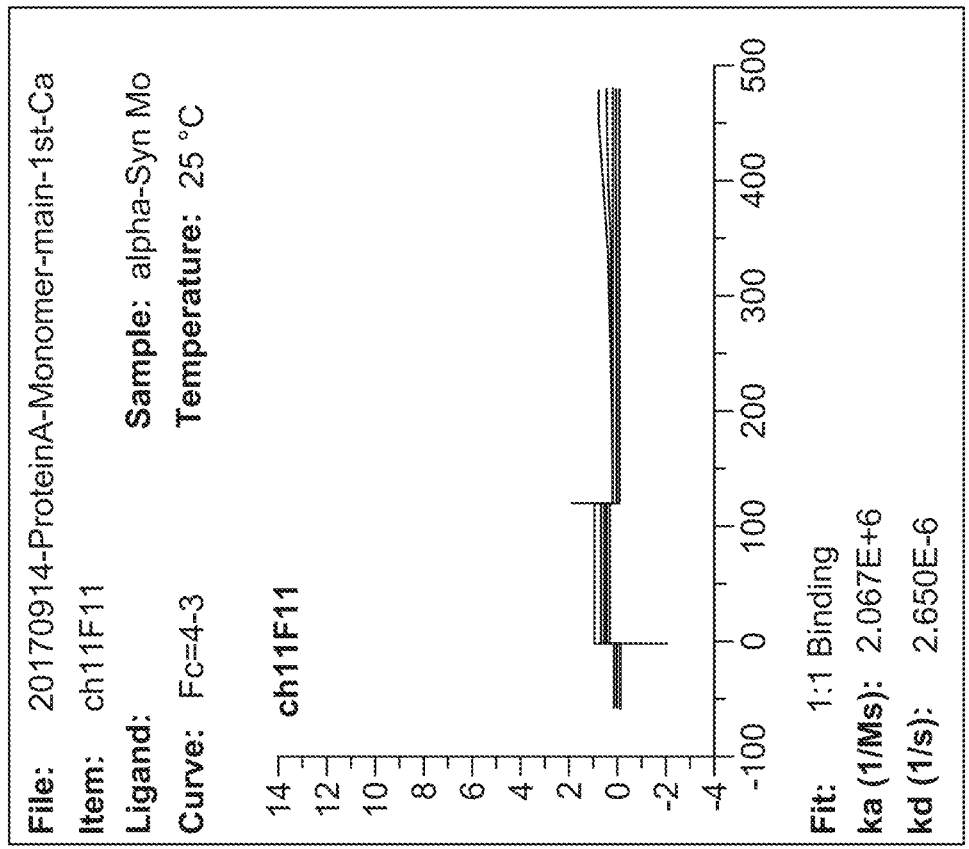
Figure 3A:
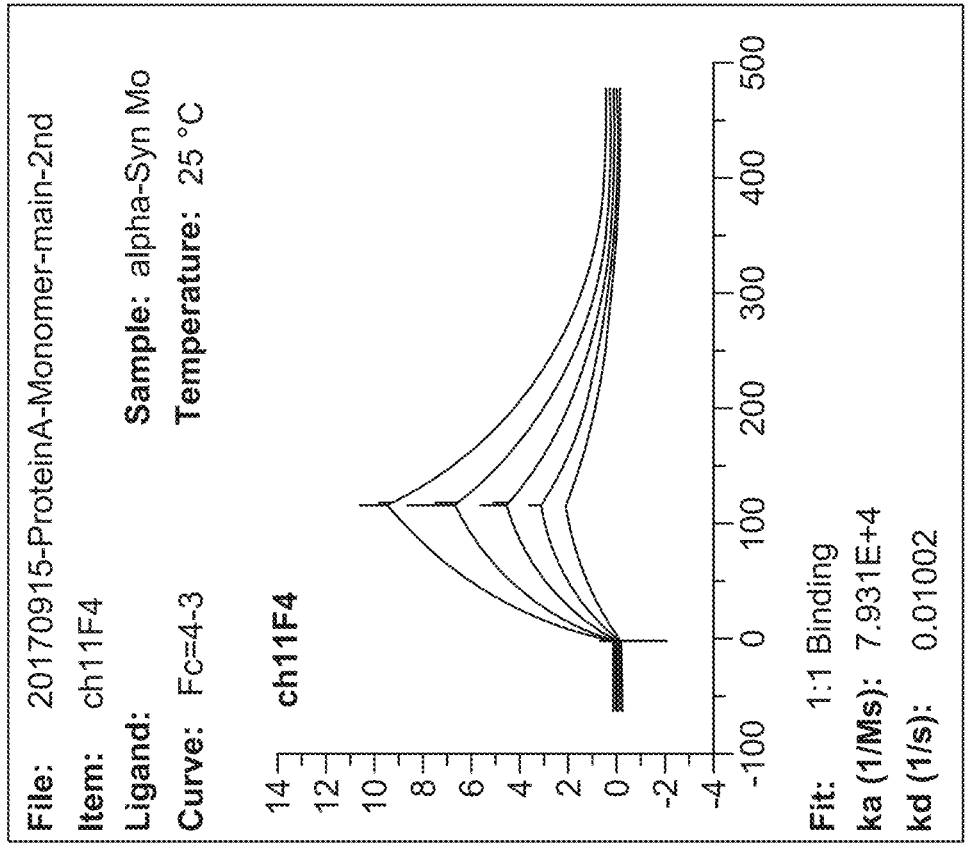
Figure 3A:
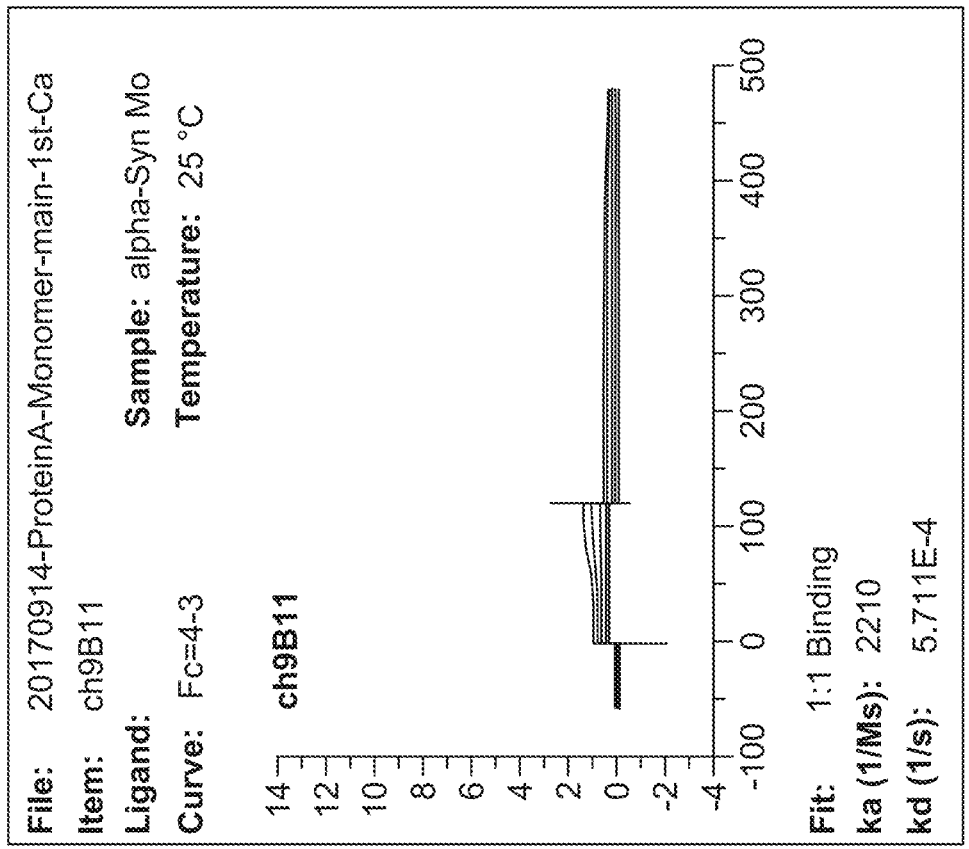
Figure 3A:
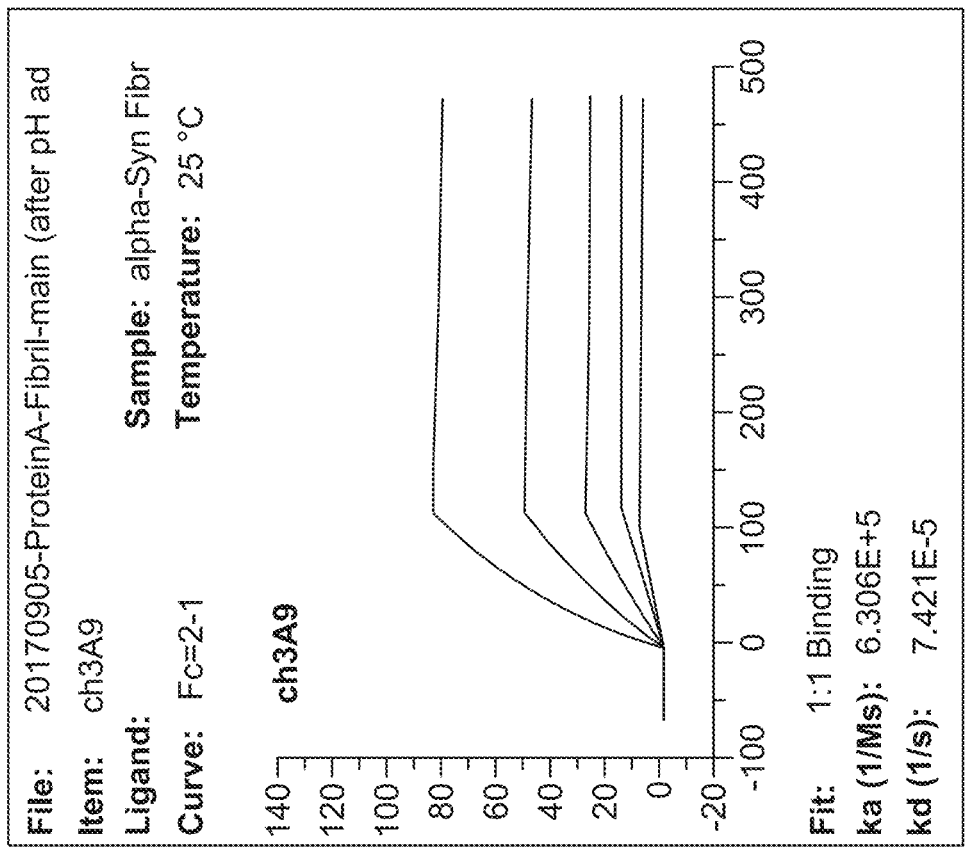
Figure 3A:
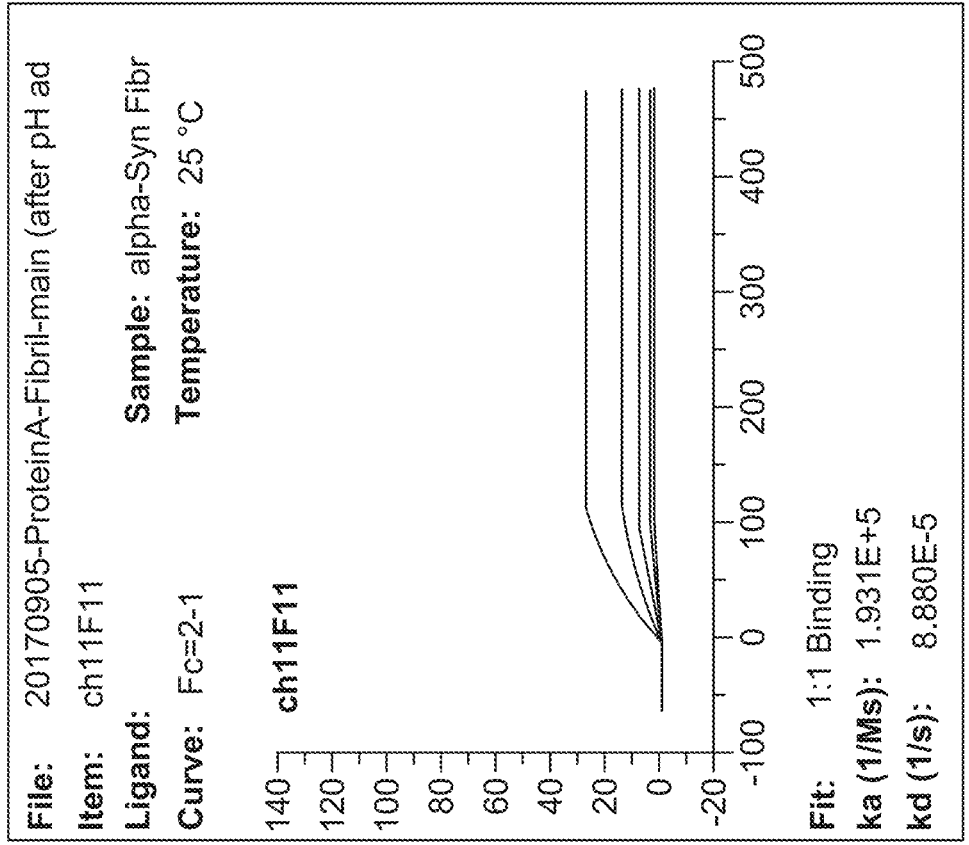
Figure 3A:
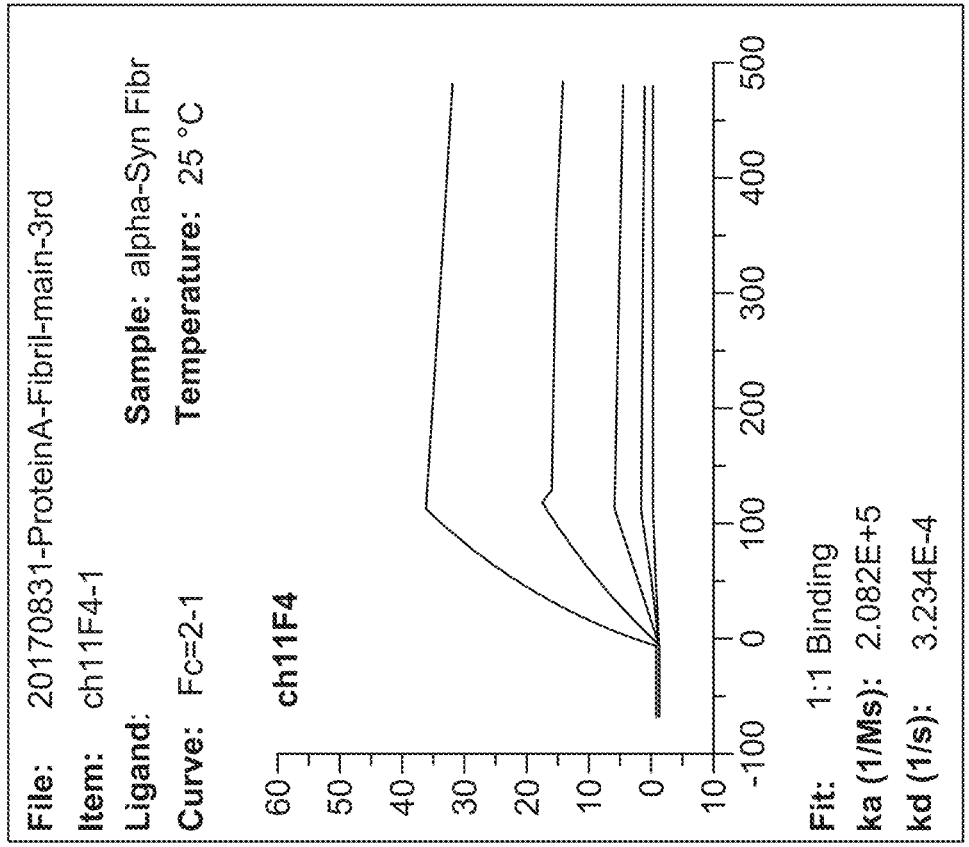
Figure 3A:
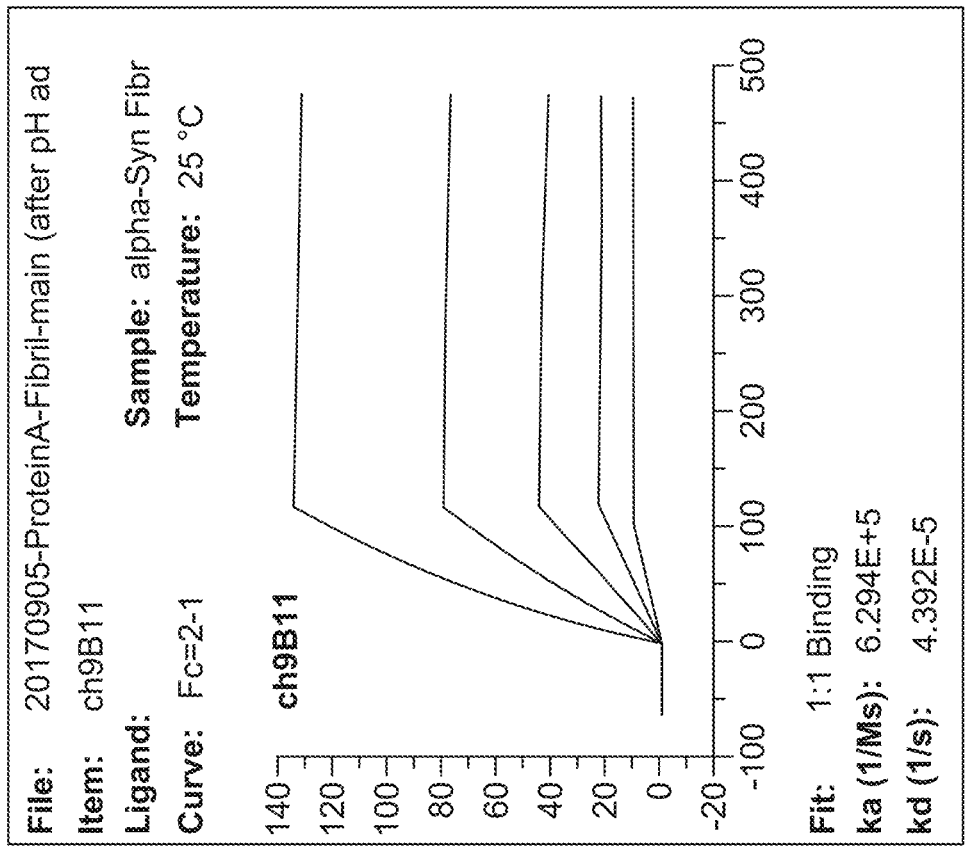

The used instrument was T200 (GE Healthcare, S/N: 1565888). Protein A is used as a chip (GE Healthcare, Cat. 29-1275-56). 10 mM Glycine-HCl pH 1.5 (GE Healthcare, Cat. BR-1003-54) was regeneration buffer. The running buffer, analyte dilution, and the sample dilution buffer were HBS-EP. The α-syn antibodies (3A9, 9B111 and 1 IF11) prepared in Example 1 were diluted with 1× HBS-EP (GE Healthcare, Cat. BR-1006-69), and alpha-synuclein monomer (1 mg/ml) and fibril protein (3 mg/ml) were serially diluted in duplicate and analyzed at 6 concentrations (0, 0.39, 1.56, 6.25, 25, 100 nM) including 0 nM in total. For the capture, the monomer was for RU of 800 (theoretical), and a fibril was for RU of 100 (theoretical). The capture phase was performed at contact time of 60 seconds, a flow rate of 30 μl/min, and a stabilization period of 180 seconds. The association phase was performed at the association time of 120 seconds and the flow rate was 30 μl/min. The dissociation phase was performed at the dissociation time of 360 seconds and the flow rate of 30 μl/min. The regeneration phase was performed twice time at the regeneration time of 240 seconds (primary) and 60 seconds (secondary) and a flow rate of 30 μl/min. The fitting was carried out suing 1:1 binding model, and the evaluation software was BIACore T200 Evaluation software (GE healthcare). The results are shown in FIGS. 3A and 3B. Among four alpha-synuclein antibodies analyzed, 3A9, 9B11, and 11F11, which preferentially bind to aggregates in the other methods described above, bind only to aggregates in BIAcore with about 1 to $3\times10^{-9}$ M of high affinity.

Examples 2-4. Octet Analysis Using Mouse Monoclonal Anti α-Syn Antibody

Quantitative analysis of the binding of the alpha-synuclein antibodies (3A9, 9B11, 11F11) prepared in Example 1 to monomer and aggregate antigen was performed using Octet.

Specifically, the running buffer was 1×KB buffer (cat. 18-1092) or 1×PBS buffer at 1000 rpm, and the immobilization buffer was sodium acetate, pH 5 (10 mM, Cat 18-1068. α-syn monomers was immobilized the α-syn antigen, and fibrils was immobilized the test antibody. The target concentrations were 20 μg/ml for the monomer and 0.4 μg/ml for the fibril. The kinetics concentration was diluted sequentially two times from 50 nM for monomers and from 100 nM for fibrils, to give 7 points in total, respectively. Association/dissociation time was 5 min/20 min for monomer and 5 min/25 min for fibril. Biosensor was ARG2 and fitting was performed using 1:1 fitting model.

Figure 4:
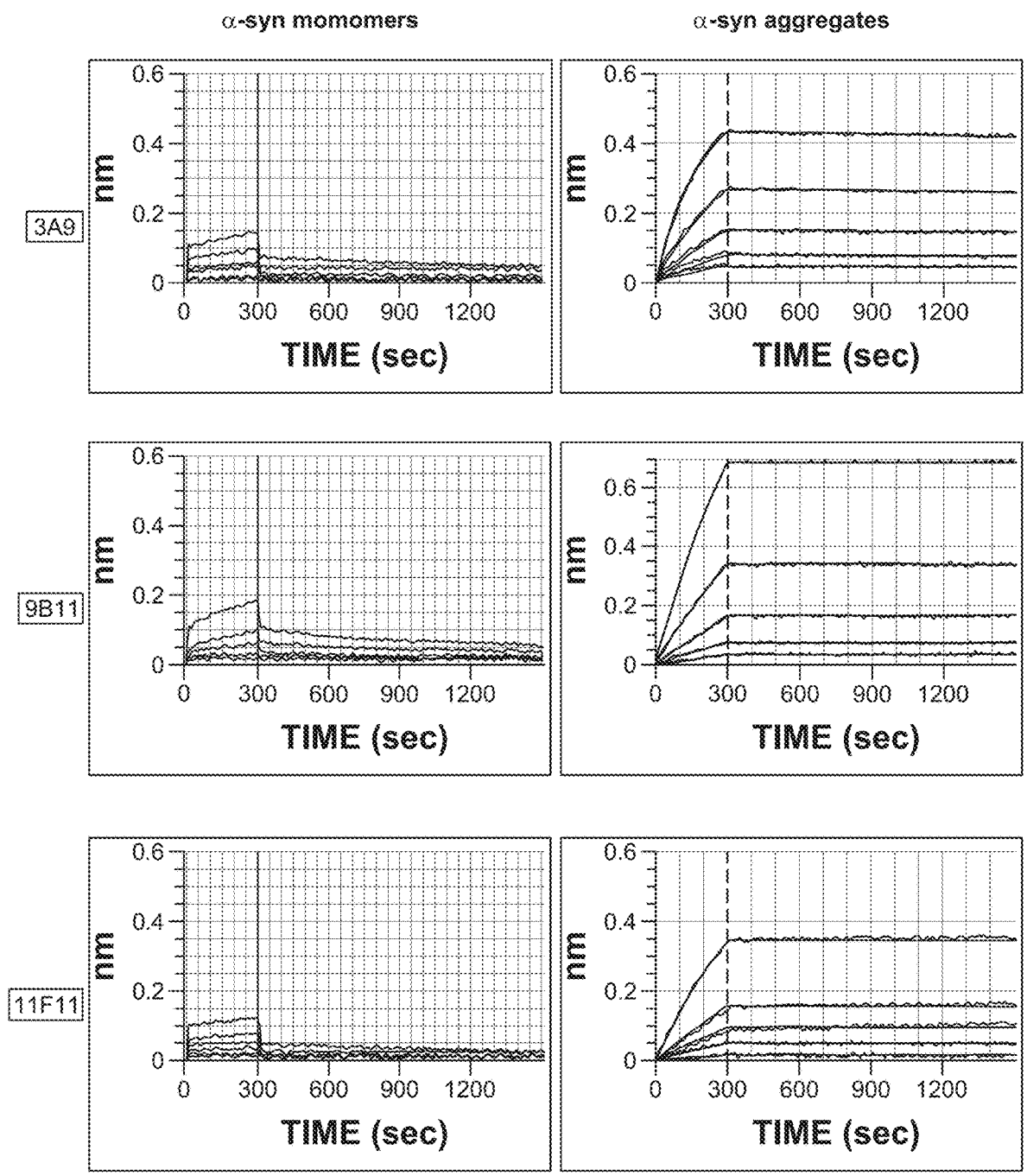
FIG. 4 is Octet analysis results for the preferential binding specificity of the monoclonal antibody produced in an embodiment of the present invention to α-syn aggregates. The results show that the antibody of the present invention preferentially binds to α-syn aggregates and is consistent with the result of FIG. 1. The #274 antibody used as a comparative group was found to bind well to monomers and aggregates.

The results are shown in FIG. 4. As shown therein, 3A9, 9B11 and 11F11 showed little binding to monomers (dotted box) and good binding to aggregates (upcline graph in dotted boxes). These results are similar to or consistent with the results in Dot blot, Octet and ELISA. As a result, among the four α-syn antibodies tested, antibodies that preferentially bind to the aggregates in the other methods, 3A9, 9B11 and 11F11 also binds only to aggregates in the Octet analysis.

Examples 2-5. Dot Blot Using scFv of Anti α-Syn Antibody

Dot blotting was performed as described in Example 2-1 using scFv anti α-syn antibodies selected in Example 1-2. Antigens were loaded in the order of 6.25ng, 12.5ng, 25ng and 50ng from the first line on the left. Antibodies were treated at a concentration of 1 μg/ml and confirmed by anti-human Fc-HRP 2nd Ab.

Figure 5:
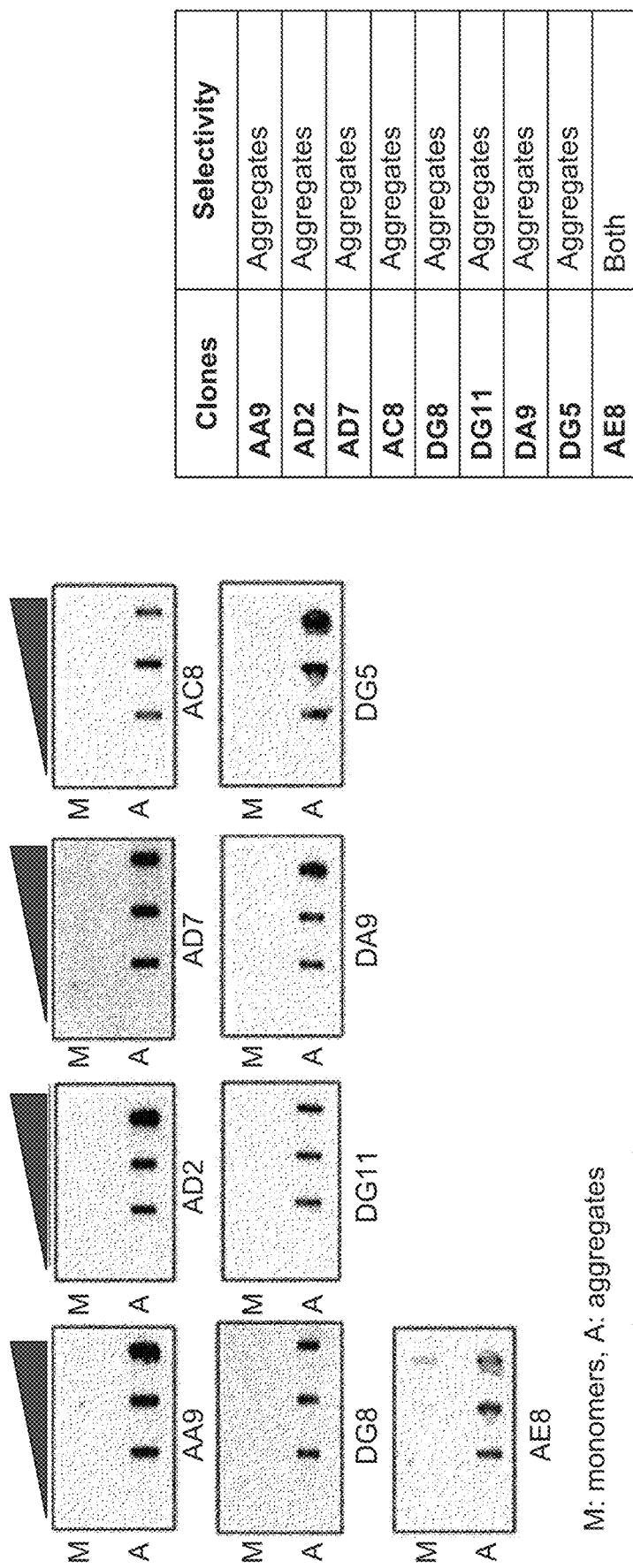
FIG. 5 is a dot-blot result showing that the monoclonal antibody selected by phage display technique in an embodiment of the present invention preferentially binds to α-syn aggregates, as a result of measuring whether or not the monoclonal antibody specifically recognizes the native α-syn in the aggregated form.

The results are shown in FIG. 5. M represents a monomeric antigen, and A represents an aggregate antigen. Selective binding of each antibody to monomers or aggregates was shown in the right table. It was shown that AA9, AD2, AD7, AC8, DG8, DG11, DA9, and DG5 bound only to the aggregates, while AE8 preferentially bound to the aggregates and bound weakly to the monomers.

Examples 2-6. Octet Analysis Using scFv Anti α-Syn Antibody

Octet analysis was performed as described in Examples 2-4 using the scFv anti-α-syn antibodies selected in Example 1-2. The results are shown in FIG. 6. These antibodies were found to have a high affinity of $\sim10^{-9}$ to $\sim10^{-11}$ M to α-syn aggregates.

Example 3. Inhibitory Effect of Mouse Monoclonal Anti α-Syn Antibody on Cell-Mediated Transport of Alpha-Synuclein Aggregate Since the intercellular transfer of alpha-synuclein aggregates is presented as a pathogenic cause of alpha-synuclein aggregate-related diseases, antibodies capable of inhibiting them may be useful as therapeutic agents. For this purpose, BiFC (bimolecular fluorescence complementation) analysis was performed as follows. The BiFc principle is shown schematically on the top of FIG. 7.

Cell Culture for BiFC Analysis

SH-SY5Y human neuroblastoma cell lines expressing alpha-synuclein and a half of Venus fluorescent proteins (Venus 1-aSyn (VlS) and αSyn-Venus2 (SV2)), respectively, were cultured as previously described (Lee H J et al., J. Neurosci. 2004; 24: 1888-1896), Prior to the experiment, 180,000 cells expressing VlS and SV2 were mixed on a cover slip and cultured for 3 days. Co-culture was sub-cultured every 48 hours to confirm the continuous intercellular migration of alpha-synuclein. Because the degree of transfer was maximum at the passage number of 6 in a separate experiment (data not shown), the inhibitory effect of the antibody on the cell-to-cell transport was analyzed using the co-culture of six passages.

BiFC Experiment/Antibody Treatment

On the day before imaging, 50 µg/ml of IgG or test antibody (3A9, 9B11, 11F11) was added to the co-culture. The signal in the Venus channel in each co-culture represents the aggregates produced by the aggregation of alpha-synuclein, which was considered as the aggregate formed by the migration of α-syn from one cell to another cell. These signals were automatically analyzed with the IN Cell Analyzer (instrument setup: puncta size: 0.1-0.4 m, intensity: 4000-7000).

Figure 7:
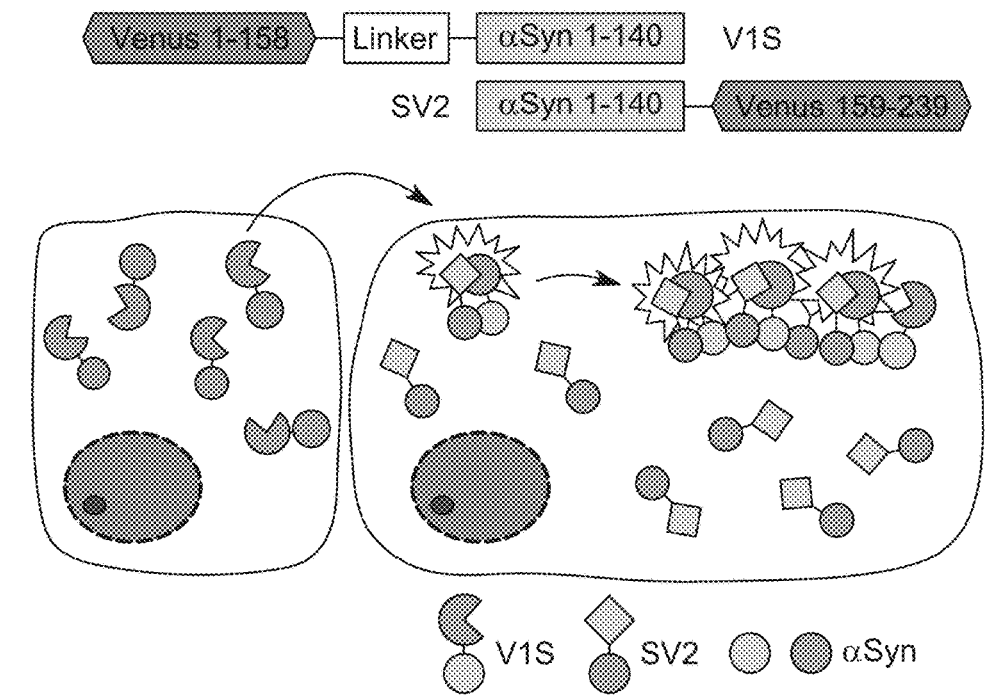
FIG. 7 shows the principle and the experiment result of analyzing whether the monoclonal antibody produced in an embodiment of present invention inhibits cell-to-cell transmission of α-syn. As shown here, α-syn released from one cell is propagated into other cell and forms aggregates by meeting another α-syn. The number of cells exhibiting intercellular transfer of α-syn leading to aggregate formation, versus a negative control IgG, was significantly reduced when the antibodies 9B111, 3A9 and 11F11 according to the present invention were treated. This result indicates that the antibody of the present invention, which specifically binds to aggregates with high affinity, can inhibit intercellular transfer of α-syn effectively.
Figure 7:
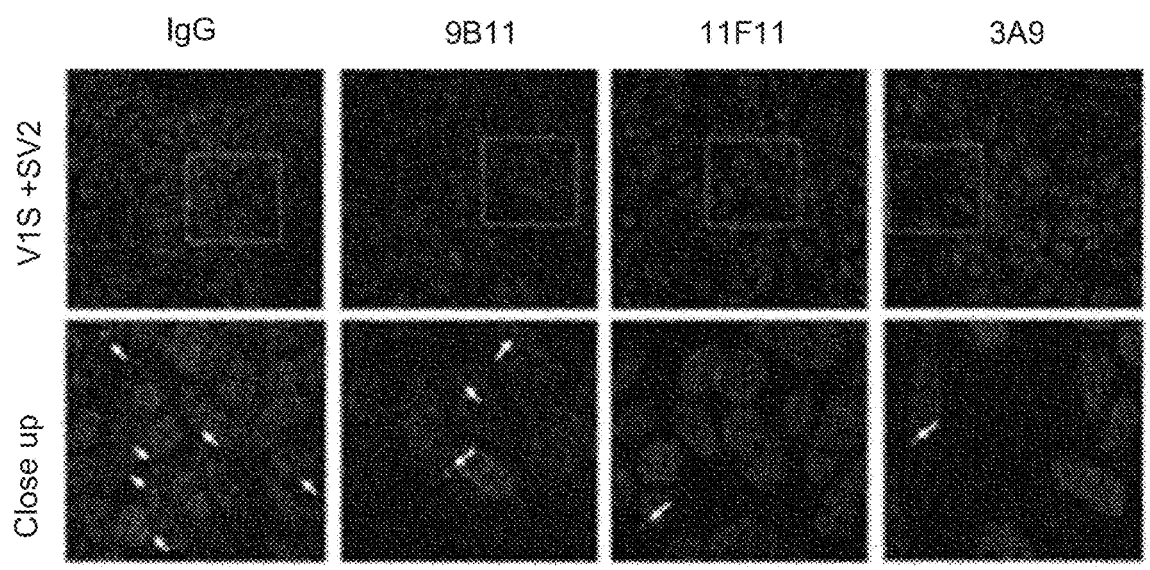

The results are shown in FIG. 7. As shown in the figure, α-synuclein which came out of one cell met α-syn of other cells and formed aggregates. The graph on the right side shows the intensity of the signal. In the 9B11, 11F11, and 3A9 treatment groups, the number of cells showing a signal indicating intercellular transfer of α-syn leading to formation of aggregates, compared to the negative control IgG, was decreased. The result indicates that the antibodies of present invention can effectively inhibit intercellular transfer of aggregates.

Example 4. Analysis of the In Vivo Removal Effect of Alpha-Synuclein Aggregates by Mouse Monoclonal Anti α-Syn Antibody In order to analyze the effect in vivo of the α-syn antibody produced in the present invention, 10 mg/kg of human alpha-synuclein or IgG was transfected into transgenic mice (mThy-1 human α-synuclein, UC San Diego) were administered intraperitoneally every week for 3 months to transgenic mice overexpressing human alpha-synuclein (mThy-1 human α-synuclein, UC San Diego). Six mice per group were used, and non-transgenic littermates were used as controls. The perfusion was then performed as follows.

After completion of the last administration, for pathological analysis of brain, the animals were anesthetized with chloral hydrate according to humanitarian regulations and then cardiopulmonary with 0.9% saline. The saggital section of the perfused brain was stored in 4% paraformaldehyde (pH 7.4, 4° C.) in phosphate buffer until subsequent analysis and the other half was stored at frozen (70° C.).

Pathological analysis was performed as follows. The half of brain fixed in paraformaldehyde was cut into a continuous section of 40 m thick by free-floating method using a vibratome. In order to confirm the expression level of α-syn in the brains of administered groups, the sections containing cortex, striatum and hippocampus were incubated with α-syn antibody (p129 α-syn antibody, abcam, ab59264 or total α-syn antibody, which is a marker of the aggregate, Cell Signaling Technology, #2642) overnight at 4° C. In order to identify the activity of astrocytes or the activity of microglia, the cut samples were treated with antibody to GFAP (glial fibrillary acidic protein)(AB5804, millipore) or Iba1(019-19741, Wako) (019-19741, Wako), respectively. In order to identify the degree of neuroinflammation, the cut samples were treated with antibody to IL-6 (NB600-1131, Novus Biologicals) or IL-10(ab9722, abcam), respectively. After incubation with the primary antibody, biotin-conjugated goat anti-rabbit IgG (1:100, Vector Laboratories) and Avidin D-horseradish peroxidase (1:200, ABC Elite, Vector Laboratories) were treated and detected with diaminobenzidine (DAB). Each immunostained sections were observed with a bright field microscope to measure optical density.

Figure 8A:
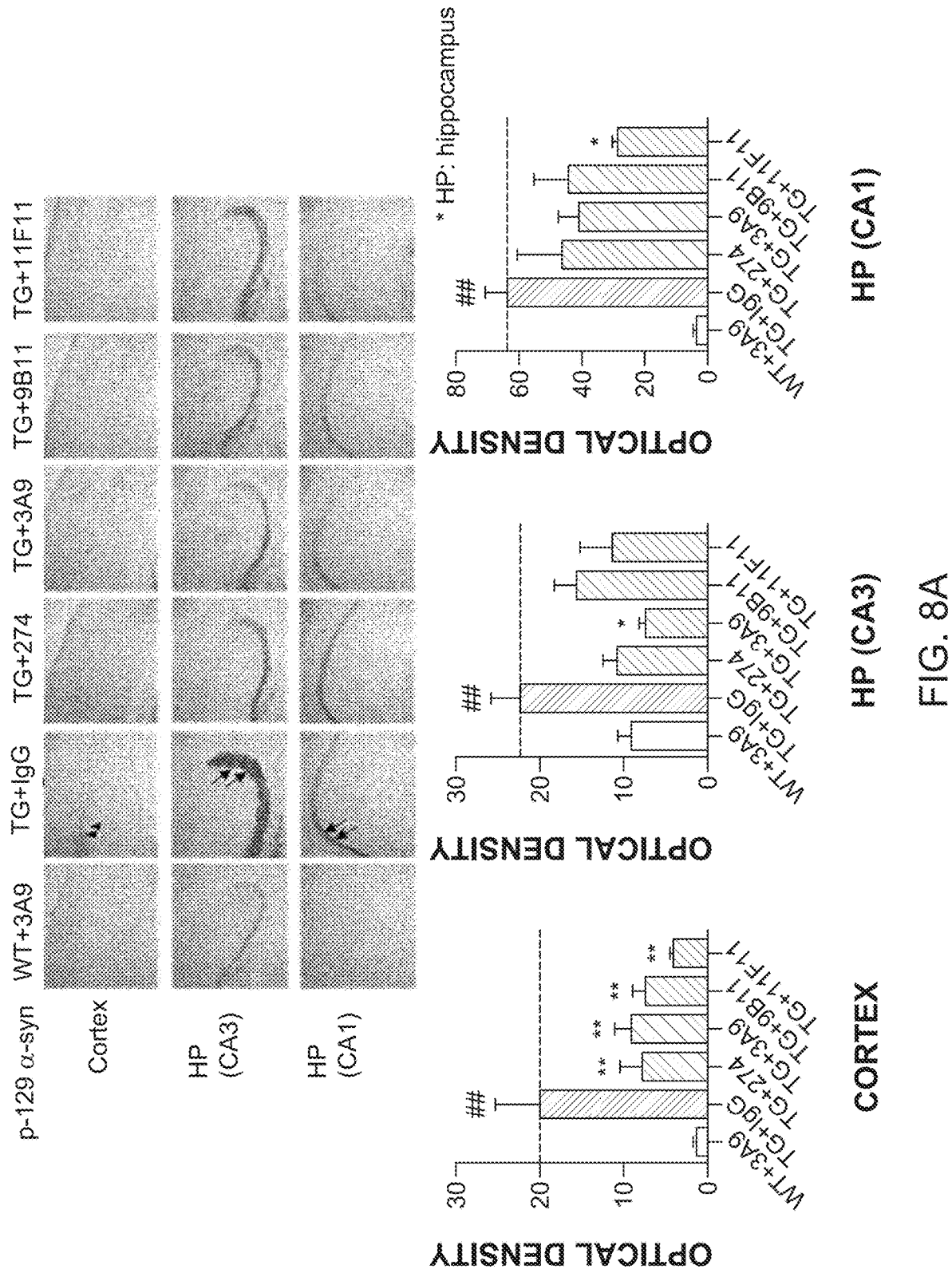
FIG. 8A shows the result of analyzing whether the monoclonal antibody produced in an embodiment of present invention removes α-syn aggregates in a mouse animal model (TG) overexpressing human α-syn, by staining the mouse brain tissue with p-129 α-syn after administering the antibody to the mouse and measuring it. In the figure, HP is hHippocampus, p-129 α-syn is a marker of aggregates in the form of phosphorylated 129th residue of α-syn, and arrow indicates phosphorylated α-syn. This result shows that the antibody of the present invention can remarkably eliminate α-syn. WT and IgG are negative controls, and antibody 274 is a comparative group that binds both monomers and aggregates. These results indicate that the antibody of the present invention can effectively inhibit the accumulation of α-syn aggregates and thus can be effectively used for the prevention and/or treatment of diseases related to α-syn-pathogenesis.
Figure 8B:
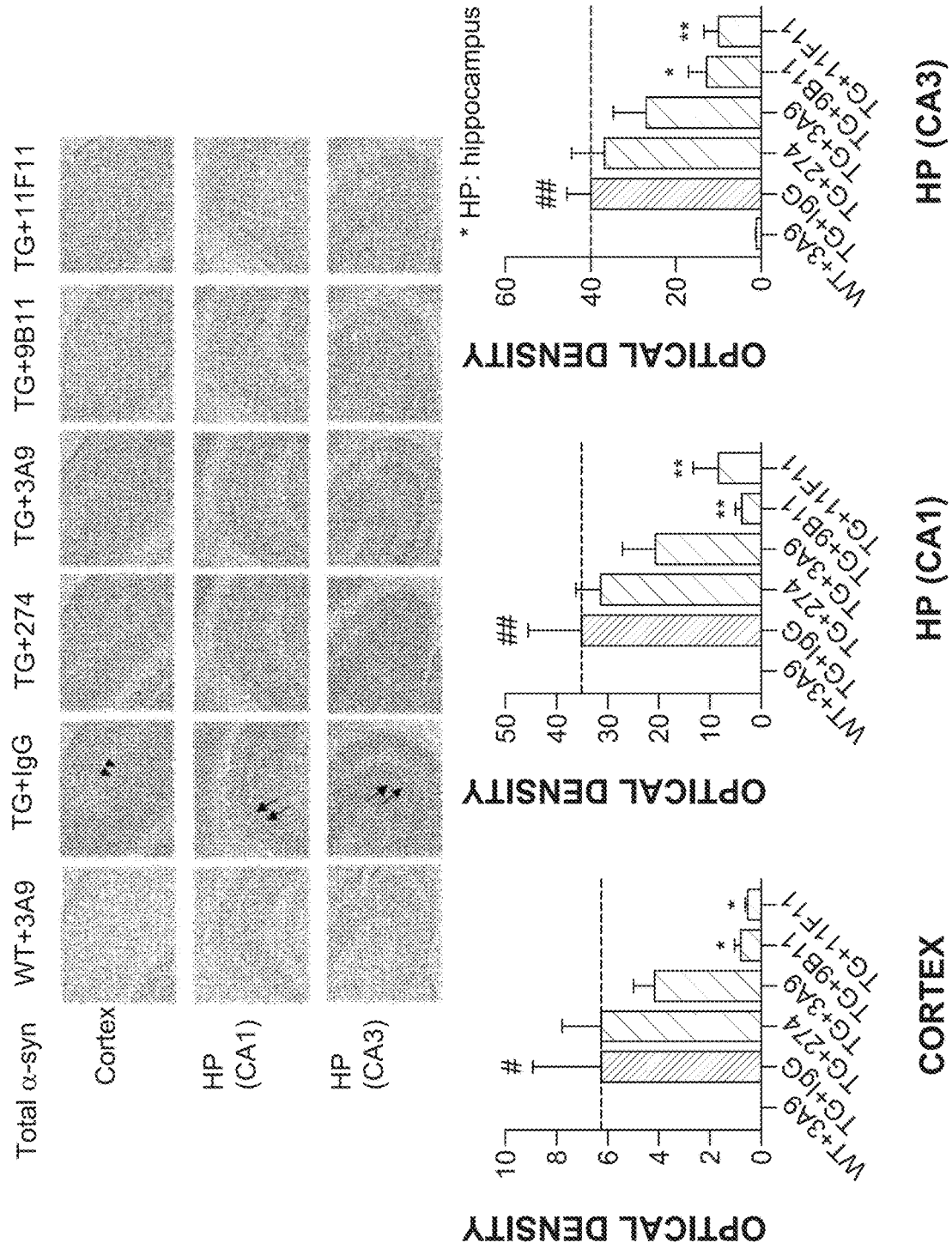
FIG. 8B is a result of the same experiment as in FIG. 8A, but as a marker, using an antibody against total α-syn. The arrow represents human α-syn. The 9B11, 11F4, and 11F11 antibodies effectively inhibited the accumulation of α-syn. The α-syn detection indicates that the antibody of the present invention has the ability to clear the synuclein itself and inhibit the cell to cell transmission of α-syn. In another aspect, it can also be interpreted as inhibiting the formation of monomers into aggregates, or removing all of the monomers.
Figure 9A:
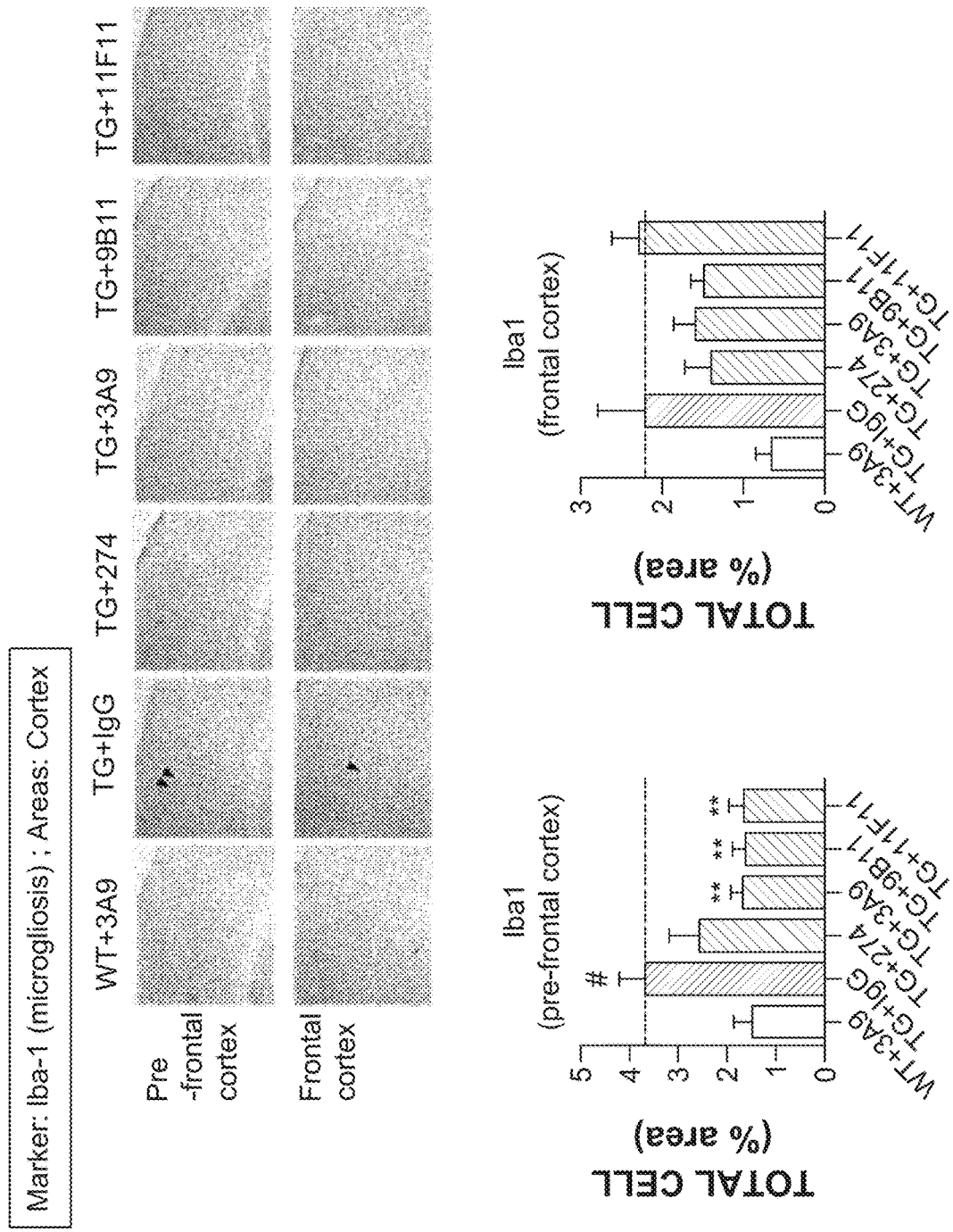
FIG. 9A shows the result of analyzing whether the monoclonal antibody produced in an embodiment of present invention can reduce microgliosis in vivo by staining the mouse brain tissue with Iba-1(microgliosis) antibody as a marker after administering the antibody to the mouse and measuring it. The arrow indicates activated microglia, and the result indicates that microglial activation is significantly reduced in the brains of mice administering the 3A9, 9B11, and 11F11 antibodies.
Figure 9B:
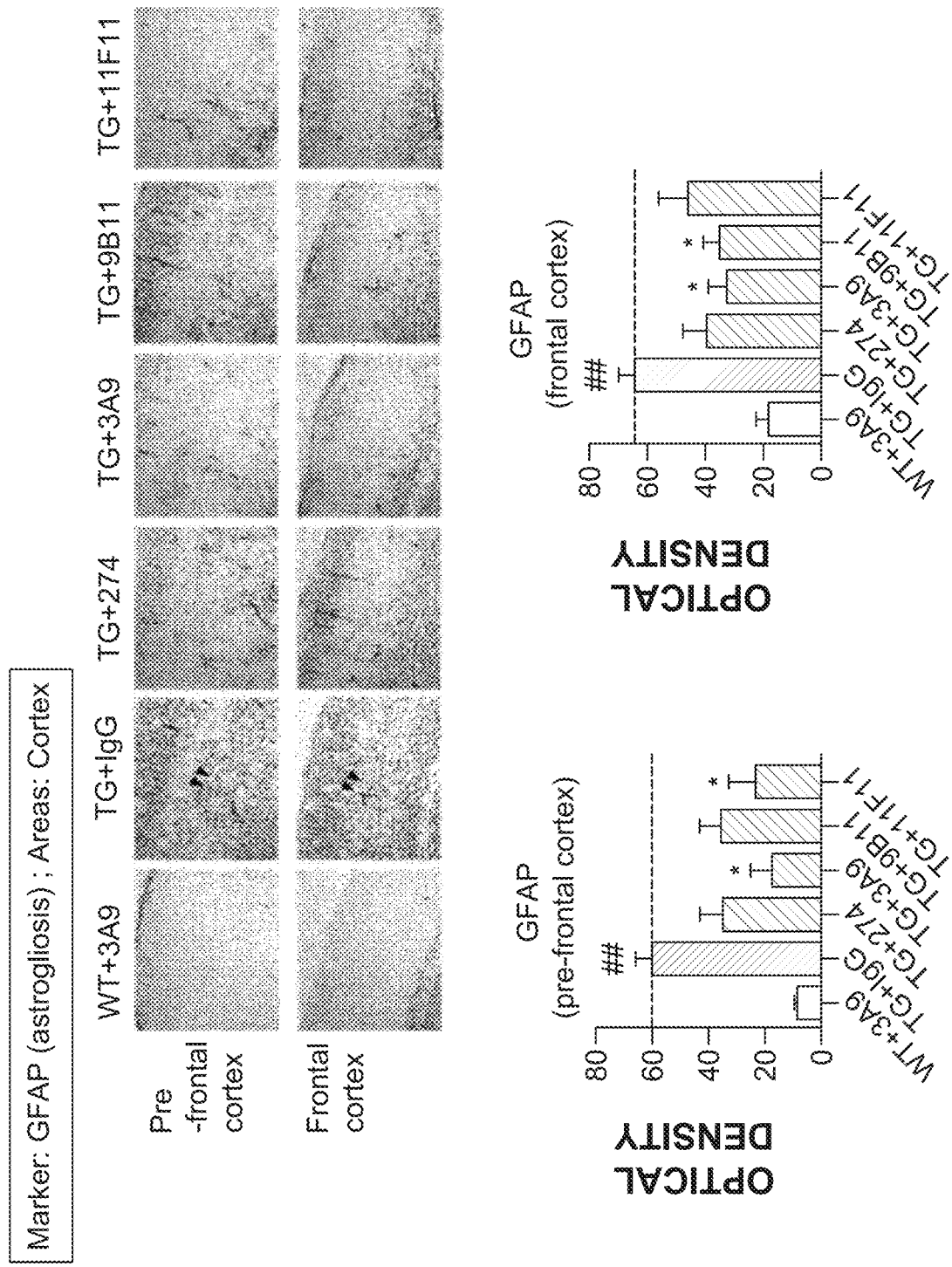
FIG. 9B shows the result of analyzing whether the monoclonal antibody produced in an embodiment of present invention can reduce the microgliosis in vivo by staining the mouse brain tissue with GFAP (astrogliosis) antibody after administering the antibody to the mouse and measuring it. The arrow indicates activated astrocytes, and the result indicates that the antibodies 3A9, 9B11, and 11F11 effectively inhibit astrogliosis to a significant level.
Figure 9C:
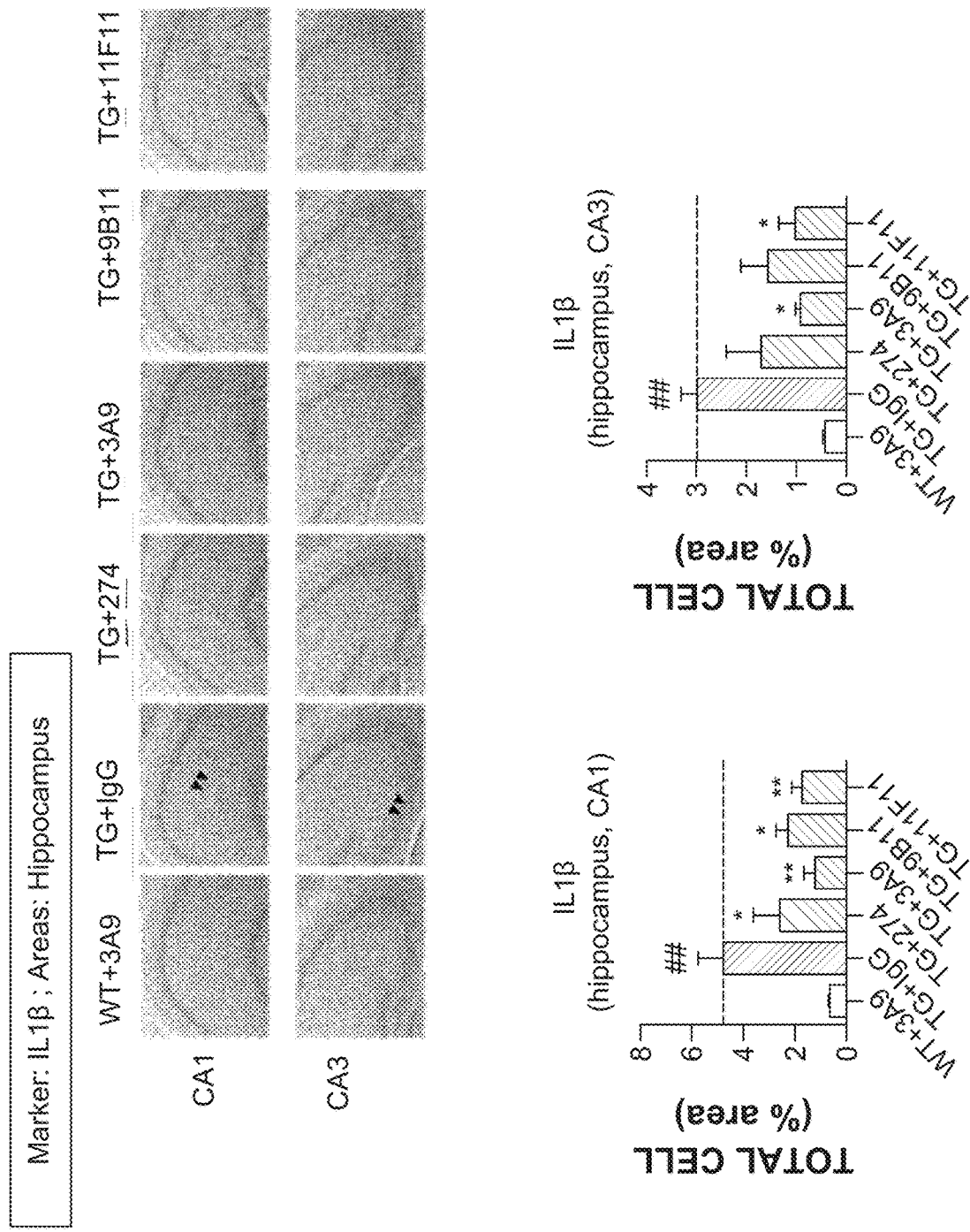
FIG. 9C shows the result of analyzing whether the monoclonal antibody produced in an embodiment of present invention can reduce inflammatory cytokines in vivo by staining the mouse brain tissue with IL-1 beta antibody as a marker after administering the antibody to the mouse and measuring it. The arrows indicate cells expressing IL-1 beta. IL-1 beta induces inflammation and death of various nerve cells. IL-1 beta is significantly reduced in the brain tissue of mice administered with the antibody of the present invention.
Figure 9D:
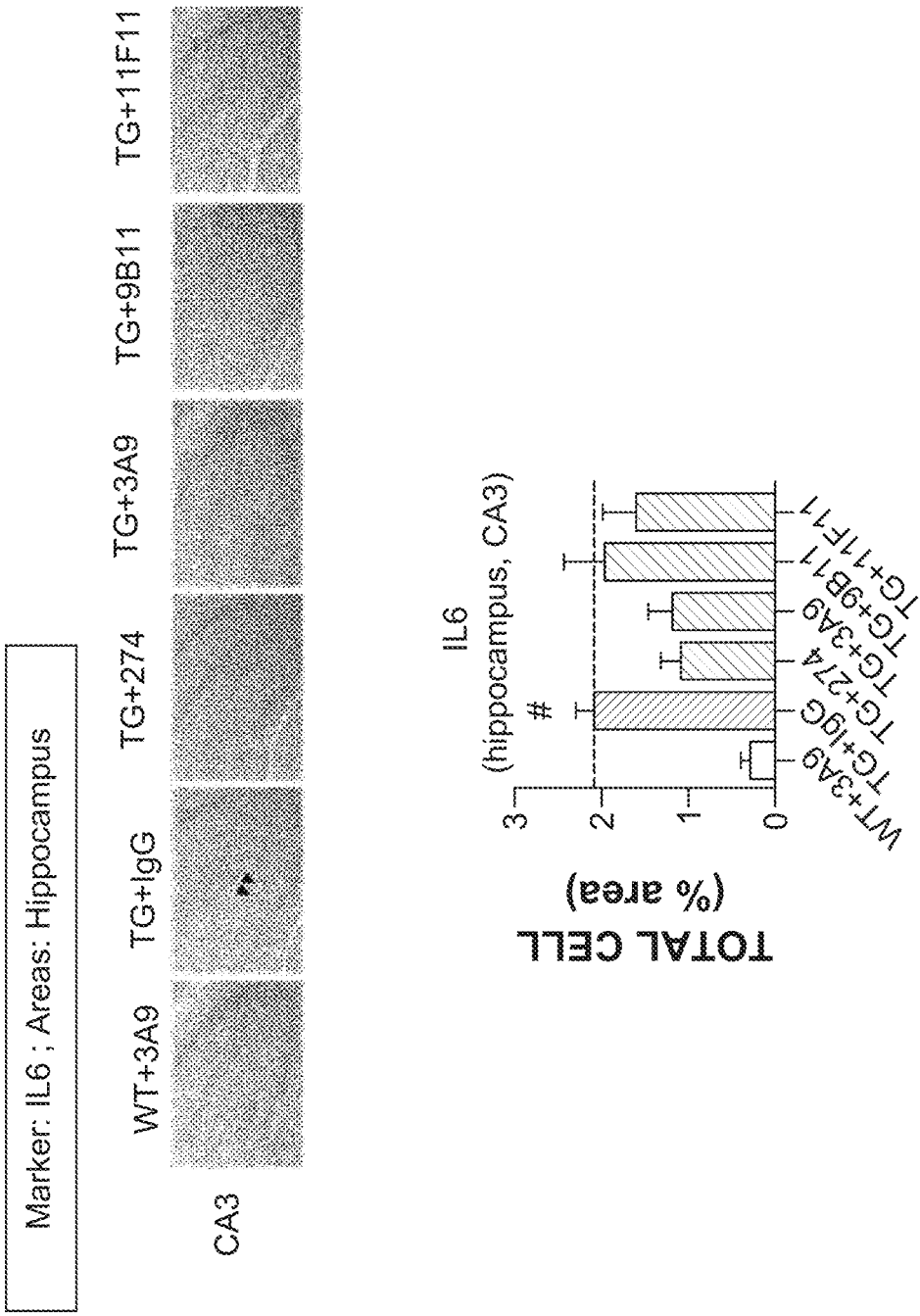
FIG. 9D shows the result of analyzing whether the monoclonal antibody produced in an embodiment of present invention can reduce inflammatory cytokines in vivo by staining the mouse brain tissue with IL-6 antibody as a marker after administering the antibody to the mouse and measuring it. The arrows indicate cells expressing IL-6 of an inflammatory cytokine. The result indicates that IL-6 has been reduced in the brain tissue of mice administered with the antibody of the present invention.

The results are shown in FIGS. 8A and 8B. FIG. 8A is a graph showing the results of analysis of p-129 α-syn antibody (an antibody recognizing α-syn phosphorylated at Ser 129), which is a marker of α-syn aggregates. As a result, TG (TransGenic) mouse showed a significant decrease in aggregate levels in CA1 and CA3 of cortex and hippocampus, compared to control mice administered only IgG (the related part is indicated by arrowheads in IgG sample). FIG. 8B shows the result of staining with total alpha-syn antibody. Increased human α-syn in TG mice was effectively removed by the administration of antibodies. These results indicate that the antibody according to the present invention effectively reduces α-syn aggregates and can be effectively used for the treatment of α-synucleinopathy such as Parkinson's disease.

Example 5: Analysis for the Reduction of Microgliosis and Astrogliosis and Reduction of Inflammatory Cytokine Release of Mouse Monoclonal Anti α-Syn Antibody Gliosis is a nonspecific reaction in glial cells that responds to damage of the central nervous system triggered by BBB damage, TGF-beta or interleukin. Representative examples include microgliosis and astrogliosis, for which markers are Iba-1 and GFAP proteins, respectively.

As described in Example 4, the effect of the antibody according to the present invention on the reduction of microgliosis and astrogliosis and inflammatory cytokine release triggered thereby was analyzed in mice.

The results are shown in FIGS. 9A, 9B, 9C and 9D. As shown therein, the antibodies of the present invention were found to reduce microgliosis and astrogliosis, and the release of the inflammatory cytokines, IL-1beta and IL-6, which triggers microgliosis and astrogliosis compared to the control.

Example 6. Detection of Lewy Bodies in Human Brain Tissue by Mouse Monoclonal Anti α-Syn Antibody The Lewy bodies and Lewy neurites in the paraffin-embedded brain sections obtained from patients died of Parkinson's disease with a thickness of ten micrometers (Dr. Halliday, University of Sydney) were stained by using antibodies of present invention in Example 5 as follows. Tissue sections were treated with 90% formic acid for 3 minutes for antigen retrieval and then peroxidase activity of the tissue was inhibited by 1% H2O2 (50% ethanol base). 10% normal horse serum was treated to prevent non-specific binding of tissues. After washing with phosphate buffer, the adjacent sections were treated with 3A9, 11F11 and 11F11 antibodies of the present invention at 4° C. overnight. After washing with phosphate buffer, biotin-conjugated anti-human IgG antibody was treated at 37° C. for 30 minutes, and the avidin-biotin complex was reacted at room temperature for 30 minutes (Vectastatin Elite kit; Vector Laboratories). Then, the color was developed with DAB containing 0.005% $H_2O_2$. Each section was counter-stained with 0.5% cresyl violet, to discriminate each cell.

Figure 10A:
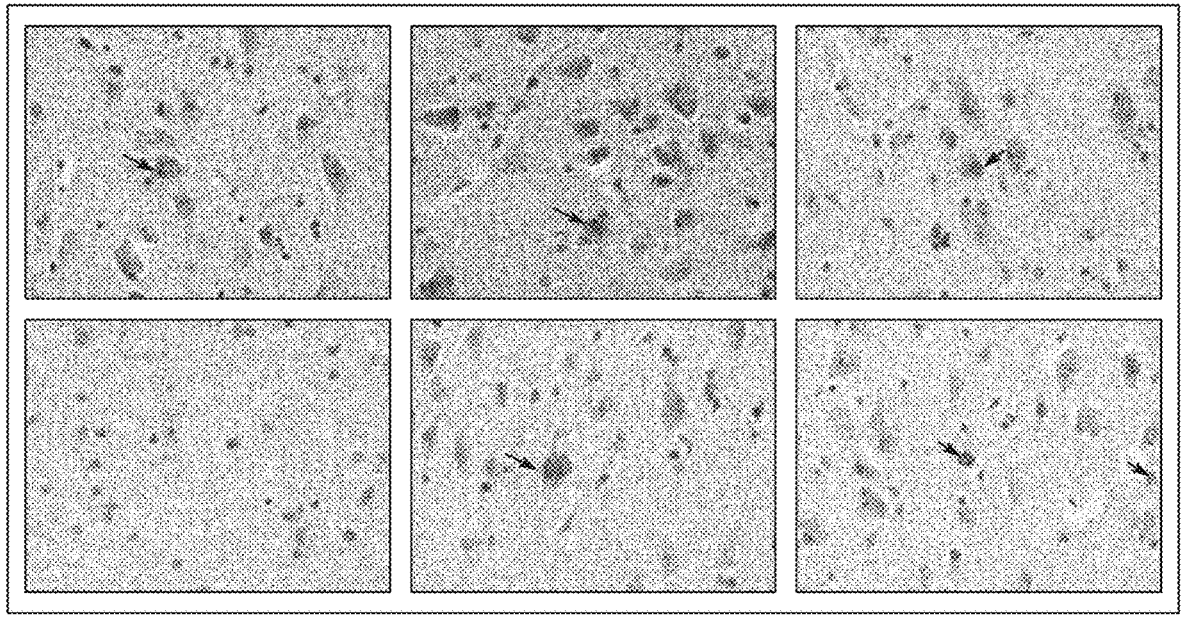
FIGS. 10A and 10B show the result of measuring that monoclonal antibodies 3A9 and 11F11 produced in an embodiment of the present invention can specifically recognize Lewy bodies and Lewy neurites in human brain tissue, respectively. It shows that the antibodies of the present invention bind to the Lewy bodies (arrow) and the Lewy neurites (lower left thread-like shape). These results indicate that the antibody of the present invention can specifically bind to α-syn aggregates in human brain tissue and can be effectively used for the prevention and/or treatment of diseases related to the α-syn pathogenesis.
Figure 10B:
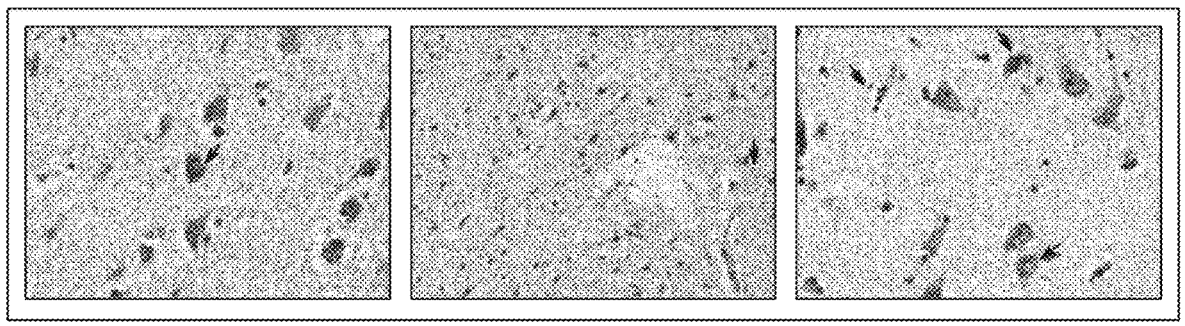

The results are shown in FIGS. 10A and 10B. As shown therein, the antibody according to the present invention was shown to be effectively bound to Lewy bodies and Lewy neurites (indicated by an arrow). This result implies that it is able to bind effectively to α-syn aggregates, a component of Lewy bodies of human brain tissue. It is shown that antibodies delivered to the human brain can effectively and specifically bind to α-syn aggregates.

Example 7. Epitope Analysis of Mouse Monoclonal Anti α-Syn Antibody

The epitope mapping for the 3A9 and 11F11 antibodies according to the present invention was performed by requesting PEPSCAN (The Netherlands) for peptide allele analysis.

Figure 11:
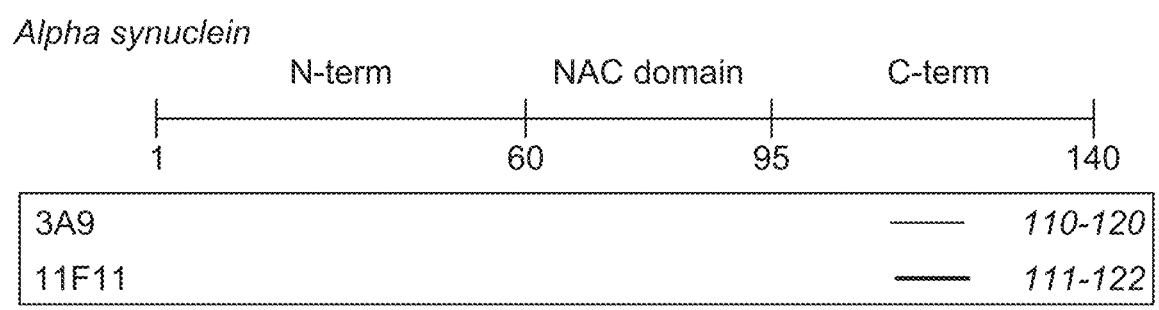
FIG. 11 is a graphical representation of the epitope mapping results of the antibodies produced in the present invention, and the antibodies of the present invention bind mostly to the C-terminal region. The α-syn antibodies recognizing the N-terminal do not recognize aggregates of other diseases such as multiple system atrophy (MSA) belonging to synucleinopathy, but the α-syn antibodies recognizing the C-terminal have an advantage of recognizing not only Parkinson's disease but also the aggregates of other various synucleinopathy diseases.

The results are shown in FIG. 11. As shown in FIG. 11, the antibody according to the present invention was found to recognize C-terminal part, especially, the part of amino acid residue of 110 to 122 as described above, with aggregation preferred binding.

It will be understood by those of ordinary skill in the art that various changes in form and details may be made therein without departing from the spirit and scope of the present invention as defined by the appended claims.

---

The invention claimed is:

1. An antibody or an antigen-binding fragment thereof that specifically binds to α-synuclein ("α-syn") aggregates, wherein said antibody or antigen-binding fragment has heavy chain complementarity determining regions (CDR) 1-3 (HCDR1-3) and light chain CDR 1-3 (LCDR1-3) that comprise
   a) SEQ ID NOs: 1, 15, 29, 43, 57, and 71, respectively;
   b) SEQ ID NOs: 2, 16, 30, 44, 58 and 72, respectively;
   c) SEQ ID NOs: 3, 17, 31, 45, 59 and 73, respectively;
   d) SEQ ID NOs: 4, 18, 32, 46, 60 and 74, respectively;
   e) SEQ ID NOs: 5, 19, 33, 47, 61 and 75, respectively;
   f) SEQ ID NOs: 6, 20, 34, 48, 62 and 76, respectively;
   g) SEQ ID NOs: 7, 21, 35, 49, 63 and 77, respectively;
   h) SEQ ID NOs: 8, 22, 36, 50, 64 and 78, respectively;
   i) SEQ ID NOs: 9, 23, 37, 51, 65 and 79, respectively;
   j) SEQ ID NOs: 10, 24, 38, 52, 66 and 80, respectively;
   k) SEQ ID NOs: 11, 25, 39, 53, 67 and 81, respectively;
   l) SEQ ID NOs: 12, 26, 40, 54, 68 and 82, respectively;
   m) SEQ ID NOs: 13, 27, 41, 55, 69 and 83, respectively;
   n) SEQ ID NOs: 14, 28, 42, 56, 70 and 84, respectively, or
   o) the HCDR1-3 of the heavy chain variable region (VH) set forth in SEQ ID NO: 85 as determined by the Kabat numbering system, and the LCDR1-3 of the light chain variable region (VL) set forth in SEQ ID NO: 99 as determined by the Kabat numbering system, respectively.

2. The antibody or antigen-binding fragment of claim 1, wherein said antibody or antigen-binding fragment comprises a VH amino acid sequence selected from SEQ ID NOs: 85 to 98, or an amino acid sequence having at least 90% or at least 95% sequence identity to the selected sequence.

3. The antibody or antigen-binding fragment of claim 1, wherein said antibody or antigen-binding fragment comprises a VL amino acid sequence selected from SEQ ID NOs: 99 to 112, or an amino acid sequence having at least 90% or at least 95% sequence identity to the selected sequence.

4. The antibody or antigen-binding fragment of claim 1, comprising VH and VL amino acid sequences of:
   SEQ ID NOs: 85 and 99, respectively;
   SEQ ID NOs: 86 and 100, respectively;
   SEQ ID NOs: 87 and 101, respectively;
   SEQ ID NOs: 88 and 102, respectively;
   SEQ ID NOs: 89 and 103, respectively;
   SEQ ID NOs: 90 and 104, respectively;
   SEQ ID NOs: 91 and 105, respectively;
   SEQ ID NOs: 92 and 106, respectively;
   SEQ ID NOs: 93 and 107, respectively;
   SEQ ID NOs: 94 and 108, respectively;
   SEQ ID NOs: 95 and 109, respectively;
   SEQ ID NOs: 96 and 110, respectively;
   SEQ ID NOs: 97 and 111, respectively; or
   SEQ ID NOs: 98 and 112, respectively.

5. The antibody or antigen-binding fragment of claim 1, wherein the antibody or antigen-binding fragment is a monoclonal antibody, Fab, Fab', F(ab'), diabody or scFv.

6. The antibody or antigen-binding fragment of claim 5, wherein the antibody is a humanized antibody or chimeric antibody.

7. The antibody or antigen-binding fragment of claim 5, wherein the antibody is of isotype subtype IgG1, IgG2, IgG3 or IgG4 type.

8. The antibody of claim 1, wherein the antibody comprises heavy chain and light chain amino acid sequences of:
SEQ ID NOs: 113 and 141, respectively;
SEQ ID NOs: 114 and 142, respectively;
SEQ ID NOs: 115 and 143, respectively;
SEQ ID NOs: 116 and 144, respectively;
SEQ ID NOs: 117 and 145, respectively;
SEQ ID NOs: 118 and 146, respectively;
SEQ ID NOs: 119 and 4 147, respectively;
SEQ ID NOs: 120 and 148, respectively;
SEQ ID NOs: 121 and 149, respectively;
SEQ ID NOs: 122 and 150, respectively;
SEQ ID NOs: 123 and 151, respectively;
SEQ ID NOs: 124 and 152, respectively;
SEQ ID NOs: 125 and 153, respectively; or
SEQ ID NOs: 126 and 154, respectively.

9. The antibody or antigen-binding fragment of claim 1, wherein the antibody or antigen-binding fragment has at least one property selected from
   a) inhibits intercellular transfer of α-syn aggregates;
   b) degrades α-syn aggregates; or
   c) inhibits formation of αsyn aggregates.

10. An antibody that specifically binds to α-synuclein ("α-syn") aggregates, wherein the antibody comprises heavy chain and light chain amino acid sequences of:
SEQ ID NOs: 127 and 155, respectively;
SEQ ID NOs: 128 and 156, respectively;
SEQ ID NOs: 129 and 157, respectively;
SEQ ID NOs: 130 and 158, respectively;
SEQ ID NOs: 131 and 159, respectively;
SEQ ID NOs: 132 and 160, respectively;
SEQ ID NOs: 133 and 161, respectively;
SEQ ID NOs: 134 and 162, respectively;
SEQ ID NOs: 135 and 163, respectively;
SEQ ID NOs: 136 and 164, respectively;
SEQ ID NOs: 137 and 165, respectively;
SEQ ID NOs: 138 and 166, respectively;
SEQ ID NOs: 139 and 167, respectively; or
SEQ ID NOs: 140 and 168, respectively.

11. An antibody or an antigen-binding fragment thereof that specifically binds to alpha-synuclein ("α-syn") aggregates, wherein:
   i) the HCDR1-3 of the antibody or antigen-binding fragment are the H-CDRs of the heavy chain variable region (VH) set forth in SEQ ID NO: 85 as determined by the Kabat numbering system, and
   ii) the LCDR1-3 of the antibody or antigen-binding fragment are the L-CDRs of the light chain variable region (VL) set forth in SEQ ID NO: 99 as determined by the Kabat numbering system, and
   wherein the antibody is humanized.

12. Isolated polynucleotide(s encoding the heavy and light chain amino acid sequences of the antibody or antigen-binding fragment of claim 1.

13. A cell comprising the isolated polynucleotide(s) of claim 12.

14. A method of preparing an antibody or an antigen-binding fragment thereof that specifically binds to α-syn aggregates, comprising:
   culturing the cell of claim 13 under conditions that allow expression of the antibody or antigen-binding fragment; and
   isolating the antibody or antigen-binding fragment from the cell culture.

15. A pharmaceutical composition comprising the antibody or antigen-binding fragment of claim 1, a pharmaceutically acceptable carrier or excipient.

16. A method for detecting α-syn aggregates in a biological sample in vivo or in vitro, comprising contacting the biological sample with the antibody or antigen-binding fragment of claim 1.

17. A method for treating an α-synucleinopathy in a human subject in need thereof, comprising administering the antibody or antigen-binding fragment of claim 1, the subject.

18. The method of claim 17, wherein the α-synucleinopathy is Parkinson's disease (PD), Parkinson's disease dementia (PDD), dementia with Lewy bodies (DLB), Lewy body variants of Alzheimer's disease (LBV), combined Alzheimer's and Parkinson's disease, or multiple system atrophy (MSA).

19. A method for diagnosing an α-synucleinopathy in a subject, comprising
   measuring the concentration and/or intercellular location of α-syn aggregates in a sample from the subject using the antibody or antigen-binding fragment of claim 1; and
   comparing the concentration and/or the intercellular location of α-syn aggregates measured in the subject sample with the results of a control sample, wherein the similarity or difference to the results of the control sample indicates whether the subject suffers from an α-synucleinopathy.

20. The method of claim 19, wherein the α-synucleinopathy is Parkinson's disease (PD), Parkinson's disease dementia (PDD), dementia with Lewy bodies (DLB), Lewy body variants of Alzheimer's disease (LBV), combined Alzheimer's and Parkinson's disease, or multiple system atrophy (MSA).

* * * * *

UNITED STATES PATENT AND TRADEMARK OFFICE
CERTIFICATE OF CORRECTION

| | | |
|---|---|---|
| PATENT NO. | : 12,049,493 B2 | Page 1 of 1 |
| APPLICATION NO. | : 16/475853 | |
| DATED | : July 30, 2024 | |
| INVENTOR(S) | : Ahn et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1421 days.

Signed and Sealed this
Third Day of December, 2024

Katherine Kelly Vidal
*Director of the United States Patent and Trademark Office*

SEQUENCE LISTING

```
<160> NUMBER OF SEQ ID NOS: 225

<210> SEQ ID NO 1
<211> LENGTH: 10
<212> TYPE: PRT
<213> ORGANISM: Mus musculus
<220> FEATURE:
<221> NAME/KEY: misc_feature
<223> OTHER INFORMATION: Mus musculus 1E4 CDR H1

<400> SEQUENCE: 1

Gly Tyr Ala Phe Thr Asn Tyr Leu Ile Glu
1               5                   10

<210> SEQ ID NO 2
<211> LENGTH: 10
<212> TYPE: PRT
<213> ORGANISM: Mus musculus
<220> FEATURE:
<221> NAME/KEY: misc_feature
<223> OTHER INFORMATION: Mus musculus 9B11 CDR H1

<400> SEQUENCE: 2

Gly Phe Thr Phe Asn Thr Tyr Ala Met Asn
1               5                   10

<210> SEQ ID NO 3
<211> LENGTH: 10
<212> TYPE: PRT
<213> ORGANISM: Mus musculus
<220> FEATURE:
<221> NAME/KEY: misc_feature
<223> OTHER INFORMATION: Mus musculus 3A9 CDR H1

<400> SEQUENCE: 3

Gly Phe Thr Phe Ser Ser Tyr Ala Met Ser
1               5                   10

<210> SEQ ID NO 4
<211> LENGTH: 10
<212> TYPE: PRT
<213> ORGANISM: Mus musculus
<220> FEATURE:
<221> NAME/KEY: misc_feature
```

<223> OTHER INFORMATION: Mus musculus 10F10 CDR H1

<400> SEQUENCE: 4

Gly Tyr Ser Ile Thr Gly Gly Phe Tyr Trp
1               5                   10

<210> SEQ ID NO 5
<211> LENGTH: 10
<212> TYPE: PRT
<213> ORGANISM: Mus musculus
<220> FEATURE:
<221> NAME/KEY: misc_feature
<223> OTHER INFORMATION: Mus musculus 11F11 CDR H1

<400> SEQUENCE: 5

Gly Phe Thr Phe Ser Asp Phe Tyr Met Glu
1               5                   10

<210> SEQ ID NO 6
<211> LENGTH: 10
<212> TYPE: PRT
<213> ORGANISM: Homo sapiens
<220> FEATURE:
<221> NAME/KEY: misc_feature
<223> OTHER INFORMATION: Homo sapiens AC8 CDR H1

<400> SEQUENCE: 6

Gly Phe Thr Phe Ser Asp Tyr Ser Met Ser
1               5                   10

<210> SEQ ID NO 7
<211> LENGTH: 10
<212> TYPE: PRT
<213> ORGANISM: Homo sapiens
<220> FEATURE:
<221> NAME/KEY: misc_feature
<223> OTHER INFORMATION: Homo sapiens AE8 CDR H1

<400> SEQUENCE: 7

Gly Phe Thr Phe Ser Asn Tyr Ala Met Ser
1               5                   10

<210> SEQ ID NO 8
<211> LENGTH: 10
<212> TYPE: PRT
<213> ORGANISM: Homo sapiens
<220> FEATURE:
<221> NAME/KEY: misc_feature
<223> OTHER INFORMATION: Homo sapiens AA9 CDR H1

<400> SEQUENCE: 8

Gly Phe Thr Phe Ser Ser Tyr Ser Met Ser
1               5                   10

<210> SEQ ID NO 9
<211> LENGTH: 10
<212> TYPE: PRT
<213> ORGANISM: Homo sapiens
<220> FEATURE:
<221> NAME/KEY: misc_feature
<223> OTHER INFORMATION: Homo sapiens DG5 CDR H1

<400> SEQUENCE: 9

Gly Phe Thr Phe Ser Asn Tyr Ala Met Ser
1               5                   10

<210> SEQ ID NO 10

```
<211> LENGTH: 10
<212> TYPE: PRT
<213> ORGANISM: Homo sapiens
<220> FEATURE:
<221> NAME/KEY: misc_feature
<223> OTHER INFORMATION: Homo sapiens AD2 CDR H1

<400> SEQUENCE: 10

Gly Phe Thr Phe Ser Asn Tyr Ala Met Ser
1               5                   10

<210> SEQ ID NO 11
<211> LENGTH: 10
<212> TYPE: PRT
<213> ORGANISM: Homo sapiens
<220> FEATURE:
<221> NAME/KEY: misc_feature
<223> OTHER INFORMATION: Homo sapiens AD7 CDR H1

<400> SEQUENCE: 11

Gly Phe Thr Phe Ser Gly Tyr Ala Met Ser
1               5                   10

<210> SEQ ID NO 12
<211> LENGTH: 10
<212> TYPE: PRT
<213> ORGANISM: Homo sapiens
<220> FEATURE:
<221> NAME/KEY: misc_feature
<223> OTHER INFORMATION: Homo sapiens DG11 CDR H1

<400> SEQUENCE: 12

Gly Phe Thr Phe Ser Asp Tyr Ala Met Ser
1               5                   10

<210> SEQ ID NO 13
<211> LENGTH: 10
<212> TYPE: PRT
<213> ORGANISM: Homo sapiens
<220> FEATURE:
<221> NAME/KEY: misc_feature
<223> OTHER INFORMATION: Homo sapiens DG8 CDR H1

<400> SEQUENCE: 13

Gly Phe Thr Phe Ser Asp His Ala Met Ser
1               5                   10

<210> SEQ ID NO 14
<211> LENGTH: 10
<212> TYPE: PRT
<213> ORGANISM: Homo sapiens
<220> FEATURE:
<221> NAME/KEY: misc_feature
<223> OTHER INFORMATION: Homo sapiens DA9 CDR H1

<400> SEQUENCE: 14

Gly Phe Thr Phe Ser Asn Tyr Ala Met Ser
1               5                   10

<210> SEQ ID NO 15
<211> LENGTH: 10
<212> TYPE: PRT
<213> ORGANISM: Mus musculus
<220> FEATURE:
<221> NAME/KEY: misc_feature
<223> OTHER INFORMATION: Mus musculus 1E4 CDR H2

<400> SEQUENCE: 15
```

```
Val Ile Asn Pro Gly Ser Gly Gly Thr Asn
1               5                   10
```

<210> SEQ ID NO 16
<211> LENGTH: 19
<212> TYPE: PRT
<213> ORGANISM: Mus musculus
<220> FEATURE:
<221> NAME/KEY: misc_feature
<223> OTHER INFORMATION: Mus musculus 9B11 CDR H2

<400> SEQUENCE: 16

```
Arg Ile Arg Ser Lys Ser Asn Asn Tyr Ala Thr Tyr Tyr Ala Asp Ser
1               5                   10                  15

Val Lys Asp
```

<210> SEQ ID NO 17
<211> LENGTH: 17
<212> TYPE: PRT
<213> ORGANISM: Mus musculus
<220> FEATURE:
<221> NAME/KEY: misc_feature
<223> OTHER INFORMATION: Mus musculus 3A9 CDR H2

<400> SEQUENCE: 17

```
Thr Ile Ser Asn Gly Gly Gly Tyr Thr Tyr Tyr Pro Asp Ser Val Lys
1               5                   10                  15

Gly
```

<210> SEQ ID NO 18
<211> LENGTH: 16
<212> TYPE: PRT
<213> ORGANISM: Mus musculus
<220> FEATURE:
<221> NAME/KEY: misc_feature
<223> OTHER INFORMATION: Mus musculus 10F10 CDR H2

<400> SEQUENCE: 18

```
Tyr Ile Asn Tyr Asp Gly Ser Ser Asp Tyr Ser Pro Ser Leu Lys Asn
1               5                   10                  15
```

<210> SEQ ID NO 19
<211> LENGTH: 19
<212> TYPE: PRT
<213> ORGANISM: Mus musculus
<220> FEATURE:
<221> NAME/KEY: misc_feature
<223> OTHER INFORMATION: Mus musculus 11F11 CDR H2

<400> SEQUENCE: 19

```
Ala Ser Arg Asn Lys Ala Asn Asp Tyr Thr Thr Glu Tyr Ser Ala Ser
1               5                   10                  15

Val Lys Gly
```

<210> SEQ ID NO 20
<211> LENGTH: 17
<212> TYPE: PRT
<213> ORGANISM: Homo sapiens
<220> FEATURE:
<221> NAME/KEY: misc_feature
<223> OTHER INFORMATION: Homo sapiens AC8 CDR H2

<400> SEQUENCE: 20

```
Gly Ile Ser Ser Gly Gly Ser Ser Lys Tyr Tyr Ala Asp Ser Val Lys
1               5                   10                  15
```

Gly

```
<210> SEQ ID NO 21
<211> LENGTH: 17
<212> TYPE: PRT
<213> ORGANISM: Homo sapiens
<220> FEATURE:
<221> NAME/KEY: misc_feature
<223> OTHER INFORMATION: Homo sapiens AE8 CDR H2

<400> SEQUENCE: 21

Ala Ile Ser Ser Gly Gly Gly Asn Ile Tyr Tyr Ala Asp Ser Val Lys
1               5                   10                  15

Gly

<210> SEQ ID NO 22
<211> LENGTH: 17
<212> TYPE: PRT
<213> ORGANISM: Homo sapiens
<220> FEATURE:
<221> NAME/KEY: misc_feature
<223> OTHER INFORMATION: Homo sapiens AA9 CDR H2

<400> SEQUENCE: 22

Ala Ile Tyr Pro Gly Ser Ser Asn Lys Tyr Tyr Ala Asp Ser Val Lys
1               5                   10                  15

Gly

<210> SEQ ID NO 23
<211> LENGTH: 17
<212> TYPE: PRT
<213> ORGANISM: Homo sapiens
<220> FEATURE:
<221> NAME/KEY: misc_feature
<223> OTHER INFORMATION: Homo sapiens DG5 CDR H2

<400> SEQUENCE: 23

Val Ile Ser Pro Gly Ser Gly Asn Thr Tyr Tyr Ala Asp Ser Val Lys
1               5                   10                  15

Gly

<210> SEQ ID NO 24
<211> LENGTH: 17
<212> TYPE: PRT
<213> ORGANISM: Homo sapiens
<220> FEATURE:
<221> NAME/KEY: misc_feature
<223> OTHER INFORMATION: Homo sapiens AD2 CDR H2

<400> SEQUENCE: 24

Ala Ile Ser His Ser Gly Ser Ser Lys Tyr Tyr Ala Asp Ser Val Lys
1               5                   10                  15

Gly

<210> SEQ ID NO 25
<211> LENGTH: 17
<212> TYPE: PRT
<213> ORGANISM: Homo sapiens
<220> FEATURE:
<221> NAME/KEY: misc_feature
<223> OTHER INFORMATION: Homo sapiens AD7 CDR H2

<400> SEQUENCE: 25

Ala Ile Ser Pro Asn Gly Gly Asn Lys Tyr Tyr Ala Asp Ser Val Lys
1               5                   10                  15
```

Gly

<210> SEQ ID NO 26
<211> LENGTH: 17
<212> TYPE: PRT
<213> ORGANISM: Homo sapiens
<220> FEATURE:
<221> NAME/KEY: misc_feature
<223> OTHER INFORMATION: Homo sapiens DG11 CDR H2

<400> SEQUENCE: 26

Val Ile Ser Pro Gly Ser Gly Ser Lys Tyr Tyr Ala Asp Ser Val Lys
1               5                   10                  15
Gly

<210> SEQ ID NO 27
<211> LENGTH: 17
<212> TYPE: PRT
<213> ORGANISM: Homo sapiens
<220> FEATURE:
<221> NAME/KEY: misc_feature
<223> OTHER INFORMATION: Homo sapiens DG8 CDR H2

<400> SEQUENCE: 27

Val Ile Ser His Gly Asn Gly Ser Lys Tyr Tyr Ala Asp Ser Val Lys
1               5                   10                  15
Gly

<210> SEQ ID NO 28
<211> LENGTH: 17
<212> TYPE: PRT
<213> ORGANISM: Homo sapiens
<220> FEATURE:
<221> NAME/KEY: misc_feature
<223> OTHER INFORMATION: Homo sapiens DA9 CDR H2

<400> SEQUENCE: 28

Val Ile Ser Pro Ser Asp Ser Asn Thr Tyr Tyr Ala Asp Ser Val Lys
1               5                   10                  15
Gly

<210> SEQ ID NO 29
<211> LENGTH: 6
<212> TYPE: PRT
<213> ORGANISM: Mus musculus
<220> FEATURE:
<221> NAME/KEY: misc_feature
<223> OTHER INFORMATION: Mus musculus 1E4 CDR H3

<400> SEQUENCE: 29

Gly Asn Tyr Asp Thr Tyr
1               5

<210> SEQ ID NO 30
<211> LENGTH: 5
<212> TYPE: PRT
<213> ORGANISM: Mus musculus
<220> FEATURE:
<221> NAME/KEY: misc_feature
<223> OTHER INFORMATION: Mus musculus 9B11 CDR H3

<400> SEQUENCE: 30

Gln Asp Phe Asp Tyr
1               5

```
<210> SEQ ID NO 31
<211> LENGTH: 13
<212> TYPE: PRT
<213> ORGANISM: Mus musculus
<220> FEATURE:
<221> NAME/KEY: misc_feature
<223> OTHER INFORMATION: Mus musculus 3A9 CDR H3

<400> SEQUENCE: 31

His Ile Thr Thr Val Arg Pro Thr Lys Tyr Phe Asp Tyr
1               5                   10

<210> SEQ ID NO 32
<211> LENGTH: 6
<212> TYPE: PRT
<213> ORGANISM: Mus musculus
<220> FEATURE:
<221> NAME/KEY: misc_feature
<223> OTHER INFORMATION: Mus musculus 10F10 CDR H3

<400> SEQUENCE: 32

Val Arg Gly Asp Tyr Asp
1               5

<210> SEQ ID NO 33
<211> LENGTH: 9
<212> TYPE: PRT
<213> ORGANISM: Mus musculus
<220> FEATURE:
<221> NAME/KEY: misc_feature
<223> OTHER INFORMATION: Mus musculus 11F11 CDR H3

<400> SEQUENCE: 33

Asp Ala His Gly Lys Pro Phe Ala Tyr
1               5

<210> SEQ ID NO 34
<211> LENGTH: 7
<212> TYPE: PRT
<213> ORGANISM: Homo sapiens
<220> FEATURE:
<221> NAME/KEY: misc_feature
<223> OTHER INFORMATION: Homo sapiens AC8 CDR H3

<400> SEQUENCE: 34

Ile Phe His Asn Phe Asp Tyr
1               5

<210> SEQ ID NO 35
<211> LENGTH: 7
<212> TYPE: PRT
<213> ORGANISM: Homo sapiens
<220> FEATURE:
<221> NAME/KEY: misc_feature
<223> OTHER INFORMATION: Homo sapiens AE8 CDR H3

<400> SEQUENCE: 35

Arg Pro Leu Tyr Phe Asp Tyr
1               5

<210> SEQ ID NO 36
<211> LENGTH: 7
<212> TYPE: PRT
<213> ORGANISM: Homo sapiens
<220> FEATURE:
<221> NAME/KEY: misc_feature
<223> OTHER INFORMATION: Homo sapiens AA9 CDR H3
```

```
<400> SEQUENCE: 36

His Ala Ala Thr Phe Asp Tyr
1               5

<210> SEQ ID NO 37
<211> LENGTH: 18
<212> TYPE: PRT
<213> ORGANISM: Homo sapiens
<220> FEATURE:
<221> NAME/KEY: misc_feature
<223> OTHER INFORMATION: Homo sapiens DG5 CDR H3

<400> SEQUENCE: 37

Val Thr Ile Ala Cys Pro Thr Lys Arg Cys Ser Tyr Ser Asn Gly Met
1               5                   10                  15

Asp Val

<210> SEQ ID NO 38
<211> LENGTH: 7
<212> TYPE: PRT
<213> ORGANISM: Homo sapiens
<220> FEATURE:
<221> NAME/KEY: misc_feature
<223> OTHER INFORMATION: Homo sapiens AD2 CDR H3

<400> SEQUENCE: 38

Ser Gly Asn Asn Phe Asp Tyr
1               5

<210> SEQ ID NO 39
<211> LENGTH: 7
<212> TYPE: PRT
<213> ORGANISM: Homo sapiens
<220> FEATURE:
<221> NAME/KEY: misc_feature
<223> OTHER INFORMATION: Homo sapiens AD7 CDR H3

<400> SEQUENCE: 39

Arg Pro Val Tyr Phe Asp Tyr
1               5

<210> SEQ ID NO 40
<211> LENGTH: 18
<212> TYPE: PRT
<213> ORGANISM: Homo sapiens
<220> FEATURE:
<221> NAME/KEY: misc_feature
<223> OTHER INFORMATION: Homo sapiens DG11 CDR H3

<400> SEQUENCE: 40

Val Thr Ile Ser Cys Ala Arg Met Arg Cys Ser Tyr Ala Asp Gly Met
1               5                   10                  15

Asp Val

<210> SEQ ID NO 41
<211> LENGTH: 18
<212> TYPE: PRT
<213> ORGANISM: Homo sapiens
<220> FEATURE:
<221> NAME/KEY: misc_feature
<223> OTHER INFORMATION: Homo sapiens DG8 CDR H3

<400> SEQUENCE: 41

Val Ala Ser Arg Cys Arg Arg Gly Arg Cys Ser Tyr Ser Asp Gly Met
1               5                   10                  15
```

Asp Val

<210> SEQ ID NO 42
<211> LENGTH: 18
<212> TYPE: PRT
<213> ORGANISM: Homo sapiens
<220> FEATURE:
<221> NAME/KEY: misc_feature
<223> OTHER INFORMATION: Homo sapiens DA9 CDR H3

<400> SEQUENCE: 42

Val Thr Leu Ser Cys Arg Ala Ser Arg Cys Ser Tyr Ser Asn Gly Met
1               5                   10                  15

Asp Val

<210> SEQ ID NO 43
<211> LENGTH: 16
<212> TYPE: PRT
<213> ORGANISM: Mus musculus
<220> FEATURE:
<221> NAME/KEY: misc_feature
<223> OTHER INFORMATION: Mus musculus 1E4 CDR L1

<400> SEQUENCE: 43

Arg Ser Ser Gln Ser Leu Val His Ser Asn Gly Asn Thr Tyr Leu His
1               5                   10                  15

<210> SEQ ID NO 44
<211> LENGTH: 16
<212> TYPE: PRT
<213> ORGANISM: Mus musculus
<220> FEATURE:
<221> NAME/KEY: misc_feature
<223> OTHER INFORMATION: Mus musculus 9B11 CDR L1

<400> SEQUENCE: 44

Arg Ser Ser Gln Ser Leu Val His Ser Asn Gly Asn Thr Tyr Leu His
1               5                   10                  15

<210> SEQ ID NO 45
<211> LENGTH: 11
<212> TYPE: PRT
<213> ORGANISM: Mus musculus
<220> FEATURE:
<221> NAME/KEY: misc_feature
<223> OTHER INFORMATION: Mus musculus 3A9 CDR L1

<400> SEQUENCE: 45

Lys Ala Ser Gln Asn Val Gly Thr Thr Val Ala
1               5                   10

<210> SEQ ID NO 46
<211> LENGTH: 16
<212> TYPE: PRT
<213> ORGANISM: Mus musculus
<220> FEATURE:
<221> NAME/KEY: misc_feature
<223> OTHER INFORMATION: Mus musculus 10F10 CDR L1

<400> SEQUENCE: 46

Lys Ser Ser Gln Ser Leu Leu Asp Ser Asp Gly Glu Thr Tyr Leu Asn
1               5                   10                  15

<210> SEQ ID NO 47
<211> LENGTH: 17
<212> TYPE: PRT
<213> ORGANISM: Mus musculus

```
<220> FEATURE:
<221> NAME/KEY: misc_feature
<223> OTHER INFORMATION: Mus musculus 11F11 CDR L1

<400> SEQUENCE: 47

Lys Ser Ser Gln Ser Leu Leu Tyr Ser Ser Asn Gln Lys Asn Tyr Leu
1               5                   10                  15

Ala

<210> SEQ ID NO 48
<211> LENGTH: 13
<212> TYPE: PRT
<213> ORGANISM: Homo sapiens
<220> FEATURE:
<221> NAME/KEY: misc_feature
<223> OTHER INFORMATION: Homo sapiens AC8 CDR L1

<400> SEQUENCE: 48

Ser Gly Ser Ser Ser Asn Ile Gly Ser Asn Asn Val Tyr
1               5                   10

<210> SEQ ID NO 49
<211> LENGTH: 13
<212> TYPE: PRT
<213> ORGANISM: Homo sapiens
<220> FEATURE:
<221> NAME/KEY: misc_feature
<223> OTHER INFORMATION: Homo sapiens AE8 CDR L1

<400> SEQUENCE: 49

Ser Gly Ser Ser Ser Asn Ile Gly Asn Asn Ser Val Asn
1               5                   10

<210> SEQ ID NO 50
<211> LENGTH: 13
<212> TYPE: PRT
<213> ORGANISM: Homo sapiens
<220> FEATURE:
<221> NAME/KEY: misc_feature
<223> OTHER INFORMATION: Homo sapiens AA9 CDR L1

<400> SEQUENCE: 50

Ser Gly Ser Ser Ser Asn Ile Gly Ser Asn Tyr Val Ser
1               5                   10

<210> SEQ ID NO 51
<211> LENGTH: 13
<212> TYPE: PRT
<213> ORGANISM: Homo sapiens
<220> FEATURE:
<221> NAME/KEY: misc_feature
<223> OTHER INFORMATION: Homo sapiens DG5 CDR L1

<400> SEQUENCE: 51

Ser Gly Ser Ser Ser Asn Ile Gly Ser Asn Ala Val Ser
1               5                   10

<210> SEQ ID NO 52
<211> LENGTH: 13
<212> TYPE: PRT
<213> ORGANISM: Homo sapiens
<220> FEATURE:
<221> NAME/KEY: misc_feature
<223> OTHER INFORMATION: Homo sapiens AD2 CDR L1

<400> SEQUENCE: 52

Thr Gly Ser Ser Ser Asn Ile Gly Asn Asn Ser Val Ser
```

<210> SEQ ID NO 53
<211> LENGTH: 13
<212> TYPE: PRT
<213> ORGANISM: Homo sapiens
<220> FEATURE:
<221> NAME/KEY: misc_feature
<223> OTHER INFORMATION: Homo sapiens AD7 CDR L1

<400> SEQUENCE: 53

Thr Gly Ser Ser Ser Asn Ile Gly Ser Asn Ala Val Asn
1               5                   10

<210> SEQ ID NO 54
<211> LENGTH: 13
<212> TYPE: PRT
<213> ORGANISM: Homo sapiens
<220> FEATURE:
<221> NAME/KEY: misc_feature
<223> OTHER INFORMATION: Homo sapiens DG11 CDR L1

<400> SEQUENCE: 54

Thr Gly Ser Ser Ser Asn Ile Gly Ser Asn Ser Val Ser
1               5                   10

<210> SEQ ID NO 55
<211> LENGTH: 13
<212> TYPE: PRT
<213> ORGANISM: Homo sapiens
<220> FEATURE:
<221> NAME/KEY: misc_feature
<223> OTHER INFORMATION: Homo sapiens DG8 CDR L1

<400> SEQUENCE: 55

Ser Gly Ser Ser Ser Asn Ile Gly Ser Asn Ser Val Ser
1               5                   10

<210> SEQ ID NO 56
<211> LENGTH: 13
<212> TYPE: PRT
<213> ORGANISM: Homo sapiens
<220> FEATURE:
<221> NAME/KEY: misc_feature
<223> OTHER INFORMATION: Homo sapiens DA9 CDR L1

<400> SEQUENCE: 56

Ser Gly Ser Pro Ser Asn Ile Gly Asn Asn Ser Val Ser
1               5                   10

<210> SEQ ID NO 57
<211> LENGTH: 7
<212> TYPE: PRT
<213> ORGANISM: Mus musculus
<220> FEATURE:
<221> NAME/KEY: misc_feature
<223> OTHER INFORMATION: Mus musculus 1E4 CDR L2

<400> SEQUENCE: 57

Lys Val Ser Asn Arg Phe Ser
1               5

<210> SEQ ID NO 58
<211> LENGTH: 7
<212> TYPE: PRT
<213> ORGANISM: Mus musculus
<220> FEATURE:
<221> NAME/KEY: misc_feature

```
<223> OTHER INFORMATION: Mus musculus 9B11 CDR L2

<400> SEQUENCE: 58

Lys Val Ser Asn Arg Phe Ser
1               5

<210> SEQ ID NO 59
<211> LENGTH: 7
<212> TYPE: PRT
<213> ORGANISM: Mus musculus
<220> FEATURE:
<221> NAME/KEY: misc_feature
<223> OTHER INFORMATION: Mus musculus 3A9 CDR L2

<400> SEQUENCE: 59

Ser Ala Ser Asn Arg Tyr Thr
1               5

<210> SEQ ID NO 60
<211> LENGTH: 7
<212> TYPE: PRT
<213> ORGANISM: Mus musculus
<220> FEATURE:
<221> NAME/KEY: misc_feature
<223> OTHER INFORMATION: Mus musculus 10F10 CDR L2

<400> SEQUENCE: 60

Leu Val Ser Lys Leu Asp Ser
1               5

<210> SEQ ID NO 61
<211> LENGTH: 7
<212> TYPE: PRT
<213> ORGANISM: Mus musculus
<220> FEATURE:
<221> NAME/KEY: misc_feature
<223> OTHER INFORMATION: Mus musculus 11F11 CDR L2

<400> SEQUENCE: 61

Trp Ala Ser Thr Arg Glu Ser
1               5

<210> SEQ ID NO 62
<211> LENGTH: 7
<212> TYPE: PRT
<213> ORGANISM: Homo sapiens
<220> FEATURE:
<221> NAME/KEY: misc_feature
<223> OTHER INFORMATION: Homo sapiens AC8 CDR L2

<400> SEQUENCE: 62

Tyr Asp Ser Gln Arg Pro Ser
1               5

<210> SEQ ID NO 63
<211> LENGTH: 7
<212> TYPE: PRT
<213> ORGANISM: Homo sapiens
<220> FEATURE:
<221> NAME/KEY: misc_feature
<223> OTHER INFORMATION: Homo sapiens AE8 CDR L2

<400> SEQUENCE: 63

Ala Asn Asn Asn Arg Pro Ser
1               5

<210> SEQ ID NO 64
```

```
<211> LENGTH: 7
<212> TYPE: PRT
<213> ORGANISM: Homo sapiens
<220> FEATURE:
<221> NAME/KEY: misc_feature
<223> OTHER INFORMATION: Homo sapiens AA9 CDR L2

<400> SEQUENCE: 64

Gly Asp Asn Lys Arg Pro Ser
1               5

<210> SEQ ID NO 65
<211> LENGTH: 7
<212> TYPE: PRT
<213> ORGANISM: Homo sapiens
<220> FEATURE:
<221> NAME/KEY: misc_feature
<223> OTHER INFORMATION: Homo sapiens DG5 CDR L2

<400> SEQUENCE: 65

Ser Asn Ser Asn Arg Pro Ser
1               5

<210> SEQ ID NO 66
<211> LENGTH: 7
<212> TYPE: PRT
<213> ORGANISM: Homo sapiens
<220> FEATURE:
<221> NAME/KEY: misc_feature
<223> OTHER INFORMATION: Homo sapiens AD2 CDR L2

<400> SEQUENCE: 66

Ser Asp Asn Asn Arg Pro Ser
1               5

<210> SEQ ID NO 67
<211> LENGTH: 7
<212> TYPE: PRT
<213> ORGANISM: Homo sapiens
<220> FEATURE:
<221> NAME/KEY: misc_feature
<223> OTHER INFORMATION: Homo sapiens AD7 CDR L2

<400> SEQUENCE: 67

Ser Asn Asn His Arg Pro Ser
1               5

<210> SEQ ID NO 68
<211> LENGTH: 7
<212> TYPE: PRT
<213> ORGANISM: Homo sapiens
<220> FEATURE:
<221> NAME/KEY: misc_feature
<223> OTHER INFORMATION: Homo sapiens DG11 CDR L2

<400> SEQUENCE: 68

Ala Asn Ser Asn Arg Pro Ser
1               5

<210> SEQ ID NO 69
<211> LENGTH: 7
<212> TYPE: PRT
<213> ORGANISM: Homo sapiens
<220> FEATURE:
<221> NAME/KEY: misc_feature
<223> OTHER INFORMATION: Homo sapiens DG8 CDR L2

<400> SEQUENCE: 69
```

```
Ala Asn Asn Asn Arg Pro Ser
1               5

<210> SEQ ID NO 70
<211> LENGTH: 7
<212> TYPE: PRT
<213> ORGANISM: Homo sapiens
<220> FEATURE:
<221> NAME/KEY: misc_feature
<223> OTHER INFORMATION: Homo sapiens DA9 CDR L2

<400> SEQUENCE: 70

Ala Asn Ser His Arg Pro Ser
1               5

<210> SEQ ID NO 71
<211> LENGTH: 9
<212> TYPE: PRT
<213> ORGANISM: Mus musculus
<220> FEATURE:
<221> NAME/KEY: misc_feature
<223> OTHER INFORMATION: Mus musculus 1E4 CDR L3

<400> SEQUENCE: 71

Ser Gln Ser Thr His Val Pro Arg Thr
1               5

<210> SEQ ID NO 72
<211> LENGTH: 9
<212> TYPE: PRT
<213> ORGANISM: Mus musculus
<220> FEATURE:
<221> NAME/KEY: misc_feature
<223> OTHER INFORMATION: Mus musculus 9B11 CDR L3

<400> SEQUENCE: 72

Ser Gln Ser Thr His Val Pro Leu Thr
1               5

<210> SEQ ID NO 73
<211> LENGTH: 9
<212> TYPE: PRT
<213> ORGANISM: Mus musculus
<220> FEATURE:
<221> NAME/KEY: misc_feature
<223> OTHER INFORMATION: Mus musculus 3A9 CDR L3

<400> SEQUENCE: 73

Gln Gln Tyr Ser Asn Tyr Pro Leu Thr
1               5

<210> SEQ ID NO 74
<211> LENGTH: 9
<212> TYPE: PRT
<213> ORGANISM: Mus musculus
<220> FEATURE:
<221> NAME/KEY: misc_feature
<223> OTHER INFORMATION: Mus musculus 10F10 CDR L3

<400> SEQUENCE: 74

Trp Gln Gly Thr His Phe Pro Gln Thr
1               5

<210> SEQ ID NO 75
<211> LENGTH: 9
<212> TYPE: PRT
<213> ORGANISM: Mus musculus
<220> FEATURE:
```

```
<221> NAME/KEY: misc_feature
<223> OTHER INFORMATION: Mus musculus 11F11 CDR L3

<400> SEQUENCE: 75

Gln Gln Tyr Tyr Ser Tyr Pro Trp Thr
1               5

<210> SEQ ID NO 76
<211> LENGTH: 11
<212> TYPE: PRT
<213> ORGANISM: Homo sapiens
<220> FEATURE:
<221> NAME/KEY: misc_feature
<223> OTHER INFORMATION: Homo sapiens AC8 CDR L3

<400> SEQUENCE: 76

Ala Ser Trp Asp Ala Ser Leu Ser Ala Tyr Val
1               5                   10

<210> SEQ ID NO 77
<211> LENGTH: 11
<212> TYPE: PRT
<213> ORGANISM: Homo sapiens
<220> FEATURE:
<221> NAME/KEY: misc_feature
<223> OTHER INFORMATION: Homo sapiens AE8 CDR L3

<400> SEQUENCE: 77

Gly Ser Trp Asp Ala Ser Leu Asn Gly Tyr Val
1               5                   10

<210> SEQ ID NO 78
<211> LENGTH: 11
<212> TYPE: PRT
<213> ORGANISM: Homo sapiens
<220> FEATURE:
<221> NAME/KEY: misc_feature
<223> OTHER INFORMATION: Homo sapiens AA9 CDR L3

<400> SEQUENCE: 78

Gly Ala Trp Asp Asp Ser Leu Ser Gly Tyr Val
1               5                   10

<210> SEQ ID NO 79
<211> LENGTH: 11
<212> TYPE: PRT
<213> ORGANISM: Homo sapiens
<220> FEATURE:
<221> NAME/KEY: misc_feature
<223> OTHER INFORMATION: Homo sapiens DG5 CDR L3

<400> SEQUENCE: 79

Ala Ala Trp Asp Ala Ser Leu Ser Gly Tyr Val
1               5                   10

<210> SEQ ID NO 80
<211> LENGTH: 11
<212> TYPE: PRT
<213> ORGANISM: Homo sapiens
<220> FEATURE:
<221> NAME/KEY: misc_feature
<223> OTHER INFORMATION: Homo sapiens AD2 CDR L3

<400> SEQUENCE: 80

Gly Ser Trp Asp Ala Ser Leu Ser Gly Tyr Val
1               5                   10
```

```
<210> SEQ ID NO 81
<211> LENGTH: 11
<212> TYPE: PRT
<213> ORGANISM: Homo sapiens
<220> FEATURE:
<221> NAME/KEY: misc_feature
<223> OTHER INFORMATION: Homo sapiens AD7 CDR L3

<400> SEQUENCE: 81

Gly Ala Trp Asp Ser Ser Leu Asn Gly Tyr Val
1               5                   10

<210> SEQ ID NO 82
<211> LENGTH: 11
<212> TYPE: PRT
<213> ORGANISM: Homo sapiens
<220> FEATURE:
<221> NAME/KEY: misc_feature
<223> OTHER INFORMATION: Homo sapiens DG11 CDR L3

<400> SEQUENCE: 82

Ala Ala Trp Asp Ala Ser Leu Ser Ala Tyr Val
1               5                   10

<210> SEQ ID NO 83
<211> LENGTH: 11
<212> TYPE: PRT
<213> ORGANISM: Homo sapiens
<220> FEATURE:
<221> NAME/KEY: misc_feature
<223> OTHER INFORMATION: Homo sapiens DG8 CDR L3

<400> SEQUENCE: 83

Gly Ala Trp Asp Ser Ser Leu Ser Ala Tyr Val
1               5                   10

<210> SEQ ID NO 84
<211> LENGTH: 11
<212> TYPE: PRT
<213> ORGANISM: Homo sapiens
<220> FEATURE:
<221> NAME/KEY: misc_feature
<223> OTHER INFORMATION: Homo sapiens DA9 CDR L3

<400> SEQUENCE: 84

Gly Ser Trp Asp Ala Ser Leu Asn Gly Tyr Val
1               5                   10

<210> SEQ ID NO 85
<211> LENGTH: 115
<212> TYPE: PRT
<213> ORGANISM: Artificial Sequence
<220> FEATURE:
<223> OTHER INFORMATION: Synthetic: 1E4 Heavy chain variable VH region

<400> SEQUENCE: 85

Glu Val Gln Leu Gln Glu Ser Gly Ala Glu Leu Val Arg Pro Gly Thr
1               5                   10                  15

Ser Val Lys Val Ser Cys Lys Ala Ser Gly Tyr Ala Phe Thr Asn Tyr
                20                  25                  30

Leu Ile Glu Trp Val Lys Gln Arg Pro Gly Gln Gly Leu Glu Trp Ile
            35                  40                  45

Gly Val Ile Asn Pro Gly Ser Gly Gly Thr Asn Tyr Asn Glu Lys Phe
        50                  55                  60

Lys Gly Lys Ala Thr Leu Thr Ala Asp Lys Ser Ser Ser Thr Ala Tyr
65                  70                  75                  80
```

Met Gln Leu Ser Ser Leu Thr Ser Asp Asp Ser Ala Val Tyr Phe Cys
                85                  90                  95

Ala Ser Gly Asn Tyr Asp Thr Tyr Trp Gly Gln Gly Thr Leu Val Thr
            100                 105                 110

Val Ser Ala
        115

<210> SEQ ID NO 86
<211> LENGTH: 116
<212> TYPE: PRT
<213> ORGANISM: Artificial Sequence
<220> FEATURE:
<223> OTHER INFORMATION: Synthetic: 9B11 Heavy chain variable VH region

<400> SEQUENCE: 86

Glu Val Gln Leu Gln Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gln Asp Phe Asp Tyr Trp Gly Gln Gly Thr Thr Leu
            100                 105                 110

Thr Val Ser Ser
        115

<210> SEQ ID NO 87
<211> LENGTH: 122
<212> TYPE: PRT
<213> ORGANISM: Artificial Sequence
<220> FEATURE:
<223> OTHER INFORMATION: Synthetic: 3A9 Heavy chain variable VH region

<400> SEQUENCE: 87

Glu Val Gln Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Asn Gly Gly Gly Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg His Ile Thr Thr Val Arg Pro Thr Lys Tyr Phe Asp Tyr Trp
            100                 105                 110

Gly Gln Gly Thr Thr Leu Thr Val Ser Ser
        115                 120

```
<210> SEQ ID NO 88
<211> LENGTH: 113
<212> TYPE: PRT
<213> ORGANISM: Artificial Sequence
<220> FEATURE:
<223> OTHER INFORMATION: Synthetic: 10F10 Heavy chain variable VH region

<400> SEQUENCE: 88
```

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Gly Gly
            20                  25                  30

Phe Tyr Trp Asn Trp Ile Arg Gln Phe Pro Gly Asn Asn Leu Glu Trp
        35                  40                  45

Met Gly Tyr Ile Asn Tyr Asp Gly Ser Ser Asp Tyr Ser Pro Ser Leu
    50                  55                  60

Lys Asn Arg Ile Ser Ile Thr Arg Asp Thr Ser Lys Asn Gln Phe Phe
65                  70                  75                  80

Leu Asn Leu Asn Ser Val Thr Thr Glu Asp Thr Ala Thr Tyr Tyr Cys
                85                  90                  95

Val Arg Gly Asp Tyr Asp Trp Gly Gln Gly Thr Thr Leu Thr Val Ser
            100                 105                 110

Ser

```
<210> SEQ ID NO 89
<211> LENGTH: 120
<212> TYPE: PRT
<213> ORGANISM: Artificial Sequence
<220> FEATURE:
<223> OTHER INFORMATION: Synthetic: 11F11 Heavy chain variable VH region

<400> SEQUENCE: 89
```

Glu Val Gln Leu Gln Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp Ala His Gly Lys Pro Phe Ala Tyr Trp Gly Gln
            100                 105                 110

Gly Thr Leu Val Thr Val Ser Ala
        115                 120

```
<210> SEQ ID NO 90
<211> LENGTH: 116
<212> TYPE: PRT
<213> ORGANISM: Artificial Sequence
<220> FEATURE:
<223> OTHER INFORMATION: Synthetic: AC8 Heavy chain variable VH region

<400> SEQUENCE: 90
```

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Asp Tyr
            20                  25                  30

Ser Met Ser Trp Val Arg Gln Ala Pro Gly Lys Gly Leu Glu Trp Val
        35                  40                  45

Ser Gly Ile Ser Ser Gly Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Phe His Asn Phe Asp Tyr Trp Gly Gln Gly Thr Leu Val
            100                 105                 110

Thr Val Ser Ser
        115

<210> SEQ ID NO 91
<211> LENGTH: 116
<212> TYPE: PRT
<213> ORGANISM: Artificial Sequence
<220> FEATURE:
<223> OTHER INFORMATION: Synthetic: AE8 Heavy chain variable VH region

<400> SEQUENCE: 91

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Ser Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Pro Leu Tyr Phe Asp Tyr Trp Gly Gln Gly Thr Leu Val
            100                 105                 110

Thr Val Ser Ser
        115

<210> SEQ ID NO 92
<211> LENGTH: 116
<212> TYPE: PRT
<213> ORGANISM: Artificial Sequence
<220> FEATURE:
<223> OTHER INFORMATION: Synthetic: AA9 Heavy chain variable VH region

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ala Ile Tyr Pro Gly Ser Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Arg His Ala Ala Thr Phe Asp Tyr Trp Gly Gln Gly Thr Leu Val
            100                 105                 110

Thr Val Ser Ser
        115

<210> SEQ ID NO 93
<211> LENGTH: 127
<212> TYPE: PRT
<213> ORGANISM: Artificial Sequence
<220> FEATURE:
<223> OTHER INFORMATION: Synthetic: DG5 Heavy chain variable VH region

<400> SEQUENCE: 93

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Val Ile Ser Pro Gly Ser Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Thr Ile Ala Cys Pro Thr Lys Arg Cys Ser Tyr Ser Asn
            100                 105                 110

Gly Met Asp Val Trp Gly Gln Gly Thr Leu Val Thr Val Ser Ser
        115                 120                 125

<210> SEQ ID NO 94
<211> LENGTH: 116
<212> TYPE: PRT
<213> ORGANISM: Artificial Sequence
<220> FEATURE:
<223> OTHER INFORMATION: Synthetic: AD2 Heavy chain variable VH region

<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser His Ser Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Asn Asn Phe Asp Tyr Trp Gly Gln Gly Thr Leu Val
            100                 105                 110

Thr Val Ser Ser
        115

<210> SEQ ID NO 95
<211> LENGTH: 116
<212> TYPE: PRT
<213> ORGANISM: Artificial Sequence
<220> FEATURE:
<223> OTHER INFORMATION: Synthetic: AD7 Heavy chain variable VH region

<400> SEQUENCE: 95

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Met Ser Trp Val Arg Gln Ala Pro Gly Lys Gly Leu Glu Trp Val
        35                  40                  45

Ser Ala Ile Ser Pro Asn Gly Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Pro Val Tyr Phe Asp Tyr Trp Gly Gln Gly Thr Leu Val
            100                 105                 110

Thr Val Ser Ser
        115

<210> SEQ ID NO 96
<211> LENGTH: 127
<212> TYPE: PRT
<213> ORGANISM: Artificial Sequence
<220> FEATURE:
<223> OTHER INFORMATION: Synthetic: DG11 Heavy chain variable VH region

<400> SEQUENCE: 96

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Val Ile Ser Pro Gly Ser Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Thr Ile Ser Cys Ala Arg Met Arg Cys Ser Tyr Ala Asp
            100                 105                 110

Gly Met Asp Val Trp Gly Gln Gly Thr Leu Val Thr Val Ser Ser
        115                 120                 125

<210> SEQ ID NO 97
<211> LENGTH: 127
<212> TYPE: PRT
<213> ORGANISM: Artificial Sequence
<220> FEATURE:
<223> OTHER INFORMATION: Synthetic: DG8 Heavy chain variable VH region

<400> SEQUENCE: 97

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Ala Met Ser Trp Val Arg Gln Ala Pro Gly Lys Gly Leu Glu Trp Val
        35                  40                  45

Ser Val Ile Ser His Gly Asn Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ala Ser Arg Cys Arg Gly Arg Cys Ser Tyr Ser Asp
            100                 105                 110

Gly Met Asp Val Trp Gly Gln Gly Thr Leu Val Thr Val Ser Ser
        115                 120                 125

<210> SEQ ID NO 98
<211> LENGTH: 127
<212> TYPE: PRT
<213> ORGANISM: Artificial Sequence
<220> FEATURE:
<223> OTHER INFORMATION: Synthetic: DA9 Heavy chain variable VH region

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Val Ile Ser Pro Ser Asp Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Thr Leu Ser Cys Arg Ala Ser Arg Cys Ser Tyr Ser Asn
            100                 105                 110

Gly Met Asp Val Trp Gly Gln Gly Thr Leu Val Thr Val Ser Ser
        115                 120                 125

<210> SEQ ID NO 99
<211> LENGTH: 112
<212> TYPE: PRT
<213> ORGANISM: Artificial Sequence
<220> FEATURE:
<223> OTHER INFORMATION: Synthetic: 1E4 Light chain variable VL region

<400> SEQUENCE: 99

Asp Ile Val Met Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile

```
                65                  70                  75                  80
Ser Arg Val Glu Ala Glu Asp Leu Gly Val Tyr Phe Cys Ser Gln Ser
                    85                  90                  95

Thr His Val Pro Arg Thr Phe Gly Gly Gly Thr Lys Leu Glu Ile Lys
                    100                 105                 110

<210> SEQ ID NO 100
<211> LENGTH: 112
<212> TYPE: PRT
<213> ORGANISM: Artificial Sequence
<220> FEATURE:
<223> OTHER INFORMATION: Synthetic: 9B11 Light chain variable VL region

<400> SEQUENCE: 100

Asp Ile Val Met Thr Gln Ser Pro Leu Ser Leu Pro Val Ser Leu Gly
1               5                   10                  15

Asp Gln Ala Ser Ile Ser Cys Arg Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                    85                  90                  95

Thr His Val Pro Leu Thr Phe Gly Ala Gly Thr Lys Leu Glu Gln Lys
                    100                 105                 110

<210> SEQ ID NO 101
<211> LENGTH: 107
<212> TYPE: PRT
<213> ORGANISM: Artificial Sequence
<220> FEATURE:
<223> OTHER INFORMATION: Synthetic: 3A9 Light chain variable VL region

<400> SEQUENCE: 101

Asp Ile Val Met Thr Gln Ser Pro Lys Phe Met Ser Thr Ser Val Gly
1               5                   10                  15

Asp Arg Val Ser Ile Thr Cys Lys Ala Ser Gln Asn Val Gly Thr Thr
                20                  25                  30

Val Ala Trp Tyr Gln Gln Lys Pro Gly Gln Ser Pro Lys Leu Leu Ile
            35                  40                  45

Tyr Ser Ala Ser Asn Arg Tyr Thr Gly Val Pro Asp Arg Phe Thr Gly
        50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Asn Tyr Pro Leu
                    85                  90                  95

Thr Phe Gly Ala Gly Thr Lys Leu Glu Leu Arg
                    100                 105

<210> SEQ ID NO 102
<211> LENGTH: 112
<212> TYPE: PRT
<213> ORGANISM: Artificial Sequence
<220> FEATURE:
<223> OTHER INFORMATION: Synthetic: 10F10 Light chain variable VL region

<400> SEQUENCE: 102
```

Asp Ile Val Met Thr Gln Ser Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Glu Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 103
<211> LENGTH: 113
<212> TYPE: PRT
<213> ORGANISM: Artificial Sequence
<220> FEATURE:
<223> OTHER INFORMATION: Synthetic: 11F11 Light chain variable VL region

<400> SEQUENCE: 103

Asp Ile Val Met Thr Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Trp Thr Phe Gly Gly Gly Thr Lys Leu Glu Ile
            100                 105                 110

Lys

<210> SEQ ID NO 104
<211> LENGTH: 111
<212> TYPE: PRT
<213> ORGANISM: Artificial Sequence
<220> FEATURE:
<223> OTHER INFORMATION: Synthetic: AC8 Light chain variable VL region

<400> SEQUENCE: 104

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Asn Val Tyr Trp Tyr Gln Gln Leu Pro Gly Thr Ala Pro Lys Leu Leu
        35                  40                  45

Ile Tyr Tyr Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

```
Ser Glu Asp Glu Ala Asp Tyr Tyr Cys Ala Ser Trp Asp Ala Ser Leu
                85                  90                  95

Ser Ala Tyr Val Phe Gly Gly Gly Thr Lys Leu Thr Val Leu Gly
            100                 105                 110

<210> SEQ ID NO 105
<211> LENGTH: 111
<212> TYPE: PRT
<213> ORGANISM: Artificial Sequence
<220> FEATURE:
<223> OTHER INFORMATION: Synthetic: AE8 Light chain variable VL region

<400> SEQUENCE: 105

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Ser Val Asn Trp Tyr Gln Gln Leu Pro Gly Thr Ala Pro Lys Leu Leu
            35                  40                  45

Ile Tyr Ala Asn Asn Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Gly Tyr Val Phe Gly Gly Gly Thr Lys Leu Thr Val Leu Gly
            100                 105                 110

<210> SEQ ID NO 106
<211> LENGTH: 111
<212> TYPE: PRT
<213> ORGANISM: Artificial Sequence
<220> FEATURE:
<223> OTHER INFORMATION: Synthetic: AA9 Light chain variable VL region

<400> SEQUENCE: 106

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
            35                  40                  45

Ile Tyr Gly Asp Asn Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Gly Tyr Val Phe Gly Gly Gly Thr Lys Leu Thr Val Leu Gly
            100                 105                 110

<210> SEQ ID NO 107
<211> LENGTH: 111
<212> TYPE: PRT
<213> ORGANISM: Artificial Sequence
<220> FEATURE:
<223> OTHER INFORMATION: Synthetic: DG5 Light chain variable VL region

<400> SEQUENCE: 107
```

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Ala Val Ser Trp Tyr Gln Gln Leu Pro Gly Thr Ala Pro Lys Leu Leu
            35                  40                  45

Ile Tyr Ser Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ala Ser Leu
                85                  90                  95

Ser Gly Tyr Val Phe Gly Gly Gly Thr Lys Leu Thr Val Leu Gly
            100                 105                 110

<210> SEQ ID NO 108
<211> LENGTH: 111
<212> TYPE: PRT
<213> ORGANISM: Artificial Sequence
<220> FEATURE:
<223> OTHER INFORMATION: Synthetic: AD2 Light chain variable VL region

<400> SEQUENCE: 108

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Asn Asn
                20                  25                  30

Ser Val Ser Trp Tyr Gln Gln Leu Pro Gly Thr Ala Pro Lys Leu Leu
            35                  40                  45

Ile Tyr Ser Asp Asn Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Ser Gly Tyr Val Phe Gly Gly Gly Thr Lys Leu Thr Val Leu Gly
            100                 105                 110

<210> SEQ ID NO 109
<211> LENGTH: 111
<212> TYPE: PRT
<213> ORGANISM: Artificial Sequence
<220> FEATURE:
<223> OTHER INFORMATION: Synthetic: AD7 Light chain variable VL region

<400> SEQUENCE: 109

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ser Asn
                20                  25                  30

Ala Val Asn Trp Tyr Gln Gln Leu Pro Gly Thr Ala Pro Lys Leu Leu
            35                  40                  45

Ile Tyr Ser Asn Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95
```

```
Asn Gly Tyr Val Phe Gly Gly Gly Thr Lys Leu Thr Val Leu Gly
            100                 105                 110
```

<210> SEQ ID NO 110
<211> LENGTH: 111
<212> TYPE: PRT
<213> ORGANISM: Artificial Sequence
<220> FEATURE:
<223> OTHER INFORMATION: Synthetic: DG11 Light chain variable VL region

<400> SEQUENCE: 110

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Ala Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ala Ser Leu
                85                  90                  95

Ser Ala Tyr Val Phe Gly Gly Gly Thr Lys Leu Thr Val Leu Gly
            100                 105                 110
```

<210> SEQ ID NO 111
<211> LENGTH: 111
<212> TYPE: PRT
<213> ORGANISM: Artificial Sequence
<220> FEATURE:
<223> OTHER INFORMATION: Synthetic: DG8 Light chain variable VL region

<400> SEQUENCE: 111

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Ala Asn Asn Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Ala Tyr Val Phe Gly Gly Gly Thr Lys Leu Thr Val Leu Gly
            100                 105                 110
```

<210> SEQ ID NO 112
<211> LENGTH: 111
<212> TYPE: PRT
<213> ORGANISM: Artificial Sequence
<220> FEATURE:
<223> OTHER INFORMATION: Synthetic: DA9 Light chain variable VL region

<400> SEQUENCE: 112

```
Gln Ser Val Leu Thr Gln Pro Pro Ser Ala Ser Gly Thr Pro Gly Gln
1               5                   10                  15
```

```
Arg Val Thr Ile Ser Cys Ser Gly Ser Pro Ser Asn Ile Gly Asn Asn
            20                  25                  30

Ser Val Ser Trp Tyr Gln Gln Leu Pro Gly Thr Ala Pro Lys Leu Leu
        35                  40                  45

Ile Tyr Ala Asn Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Gly Tyr Val Phe Gly Gly Gly Thr Lys Leu Thr Val Leu Gly
            100                 105                 110

<210> SEQ ID NO 113
<211> LENGTH: 445
<212> TYPE: PRT
<213> ORGANISM: Artificial Sequence
<220> FEATURE:
<223> OTHER INFORMATION: Synthetic: 1E4 Full length heavy chain
      comprising mouse IgG2a constant region

<400> SEQUENCE: 113

Glu Val Gln Leu Gln Glu Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Asp Asp Ser Ala Val Tyr Phe Cys
                85                  90                  95

Ala Ser Gly Asn Tyr Asp Thr Tyr Trp Gly Gln Gly Thr Leu Val Thr
            100                 105                 110

Val Ser Ala Ala Lys Thr Thr Ala Pro Ser Val Tyr Pro Leu Ala Pro
        115                 120                 125

Val Cys Gly Asp Thr Thr Gly Ser Ser Val Thr Leu Gly Cys Leu Val
    130                 135                 140

Lys Gly Tyr Phe Pro Glu Pro Val Thr Leu Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Thr Ser Ser Thr Trp Pro Ser
            180                 185                 190

Gln Ser Ile Thr Cys Asn Val Ala His Pro Ala Ser Ser Thr Lys Val
        195                 200                 205

Asp Lys Lys Ile Glu Pro Arg Gly Pro Thr Ile Lys Pro Cys Pro Pro
    210                 215                 220

Cys Lys Cys Pro Ala Pro Asn Leu Leu Gly Gly Pro Ser Val Phe Ile
225                 230                 235                 240

Phe Pro Pro Lys Ile Lys Asp Val Leu Met Ile Ser Leu Ser Pro Ile
                245                 250                 255

Val Thr Cys Val Val Val Asp Val Ser Glu Asp Asp Pro Asp Val Gln
            260                 265                 270
```

```
Ile Ser Trp Phe Val Asn Asn Val Glu Val His Thr Ala Gln Thr Gln
        275                 280                 285

Thr His Arg Glu Asp Tyr Asn Ser Thr Leu Arg Val Val Ser Ala Leu
    290                 295                 300

Pro Ile Gln His Gln Asp Trp Met Ser Gly Lys Glu Phe Lys Cys Lys
305                 310                 315                 320

Val Asn Asn Lys Asp Leu Pro Ala Pro Ile Glu Arg Thr Ile Ser Lys
                325                 330                 335

Pro Lys Gly Ser Val Arg Ala Pro Gln Val Tyr Val Leu Pro Pro Pro
            340                 345                 350

Glu Glu Glu Met Thr Lys Lys Gln Val Thr Leu Thr Cys Met Val Thr
                355                 360                 365

Asp Phe Met Pro Glu Asp Ile Tyr Val Glu Trp Thr Asn Asn Gly Lys
    370                 375                 380

Thr Glu Leu Asn Tyr Lys Asn Thr Glu Pro Val Leu Asp Ser Asp Gly
385                 390                 395                 400

Ser Tyr Phe Met Tyr Ser Lys Leu Arg Val Glu Lys Lys Asn Trp Val
                405                 410                 415

Glu Arg Asn Ser Tyr Ser Cys Ser Val Val His Glu Gly Leu His Asn
            420                 425                 430

His His Thr Thr Lys Ser Phe Ser Arg Thr Pro Gly Lys
        435                 440                 445

<210> SEQ ID NO 114
<211> LENGTH: 446
<212> TYPE: PRT
<213> ORGANISM: Artificial Sequence
<220> FEATURE:
<223> OTHER INFORMATION: Synthetic: 9B11 Full length heavy chain
      comprising mouse IgG2a constant region

<400> SEQUENCE: 114

Glu Val Gln Leu Gln Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gln Asp Phe Asp Tyr Trp Gly Gln Gly Thr Thr Leu
            100                 105                 110

Thr Val Ser Ser Ala Lys Thr Thr Ala Pro Ser Val Tyr Pro Leu Ala
        115                 120                 125

Pro Val Cys Gly Asp Thr Thr Gly Ser Ser Val Thr Leu Gly Cys Leu
    130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Thr Ser Ser Thr Trp Pro
```

```
            180                 185                 190
Ser Gln Ser Ile Thr Cys Asn Val Ala His Pro Ala Ser Ser Thr Lys
        195                 200                 205
Val Asp Lys Lys Ile Glu Pro Arg Gly Pro Thr Ile Lys Pro Cys Pro
        210                 215                 220
Pro Cys Lys Cys Pro Ala Pro Asn Leu Leu Gly Gly Pro Ser Val Phe
225                 230                 235                 240
Ile Phe Pro Pro Lys Ile Lys Asp Val Leu Met Ile Ser Leu Ser Pro
                245                 250                 255
Ile Val Thr Cys Val Val Val Asp Val Ser Glu Asp Asp Pro Asp Val
            260                 265                 270
Gln Ile Ser Trp Phe Val Asn Asn Val Glu Val His Thr Ala Gln Thr
        275                 280                 285
Gln Thr His Arg Glu Asp Tyr Asn Ser Thr Leu Arg Val Val Ser Ala
        290                 295                 300
Leu Pro Ile Gln His Gln Asp Trp Met Ser Gly Lys Glu Phe Lys Cys
305                 310                 315                 320
Lys Val Asn Asn Lys Asp Leu Pro Ala Pro Ile Glu Arg Thr Ile Ser
                325                 330                 335
Lys Pro Lys Gly Ser Val Arg Ala Pro Gln Val Tyr Val Leu Pro Pro
                340                 345                 350
Pro Glu Glu Glu Met Thr Lys Lys Gln Val Thr Leu Thr Cys Met Val
            355                 360                 365
Thr Asp Phe Met Pro Glu Asp Ile Tyr Val Glu Trp Thr Asn Asn Gly
        370                 375                 380
Lys Thr Glu Leu Asn Tyr Lys Asn Thr Glu Pro Val Leu Asp Ser Asp
385                 390                 395                 400
Gly Ser Tyr Phe Met Tyr Ser Lys Leu Arg Val Glu Lys Lys Asn Trp
                405                 410                 415
Val Glu Arg Asn Ser Tyr Ser Cys Ser Val Val His Glu Gly Leu His
                420                 425                 430
Asn His His Thr Thr Lys Ser Phe Ser Arg Thr Pro Gly Lys
            435                 440                 445

<210> SEQ ID NO 115
<211> LENGTH: 452
<212> TYPE: PRT
<213> ORGANISM: Artificial Sequence
<220> FEATURE:
<223> OTHER INFORMATION: Synthetic: 3A9 Full length heavy chain
      comprising mouse IgG2a constant region

<400> SEQUENCE: 115

Glu Val Gln Leu Gln Glu Ser Gly Gly Gly Leu Val Lys Pro Gly Gly
1               5                   10                  15
Ser Leu Lys Leu Ser Cys Ala Ala Ser Gly Phe Thr Phe Ser Ser Tyr
            20                  25                  30
Ala Met Ser Trp Val Arg Gln Thr Pro Glu Lys Arg Leu Glu Trp Val
        35                  40                  45
Ala Thr Ile Ser Asn Gly Gly Gly Tyr Thr Tyr Tyr Pro Asp Ser Val
    50                  55                  60
Lys Gly Arg Phe Thr Ile Ser Arg Asp Asn Ala Lys Asn Thr Leu Tyr
65                  70                  75                  80
Leu Gln Met Ser Ser Leu Arg Ser Glu Asp Thr Ala Met Tyr Tyr Cys
                85                  90                  95
```

```
Ala Arg His Ile Thr Thr Val Arg Pro Thr Lys Tyr Phe Asp Tyr Trp
            100                 105                 110

Gly Gln Gly Thr Thr Leu Thr Val Ser Ser Ala Lys Thr Thr Ala Pro
        115                 120                 125

Ser Val Tyr Pro Leu Ala Pro Val Cys Gly Asp Thr Thr Gly Ser Ser
    130                 135                 140

Val Thr Leu Gly Cys Leu Val Lys Gly Tyr Phe Pro Glu Pro Val Thr
145                 150                 155                 160

Leu Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Thr Ser Ser Thr Trp Pro Ser Gln Ser Ile Thr Cys Asn Val Ala His
        195                 200                 205

Pro Ala Ser Ser Thr Lys Val Asp Lys Lys Ile Glu Pro Arg Gly Pro
    210                 215                 220

Thr Ile Lys Pro Cys Pro Pro Cys Lys Cys Pro Ala Pro Asn Leu Leu
225                 230                 235                 240

Gly Gly Pro Ser Val Phe Ile Phe Pro Pro Lys Ile Lys Asp Val Leu
                245                 250                 255

Met Ile Ser Leu Ser Pro Ile Val Thr Cys Val Val Val Asp Val Ser
            260                 265                 270

Glu Asp Asp Pro Asp Val Gln Ile Ser Trp Phe Val Asn Asn Val Glu
        275                 280                 285

Val His Thr Ala Gln Thr Gln Thr His Arg Glu Asp Tyr Asn Ser Thr
    290                 295                 300

Leu Arg Val Val Ser Ala Leu Pro Ile Gln His Gln Asp Trp Met Ser
305                 310                 315                 320

Gly Lys Glu Phe Lys Cys Lys Val Asn Asn Lys Asp Leu Pro Ala Pro
                325                 330                 335

Ile Glu Arg Thr Ile Ser Lys Pro Lys Gly Ser Val Arg Ala Pro Gln
            340                 345                 350

Val Tyr Val Leu Pro Pro Pro Glu Glu Glu Met Thr Lys Lys Gln Val
        355                 360                 365

Thr Leu Thr Cys Met Val Thr Asp Phe Met Pro Glu Asp Ile Tyr Val
    370                 375                 380

Glu Trp Thr Asn Asn Gly Lys Thr Glu Leu Asn Tyr Lys Asn Thr Glu
385                 390                 395                 400

Pro Val Leu Asp Ser Asp Gly Ser Tyr Phe Met Tyr Ser Lys Leu Arg
                405                 410                 415

Val Glu Lys Lys Asn Trp Val Glu Arg Asn Ser Tyr Ser Cys Ser Val
            420                 425                 430

Val His Glu Gly Leu His Asn His His Thr Thr Lys Ser Phe Ser Arg
        435                 440                 445

Thr Pro Gly Lys
    450

<210> SEQ ID NO 116
<211> LENGTH: 443
<212> TYPE: PRT
<213> ORGANISM: Artificial Sequence
<220> FEATURE:
<223> OTHER INFORMATION: Synthetic: 10F10 Full length heavy chain
      comprising mouse IgG2a constant region

<400> SEQUENCE: 116
```

```
Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Gly Gly
            20                  25                  30

Phe Tyr Trp Asn Trp Ile Arg Gln Phe Pro Gly Asn Asn Leu Glu Trp
            35                  40                  45

Met Gly Tyr Ile Asn Tyr Asp Gly Ser Ser Asp Tyr Ser Pro Ser Leu
    50                  55                  60

Lys Asn Arg Ile Ser Ile Thr Arg Asp Thr Ser Lys Asn Gln Phe Phe
65                  70                  75                  80

Leu Asn Leu Asn Ser Val Thr Thr Glu Asp Thr Ala Thr Tyr Tyr Cys
                85                  90                  95

Val Arg Gly Asp Tyr Asp Trp Gly Gln Gly Thr Thr Leu Thr Val Ser
            100                 105                 110

Ser Ala Lys Thr Thr Ala Pro Ser Val Tyr Pro Leu Ala Pro Val Cys
            115                 120                 125

Gly Asp Thr Thr Gly Ser Ser Val Thr Leu Gly Cys Leu Val Lys Gly
    130                 135                 140

Tyr Phe Pro Glu Pro Val Thr Leu Thr Trp Asn Ser Gly Ser Leu Ser
145                 150                 155                 160

Ser Gly Val His Thr Phe Pro Ala Val Leu Gln Ser Asp Leu Tyr Thr
            165                 170                 175

Leu Ser Ser Ser Val Thr Val Thr Ser Ser Thr Trp Pro Ser Gln Ser
            180                 185                 190

Ile Thr Cys Asn Val Ala His Pro Ala Ser Ser Thr Lys Val Asp Lys
            195                 200                 205

Lys Ile Glu Pro Arg Gly Pro Thr Ile Lys Pro Cys Pro Pro Cys Lys
            210                 215                 220

Cys Pro Ala Pro Asn Leu Leu Gly Gly Pro Ser Val Phe Ile Phe Pro
225                 230                 235                 240

Pro Lys Ile Lys Asp Val Leu Met Ile Ser Leu Ser Pro Ile Val Thr
            245                 250                 255

Cys Val Val Val Asp Val Ser Glu Asp Asp Pro Asp Val Gln Ile Ser
            260                 265                 270

Trp Phe Val Asn Asn Val Glu Val His Thr Ala Gln Thr Gln Thr His
            275                 280                 285

Arg Glu Asp Tyr Asn Ser Thr Leu Arg Val Val Ser Ala Leu Pro Ile
            290                 295                 300

Gln His Gln Asp Trp Met Ser Gly Lys Glu Phe Lys Cys Lys Val Asn
305                 310                 315                 320

Asn Lys Asp Leu Pro Ala Pro Ile Glu Arg Thr Ile Ser Lys Pro Lys
            325                 330                 335

Gly Ser Val Arg Ala Pro Gln Val Tyr Val Leu Pro Pro Pro Glu Glu
            340                 345                 350

Glu Met Thr Lys Lys Gln Val Thr Leu Thr Cys Met Val Thr Asp Phe
            355                 360                 365

Met Pro Glu Asp Ile Tyr Val Glu Trp Thr Asn Asn Gly Lys Thr Glu
    370                 375                 380

Leu Asn Tyr Lys Asn Thr Glu Pro Val Leu Asp Ser Asp Gly Ser Tyr
385                 390                 395                 400

Phe Met Tyr Ser Lys Leu Arg Val Glu Lys Lys Asn Trp Val Glu Arg
                405                 410                 415
```

-continued

Asn Ser Tyr Ser Cys Ser Val Val His Glu Gly Leu His Asn His His
            420                 425                 430

Thr Thr Lys Ser Phe Ser Arg Thr Pro Gly Lys
        435                 440

<210> SEQ ID NO 117
<211> LENGTH: 450
<212> TYPE: PRT
<213> ORGANISM: Artificial Sequence
<220> FEATURE:
<223> OTHER INFORMATION: Synthetic: 11F11 Full length heavy chain
      comprising mouse IgG2a constant region

<400> SEQUENCE: 117

Glu Val Gln Leu Gln Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp Ala His Gly Lys Pro Phe Ala Tyr Trp Gly Gln
            100                 105                 110

Gly Thr Leu Val Thr Val Ser Ala Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

```
Arg Thr Ile Ser Lys Pro Lys Gly Ser Val Arg Ala Pro Gln Val Tyr
            340                 345                 350

Val Leu Pro Pro Glu Glu Glu Met Thr Lys Lys Gln Val Thr Leu
            355                 360                 365

Thr Cys Met Val Thr Asp Phe Met Pro Glu Asp Ile Tyr Val Glu Trp
        370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
            435                 440                 445

Gly Lys
    450

<210> SEQ ID NO 118
<211> LENGTH: 446
<212> TYPE: PRT
<213> ORGANISM: Artificial Sequence
<220> FEATURE:
<223> OTHER INFORMATION: AC8 Full length heavy chain comprising mouse
      IgG2a constant region

<400> SEQUENCE: 118

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Met Ser Trp Val Arg Gln Ala Pro Gly Lys Gly Leu Glu Trp Val
        35                  40                  45

Ser Gly Ile Ser Ser Gly Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Phe His Asn Phe Asp Tyr Trp Gly Gln Gly Thr Leu Val
            100                 105                 110

Thr Val Ser Ser Ala Lys Thr Thr Ala Pro Ser Val Tyr Pro Leu Ala
        115                 120                 125

Pro Val Cys Gly Asp Thr Thr Gly Ser Ser Val Thr Leu Gly Cys Leu
    130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Thr Ser Ser Thr Trp Pro
            180                 185                 190

Ser Gln Ser Ile Thr Cys Asn Val Ala His Pro Ala Ser Ser Thr Lys
        195                 200                 205

Val Asp Lys Lys Ile Glu Pro Arg Gly Pro Thr Ile Lys Pro Cys Pro
    210                 215                 220

Pro Cys Lys Cys Pro Ala Pro Asn Leu Leu Gly Gly Pro Ser Val Phe
```

```
                    225                 230                 235                 240
        Ile Phe Pro Pro Lys Ile Lys Asp Val Leu Met Ile Ser Leu Ser Pro
                        245                 250                 255

Ile Val Thr Cys Val Val Val Asp Val Ser Glu Asp Pro Asp Val
                        260                 265                 270

Gln Ile Ser Trp Phe Val Asn Asn Val Glu Val His Thr Ala Gln Thr
                        275                 280                 285

Gln Thr His Arg Glu Asp Tyr Asn Ser Thr Leu Arg Val Val Ser Ala
                    290                 295                 300

Leu Pro Ile Gln His Gln Asp Trp Met Ser Gly Lys Glu Phe Lys Cys
        305                 310                 315                 320

Lys Val Asn Asn Lys Asp Leu Pro Ala Pro Ile Glu Arg Thr Ile Ser
                        325                 330                 335

Lys Pro Lys Gly Ser Val Arg Ala Pro Gln Val Tyr Val Leu Pro Pro
                        340                 345                 350

Pro Glu Glu Glu Met Thr Lys Lys Gln Val Thr Leu Thr Cys Met Val
                        355                 360                 365

Thr Asp Phe Met Pro Glu Asp Ile Tyr Val Glu Trp Thr Asn Asn Gly
                    370                 375                 380

Lys Thr Glu Leu Asn Tyr Lys Asn Thr Glu Pro Val Leu Asp Ser Asp
        385                 390                 395                 400

Gly Ser Tyr Phe Met Tyr Ser Lys Leu Arg Val Glu Lys Lys Asn Trp
                        405                 410                 415

Val Glu Arg Asn Ser Tyr Ser Cys Ser Val Val His Glu Gly Leu His
                        420                 425                 430

Asn His His Thr Thr Lys Ser Phe Ser Arg Thr Pro Gly Lys
                    435                 440                 445

<210> SEQ ID NO 119
<211> LENGTH: 446
<212> TYPE: PRT
<213> ORGANISM: Artificial Sequence
<220> FEATURE:
<223> OTHER INFORMATION: AE8 Full length heavy chain comprising mouse
      IgG2a constant region

<400> SEQUENCE: 119

Glu Val Gln Leu Leu Glu Ser Gly Gly Gly Leu Val Gln Pro Gly Gly
        1               5                   10                  15

Ser Leu Arg Leu Ser Cys Ala Ala Ser Gly Phe Thr Phe Ser Asn Tyr
                        20                  25                  30

Ala Met Ser Trp Val Arg Gln Ala Pro Gly Lys Gly Leu Glu Trp Val
                        35                  40                  45

Ser Ala Ile Ser Gly Gly Gly Asn Ile Tyr Tyr Ala Asp Ser Val
                    50                  55                  60

Lys Gly Arg Phe Thr Ile Ser Arg Asp Asn Ser Lys Asn Thr Leu Tyr
        65                  70                  75                  80

Leu Gln Met Asn Ser Leu Arg Ala Glu Asp Thr Ala Val Tyr Tyr Cys
                        85                  90                  95

Ala Arg Arg Pro Leu Tyr Phe Asp Tyr Trp Gly Gln Gly Thr Leu Val
                        100                 105                 110

Thr Val Ser Ser Ala Lys Thr Thr Ala Pro Ser Val Tyr Pro Leu Ala
                    115                 120                 125

Pro Val Cys Gly Asp Thr Gly Ser Ser Val Thr Leu Gly Cys Leu
                    130                 135                 140
```

-continued

```
Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Thr Ser Ser Thr Trp Pro
            180                 185                 190

Ser Gln Ser Ile Thr Cys Asn Val Ala His Pro Ala Ser Ser Thr Lys
        195                 200                 205

Val Asp Lys Lys Ile Glu Pro Arg Gly Pro Thr Ile Lys Pro Cys Pro
210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
                245                 250                 255

Ile Val Thr Cys Val Val Val Asp Val Ser Glu Asp Asp Pro Asp Val
            260                 265                 270

Gln Ile Ser Trp Phe Val Asn Asn Val Glu Val His Thr Ala Gln Thr
        275                 280                 285

Gln Thr His Arg Glu Asp Tyr Asn Ser Thr Leu Arg Val Val Ser Ala
290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335

Lys Pro Lys Gly Ser Val Arg Ala Pro Gln Val Tyr Val Leu Pro Pro
            340                 345                 350

Pro Glu Glu Glu Met Thr Lys Lys Gln Val Thr Leu Thr Cys Met Val
        355                 360                 365

Thr Asp Phe Met Pro Glu Asp Ile Tyr Val Glu Trp Thr Asn Asn Gly
370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
                405                 410                 415

Val Glu Arg Asn Ser Tyr Ser Cys Ser Val Val His Glu Gly Leu His
            420                 425                 430

Asn His His Thr Thr Lys Ser Phe Ser Arg Thr Pro Gly Lys
        435                 440                 445

<210> SEQ ID NO 120
<211> LENGTH: 446
<212> TYPE: PRT
<213> ORGANISM: Artificial Sequence
<220> FEATURE:
<223> OTHER INFORMATION: AA9 Full length heavy chain comprising mouse
      IgG2a constant region

<400> SEQUENCE: 120

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ala Ile Tyr Pro Gly Ser Ser Asn Lys Tyr Tyr Ala Asp Ser Val
50                  55                  60
```

-continued

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg His Ala Ala Thr Phe Asp Tyr Trp Gly Gln Gly Thr Leu Val
            100                 105                 110

Thr Val Ser Ser Ala Lys Thr Thr Ala Pro Ser Val Tyr Pro Leu Ala
            115                 120                 125

Pro Val Cys Gly Asp Thr Thr Gly Ser Ser Val Thr Leu Gly Cys Leu
130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Thr Ser Ser Thr Trp Pro
            180                 185                 190

Ser Gln Ser Ile Thr Cys Asn Val Ala His Pro Ala Ser Ser Thr Lys
            195                 200                 205

Val Asp Lys Lys Ile Glu Pro Arg Gly Pro Thr Ile Lys Pro Cys Pro
210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
                245                 250                 255

Ile Val Thr Cys Val Val Val Asp Val Ser Glu Asp Asp Pro Asp Val
            260                 265                 270

Gln Ile Ser Trp Phe Val Asn Asn Val Glu Val His Thr Ala Gln Thr
            275                 280                 285

Gln Thr His Arg Glu Asp Tyr Asn Ser Thr Leu Arg Val Val Ser Ala
290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335

Lys Pro Lys Gly Ser Val Arg Ala Pro Gln Val Tyr Val Leu Pro Pro
            340                 345                 350

Pro Glu Glu Glu Met Thr Lys Lys Gln Val Thr Leu Thr Cys Met Val
            355                 360                 365

Thr Asp Phe Met Pro Glu Asp Ile Tyr Val Glu Trp Thr Asn Asn Gly
370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
                405                 410                 415

Val Glu Arg Asn Ser Tyr Ser Cys Ser Val Val His Glu Gly Leu His
            420                 425                 430

Asn His His Thr Thr Lys Ser Phe Ser Arg Thr Pro Gly Lys
            435                 440                 445

<210> SEQ ID NO 121
<211> LENGTH: 457
<212> TYPE: PRT
<213> ORGANISM: Artificial Sequence
<220> FEATURE:

<223> OTHER INFORMATION: DG5 Full length heavy chain comprising mouse
     IgG2a constant region

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Val Ile Ser Pro Gly Ser Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Thr Ile Ala Cys Pro Thr Lys Arg Cys Ser Tyr Ser Asn
            100                 105                 110

Gly Met Asp Val Trp Gly Gln Gly Thr Leu Val Thr Val Ser Ser Ala
        115                 120                 125

Lys Thr Thr Ala Pro Ser Val Tyr Pro Leu Ala Pro Val Cys Gly Asp
    130                 135                 140

Thr Thr Gly Ser Ser Val Thr Leu Gly Cys Leu Val Lys Gly Tyr Phe
145                 150                 155                 160

Pro Glu Pro Val Thr Leu Thr Trp Asn Ser Gly Ser Leu Ser Ser Gly
                165                 170                 175

Val His Thr Phe Pro Ala Val Leu Gln Ser Asp Leu Tyr Thr Leu Ser
            180                 185                 190

Ser Ser Val Thr Val Thr Ser Ser Thr Trp Pro Ser Gln Ser Ile Thr
        195                 200                 205

Cys Asn Val Ala His Pro Ala Ser Ser Thr Lys Val Asp Lys Lys Ile
    210                 215                 220

Glu Pro Arg Gly Pro Thr Ile Lys Pro Cys Pro Pro Cys Lys Cys Pro
225                 230                 235                 240

Ala Pro Asn Leu Leu Gly Gly Pro Ser Val Phe Ile Phe Pro Pro Lys
                245                 250                 255

Ile Lys Asp Val Leu Met Ile Ser Leu Ser Pro Ile Val Thr Cys Val
            260                 265                 270

Val Val Asp Val Ser Glu Asp Asp Pro Asp Val Gln Ile Ser Trp Phe
        275                 280                 285

Val Asn Asn Val Glu Val His Thr Ala Gln Thr Gln Thr His Arg Glu
    290                 295                 300

Asp Tyr Asn Ser Thr Leu Arg Val Val Ser Ala Leu Pro Ile Gln His
305                 310                 315                 320

Gln Asp Trp Met Ser Gly Lys Glu Phe Lys Cys Lys Val Asn Asn Lys
                325                 330                 335

Asp Leu Pro Ala Pro Ile Glu Arg Thr Ile Ser Lys Pro Lys Gly Ser
            340                 345                 350

Val Arg Ala Pro Gln Val Tyr Val Leu Pro Pro Pro Glu Glu Glu Met
        355                 360                 365

Thr Lys Lys Gln Val Thr Leu Thr Cys Met Val Thr Asp Phe Met Pro
    370                 375                 380

Glu Asp Ile Tyr Val Glu Trp Thr Asn Asn Gly Lys Thr Glu Leu Asn
385                 390                 395                 400

Tyr Lys Asn Thr Glu Pro Val Leu Asp Ser Asp Gly Ser Tyr Phe Met
                405                 410                 415

Tyr Ser Lys Leu Arg Val Glu Lys Lys Asn Trp Val Glu Arg Asn Ser
            420                 425                 430

Tyr Ser Cys Ser Val Val His Glu Gly Leu His Asn His His Thr Thr
            435                 440                 445

Lys Ser Phe Ser Arg Thr Pro Gly Lys
        450                 455

<210> SEQ ID NO 122
<211> LENGTH: 446
<212> TYPE: PRT
<213> ORGANISM: Artificial Sequence
<220> FEATURE:
<223> OTHER INFORMATION: AD2 Full length heavy chain comprising mouse
      IgG2a constant region

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser His Ser Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Asn Asn Phe Asp Tyr Trp Gly Gln Gly Thr Leu Val
            100                 105                 110

Thr Val Ser Ser Ala Lys Thr Thr Ala Pro Ser Val Tyr Pro Leu Ala
        115                 120                 125

Pro Val Cys Gly Asp Thr Thr Gly Ser Ser Val Thr Leu Gly Cys Leu
    130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Thr Ser Ser Thr Trp Pro
            180                 185                 190

Ser Gln Ser Ile Thr Cys Asn Val Ala His Pro Ala Ser Ser Thr Lys
        195                 200                 205

Val Asp Lys Lys Ile Glu Pro Arg Gly Pro Thr Ile Lys Pro Cys Pro
    210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
                245                 250                 255

Ile Val Thr Cys Val Val Asp Val Ser Glu Asp Asp Pro Asp Val
            260                 265                 270

Gln Ile Ser Trp Phe Val Asn Asn Val Glu Val His Thr Ala Gln Thr
        275                 280                 285

Gln Thr His Arg Glu Asp Tyr Asn Ser Thr Leu Arg Val Val Ser Ala

```
                    290              295                  300
Leu Pro Ile Gln His Gln Asp Trp Met Ser Gly Lys Glu Phe Lys Cys
305                 310                  315                 320

Lys Val Asn Asn Lys Asp Leu Pro Ala Pro Ile Glu Arg Thr Ile Ser
                    325                  330                 335

Lys Pro Lys Gly Ser Val Arg Ala Pro Gln Val Tyr Val Leu Pro Pro
                340                  345                 350

Pro Glu Glu Met Thr Lys Lys Gln Val Thr Leu Thr Cys Met Val
            355                  360                 365

Thr Asp Phe Met Pro Glu Asp Ile Tyr Val Glu Trp Thr Asn Asn Gly
            370                  375                 380

Lys Thr Glu Leu Asn Tyr Lys Asn Thr Glu Pro Val Leu Asp Ser Asp
385                 390                  395                 400

Gly Ser Tyr Phe Met Tyr Ser Lys Leu Arg Val Glu Lys Lys Asn Trp
                    405                  410                 415

Val Glu Arg Asn Ser Tyr Ser Cys Ser Val Val His Glu Gly Leu His
                420                  425                 430

Asn His His Thr Thr Lys Ser Phe Ser Arg Thr Pro Gly Lys
            435                  440                 445

<210> SEQ ID NO 123
<211> LENGTH: 446
<212> TYPE: PRT
<213> ORGANISM: Artificial Sequence
<220> FEATURE:
<223> OTHER INFORMATION: AD7 Full length heavy chain comprising mouse
      IgG2a constant region

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Met Ser Trp Val Arg Gln Ala Pro Gly Lys Gly Leu Glu Trp Val
        35                  40                  45

Ser Ala Ile Ser Pro Asn Gly Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Pro Val Tyr Phe Asp Tyr Trp Gly Gln Gly Thr Leu Val
            100                 105                 110

Thr Val Ser Ser Ala Lys Thr Thr Ala Pro Ser Val Tyr Pro Leu Ala
        115                 120                 125

Pro Val Cys Gly Asp Thr Thr Gly Ser Ser Val Thr Leu Gly Cys Leu
    130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Thr Ser Ser Thr Trp Pro
            180                 185                 190

Ser Gln Ser Ile Thr Cys Asn Val Ala His Pro Ala Ser Ser Thr Lys
        195                 200                 205
```

Val Asp Lys Lys Ile Glu Pro Arg Gly Pro Thr Ile Lys Pro Cys Pro
210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
                245                 250                 255

Ile Val Thr Cys Val Val Asp Val Ser Glu Asp Pro Asp Val
                260                 265                 270

Gln Ile Ser Trp Phe Val Asn Asn Val Glu Val His Thr Ala Gln Thr
            275                 280                 285

Gln Thr His Arg Glu Asp Tyr Asn Ser Thr Leu Arg Val Val Ser Ala
        290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335

Lys Pro Lys Gly Ser Val Arg Ala Pro Gln Val Tyr Val Leu Pro Pro
            340                 345                 350

Pro Glu Glu Glu Met Thr Lys Lys Gln Val Thr Leu Thr Cys Met Val
        355                 360                 365

Thr Asp Phe Met Pro Glu Asp Ile Tyr Val Glu Trp Thr Asn Asn Gly
370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
                405                 410                 415

Val Glu Arg Asn Ser Tyr Ser Cys Ser Val Val His Glu Gly Leu His
            420                 425                 430

Asn His His Thr Thr Lys Ser Phe Ser Arg Thr Pro Gly Lys
        435                 440                 445

<210> SEQ ID NO 124
<211> LENGTH: 457
<212> TYPE: PRT
<213> ORGANISM: Artificial Sequence
<220> FEATURE:
<223> OTHER INFORMATION: DG11 Full length heavy chain comprising mouse
      IgG2a constant region

<400> SEQUENCE: 124

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Val Ile Ser Pro Gly Ser Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Thr Ile Ser Cys Ala Arg Met Arg Cys Ser Tyr Ala Asp
            100                 105                 110

Gly Met Asp Val Trp Gly Gln Gly Thr Leu Val Thr Val Ser Ser Ala
        115                 120                 125

Lys Thr Thr Ala Pro Ser Val Tyr Pro Leu Ala Pro Val Cys Gly Asp
            130                 135                 140

Thr Thr Gly Ser Ser Val Thr Leu Gly Cys Leu Val Lys Gly Tyr Phe
145                 150                 155                 160

Pro Glu Pro Val Thr Leu Thr Trp Asn Ser Gly Ser Leu Ser Ser Gly
                165                 170                 175

Val His Thr Phe Pro Ala Val Leu Gln Ser Asp Leu Tyr Thr Leu Ser
            180                 185                 190

Ser Ser Val Thr Val Thr Ser Ser Thr Trp Pro Ser Gln Ser Ile Thr
        195                 200                 205

Cys Asn Val Ala His Pro Ala Ser Ser Thr Lys Val Asp Lys Lys Ile
    210                 215                 220

Glu Pro Arg Gly Pro Thr Ile Lys Pro Cys Pro Pro Cys Lys Cys Pro
225                 230                 235                 240

Ala Pro Asn Leu Leu Gly Gly Pro Ser Val Phe Ile Phe Pro Pro Lys
                245                 250                 255

Ile Lys Asp Val Leu Met Ile Ser Leu Ser Pro Ile Val Thr Cys Val
            260                 265                 270

Val Val Asp Val Ser Glu Asp Asp Pro Asp Val Gln Ile Ser Trp Phe
        275                 280                 285

Val Asn Asn Val Glu Val His Thr Ala Gln Thr Gln Thr His Arg Glu
    290                 295                 300

Asp Tyr Asn Ser Thr Leu Arg Val Val Ser Ala Leu Pro Ile Gln His
305                 310                 315                 320

Gln Asp Trp Met Ser Gly Lys Glu Phe Lys Cys Lys Val Asn Asn Lys
                325                 330                 335

Asp Leu Pro Ala Pro Ile Glu Arg Thr Ile Ser Lys Pro Lys Gly Ser
            340                 345                 350

Val Arg Ala Pro Gln Val Tyr Val Leu Pro Pro Pro Glu Glu Glu Met
        355                 360                 365

Thr Lys Lys Gln Val Thr Leu Thr Cys Met Val Thr Asp Phe Met Pro
    370                 375                 380

Glu Asp Ile Tyr Val Glu Trp Thr Asn Asn Gly Lys Thr Glu Leu Asn
385                 390                 395                 400

Tyr Lys Asn Thr Glu Pro Val Leu Asp Ser Asp Gly Ser Tyr Phe Met
                405                 410                 415

Tyr Ser Lys Leu Arg Val Glu Lys Lys Asn Trp Val Glu Arg Asn Ser
            420                 425                 430

Tyr Ser Cys Ser Val Val His Glu Gly Leu His Asn His His Thr Thr
        435                 440                 445

Lys Ser Phe Ser Arg Thr Pro Gly Lys
    450                 455

<210> SEQ ID NO 125
<211> LENGTH: 457
<212> TYPE: PRT
<213> ORGANISM: Artificial Sequence
<220> FEATURE:
<223> OTHER INFORMATION: DG8 Full length heavy chain comprising mouse
      IgG2a constant region

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp His

-continued

```
                20                  25                  30
Ala Met Ser Trp Val Arg Gln Ala Pro Gly Lys Gly Leu Glu Trp Val
                35                  40                  45
Ser Val Ile Ser His Gly Asn Gly Ser Lys Tyr Tyr Ala Asp Ser Val
                50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Val Ala Ser Arg Cys Arg Arg Gly Arg Cys Ser Tyr Ser Asp
                100                 105                 110
Gly Met Asp Val Trp Gly Gln Gly Thr Leu Val Thr Val Ser Ser Ala
                115                 120                 125
Lys Thr Thr Ala Pro Ser Val Tyr Pro Leu Ala Pro Val Cys Gly Asp
                130                 135                 140
Thr Thr Gly Ser Ser Val Thr Leu Gly Cys Leu Val Lys Gly Tyr Phe
145                 150                 155                 160
Pro Glu Pro Val Thr Leu Thr Trp Asn Ser Gly Ser Leu Ser Ser Gly
                165                 170                 175
Val His Thr Phe Pro Ala Val Leu Gln Ser Asp Leu Tyr Thr Leu Ser
                180                 185                 190
Ser Ser Val Thr Val Thr Ser Ser Thr Trp Pro Ser Gln Ser Ile Thr
                195                 200                 205
Cys Asn Val Ala His Pro Ala Ser Ser Thr Lys Val Asp Lys Lys Ile
                210                 215                 220
Glu Pro Arg Gly Pro Thr Ile Lys Pro Cys Pro Pro Cys Lys Cys Pro
225                 230                 235                 240
Ala Pro Asn Leu Leu Gly Gly Pro Ser Val Phe Ile Phe Pro Pro Lys
                245                 250                 255
Ile Lys Asp Val Leu Met Ile Ser Leu Ser Pro Ile Val Thr Cys Val
                260                 265                 270
Val Val Asp Val Ser Glu Asp Asp Pro Asp Val Gln Ile Ser Trp Phe
                275                 280                 285
Val Asn Asn Val Glu Val His Thr Ala Gln Thr Gln Thr His Arg Glu
                290                 295                 300
Asp Tyr Asn Ser Thr Leu Arg Val Val Ser Ala Leu Pro Ile Gln His
305                 310                 315                 320
Gln Asp Trp Met Ser Gly Lys Glu Phe Lys Cys Lys Val Asn Asn Lys
                325                 330                 335
Asp Leu Pro Ala Pro Ile Glu Arg Thr Ile Ser Lys Pro Lys Gly Ser
                340                 345                 350
Val Arg Ala Pro Gln Val Tyr Val Leu Pro Pro Pro Glu Glu Glu Met
                355                 360                 365
Thr Lys Lys Gln Val Thr Leu Thr Cys Met Val Thr Asp Phe Met Pro
                370                 375                 380
Glu Asp Ile Tyr Val Glu Trp Thr Asn Asn Gly Lys Thr Glu Leu Asn
385                 390                 395                 400
Tyr Lys Asn Thr Glu Pro Val Leu Asp Ser Asp Gly Ser Tyr Phe Met
                405                 410                 415
Tyr Ser Lys Leu Arg Val Glu Lys Lys Asn Trp Val Glu Arg Asn Ser
                420                 425                 430
Tyr Ser Cys Ser Val Val His Glu Gly Leu His Asn His His Thr Thr
                435                 440                 445
```

```
Lys Ser Phe Ser Arg Thr Pro Gly Lys
    450                 455
```

<210> SEQ ID NO 126
<211> LENGTH: 457
<212> TYPE: PRT
<213> ORGANISM: Artificial Sequence
<220> FEATURE:
<223> OTHER INFORMATION: DA9 Full length heavy chain comprising mouse
      IgG2a constant region

<400> SEQUENCE: 126

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Val Ile Ser Pro Ser Asp Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Thr Leu Ser Cys Arg Ala Ser Arg Cys Ser Tyr Ser Asn
            100                 105                 110

Gly Met Asp Val Trp Gly Gln Gly Thr Leu Val Thr Val Ser Ser Ala
        115                 120                 125

Lys Thr Thr Ala Pro Ser Val Tyr Pro Leu Ala Pro Val Cys Gly Asp
    130                 135                 140

Thr Thr Gly Ser Ser Val Thr Leu Gly Cys Leu Val Lys Gly Tyr Phe
145                 150                 155                 160

Pro Glu Pro Val Thr Leu Thr Trp Asn Ser Gly Ser Leu Ser Ser Gly
                165                 170                 175

Val His Thr Phe Pro Ala Val Leu Gln Ser Asp Leu Tyr Thr Leu Ser
            180                 185                 190

Ser Ser Val Thr Val Thr Ser Ser Thr Trp Pro Ser Gln Ser Ile Thr
        195                 200                 205

Cys Asn Val Ala His Pro Ala Ser Ser Thr Lys Val Asp Lys Lys Ile
    210                 215                 220

Glu Pro Arg Gly Pro Thr Ile Lys Pro Cys Pro Pro Cys Lys Cys Pro
225                 230                 235                 240

Ala Pro Asn Leu Leu Gly Gly Pro Ser Val Phe Ile Phe Pro Pro Lys
                245                 250                 255

Ile Lys Asp Val Leu Met Ile Ser Leu Ser Pro Ile Val Thr Cys Val
            260                 265                 270

Val Val Asp Val Ser Glu Asp Asp Pro Asp Val Gln Ile Ser Trp Phe
        275                 280                 285

Val Asn Asn Val Glu Val His Thr Ala Gln Thr Gln Thr His Arg Glu
    290                 295                 300

Asp Tyr Asn Ser Thr Leu Arg Val Val Ser Ala Leu Pro Ile Gln His
305                 310                 315                 320

Gln Asp Trp Met Ser Gly Lys Glu Phe Lys Cys Lys Val Asn Asn Lys
                325                 330                 335

Asp Leu Pro Ala Pro Ile Glu Arg Thr Ile Ser Lys Pro Lys Gly Ser
```

```
            340                 345                 350
Val Arg Ala Pro Gln Val Tyr Val Leu Pro Pro Glu Glu Glu Met
            355                 360                 365

Thr Lys Lys Gln Val Thr Leu Thr Cys Met Val Thr Asp Phe Met Pro
370                 375                 380

Glu Asp Ile Tyr Val Glu Trp Thr Asn Asn Gly Lys Thr Glu Leu Asn
385                 390                 395                 400

Tyr Lys Asn Thr Glu Pro Val Leu Asp Ser Asp Gly Ser Tyr Phe Met
                405                 410                 415

Tyr Ser Lys Leu Arg Val Glu Lys Lys Asn Trp Val Glu Arg Asn Ser
                420                 425                 430

Tyr Ser Cys Ser Val Val His Glu Gly Leu His Asn His His Thr Thr
                435                 440                 445

Lys Ser Phe Ser Arg Thr Pro Gly Lys
                450                 455

<210> SEQ ID NO 127
<211> LENGTH: 445
<212> TYPE: PRT
<213> ORGANISM: Artificial Sequence
<220> FEATURE:
<223> OTHER INFORMATION: 1E4 Full length heavy chain comprising human
      IgG1 constant region

<400> SEQUENCE: 127

Glu Val Gln Leu Gln Glu Ser Gly Ala Glu Leu Val Arg Pro Gly Thr
1               5                   10                  15

Ser Val Lys Val Ser Cys Lys Ala Ser Gly Tyr Ala Phe Thr Asn Tyr
                20                  25                  30

Leu Ile Glu Trp Val Lys Gln Arg Pro Gly Gln Gly Leu Glu Trp Ile
            35                  40                  45

Gly Val Ile Asn Pro Gly Ser Gly Gly Thr Asn Tyr Asn Glu Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Ser Gly Asn Tyr Asp Thr Tyr Trp Gly Gln Gly Thr Leu Val Thr
                100                 105                 110

Val Ser Ala Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

Pro Pro Cys Pro Ala Pro Glu Leu Leu Gly Gly Pro Ser Val Phe Leu
225                 230                 235                 240
```

```
Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 128
<211> LENGTH: 446
<212> TYPE: PRT
<213> ORGANISM: Artificial Sequence
<220> FEATURE:
<223> OTHER INFORMATION: 9B11 Full length heavy chain comprising human
      IgG1 constant region

<400> SEQUENCE: 128

Glu Val Gln Leu Gln Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gln Asp Phe Asp Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 129
<211> LENGTH: 452
<212> TYPE: PRT
<213> ORGANISM: Artificial Sequence
<220> FEATURE:
<223> OTHER INFORMATION: 3A9 Full length heavy chain comprising human
      IgG1 constant region

<400> SEQUENCE: 129

Glu Val Gln Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Asn Gly Gly Gly Tyr Thr Tyr Tyr Pro Asp Ser Val
    50                  55                  60

Lys Gly Arg Phe Thr Ile Ser Arg Asp Asn Ala Lys Asn Thr Leu Tyr
```

```
            65                  70                  75                  80
        Leu Gln Met Ser Ser Leu Arg Ser Glu Asp Thr Ala Met Tyr Tyr Cys
                            85                  90                  95

Ala Arg His Ile Thr Thr Val Arg Pro Thr Lys Tyr Phe Asp Tyr Trp
                        100                 105                 110

Gly Gln Gly Thr Thr Leu Thr Val Ser Ser Ala Ser Thr Lys Gly Pro
                        115                 120                 125

Ser Val Phe Pro Leu Ala Pro Ser Ser Lys Ser Thr Ser Gly Gly Thr
                130                 135                 140

Ala Ala Leu Gly Cys Leu Val Lys Asp Tyr Phe Pro Glu Pro Val Thr
        145                 150                 155                 160

Val Ser Trp Asn Ser Gly Ala Leu Thr Ser Gly Val His Thr Phe Pro
                        165                 170                 175

Ala Val Leu Gln Ser Ser Gly Leu Tyr Ser Leu Ser Ser Val Val Thr
                        180                 185                 190

Val Pro Ser Ser Ser Leu Gly Thr Gln Thr Tyr Ile Cys Asn Val Asn
                        195                 200                 205

His Lys Pro Ser Asn Thr Lys Val Asp Lys Lys Val Glu Pro Lys Ser
                210                 215                 220

Cys Asp Lys Thr His Thr Cys Pro Pro Cys Pro Ala Pro Glu Leu Leu
        225                 230                 235                 240

Gly Gly Pro Ser Val Phe Leu Phe Pro Pro Lys Pro Lys Asp Thr Leu
                        245                 250                 255

Met Ile Ser Arg Thr Pro Glu Val Thr Cys Val Val Val Asp Val Ser
                        260                 265                 270

His Glu Asp Pro Glu Val Lys Phe Asn Trp Tyr Val Asp Gly Val Glu
                        275                 280                 285

Val His Asn Ala Lys Thr Lys Pro Arg Glu Glu Gln Tyr Asn Ser Thr
                290                 295                 300

Tyr Arg Val Val Ser Val Leu Thr Val Leu His Gln Asp Trp Leu Asn
        305                 310                 315                 320

Gly Lys Glu Tyr Lys Cys Lys Val Ser Asn Lys Ala Leu Pro Ala Pro
                        325                 330                 335

Ile Glu Lys Thr Ile Ser Lys Ala Lys Gly Gln Pro Arg Glu Pro Gln
                        340                 345                 350

Val Tyr Thr Leu Pro Pro Ser Arg Glu Glu Met Thr Lys Asn Gln Val
                        355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
        385                 390                 395                 400

Pro Val Leu Asp Ser Asp Gly Ser Phe Phe Leu Tyr Ser Lys Leu Thr
                        405                 410                 415

Val Asp Lys Ser Arg Trp Gln Gln Gly Asn Val Phe Ser Cys Ser Val
                        420                 425                 430

Met His Glu Ala Leu His Asn His Tyr Thr Gln Lys Ser Leu Ser Leu
                        435                 440                 445

Ser Pro Gly Lys
                450

<210> SEQ ID NO 130
<211> LENGTH: 443
<212> TYPE: PRT
<213> ORGANISM: Artificial Sequence
```

<220> FEATURE:
<223> OTHER INFORMATION: 10F10 Full length heavy chain comprising human
     IgG1 constant region

<400> SEQUENCE: 130

```
Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Gly Gly
            20                  25                  30

Phe Tyr Trp Asn Trp Ile Arg Gln Phe Pro Gly Asn Asn Leu Glu Trp
        35                  40                  45

Met Gly Tyr Ile Asn Tyr Asp Gly Ser Ser Asp Tyr Ser Pro Ser Leu
    50                  55                  60

Lys Asn Arg Ile Ser Ile Thr Arg Asp Thr Ser Lys Asn Gln Phe Phe
65                  70                  75                  80

Leu Asn Leu Asn Ser Val Thr Thr Glu Asp Thr Ala Thr Tyr Tyr Cys
                85                  90                  95

Val Arg Gly Asp Tyr Asp Trp Gly Gln Gly Thr Thr Leu Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
```

```
385             390             395             400
Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 131
<211> LENGTH: 450
<212> TYPE: PRT
<213> ORGANISM: Artificial Sequence
<220> FEATURE:
<223> OTHER INFORMATION: 11F11 Full length heavy chain comprising human
      IgG1 constant region

<400> SEQUENCE: 131

Glu Val Gln Leu Gln Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
            35                  40                  45

Ala Ala Ser Arg Asn Lys Ala Asn Asp Tyr Thr Thr Glu Tyr Ser Ala
50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
            85                  90                  95

Tyr Cys Ala Arg Asp Ala His Gly Lys Pro Phe Ala Tyr Trp Gly Gln
            100                 105                 110

Gly Thr Leu Val Thr Val Ser Ala Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 132
<211> LENGTH: 446
<212> TYPE: PRT
<213> ORGANISM: Artificial Sequence
<220> FEATURE:
<223> OTHER INFORMATION: Synthetic: AC8 Full length heavy chain
      comprising human IgG1 constant region

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Met Ser Trp Val Arg Gln Ala Pro Gly Lys Gly Leu Glu Trp Val
        35                  40                  45

Ser Gly Ile Ser Ser Gly Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Ile Phe His Asn Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205
```

```
Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 133
<211> LENGTH: 446
<212> TYPE: PRT
<213> ORGANISM: Artificial Sequence
<220> FEATURE:
<223> OTHER INFORMATION: Synthetic: AE8 Full length heavy chain
      comprising human IgG1 constant region

<400> SEQUENCE: 133

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Ser Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Pro Leu Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
```

```
                115                 120                 125
Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 134
<211> LENGTH: 446
<212> TYPE: PRT
<213> ORGANISM: Artificial Sequence
<220> FEATURE:
<223> OTHER INFORMATION: Synthetic: AA9 Full length heavy chain
      comprising human IgG1 constant region

<400> SEQUENCE: 134

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ser Met Ser Trp Val Arg Gln Ala Pro Gly Lys Gly Leu Glu Trp Val
         35                  40                  45
Ser Ala Ile Tyr Pro Gly Ser Ser Asn Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
             85                  90                  95
Ala Arg His Ala Ala Thr Phe Asp Tyr Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Lys Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445
```

<210> SEQ ID NO 135
<211> LENGTH: 457
<212> TYPE: PRT
<213> ORGANISM: Artificial Sequence
<220> FEATURE:
<223> OTHER INFORMATION: Synthetic: DG5 Full length heavy chain comprising human IgG1 constant region

<400> SEQUENCE: 135

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Val Ile Ser Pro Gly Ser Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Thr Ile Ala Cys Pro Thr Lys Arg Cys Ser Tyr Ser Asn
            100                 105                 110

Gly Met Asp Val Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365
```

```
Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 136
<211> LENGTH: 446
<212> TYPE: PRT
<213> ORGANISM: Artificial Sequence
<220> FEATURE:
<223> OTHER INFORMATION: Synthetic: AD2 Full length heavy chain
      comprising human IgG1 constant region

<400> SEQUENCE: 136

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser His Ser Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Asn Asn Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

```
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
        290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 137
<211> LENGTH: 446
<212> TYPE: PRT
<213> ORGANISM: Artificial Sequence
<220> FEATURE:
<223> OTHER INFORMATION: Synthetic: AD7 Full length heavy chain
      comprising human IgG1 constant region

<400> SEQUENCE: 137

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Gly Tyr
            20                  25                  30
Ala Met Ser Trp Val Arg Gln Ala Pro Gly Lys Gly Leu Glu Trp Val
        35                  40                  45
Ser Ala Ile Ser Pro Asn Gly Gly Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Arg Pro Val Tyr Phe Asp Tyr Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
```

```
                    180                 185                 190
Gly Thr Gln Thr Tyr Ile Cys Asn Val Asn His Lys Pro Ser Asn Thr
                195                 200                 205
Lys Val Asp Lys Lys Val Glu Pro Lys Ser Cys Asp Lys Thr His Thr
                210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
                260                 265                 270
Lys Phe Asn Trp Tyr Val Asp Gly Val Glu Val His Asn Ala Lys Thr
                275                 280                 285
Lys Pro Arg Glu Glu Gln Tyr Asn Ser Thr Tyr Arg Val Val Ser Val
                290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
                340                 345                 350
Ser Arg Glu Glu Met Thr Lys Asn Gln Val Ser Leu Thr Cys Leu Val
                355                 360                 365
Lys Gly Phe Tyr Pro Ser Asp Ile Ala Val Glu Trp Glu Ser Asn Gly
                370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
                420                 425                 430
Asn His Tyr Thr Gln Lys Ser Leu Ser Leu Ser Pro Gly Lys
                435                 440                 445

<210> SEQ ID NO 138
<211> LENGTH: 457
<212> TYPE: PRT
<213> ORGANISM: Artificial Sequence
<220> FEATURE:
<223> OTHER INFORMATION: Synthetic: DG11 Full length heavy chain
      comprising human IgG1 constant region

<400> SEQUENCE: 138

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Asp Tyr
                20                  25                  30
Ala Met Ser Trp Val Arg Gln Ala Pro Gly Lys Gly Leu Glu Trp Val
                35                  40                  45
Ser Val Ile Ser Pro Gly Ser Gly Ser Lys Tyr Tyr Ala Asp Ser Val
                50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
```

-continued

```
Ala Lys Val Thr Ile Ser Cys Ala Arg Met Arg Cys Ser Tyr Ala Asp
            100                 105                 110

Gly Met Asp Val Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 139
<211> LENGTH: 457
<212> TYPE: PRT
<213> ORGANISM: Artificial Sequence
<220> FEATURE:
<223> OTHER INFORMATION: Synthetic: DG8 Full length heavy chain
      comprising human IgG1 constant region

<400> SEQUENCE: 139
```

```
Glu Val Gln Leu Leu Glu Ser Gly Gly Gly Leu Val Gln Pro Gly Gly
 1               5                  10                 15

Ser Leu Arg Leu Ser Cys Ala Ala Ser Gly Phe Thr Phe Ser Asp His
             20                  25                  30

Ala Met Ser Trp Val Arg Gln Ala Pro Gly Lys Gly Leu Glu Trp Val
         35                  40                  45

Ser Val Ile Ser His Gly Asn Gly Ser Lys Tyr Tyr Ala Asp Ser Val
 50                  55                  60

Lys Gly Arg Phe Thr Ile Ser Arg Asp Asn Ser Lys Asn Thr Leu Tyr
 65              70                  75                  80

Leu Gln Met Asn Ser Leu Arg Ala Glu Asp Thr Ala Val Tyr Tyr Cys
             85                  90                  95

Ala Arg Val Ala Ser Arg Cys Arg Arg Gly Arg Cys Ser Tyr Ser Asp
             100                 105                 110

Gly Met Asp Val Trp Gly Gln Gly Thr Leu Val Thr Val Ser Ser Ala
         115                 120                 125

Ser Thr Lys Gly Pro Ser Val Phe Pro Leu Ala Pro Ser Ser Lys Ser
 130                 135                 140

Thr Ser Gly Gly Thr Ala Ala Leu Gly Cys Leu Val Lys Asp Tyr Phe
 145                 150                 155                 160

Pro Glu Pro Val Thr Val Ser Trp Asn Ser Gly Ala Leu Thr Ser Gly
                 165                 170                 175

Val His Thr Phe Pro Ala Val Leu Gln Ser Ser Gly Leu Tyr Ser Leu
             180                 185                 190

Ser Ser Val Val Thr Val Pro Ser Ser Ser Leu Gly Thr Gln Thr Tyr
             195                 200                 205

Ile Cys Asn Val Asn His Lys Pro Ser Asn Thr Lys Val Asp Lys Lys
 210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
             245                 250                 255

Pro Lys Asp Thr Leu Met Ile Ser Arg Thr Pro Glu Val Thr Cys Val
             260                 265                 270

Val Val Asp Val Ser His Glu Asp Pro Glu Val Lys Phe Asn Trp Tyr
             275                 280                 285

Val Asp Gly Val Glu Val His Asn Ala Lys Thr Lys Pro Arg Glu Glu
 290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
             325                 330                 335

Ala Leu Pro Ala Pro Ile Glu Lys Thr Ile Ser Lys Ala Lys Gly Gln
             340                 345                 350

Pro Arg Glu Pro Gln Val Tyr Thr Leu Pro Pro Ser Arg Glu Glu Met
             355                 360                 365

Thr Lys Asn Gln Val Ser Leu Thr Cys Leu Val Lys Gly Phe Tyr Pro
 370                 375                 380

Ser Asp Ile Ala Val Glu Trp Glu Ser Asn Gly Gln Pro Glu Asn Asn
 385                 390                 395                 400

Tyr Lys Thr Thr Pro Pro Val Leu Asp Ser Asp Gly Ser Phe Phe Leu
             405                 410                 415
```

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 140
<211> LENGTH: 457
<212> TYPE: PRT
<213> ORGANISM: Artificial Sequence
<220> FEATURE:
<223> OTHER INFORMATION: Synthetic: DA9 Full length heavy chain
      comprising human IgG1 constant region

<400> SEQUENCE: 140

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Val Ile Ser Pro Ser Asp Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Thr Leu Ser Cys Arg Ala Ser Arg Cys Ser Tyr Ser Asn
            100                 105                 110

Gly Met Asp Val Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
                340                 345                 350

Pro Arg Glu Pro Gln Val Tyr Thr Leu Pro Pro Ser Arg Glu Glu Met
                355                 360                 365

Thr Lys Asn Gln Val Ser Leu Thr Cys Leu Val Lys Gly Phe Tyr Pro
            370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
                420                 425                 430

Phe Ser Cys Ser Val Met His Glu Ala Leu His Asn His Tyr Thr Gln
                435                 440                 445

Lys Ser Leu Ser Leu Ser Pro Gly Lys
                450                 455

<210> SEQ ID NO 141
<211> LENGTH: 218
<212> TYPE: PRT
<213> ORGANISM: Artificial Sequence
<220> FEATURE:
<223> OTHER INFORMATION: Synthetic: 1E4 Full length light chain
      comprising mous kappa constant region

<400> SEQUENCE: 141

Asp Ile Val Met Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Arg Thr Phe Gly Gly Gly Thr Lys Leu Glu Ile Lys
                100                 105                 110

Ala Asp Ala Ala Pro Thr Val Ser Ile Phe Pro Pro Ser Ser Glu Gln
            115                 120                 125

Leu Thr Ser Gly Gly Ala Ser Val Val Cys Phe Leu Asn Asn Phe Tyr
        130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
                180                 185                 190

His Asn Ser Tyr Thr Cys Glu Ala Thr His Lys Thr Ser Thr Ser Pro
            195                 200                 205

Ile Val Lys Ser Phe Asn Arg Asn Glu Cys
        210                 215

<210> SEQ ID NO 142
<211> LENGTH: 218
<212> TYPE: PRT
<213> ORGANISM: Artificial Sequence
<220> FEATURE:
<223> OTHER INFORMATION: Synthetic: 9B11 Full length light chain
      comprising mous kappa constant region

<400> SEQUENCE: 142

Asp Ile Val Met Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Gln Lys
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 143
<211> LENGTH: 213
<212> TYPE: PRT
<213> ORGANISM: Artificial Sequence
<220> FEATURE:
<223> OTHER INFORMATION: Synthetic: 3A9 Full length light chain
      comprising mous kappa constant region

<400> SEQUENCE: 143

Asp Ile Val Met Thr Gln Ser Pro Lys Phe Met Ser Thr Ser Val Gly
1               5                   10                  15

Asp Arg Val Ser Ile Thr Cys Lys Ala Ser Gln Asn Val Gly Thr Thr
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser

```
                65                  70                  75                  80
Glu Asp Leu Ala Asp Tyr Phe Cys Gln Gln Tyr Ser Asn Tyr Pro Leu
                    85                  90                  95

Thr Phe Gly Ala Gly Thr Lys Leu Glu Leu Arg Ala Asp Ala Ala Pro
                100                 105                 110

Thr Val Ser Ile Phe Pro Pro Ser Glu Gln Leu Thr Ser Gly Gly
                115                 120                 125

Ala Ser Val Val Cys Phe Leu Asn Asn Phe Tyr Pro Lys Asp Ile Asn
            130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                    165                 170                 175

Thr Leu Thr Leu Thr Lys Asp Glu Tyr Glu Arg His Asn Ser Tyr Thr
                180                 185                 190

Cys Glu Ala Thr His Lys Thr Ser Thr Ser Pro Ile Val Lys Ser Phe
                195                 200                 205

Asn Arg Asn Glu Cys
            210
```

<210> SEQ ID NO 144
<211> LENGTH: 218
<212> TYPE: PRT
<213> ORGANISM: Artificial Sequence
<220> FEATURE:
<223> OTHER INFORMATION: Synthetic: 10F10 Full length light chain
      comprising mous kappa constant region

<400> SEQUENCE: 144

```
Asp Ile Val Met Thr Gln Ser Pro Leu Thr Leu Ser Val Thr Ile Gly
1               5                   10                  15

Gln Pro Ala Ser Ile Ser Cys Lys Ser Ser Gln Ser Leu Leu Asp Ser
                20                  25                  30

Asp Gly Glu Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                    85                  90                  95

Thr His Phe Pro Gln Thr Phe Gly Gly Gly Thr Lys Leu Glu Ile Lys
                100                 105                 110

Ala Asp Ala Ala Pro Thr Val Ser Ile Phe Pro Pro Ser Ser Glu Gln
            115                 120                 125

Leu Thr Ser Gly Gly Ala Ser Val Val Cys Phe Leu Asn Asn Phe Tyr
        130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                    165                 170                 175

Tyr Ser Met Ser Ser Thr Leu Thr Leu Thr Lys Asp Glu Tyr Glu Arg
                180                 185                 190

His Asn Ser Tyr Thr Cys Glu Ala Thr His Lys Thr Ser Thr Ser Pro
            195                 200                 205
```

Ile Val Lys Ser Phe Asn Arg Asn Glu Cys
    210                    215

<210> SEQ ID NO 145
<211> LENGTH: 219
<212> TYPE: PRT
<213> ORGANISM: Artificial Sequence
<220> FEATURE:
<223> OTHER INFORMATION: Synthetic: 11F11 Full length light chain
     comprising mous kappa constant region

<400> SEQUENCE: 145

Asp Ile Val Met Thr Gln Ser Pro Ser Ser Leu Ala Val Ser Val Gly
1                5                    10                 15

Glu Lys Val Thr Met Ser Cys Lys Ser Ser Gln Ser Leu Leu Tyr Ser
              20                 25               30

Ser Asn Gln Lys Asn Tyr Leu Ala Trp Tyr Gln Lys Pro Gly Gln
        35                   40                 45

Ser Pro Lys Leu Leu Ile Tyr Trp Ala Ser Thr Arg Glu Ser Gly Val
50                    55                    60

Pro Asp Arg Phe Thr Gly Ser Gly Ser Gly Thr Asp Phe Thr Leu Thr
65                   70                    75                 80

Ile Ser Ser Val Lys Ala Glu Asp Leu Ala Val Tyr Tyr Cys Gln Gln
              85                 90               95

Tyr Tyr Ser Tyr Pro Trp Thr Phe Gly Gly Gly Thr Lys Leu Glu Ile
             100                105             110

Lys Ala Asp Ala Ala Pro Thr Val Ser Ile Phe Pro Pro Ser Ser Glu
            115                120             125

Gln Leu Thr Ser Gly Gly Ala Ser Val Val Cys Phe Leu Asn Asn Phe
        130                  135             140

Tyr Pro Lys Asp Ile Asn Val Lys Trp Lys Ile Asp Gly Ser Glu Arg
145                  150                155             160

Gln Asn Gly Val Leu Asn Ser Trp Thr Asp Gln Asp Ser Lys Asp Ser
               165                170             175

Thr Tyr Ser Met Ser Ser Thr Leu Thr Leu Thr Lys Asp Glu Tyr Glu
            180                185             190

Arg His Asn Ser Tyr Thr Cys Glu Ala Thr His Lys Thr Ser Thr Ser
        195                  200             205

Pro Ile Val Lys Ser Phe Asn Arg Asn Glu Cys
    210                    215

<210> SEQ ID NO 146
<211> LENGTH: 217
<212> TYPE: PRT
<213> ORGANISM: Artificial Sequence
<220> FEATURE:
<223> OTHER INFORMATION: AC8 Full length light chain comprising mous
     kappa constant region

<400> SEQUENCE: 146

Gln Ser Val Leu Thr Gln Pro Pro Ser Ala Ser Gly Thr Pro Gly Gln
1                5                    10                 15

Arg Val Thr Ile Ser Cys Ser Gly Ser Ser Ser Asn Ile Gly Ser Asn
              20                 25               30

Asn Val Tyr Trp Tyr Gln Gln Leu Pro Gly Thr Ala Pro Lys Leu Leu
        35                   40                 45

Ile Tyr Tyr Asp Ser Gln Arg Pro Ser Gly Val Pro Asp Arg Phe Ser
50                    55                    60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Ala Ser Leu
                85                  90                  95

Ser Ala Tyr Val Phe Gly Gly Gly Thr Lys Leu Thr Val Leu Gly Ala
            100                 105                 110

Asp Ala Ala Pro Thr Val Ser Ile Phe Pro Pro Ser Ser Glu Gln Leu
            115                 120                 125

Thr Ser Gly Gly Ala Ser Val Val Cys Phe Leu Asn Asn Phe Tyr Pro
        130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215

<210> SEQ ID NO 147
<211> LENGTH: 217
<212> TYPE: PRT
<213> ORGANISM: Artificial Sequence
<220> FEATURE:
<223> OTHER INFORMATION: AE8 Full length light chain comprising mous
      kappa constant region

<400> SEQUENCE: 147

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Ser Val Asn Trp Tyr Gln Gln Leu Pro Gly Thr Ala Pro Lys Leu Leu
        35                  40                  45

Ile Tyr Ala Asn Asn Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Gly Tyr Val Phe Gly Gly Gly Thr Lys Leu Thr Val Leu Gly Ala
            100                 105                 110

Asp Ala Ala Pro Thr Val Ser Ile Phe Pro Pro Ser Ser Glu Gln Leu
            115                 120                 125

Thr Ser Gly Gly Ala Ser Val Val Cys Phe Leu Asn Asn Phe Tyr Pro
        130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215

<210> SEQ ID NO 148
<211> LENGTH: 217
<212> TYPE: PRT
<213> ORGANISM: Artificial Sequence
<220> FEATURE:
<223> OTHER INFORMATION: AA9 Full length light chain comprising mous
      kappa constant region

<400> SEQUENCE: 148

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Gly Asp Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Leu
                85                  90                  95

Ser Gly Tyr Val Phe Gly Gly Thr Lys Leu Thr Val Leu Gly Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215

<210> SEQ ID NO 149
<211> LENGTH: 217
<212> TYPE: PRT
<213> ORGANISM: Artificial Sequence
<220> FEATURE:
<223> OTHER INFORMATION: DG5 Full length light chain comprising mous
      kappa constant region

<400> SEQUENCE: 149

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ala Val Ser Trp Tyr Gln Gln Leu Pro Gly Thr Ala Pro Lys Leu Leu
        35                  40                  45

Ile Tyr Ser Asn Ser Asn Arg Pro Ser Gly Val Pro Asp Arg Phe Ser
    50                  55                  60

```
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Ala Ser Leu
                 85                  90                  95

Ser Gly Tyr Val Phe Gly Gly Gly Thr Lys Leu Thr Val Leu Gly Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215

<210> SEQ ID NO 150
<211> LENGTH: 217
<212> TYPE: PRT
<213> ORGANISM: Artificial Sequence
<220> FEATURE:
<223> OTHER INFORMATION: AD2 Full length light chain comprising mous
      kappa constant region

<400> SEQUENCE: 150

Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Asn Asn
                20                  25                  30

Ser Val Ser Trp Tyr Gln Gln Leu Pro Gly Thr Ala Pro Lys Leu Leu
            35                  40                  45

Ile Tyr Ser Asp Asn Asn Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Ala Ser Leu
                 85                  90                  95

Ser Gly Tyr Val Phe Gly Gly Gly Thr Lys Leu Thr Val Leu Gly Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
```

```
                195                 200                 205
Val Lys Ser Phe Asn Arg Asn Glu Cys
    210                 215

<210> SEQ ID NO 151
<211> LENGTH: 217
<212> TYPE: PRT
<213> ORGANISM: Artificial Sequence
<220> FEATURE:
<223> OTHER INFORMATION: AD7 Full length light chain comprising mous
      kappa constant region

<400> SEQUENCE: 151

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
                20                  25                  30

Ala Val Asn Trp Tyr Gln Gln Leu Pro Gly Thr Ala Pro Lys Leu Leu
            35                  40                  45

Ile Tyr Ser Asn Asn His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Asn Gly Tyr Val Phe Gly Gly Gly Thr Lys Leu Thr Val Leu Gly Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215

<210> SEQ ID NO 152
<211> LENGTH: 217
<212> TYPE: PRT
<213> ORGANISM: Artificial Sequence
<220> FEATURE:
<223> OTHER INFORMATION: DG11 Full length light chain comprising mous
      kappa constant region

<400> SEQUENCE: 152

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
                20                  25                  30

Ser Val Ser Trp Tyr Gln Gln Leu Pro Gly Thr Ala Pro Lys Leu Leu
            35                  40                  45

Ile Tyr Ala Asn Ser Asn Arg Pro Ser Gly Val Pro Asp Arg Phe Ser
```

```
            50                  55                  60
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Ala Ser Leu
                 85                  90                  95

Ser Ala Tyr Val Phe Gly Gly Gly Thr Lys Leu Thr Val Leu Gly Ala
            100                 105                 110

Asp Ala Ala Pro Thr Val Ser Ile Phe Pro Pro Ser Ser Glu Gln Leu
            115                 120                 125

Thr Ser Gly Gly Ala Ser Val Val Cys Phe Leu Asn Asn Phe Tyr Pro
        130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
            195                 200                 205

Val Lys Ser Phe Asn Arg Asn Glu Cys
            210                 215

<210> SEQ ID NO 153
<211> LENGTH: 217
<212> TYPE: PRT
<213> ORGANISM: Artificial Sequence
<220> FEATURE:
<223> OTHER INFORMATION: DG8 Full length light chain comprising mous
      kappa constant region

<400> SEQUENCE: 153

Gln Ser Val Leu Thr Gln Pro Pro Ser Ala Ser Gly Thr Pro Gly Gln
  1               5                  10                  15

Arg Val Thr Ile Ser Cys Ser Gly Ser Ser Asn Ile Gly Ser Asn
             20                  25                  30

Ser Val Ser Trp Tyr Gln Gln Leu Pro Gly Thr Ala Pro Lys Leu Leu
         35                  40                  45

Ile Tyr Ala Asn Asn Asn Arg Pro Ser Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ala Trp Asp Ser Ser Leu
                 85                  90                  95

Ser Ala Tyr Val Phe Gly Gly Gly Thr Lys Leu Thr Val Leu Gly Ala
            100                 105                 110

Asp Ala Ala Pro Thr Val Ser Ile Phe Pro Pro Ser Ser Glu Gln Leu
            115                 120                 125

Thr Ser Gly Gly Ala Ser Val Val Cys Phe Leu Asn Asn Phe Tyr Pro
        130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190
```

```
Asn Ser Tyr Thr Cys Glu Ala Thr His Lys Thr Ser Thr Ser Pro Ile
        195                 200                 205

Val Lys Ser Phe Asn Arg Asn Glu Cys
        210                 215
```

<210> SEQ ID NO 154
<211> LENGTH: 217
<212> TYPE: PRT
<213> ORGANISM: Artificial Sequence
<220> FEATURE:
<223> OTHER INFORMATION: DA9 Full length light chain comprising mous
      kappa constant region

<400> SEQUENCE: 154

```
Gln Ser Val Leu Thr Gln Pro Pro Ser Ala Ser Gly Thr Pro Gly Gln
1               5                   10                  15

Arg Val Thr Ile Ser Cys Ser Gly Ser Pro Ser Asn Ile Gly Asn Asn
                20                  25                  30

Ser Val Ser Trp Tyr Gln Gln Leu Pro Gly Thr Ala Pro Lys Leu Leu
            35                  40                  45

Ile Tyr Ala Asn Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Gly Tyr Val Phe Gly Gly Gly Thr Lys Leu Thr Val Leu Gly Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
        210                 215
```

<210> SEQ ID NO 155
<211> LENGTH: 219
<212> TYPE: PRT
<213> ORGANISM: Artificial Sequence
<220> FEATURE:
<223> OTHER INFORMATION: 1E4 Full length light chain comprising human
      kappa constant region

<400> SEQUENCE: 155

```
Asp Ile Val Met Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45
```

```
Pro Lys Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Arg Thr Phe Gly Gly Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
210                 215

<210> SEQ ID NO 156
<211> LENGTH: 219
<212> TYPE: PRT
<213> ORGANISM: Artificial Sequence
<220> FEATURE:
<223> OTHER INFORMATION: 9B11 Full length light chain comprising human
      kappa constant region

<400> SEQUENCE: 156

Asp Ile Val Met Thr Gln Ser Pro Leu Ser Leu Pro Val Ser Leu Gly
 1               5                  10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Leu Thr Phe Gly Ala Gly Thr Lys Leu Glu Gln Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190
```

```
Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215
```

<210> SEQ ID NO 157
<211> LENGTH: 214
<212> TYPE: PRT
<213> ORGANISM: Artificial Sequence
<220> FEATURE:
<223> OTHER INFORMATION: 3A9 Full length light chain comprising human
      kappa constant region

<400> SEQUENCE: 157

```
Asp Ile Val Met Thr Gln Ser Pro Lys Phe Met Ser Thr Ser Val Gly
1               5                   10                  15

Asp Arg Val Ser Ile Thr Cys Lys Ala Ser Gln Asn Val Gly Thr Thr
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Asn Tyr Pro Leu
                85                  90                  95

Thr Phe Gly Ala Gly Thr Lys Leu Glu Leu Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 158
<211> LENGTH: 219
<212> TYPE: PRT
<213> ORGANISM: Artificial Sequence
<220> FEATURE:
<223> OTHER INFORMATION: 10F10 Full length light chain comprising human
      kappa constant region

<400> SEQUENCE: 158

```
Asp Ile Val Met Thr Gln Ser Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Glu Thr Tyr Leu Asn Trp Leu Leu Gln Arg Pro Gly Gln Ser
        35                  40                  45
```

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 159
<211> LENGTH: 220
<212> TYPE: PRT
<213> ORGANISM: Artificial Sequence
<220> FEATURE:
<223> OTHER INFORMATION: 11F11 Full length light chain comprising human
      kappa constant region

<400> SEQUENCE: 159

Asp Ile Val Met Thr Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Trp Thr Phe Gly Gly Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr

```
                   180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220

<210> SEQ ID NO 160
<211> LENGTH: 218
<212> TYPE: PRT
<213> ORGANISM: Artificial Sequence
<220> FEATURE:
<223> OTHER INFORMATION: Synthetic: AC8 Full length light chain
      comprising human kappa constant region

<400> SEQUENCE: 160

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Asn Val Tyr Trp Tyr Gln Gln Leu Pro Gly Thr Ala Pro Lys Leu Leu
        35                  40                  45

Ile Tyr Tyr Asp Ser Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Ala Ser Leu
                85                  90                  95

Ser Ala Tyr Val Phe Gly Gly Gly Thr Lys Leu Thr Val Leu Gly Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 161
<211> LENGTH: 218
<212> TYPE: PRT
<213> ORGANISM: Artificial Sequence
<220> FEATURE:
<223> OTHER INFORMATION: Synthetic: AE8 Full length light chain
      comprising human kappa constant region

<400> SEQUENCE: 161

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Ser Val Asn Trp Tyr Gln Gln Leu Pro Gly Thr Ala Pro Lys Leu Leu
```

Ile Tyr Ala Asn Asn Arg Pro Ser Gly Val Pro Asp Arg Phe Ser
        50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Ala Ser Leu
                85                  90                  95

Asn Gly Tyr Val Phe Gly Gly Gly Thr Lys Leu Thr Val Leu Gly Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 162
<211> LENGTH: 218
<212> TYPE: PRT
<213> ORGANISM: Artificial Sequence
<220> FEATURE:
<223> OTHER INFORMATION: Synthetic: AA9 Full length light chain
      comprising human kappa constant region

<400> SEQUENCE: 162

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
                20                  25                  30

Tyr Val Ser Trp Tyr Gln Gln Leu Pro Gly Thr Ala Pro Lys Leu Leu
            35                  40                  45

Ile Tyr Gly Asp Asn Lys Arg Pro Ser Gly Val Pro Asp Arg Phe Ser
        50                  55                  60

Gly Ser Lys Ser Gly Thr Ser Ala Ser Leu Ala Ile Ser Gly Leu Arg
 65                 70                  75                  80

Ser Glu Asp Glu Ala Asp Tyr Tyr Cys Gly Ala Trp Asp Asp Ser Leu
                85                  90                  95

Ser Gly Tyr Val Phe Gly Gly Gly Thr Lys Leu Thr Val Leu Gly Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 163
<211> LENGTH: 218
<212> TYPE: PRT
<213> ORGANISM: Artificial Sequence
<220> FEATURE:
<223> OTHER INFORMATION: Synthetic: DG5 Full length light chain
      comprising human kappa constant region

<400> SEQUENCE: 163

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ala Val Ser Trp Tyr Gln Gln Leu Pro Gly Thr Ala Pro Lys Leu Leu
        35                  40                  45

Ile Tyr Ser Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ala Ser Leu
                85                  90                  95

Ser Gly Tyr Val Phe Gly Gly Gly Thr Lys Leu Thr Val Leu Gly Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 164
<211> LENGTH: 218
<212> TYPE: PRT
<213> ORGANISM: Artificial Sequence
<220> FEATURE:
<223> OTHER INFORMATION: Synthetic: AD2 Full length light chain
      comprising human kappa constant region

<400> SEQUENCE: 164

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

```
Ser Val Ser Trp Tyr Gln Gln Leu Pro Gly Thr Ala Pro Lys Leu Leu
        35                  40                  45

Ile Tyr Ser Asp Asn Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Ala Ser Leu
                 85                  90                  95

Ser Gly Tyr Val Phe Gly Gly Gly Thr Lys Leu Thr Val Leu Gly Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 165
<211> LENGTH: 218
<212> TYPE: PRT
<213> ORGANISM: Artificial Sequence
<220> FEATURE:
<223> OTHER INFORMATION: Synthetic: AD7 Full length light chain
      comprising human kappa constant region

<400> SEQUENCE: 165

Gln Ser Val Leu Thr Gln Pro Pro Ser Ala Ser Gly Thr Pro Gly Gln
 1               5                  10                  15

Arg Val Thr Ile Ser Cys Thr Gly Ser Ser Asn Ile Gly Ser Asn
                20                  25                  30

Ala Val Asn Trp Tyr Gln Gln Leu Pro Gly Thr Ala Pro Lys Leu Leu
            35                  40                  45

Ile Tyr Ser Asn Asn His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ala Trp Asp Ser Ser Leu
                 85                  90                  95

Asn Gly Tyr Val Phe Gly Gly Gly Thr Lys Leu Thr Val Leu Gly Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175
```

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 166
<211> LENGTH: 218
<212> TYPE: PRT
<213> ORGANISM: Artificial Sequence
<220> FEATURE:
<223> OTHER INFORMATION: Synthetic: DG11 Full length light chain
      comprising human kappa constant region

<400> SEQUENCE: 166

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Ala Asn Ser Asn Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ala Ser Leu
                85                  90                  95

Ser Ala Tyr Val Phe Gly Gly Gly Thr Lys Leu Thr Val Leu Gly Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 167
<211> LENGTH: 218
<212> TYPE: PRT
<213> ORGANISM: Artificial Sequence
<220> FEATURE:
<223> OTHER INFORMATION: Synthetic: DG8 Full length light chain
      comprising human kappa constant region

<400> SEQUENCE: 167

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ser Val Ser Trp Tyr Gln Gln Leu Pro Gly Thr Ala Pro Lys Leu Leu
            35                  40                  45

Ile Tyr Ala Asn Asn Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ala Trp Asp Ser Ser Leu
                     85                  90                  95

Ser Ala Tyr Val Phe Gly Gly Gly Thr Lys Leu Thr Val Leu Gly Arg
                 100                 105                 110

Thr Val Ala Ala Pro Ser Val Phe Ile Phe Pro Pro Ser Asp Glu Gln
             115                 120                 125

Leu Lys Ser Gly Thr Ala Ser Val Val Cys Leu Leu Asn Asn Phe Tyr
         130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                 165                 170                 175

Tyr Ser Leu Ser Ser Thr Leu Thr Leu Ser Lys Ala Asp Tyr Glu Lys
             180                 185                 190

His Lys Val Tyr Ala Cys Glu Val Thr His Gln Gly Leu Ser Ser Pro
         195                 200                 205

Val Thr Lys Ser Phe Asn Arg Gly Glu Cys
     210                 215

<210> SEQ ID NO 168
<211> LENGTH: 218
<212> TYPE: PRT
<213> ORGANISM: Artificial Sequence
<220> FEATURE:
<223> OTHER INFORMATION: Synthetic: DA9 Full length light chain
      comprising human kappa constant region

<400> SEQUENCE: 168

Gln Ser Val Leu Thr Gln Pro Pro Ser Ala Ser Gly Thr Pro Gly Gln
1               5                   10                  15

Arg Val Thr Ile Ser Cys Ser Gly Ser Pro Ser Asn Ile Gly Asn Asn
             20                  25                  30

Ser Val Ser Trp Tyr Gln Gln Leu Pro Gly Thr Ala Pro Lys Leu Leu
         35                  40                  45

Ile Tyr Ala Asn Ser His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Ala Ser Leu
                     85                  90                  95

Asn Gly Tyr Val Phe Gly Gly Gly Thr Lys Leu Thr Val Leu Gly Arg
                 100                 105                 110

Thr Val Ala Ala Pro Ser Val Phe Ile Phe Pro Pro Ser Asp Glu Gln
             115                 120                 125

Leu Lys Ser Gly Thr Ala Ser Val Val Cys Leu Leu Asn Asn Phe Tyr
         130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr 165                 170                 175
Tyr Ser Leu Ser Ser Thr Leu Thr Leu Ser Lys Ala Asp Tyr Glu Lys
        180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 169
<211> LENGTH: 1335
<212> TYPE: DNA
<213> ORGANISM: Artificial Sequence
<220> FEATURE:
<223> OTHER INFORMATION: Synthetic: 1E4 Heavy chain comprising Mouse
      IgG2a constant region

<400> SEQUENCE: 169
gaagttcagc tgcaagaatc tggcgccgaa ctcgtgcgac ctggcacctc tgtgaaagtg      60
tcttgcaagg cctctggcta cgccttcacc aactacctga tcgagtgggt caagcagagg     120
cctggacagg gacttgagtg gatcggagtg atcaatcctg gctccggcgg caccaattac     180
aacgagaagt tcaagggcaa agctaccctg accgccgaca gtcctcttc accgcttac     240 atgcagctgt ccagcctgac ctctgacgac tctgccgtgt acttctgcgc ctctggcaac     300
tacgatacct attggggcca gggcaccctg gtcacagtgt ctgctgccaa gaccaccgcc     360
cccagcgtgt accccctggc cccgtgtgc ggcgacacca ccggcagcag cgtgaccctg     420
ggctgcctgg tgaagggcta cttccccgag cccgtgaccc tgacctggaa cagcggcagc     480
ctgagcagcg gcgtgcacac cttccccgcc gtgctgcaga gcgacctgta caccctgagc     540
agcagcgtga ccgtgaccag cagcacctgg cccagccaga gcatcacctg caacgtggcc     600
caccccgcca gcagcaccaa ggtggacaag aagatcgagc cagaggccc caccatcaag     660 ccctgccccc ctgcaagtg ccccgccccc aacctgctgg gcgcccccag cgtgttcatc     720
ttccccccca agatcaagga cgtgctgatg atcagcctga gcccatcgt gacctgcgtg     780 gtggtggacg tgagcgagga cgaccccgac gtgcagatca gctggttcgt gaacaacgtg     840
gaggtgcaca ccgcccagac ccagacccac agagaggact acaacagcac cctgagagtg     900
gtgagcgccc tgcccatcca gcaccaggac tggatgagcg gcaaggagtt caagtgcaag     960
gtgaacaaca aggacctgcc cgcccccatc gagagaacca tcagcaagcc caagggcagc    1020
gtgagagccc cccaggtgta cgtgctgccc ccccccgagg aggagatgac caagaagcag    1080
gtgaccctga cctgcatggt gaccgacttc atgcccgagg acatctacgt ggagtggacc    1140
aacaacggca agaccgagct gaactacaag aacaccgagc ccgtgctgga cagcgacggc    1200
agctacttca tgtacagcaa gctgagagtg gagaagaaga ctgggtggga gaaacagc     1260 tacagctgca gcgtggtgca cgagggcctg cacaaccacc acaccaccaa gagcttcagc    1320
agaacccccg gcaag                                                    1335

<210> SEQ ID NO 170
<211> LENGTH: 1338
<212> TYPE: DNA
<213> ORGANISM: Artificial Sequence
<220> FEATURE:
<223> OTHER INFORMATION: Synthetic: 9B11 Heavy chain comprising Mouse
      IgG2a constant region

<400> SEQUENCE: 170

```
gaagttcagc tgcaagaatc tggcggcgga ctggtgcagc taagggatc tctgaagctg      60 tcttgtgccg cctccggctt caccttcaac acctacgcca tgaactgggt ccgacaggct     120
cctggcaaag gactggaatg ggtcgcccgg atcagatcca agtctaacaa ctacgccacc     180
tactacgccg actccgtgaa ggacagattc accatctctc gggacgactc ccagtccatg     240
ctgtacctgc agatgaacaa cctgaaaacc gaggacaccg ccatgtacta ctgcgtgcgg     300
caggatttcg attactgggg ccagggcaca accctgaccg tgtcctctgc caagaccacc     360
gcccccagcg tgtacccct ggcccccgtg tgcggcgaca ccaccggcag cagcgtgacc     420
ctgggctgcc tggtgaaggg ctacttcccc gagcccgtga ccctgacctg aacagcggc     480 agcctgagca gcggcgtgca caccttcccc gccgtgctgc agagcgacct gtacaccctg     540
agcagcagcg tgaccgtgac cagcagcacc tggcccagcc agagcatcac ctgcaacgtg     600
gcccaccccg ccagcagcac caaggtggac aagaagatcg agcccagagg ccccaccatc     660
aagccctgcc cccctgcaa gtgccccgcc ccaacctgc tgggcggccc cagcgtgttc     720
atcttccccc ccaagatcaa ggacgtgctg atgatcagcc tgagcccat cgtgacctgc     780 gtggtggtgg acgtgagcga ggacgacccc gacgtgcaga tcagctggtt cgtgaacaac     840
gtggaggtgc acaccgccca gacccagacc cacagagagg actacaacag caccctgaga     900
gtggtgagcg ccctgcccat ccagcaccag gactggatga gcggcaagga gttcaagtgc     960
aaggtgaaca caaggacct gcccgccccc atcgagagaa ccatcagcaa gcccaagggc    1020
agcgtgagag cccccaggt gtacgtgctg cccccccccg aggaggagat gaccaagaag    1080
caggtgaccc tgacctgcat ggtgaccgac ttcatgcccg aggacatcta cgtggagtgg    1140
accaacaacg gcaagaccga gctgaactac aagaacaccg agcccgtgct ggacagcgac    1200
ggcagctact tcatgtacag caagctgaga gtggagaaga gaactgggt ggagagaaac    1260 agctacagct gcagcgtggt gcacgagggc ctgcacaacc accacaccac caagagcttc    1320
agcagaaccc ccggcaag                                                  1338
```

<210> SEQ ID NO 171
<211> LENGTH: 1356
<212> TYPE: DNA
<213> ORGANISM: Artificial Sequence
<220> FEATURE:
<223> OTHER INFORMATION: Synthetic: 3A9 Heavy chain comprising Mouse
      IgG2a constant region

<400> SEQUENCE: 171

```
gaagttcagc tgcaagaatc tggcggcgga cttgtgaaac ctggcggctc tctgaagctg      60
tcttgtgccg cctctggctt caccttctcc tcttacgcca tgtcctgggt ccgacagacc     120
cctgagaaga gactggaatg ggtcgccacc atctctaacg gcggaggcta cacctactat     180
cccgactccg tgaagggcag attcaccatc tccagagaca acgccaagaa caccctgtac     240
ctgcagatgt ccagcctgag atctgaggac accgccatgt actactgcgc cagacatatc     300
accaccgtgc ggcccaccaa gtacttcgat tattggggcc agggcaccac actgaccgtg     360
tcctctgcca gaccaccgc cccagcgt taccccctgg cccccgtgtg cggcgacacc     420
accggcagca gcgtgaccct gggctgcctg gtgaagggct acttccccga gcccgtgacc     480
ctgacctgga cagcggcag cctgagcagc ggcgtgcaca ccttccccgc cgtgctgcag     540
agcgacctgt acaccctgag cagcagcgtg accgtgacca gcagcacctg gcccagccag     600
agcatcacct gcaacgtggc ccaccccgcc agcagcacca aggtggacaa gaagatcgag     660
```

```
cccagaggcc ccaccatcaa gccctgcccc cctgcaagt gccccgcccc caacctgctg      720
ggcggcccca gcgtgttcat cttcccccc aagatcaagg acgtgctgat gatcagcctg      780
agccccatcg tgacctgcgt ggtggtggac gtgagcgagg acgaccccga cgtgcagatc      840
agctggttcg tgaacaacgt ggaggtgcac accgcccaga cccagaccca cagagaggac      900
tacaacagca ccctgagagt ggtgagcgcc ctgcccatcc agcaccagga ctggatgagc      960
ggcaaggagt tcaagtgcaa ggtgaacaac aaggacctgc cgcccccat cgagagaacc      1020 atcagcaagc ccaagggcag cgtgagagcc ccccaggtgt acgtgctgcc ccccccgag      1080 gaggagatga ccaagaagca ggtgaccctg acctgcatgg tgaccgactt catgcccgag      1140
gacatctacg tggagtggac caacaacggc aagaccgagc tgaactacaa gaacaccgag      1200
cccgtgctgg acagcgacgg cagctacttc atgtacagca agctgagagt ggagaagaag      1260
aactgggtgg agagaaacag ctacagctgc agcgtggtgc acgagggcct gcacaaccac      1320
cacaccacca gagcttcag cagaaccccc ggcaag                                1356
```

<210> SEQ ID NO 172
<211> LENGTH: 1329
<212> TYPE: DNA
<213> ORGANISM: Artificial Sequence
<220> FEATURE:
<223> OTHER INFORMATION: Synthetic: 10F10 Heavy chain comprising Mouse
      IgG2a constant region

<400> SEQUENCE: 172

```
gaagttcagc tgcaagagtc tggccctggc ctggtcaaac cttctcagtc tctgtccctg       60
acctgctccg tgaccggata ttctatcacc ggcggcttct actggaactg gatcagacag      120
ttccccggca caacctgga atggatgggc tacatcaact acgacggctc ctccgactac      180
tcccctagcc tgaagaaccg gatctccatc accagagaca cctccaagaa ccagttcttc      240
ctgaacctga cagcgtgac caccgaggac accgccacct attattgtgt gcggggcgat      300
tatgactggg gccagggaac aacactgacc gtgtcctctg ccaagaccac cgcccccagc      360
gtgtaccccc tggccccgt gtgcggcgac accaccggca gcagcgtgac cctgggctgc      420
ctggtgaagg gctacttccc cgagcccgtg acctgacct ggaacagcgg cagcctgagc      480
agcggcgtgc acaccttccc cgccgtgctg cagagcgacc tgtacaccct gagcagcagc      540
gtgaccgtga ccagcagcac ctggcccagc cagagcatca cctgcaacgt ggcccacccc      600
gccagcagca ccaaggtgga caagaagatc gagcccagag ccccaccat caagccctgc      660 ccccctgca agtgccccgc cccaacctg ctgggcggcc ccagcgtgtt catcttcccc       720
cccaagatca aggacgtgct gatgatcagc ctgagcccca tcgtgacctg cgtggtggtg      780
gacgtgagcg aggacgaccc cgacgtgcag atcagctggt tcgtgaacaa cgtggaggtg      840
cacaccgccc agacccagac ccacagagag gactacaaca gcaccctgag agtggtgagc      900
gccctgccca tccagcacca ggactggatg agcggcaagg agttcaagtg caaggtgaac      960
aacaaggacc tgcccgcccc catcgagaga accatcagca agcccaaggg cagcgtgaga     1020
gccccccagg tgtacgtgct gccccccccc gaggaggaga tgaccaagaa gcaggtgacc     1080
ctgacctgca tggtgaccga cttcatgccc gaggacatct acgtggagtg gaccaacaac     1140
ggcaagaccg agctgaacta caagaacacc gagcccgtgc tggacagcga cggcagctac     1200
ttcatgtaca gcaagctgag agtggagaag aagaactggg tggagagaaa cagctacagc     1260
tgcagcgtgg tgcacgaggg cctgcacaac caccacacca ccaagagctt cagcagaacc     1320
```

-continued

| | |
|---|---|
| cccggcaag | 1329 |

<210> SEQ ID NO 173
<211> LENGTH: 1350
<212> TYPE: DNA
<213> ORGANISM: Artificial Sequence
<220> FEATURE:
<223> OTHER INFORMATION: Synthetic: 11F11 Heavy chain comprising Mouse
      IgG2a constant region

<400> SEQUENCE: 173

| | |
|---|---|
| gaagttcagc tgcaagaatc tggcggcgga ttggttcagc ctggcggatc tctgagactg | 60 |
| tcttgtgcca cctccggctt caccttctcc gacttctaca tggaatgggt ccgacagcct | 120 |
| cctggcaaga gactggaatg gatcgccgcc tccagaaaca aggccaacga ctacaccacc | 180 |
| gagtactccg cctctgtgaa gggcagattc atcgtgtctc gggacaccag ccagtccatc | 240 |
| ctgtacctgc agatgaatgc cctgagagcc gaggacaccg ccatctacta ctgtgctaga | 300 |
| gatgcccacg gcaagccttt tgcttattgg ggccagggca ccctggtcac cgtgtctgct | 360 |
| gccaagacca ccgcccccag cgtgtacccc ctggcccccg tgtgcggcga caccaccggc | 420 |
| agcagcgtga ccctgggctg cctggtgaag ggctacttcc ccgagcccgt gaccctgacc | 480 |
| tggaacagcg gcagcctgag cagcggcgtg cacaccttcc ccgccgtgct gcagagcgac | 540 |
| ctgtacaccc tgagcagcag cgtgaccgtg accagcagca cctggcccag ccagagcatc | 600 |
| acctgcaacg tggcccaccc cgccagcagc accaaggtgg acaagaagat cgagcccaga | 660 |
| ggccccacca tcaagccctg cccccccctgc aagtgccccg cccccaacct gctgggcggc | 720 |
| cccagcgtgt tcatcttccc ccccaagatc aaggacgtgc tgatgatcag cctgagcccc | 780 |
| atcgtgacct gcgtggtggt ggacgtgagc gaggacgacc ccgacgtgca gatcagctgg | 840 |
| ttcgtgaaca acgtggaggt gcacaccgcc cagacccaga cccacagaga ggactacaac | 900 |
| agcaccctga gtggtgagcg ccctgccatc cagcacacc aggactggat gagcggcaag | 960 |
| gagttcaagt gcaaggtgaa caacaaggac ctgcccgccc ccatcgagag aaccatcagc | 1020 |
| aagcccaagg gcagcgtgag agccccccag gtgtacgtgc tgccccccccc gaggaggag | 1080 |
| atgaccaaga agcaggtgac cctgacctgc atggtgaccg acttcatgcc cgaggacatc | 1140 |
| tacgtggagt ggaccaacaa cggcaagacc gagctgaact acaagaacac cgagcccgtg | 1200 |
| ctggacagcg acggcagcta cttcatgtac agcaagctga gtggagaa gagaactgg | 1260 |
| gtggagagaa acagctacag ctgcagcgtg gtgcacgagg cctgcacaa ccaccacacc | 1320 |
| accaagagct tcagcagaac ccccggcaag | 1350 |

<210> SEQ ID NO 174
<211> LENGTH: 1338
<212> TYPE: DNA
<213> ORGANISM: Artificial Sequence
<220> FEATURE:
<223> OTHER INFORMATION: AC8 Heavy chain comprising Mouse IgG2a constant
      region

<400> SEQUENCE: 174

| | |
|---|---|
| gaagttcagc tgctcgaatc aggaggggga ctggtccagc caggtggttc cttgcgactg | 60 |
| tcatgcgctg cttccggttt tactttagt gattactcaa tgagttgggt gagacaagca | 120 |
| cctgggaagg gtttggagtg ggtgagcggc ataagttcag gaggctcttc caagtattac | 180 |
| gcagattcag taaagggtcg ctttaccatc tcacgggata atagtaagaa cacactttac | 240 |
| cttcaaatga actctctgag agctgaggat accgcagttt attattgtgc aaagattttt | 300 |

```
cataattttg actactgggg ccaggggact cttgttaccg tcagcagcgc aagaccacc    360
gcccccagcg tgtaccccct ggcccccgtg tgcggcgaca ccaccggcag cagcgtgacc    420
ctgggctgcc tggtgaaggg ctacttcccc gagcccgtga ccctgacctg aacagcggc    480
agcctgagca gcggcgtgca caccttcccc gccgtgctgc agagcgacct gtacaccctg    540
agcagcagcg tgaccgtgac cagcagcacc tggcccagcc agagcatcac ctgcaacgtg    600
gcccaccccg ccagcagcac caaggtggac aagaagatcg agcccagagg ccccaccatc    660
aagccctgcc cccctgcaa gtgccccgcc ccaacctgc tgggcggccc cagcgtgttc    720
atcttccccc ccaagatcaa ggacgtgctg atgatcagcc tgagcccccat cgtgacctgc    780
gtggtggtgg acgtgagcga ggacgacccc gacgtgcaga tcagctggtt cgtgaacaac    840
gtggaggtgc acaccgccca gacccagacc cacagagagg actacaacag caccctgaga    900
gtggtgagcg ccctgcccat ccagcaccag gactggatga gcggcaagga gttcaagtgc    960
aaggtgaaca caaggaccct gcccgccccc atcgagagaa ccatcagcaa gcccaagggc   1020
agcgtgagag ccccccaggt gtacgtgctg ccccccccg aggaggagat gaccaagaag   1080
caggtgaccc tgacctgcat ggtgaccgac ttcatgcccg aggacatcta cgtggagtgg   1140
accaacaacg gcaagaccga gctgaactac aagaacaccg agcccgtgct ggacagcgac   1200
ggcagctact tcatgtacag caagctgaga gtggagaaga gaactgggt ggagagaaac   1260
agctacagct gcagcgtggt gcacgagggc ctgcacaacc accacaccac caagagcttc   1320
agcagaaccc ccggcaag                                                 1338
```

<210> SEQ ID NO 175
<211> LENGTH: 1338
<212> TYPE: DNA
<213> ORGANISM: Artificial Sequence
<220> FEATURE:
<223> OTHER INFORMATION: AE8 Heavy chain comprising Mouse IgG2a constant
      region

<400> SEQUENCE: 175

```
gaagtgcaac ttcttgaatc aggtggagga ctcgtacaac ccggaggtag cctgagactt     60
tcatgtgcag cctcagggtt taccttctct aactacgcca tgagctgggt acggcaggca    120
cctggcaaag gactggaatg ggtttcagca atatcctctg gcggtggtaa catctattac    180
gccgattcag tgaagggtcg attcacaatt tctagggata ctccaaaaa cacactgtac    240
ctccaaatga actcccttag agccgaagat accgctgtgt actattgtgc tcgaagaccc    300
ctctactttg actattgggg acaagggacc cttgtgaccg tatcatctgc aagaccacc    360
gcccccagcg tgtaccccct ggcccccgtg tgcggcgaca ccaccggcag cagcgtgacc    420
ctgggctgcc tggtgaaggg ctacttcccc gagcccgtga ccctgacctg aacagcggc    480
agcctgagca gcggcgtgca caccttcccc gccgtgctgc agagcgacct gtacaccctg    540
agcagcagcg tgaccgtgac cagcagcacc tggcccagcc agagcatcac ctgcaacgtg    600
gcccaccccg ccagcagcac caaggtggac aagaagatcg agcccagagg ccccaccatc    660
aagccctgcc cccctgcaa gtgccccgcc ccaacctgc tgggcggccc cagcgtgttc    720
atcttccccc ccaagatcaa ggacgtgctg atgatcagcc tgagcccccat cgtgacctgc    780
gtggtggtgg acgtgagcga ggacgacccc gacgtgcaga tcagctggtt cgtgaacaac    840
gtggaggtgc acaccgccca gacccagacc cacagagagg actacaacag caccctgaga    900
gtggtgagcg ccctgcccat ccagcaccag gactggatga gcggcaagga gttcaagtgc    960
```

```
aaggtgaaca acaaggacct gcccgccccc atcgagagaa ccatcagcaa gcccaagggc    1020
agcgtgagag ccccccaggt gtacgtgctg ccccccccg aggaggagat gaccaagaag     1080
caggtgaccc tgacctgcat ggtgaccgac ttcatgcccg aggacatcta cgtggagtgg    1140
accaacaacg gcaagaccga gctgaactac aagaacaccg agcccgtgct ggacagcgac    1200
ggcagctact tcatgtacag caagctgaga gtggagaaga gaactgggt ggagagaaac     1260 agctacagct gcagcgtggt gcacgagggc ctgcacaacc accacaccac caagagcttc    1320
agcagaaccc ccggcaag                                                  1338
```

<210> SEQ ID NO 176
<211> LENGTH: 1338
<212> TYPE: DNA
<213> ORGANISM: Artificial Sequence
<220> FEATURE:
<223> OTHER INFORMATION: AA9 Heavy chain comprising Mouse IgG2a constant region

<400> SEQUENCE: 176

```
gaggttcagc ttctggaaag cggaggggga ttggtccaac ctgggggttc acttcgtttg    60
tcatgcgccg cttccggctt tactttcagt tcatactcta tgagctgggt acggcaggct   120
ccagggaaag gacttgagtg ggtttctgca atatacctg atcaagcaa caagtactac      180 gcagattctg taaaagggcg gttcactatc tcacgtgata actcaaagaa cactctttac   240
ctccagatga atagtttgag ggcagaagac actgctgttt actattgcgc tcgtcatgcc   300
gccacatttg attattgggg acagggaact ctggttacag tgagtagtgc caagaccacc   360
gcccccagcg tgtaccccct ggccccgtg tgcggcgaca ccaccggcag cagcgtgacc    420
ctgggctgcc tggtgaaggg ctacttcccc gagcccgtga ccctgacctg aacagcggc    480 agcctgagca gcggcgtgca caccttcccc gccgtgctgc agagcgacct gtacaccctg   540
agcagcagcg tgaccgtgac cagcagcacc tggcccagcc agagcatcac ctgcaacgtg   600
gcccaccccg ccagcagcac caaggtggac aagaagatcg agcccagagg ccccaccatc   660
aagccctgcc cccctgcaa gtgccccgcc cccaacctgc tgggcggccc cagcgtgttc   720
atcttccccc ccaagatcaa ggacgtgctg atgatcagcc tgagccccat cgtgacctgc   780
gtggtggtgg acgtgagcga ggacgacccc gacgtgcaga tcagctggtt cgtgaacaac   840
gtggaggtgc acaccgccca gacccagacc cacagagagg actacaacag caccctgaga   900
gtggtgagcg ccctgcccat ccagcaccag gactggatga gcggcaagga gttcaagtgc   960
aaggtgaaca acaaggacct gcccgccccc atcgagagaa ccatcagcaa gcccaagggc  1020
agcgtgagag ccccccaggt gtacgtgctg ccccccccg aggaggagat gaccaagaag   1080
caggtgaccc tgacctgcat ggtgaccgac ttcatgcccg aggacatcta cgtggagtgg  1140
accaacaacg gcaagaccga gctgaactac aagaacaccg agcccgtgct ggacagcgac  1200
ggcagctact tcatgtacag caagctgaga gtggagaaga gaactgggt ggagagaaac   1260 agctacagct gcagcgtggt gcacgagggc ctgcacaacc accacaccac caagagcttc  1320
agcagaaccc ccggcaag                                                1338
```

<210> SEQ ID NO 177
<211> LENGTH: 1371
<212> TYPE: DNA
<213> ORGANISM: Artificial Sequence
<220> FEATURE:
<223> OTHER INFORMATION: DG5 Heavy chain comprising Mouse IgG2a constant region

<400> SEQUENCE: 177

| gaggtccaac | ttctggaatc | aggtggtggc | ctggttcagc | caggaggctc | tctccgactc | 60 |
| tcctgtgctg | cttctggctt | cacctttagt | aattacgcca | tgtcatgggt | gcgtcaggca | 120 |
| ccaggcaaag | gcttgaatg | ggtctcagtc | atctctcctg | gaagcggtaa | tacctattac | 180 |
| gcagattctg | tcaaggggag | gtttactatc | tcaagagaca | atagcaagaa | tactttgtac | 240 |
| ctgcaaatga | atagccttcg | agcagaagac | acagccgtgt | actactgcgc | acgagtcacc | 300 |
| atcgcctgcc | caacaaaacg | atgttcatac | tccaatggga | tggatgtatg | gggacaagga | 360 |
| actctcgtaa | ctgtttcatc | tgccaagacc | accgccccca | gcgtgtaccc | cctggccccc | 420 |
| gtgtgcggcg | acaccaccgg | cagcagcgtg | accctgggct | gcctggtgaa | gggctacttc | 480 |
| cccgagcccg | tgaccctgac | ctggaacagc | ggcagcctga | gcagcggcgt | gcacaccttc | 540 |
| cccgccgtgc | tgcagagcga | cctgtacacc | ctgagcagca | gcgtgaccgt | gaccagcagc | 600 |
| acctggccca | gccagagcat | cacctgcaac | gtggcccacc | cgccagcag | caccaaggtg | 660 |
| gacaagaaga | tcgagcccag | aggccccacc | atcaagccct | gccccccctg | caagtgcccc | 720 |
| gcccccaacc | tgctgggcgg | cccagcgtg | ttcatcttcc | cccccaagat | caaggacgtg | 780 |
| ctgatgatca | gcctgagccc | catcgtgacc | tgcgtggtgg | tggacgtgag | cgaggacgac | 840 |
| cccgacgtgc | agatcagctg | gttcgtgaac | aacgtggagg | tgcacaccgc | ccagacccag | 900 |
| acccacagag | aggactacaa | cagcaccctg | agagtggtga | gcgccctgcc | catccagcac | 960 |
| caggactgga | tgagcggcaa | ggagttcaag | tgcaaggtga | caacaaggga | cctgcccgcc | 1020 |
| cccatcgaga | gaaccatcag | caagcccaag | ggcagcgtga | gagccccca | ggtgtacgtg | 1080 |
| ctgccccccc | cgaggagga | gatgaccaag | aagcaggtga | ccctgacctg | catggtgacc | 1140 |
| gacttcatgc | ccgaggacat | ctacgtggag | tggaccaaca | acggcaagac | cgagctgaac | 1200 |
| tacaagaaca | ccgagcccgt | gctggacagc | gacggcagct | acttcatgta | cagcaagctg | 1260 |
| agagtggaga | agaagaactg | ggtggagaga | aacagctaca | gctgcagcgt | ggtgcacgag | 1320 |
| ggcctgcaca | accaccacac | caccaagagc | ttcagcagaa | cccccggcaa | g | 1371 |

<210> SEQ ID NO 178
<211> LENGTH: 1338
<212> TYPE: DNA
<213> ORGANISM: Artificial Sequence
<220> FEATURE:
<223> OTHER INFORMATION: AD2 Heavy chain comprising Mouse IgG2a constant region

<400> SEQUENCE: 178

| gaggtacaac | ttcttgagag | cggcggcggt | tcgtacagc | ctgggggctc | cttgcggttg | 60 |
| tcttgtgccg | cttcaggttt | cacattctct | aactacgcca | tgagctgggt | caggcaagcc | 120 |
| cccggcaaag | gttggagtg | ggtcagtgct | attagtcatt | ctgggtcctc | aaaatactac | 180 |
| gcagactcag | tgaaaggacg | atttaccata | agtcgggata | atagcaaaaa | cacactttat | 240 |
| ctccaaatga | atagtttgcg | ggccgaagac | actgctgtct | attactgtgc | caggtccgga | 300 |
| aataatttcg | attattgggg | tcagggaaca | ctggtcaccg | tcagctccgc | caagaccacc | 360 |
| gcccccagcg | tgtacccct | ggccccgtg | tgcggcgaca | ccaccggcag | cagcgtgacc | 420 |
| ctgggctgcc | tggtgaaggg | ctacttccc | gagcccgtga | ccctgacctg | gaacagcggc | 480 |
| agcctgagca | gcggcgtgca | caccttcccc | gccgtgctgc | agagcgacct | gtacaccctg | 540 |

| | |
|---|---|
| agcagcagcg tgaccgtgac cagcagcacc tggcccagcc agagcatcac ctgcaacgtg | 600 |
| gcccaccccg ccagcagcac caaggtggac aagaagatcg agcccagagg ccccaccatc | 660 |
| aagccctgcc cccctgcaa gtgccccgcc cccaacctgc tgggcggccc cagcgtgttc | 720 |
| atcttccccc ccaagatcaa ggacgtgctg atgatcagcc tgagcccat cgtgacctgc | 780 |
| gtggtggtgg acgtgagcga ggacgacccc gacgtgcaga tcagctggtt cgtgaacaac | 840 |
| gtggaggtgc acaccgccca gacccagacc cacagagagg actacaacag caccctgaga | 900 |
| gtggtgagcg ccctgcccat ccagcaccag gactggatga gcggcaagga gttcaagtgc | 960 |
| aaggtgaaca caaggacct gcccgccccc atcgagagaa ccatcagcaa gcccaagggc | 1020 |
| agcgtgagag ccccccaggt gtacgtgctg ccccccccg aggaggagat gaccaagaag | 1080 |
| caggtgaccc tgacctgcat ggtgaccgac ttcatgcccg aggacatcta cgtggagtgg | 1140 |
| accaacaacg gcaagaccga gctgaactac aagaacaccg agcccgtgct ggacagcgac | 1200 |
| ggcagctact tcatgtacag caagctgaga gtggagaaga gaactgggt ggagagaaac | 1260 |
| agctacagct gcagcgtggt gcacgagggc ctgcacaacc accaccac caagagcttc | 1320 |
| agcagaaccc ccggcaag | 1338 |

<210> SEQ ID NO 179
<211> LENGTH: 1338
<212> TYPE: DNA
<213> ORGANISM: Artificial Sequence
<220> FEATURE:
<223> OTHER INFORMATION: AD7 Heavy chain comprising Mouse IgG2a constant region

<400> SEQUENCE: 179

| | |
|---|---|
| gaagttcaac tgcttgaaag cggggggcgga ttggtccagc caggagggtc cttgcggctg | 60 |
| agctgcgctg cctccggttt taccttagt ggttatgcta tgtcatgggt tcgtcaggcc | 120 |
| ccaggtaaag gtttggagtg ggtgagtgcc atctcaccca acggaggtaa taaatattat | 180 |
| gccgactcag tcaagggggcg attcactatc tctagggaca atagcaaaaa cacactctac | 240 |
| cttcaaatga acagtcttcg agctgaagac acagcagtgt actattgcgc aaggaggccc | 300 |
| gtctatttcg attactgggg gcagggggaca ctcgtgacag tttctagtgc caagaccacc | 360 |
| gccccagcg tgtacccct ggccccgtg tgcggcgaca ccaccggcag cagcgtgacc | 420 |
| ctgggctgcc tggtgaaggg ctacttcccc gagcccgtga ccctgacctg aacagcggc | 480 |
| agcctgagca gcggcgtgca caccttcccc gccgtgctgc agagcgacct gtacaccctg | 540 |
| agcagcagcg tgaccgtgac cagcagcacc tggcccagcc agagcatcac ctgcaacgtg | 600 |
| gcccaccccg ccagcagcac caaggtggac aagaagatcg agcccagagg ccccaccatc | 660 |
| aagccctgcc cccctgcaa gtgccccgcc cccaacctgc tgggcggccc cagcgtgttc | 720 |
| atcttccccc ccaagatcaa ggacgtgctg atgatcagcc tgagcccat cgtgacctgc | 780 |
| gtggtggtgg acgtgagcga ggacgacccc gacgtgcaga tcagctggtt cgtgaacaac | 840 |
| gtggaggtgc acaccgccca gacccagacc cacagagagg actacaacag caccctgaga | 900 |
| gtggtgagcg ccctgcccat ccagcaccag gactggatga gcggcaagga gttcaagtgc | 960 |
| aaggtgaaca caaggacct gcccgccccc atcgagagaa ccatcagcaa gcccaagggc | 1020 |
| agcgtgagag ccccccaggt gtacgtgctg ccccccccg aggaggagat gaccaagaag | 1080 |
| caggtgaccc tgacctgcat ggtgaccgac ttcatgcccg aggacatcta cgtggagtgg | 1140 |
| accaacaacg gcaagaccga gctgaactac aagaacaccg agcccgtgct ggacagcgac | 1200 |

| | |
|---|---|
| ggcagctact tcatgtacag caagctgaga gtggagaaga agaactgggt ggagagaaac | 1260 |
| agctacagct gcagcgtggt gcacgagggc ctgcacaacc accacaccac caagagcttc | 1320 |
| agcagaaccc ccggcaag | 1338 |

```
<210> SEQ ID NO 180
<211> LENGTH: 1371
<212> TYPE: DNA
<213> ORGANISM: Artificial Sequence
<220> FEATURE:
<223> OTHER INFORMATION: DG11 Heavy chain comprising Mouse IgG2a
      constant region

<400> SEQUENCE: 180
```

| | |
|---|---|
| gaggtgcagc ttctggagtc tggcggaggg ctggttcaac ctggtgggtc tcttcgtctc | 60 |
| tcttgtgcag cttctggctt cactttctcc gactatgcca tgagctgggt caggcaggca | 120 |
| cctggcaaag gtctggagtg ggtctccgtg atttctcctg ctcagggag caagtattac | 180 |
| gcagactcag tgaaaggaag attcaccata tcccgagata cagtaaaaa tactctctat | 240 |
| ttgcagatga acagtctcag agccgaagat acagcagtct actattgcgc taaagttact | 300 |
| atatcttgcg ctcgaatgag gtgctcctac gcagatggta tggacgtatg ggggcagggt | 360 |
| accctggtta ccgttagctc cgccaagacc accgccccca gcgtgtaccc cctggccccc | 420 |
| gtgtgcggcg acaccaccgg cagcagcgtg accctgggct gctggtgaa gggctacttc | 480 |
| cccgagcccg tgaccctgac ctggaacagc ggcagcctga gcagcggcgt gcacaccttc | 540 |
| cccgccgtgc tgcagagcga cctgtacacc ctgagcagca gcgtgaccgt gaccagcagc | 600 |
| acctggccca gccagagcat cacctgcaac gtggcccacc ccgccagcag caccaaggtg | 660 |
| gacaagaaga tcgagcccag aggccccacc atcaagccct gcccccctg caagtgcccc | 720 |
| gcccccaacc tgctgggcgg ccccagcgtg ttcatcttcc cccccaagat caaggacgtg | 780 |
| ctgatgatca gcctgagccc catcgtgacc tgcgtggtgg tggacgtgag cgaggacgac | 840 |
| cccgacgtgc agatcagctg gttcgtgaac aacgtggagg tgcacaccgc ccagacccag | 900 |
| acccacagag aggactacaa cagcaccctg agagtggtga gcgccctgcc catccagcac | 960 |
| caggactgga tgagcggcaa ggagttcaag tgcaaggtga caacaaagga cctgcccgcc | 1020 |
| cccatcgaga gaaccatcag caagcccaag ggcagcgtga gaccccccca ggtgtacgtg | 1080 |
| ctgcccccc cgaggagga gatgaccaag aagcaggtga ccctgacctg catggtgacc | 1140 |
| gacttcatgc ccgaggacat ctacgtggag tggaccaaca acggcaagac cgagctgaac | 1200 |
| tacaagaaca ccgagcccgt gctggacagc gacggcagct acttcatgta cagcaagctg | 1260 |
| agagtggaga agaagaactg ggtggagaga aacagctaca gctgcagcgt ggtgcacgag | 1320 |
| ggcctgcaca accaccacac caccaagagc ttcagcagaa ccccggcaa g | 1371 |

```
<210> SEQ ID NO 181
<211> LENGTH: 1371
<212> TYPE: DNA
<213> ORGANISM: Artificial Sequence
<220> FEATURE:
<223> OTHER INFORMATION: DG8 Heavy chain comprising Mouse IgG2a constant
      region

<400> SEQUENCE: 181
```

| | |
|---|---|
| gaagtacaat tgcttgaaag tgggggggggc ttggtacagc ctggcggctc ccttcggctt | 60 |
| tcttgtgctg cttcaggatt taccttcagt gaccacgcca tgtcctgggt ccgtcaagct | 120 |
| ccaggtaaag ggctcgaatg ggtatctgta attagccatg gtaacggttc taagtattac | 180 |

```
gccgatagtg taaagggacg atttaccatt agtagagata attctaagaa tactctttat      240
ctccaaatga actctttgag ggccgaggac acagccgtgt actactgcgc ccgtgttgcc      300
tctcggtgtc gacggggacg atgcagttat tcagacggca tggacgtttg gggacaaggg      360
actttggtca ctgtgagttc tgccaagacc accgccccca gcgtgtaccc cctggccccc      420
gtgtgcggcg acaccaccgg cagcagcgtg accctgggct gcctggtgaa gggctacttc      480
cccgagcccg tgaccctgac ctggaacagc ggcagcctga gcagcggcgt gcacaccttc      540
cccgccgtgc tgcagagcga cctgtacacc ctgagcagca gcgtgaccgt gaccagcagc      600
acctggccca gccagagcat cacctgcaac gtggcccacc ccgccagcag caccaaggtg      660
gacaagaaga tcgagcccag aggccccacc atcaagccct gccccccctg caagtgcccc      720
gcccccaacc tgctgggcgg ccccagcgtg ttcatcttcc cccccaagat caaggacgtg      780
ctgatgatca gcctgagccc catcgtgacc tgcgtggtgg tggacgtgag cgaggacgac      840
cccgacgtgc agatcagctg gttcgtgaac aacgtggagg tgcacaccgc ccagacccag      900
acccacagag aggactacaa cagcaccctg agagtggtga gcgccctgcc catccagcac      960
caggactgga tgagcggcaa ggagttcaag tgcaaggtga caacaaggac cctgcccgcc     1020
cccatcgaga gaaccatcag caagcccaag ggcagcgtga gagcccccca ggtgtacgtg     1080
ctgccccccc ccgaggagga tgatgaccaag aagcaggtga ccctgacctg catggtgacc     1140
gacttcatgc ccgaggacat ctacgtggag tggaccaaca acggcaagac cgagctgaac     1200
tacaagaaca ccgagcccgt gctggacagc gacggcagct acttcatgta cagcaagctg     1260
agagtggaga agaagaactg ggtggagaga acagctaca gctgcagcgt ggtgcacgag     1320
ggcctgcaca ccaccacac caccaagagc ttcagcagaa cccccggcaa g               1371
```

<210> SEQ ID NO 182
<211> LENGTH: 1371
<212> TYPE: DNA
<213> ORGANISM: Artificial Sequence
<220> FEATURE:
<223> OTHER INFORMATION: DA9 Heavy chain comprising Mouse IgG2a constant
      region

<400> SEQUENCE: 182

```
gaggttcagc tcctggagtc cggtggtggc ctggttcagc ccggagggtc cttgcgtttg       60
tcttgcgctg caagcgggtt cactttctcc aactatgcta tgtcttgggt caggcaagcc      120
cctggaaagg gactcgagtg ggtcagtgta atttccccat ctgattccaa cacatattat      180
gcagacagcg ttaaggacg gttcaccatt tcccgtgata attcaaaaaa taccttgtac      240
ttgcaaatga atagtcttcg tgctgaggat accgcagttt actactgcgc ccgagttacc      300
ctgagttgca gggctagccg atgctcttac agcaatggta tggatgtatg gggtcaaggt      360
acattggtca cagtctcctc cgccaagacc accgccccca gcgtgtaccc cctggccccc      420
gtgtgcggcg acaccaccgg cagcagcgtg accctgggct gcctggtgaa gggctacttc      480
cccgagcccg tgaccctgac ctggaacagc ggcagcctga gcagcggcgt gcacaccttc      540
cccgccgtgc tgcagagcga cctgtacacc ctgagcagca gcgtgaccgt gaccagcagc      600
acctggccca gccagagcat cacctgcaac gtggcccacc ccgccagcag caccaaggtg      660
gacaagaaga tcgagcccag aggccccacc atcaagccct gccccccctg caagtgcccc      720
gcccccaacc tgctgggcgg ccccagcgtg ttcatcttcc cccccaagat caaggacgtg      780
ctgatgatca gcctgagccc catcgtgacc tgcgtggtgg tggacgtgag cgaggacgac      840
```

```
cccgacgtgc agatcagctg gttcgtgaac aacgtggagg tgcacaccgc ccagacccag    900
acccacagag aggactacaa cagcaccctg agagtggtga gcgccctgcc catccagcac    960
caggactgga tgagcggcaa ggagttcaag tgcaaggtga acaacaagga cctgcccgcc   1020
cccatcgaga gaaccatcag caagcccaag ggcagcgtga gaccccccca ggtgtacgtg   1080
ctgccccccc ccgaggagga gatgaccaag aagcaggtga ccctgacctg catggtgacc   1140
gacttcatgc ccgaggacat ctacgtggag tggaccaaca acggcaagac cgagctgaac   1200
tacaagaaca ccgagcccgt gctggacagc gacggcagct acttcatgta cagcaagctg   1260
agagtggaga gaagaactg gtggagaga aacagctaca gctgcagcgt ggtgcacgag   1320
ggcctgcaca accaccacac caccaagagc ttcagcagaa cccccggcaa g           1371
```

<210> SEQ ID NO 183
<211> LENGTH: 1335
<212> TYPE: DNA
<213> ORGANISM: Artificial Sequence
<220> FEATURE:
<223> OTHER INFORMATION: 1E4 Heavy chain comprising Human IgG1 constant
      region

<400> SEQUENCE: 183

```
gaagttcagc tgcaagaatc tggcgccgaa ctcgtgcgac ctggcaccct tgtgaaagtg     60
tcttgcaagg cctctggcta cgccttcacc aactacctga tcgagtgggt caagcagagg    120
cctggacagg gacttgagtg gatcggagtg atcaatcctg gctccggcgg caccaattac    180
aacgagaagt tcaagggcaa agctaccctg accgccgaca gtcctcttc caccgcttac    240 atgcagctgt ccagcctgac ctctgacgac tctgccgtgt acttctgcgc ctctggcaac    300
tacgatacct attggggcca gggcaccctg gtcacagtgt ctgctgcgag caccaaaggc    360
ccgagcgtgt tccgctggc gccgagcagc aaaagcacca gcggcggcac cgcggcgctg    420
ggctgcctgg tgaaagatta ttttccggaa ccggtgaccg tgagctggaa cagcggcgcg    480
ctgaccagcg gcgtgcatac ctttccggcg gtgctgcaga gcagcggcct gtatagcctg    540
agcagcgtgg tgaccgtgcc gagcagcagc ctgggcaccc agacctatat ttgcaacgtg    600
aaccataaac cgagcaacac caaagtggat aaaaaagtgg aaccgaaaag ctgcgataaa    660
acccatacct gccgcgtg cccggcgccg aactgctgg gcggcccgag cgtgtttctg     720
tttccgccga aaccgaaaga taccctgatg attagccgca cccggaagt gacctgcgtg    780 gtggtggatg tgagccatga agatccggaa gtgaaatta ctggtatgt ggatggcgtg    840 gaagtgcata acgcgaaaac caaaccgcgc gaagaacagt ataacagcac ctatcgcgtg    900
gtgagcgtgc tgaccgtgct gcatcaggat tggctgaacg gcaaagaata taatgcaaa    960 gtgagcaaca aagcgctgcc ggcgccgatt gaaaaaacca ttagcaaagc gaaaggccag   1020
ccgcgcgaac gccaggtgta tacctgccg ccgagccgcg aagaaatgac caaaaaccag   1080
gtgagcctga cctgcctggt gaaaggcttt tatccgagcg atattgcggt ggaatgggaa   1140
agcaacggcc agccggaaaa caactataaa accacccgc cggtgctgga tagcgatggc   1200 agctttttc tgtatagcaa actgaccgtg gataaaagcc gctggcagca gggcaacgtg   1260
tttagctgca gcgtgatgca tgaagcgctg cataaccatt atacccagaa aagcctgagc   1320
ctgagcccgg gcaaa                                                   1335
```

<210> SEQ ID NO 184
<211> LENGTH: 1338

<212> TYPE: DNA
<213> ORGANISM: Artificial Sequence
<220> FEATURE:
<223> OTHER INFORMATION: 9B11 Heavy chain comprising Human IgG1 constant
      region

<400> SEQUENCE: 184

```
gaagttcagc tgcaagaatc tggcggcgga ctggtgcagc ctaagggatc tctgaagctg      60
tcttgtgccg cctccggctt caccttcaac acctacgcca tgaactgggt ccgacaggct     120
cctggcaaag gactggaatg ggtcgcccgg atcagatcca agtctaacaa ctacgccacc     180
tactacgccg actccgtgaa ggacagattc accatctctc gggacgactc ccagtccatg     240
ctgtacctgc agatgaacaa cctgaaaacc gaggacaccg ccatgtacta ctgcgtgcgg     300
caggatttcg attactgggg ccagggcaca accctgaccg tgtcctctgc gagcaccaaa     360
ggcccgagcg tgtttccgct ggcgccgagc agcaaaagca ccagcggcgg caccgcggcg     420
ctgggctgcc tggtgaaaga ttattttccg aaccgtgtga ccgtgagctg aacagcggc     480
gcgctgacca gcggcgtgca tacctttccg gcggtgctgc agagcagcgg cctgtatagc     540
ctgagcagcg tggtgaccgt gccgagcagc agcctgggca cccagaccta tatttgcaac     600
gtgaaccata aaccgagcaa caccaaagtg gataaaaaag tggaaccgaa aagctgcgat     660
aaaacccata cctgcccgcc gtgcccggcg ccggaactgc tgggcggccc gagcgtgttt     720
ctgtttccgc cgaaaccgaa agataccctg atgattagcc gcaccccgga agtgacctgc     780
gtggtggtgg atgtgagcca tgaagatccg gaagtgaaat taactggta tgtggatggc     840
gtggaagtgc ataacgcgaa aaccaaaccg cgcgaagaac agtataacag cacctatcgc     900
gtggtgagcg tgctgaccgt gctgcatcag gattggctga acggcaaaga atataaatgc     960
aaagtgagca caaagcgct gccggcgccg attgaaaaaa ccattagcaa agcgaaaggc    1020
cagccgcgcg aaccgcaggt gtataccctg ccgccgagcc gcgaagaaat gaccaaaaac    1080
caggtgagcc tgacctgcct ggtgaaaggc ttttatccga cgatattgc ggtggaatgg    1140
gaaagcaacg gccagccgga aaacaactat aaaaccaccc cgccggtgct ggatagcgat    1200
ggcagcttt ttctgtatag caaactgacc gtggataaaa gccgctggca gcagggcaac    1260
gtgtttagct gcagcgtgat gcatgaagcg ctgcataacc attataccca gaaaagcctg    1320
agcctgagcc cgggcaaa                                                  1338
```

<210> SEQ ID NO 185
<211> LENGTH: 1356
<212> TYPE: DNA
<213> ORGANISM: Artificial Sequence
<220> FEATURE:
<223> OTHER INFORMATION: 3A9 Heavy chain comprising Human IgG1 constant
      region

<400> SEQUENCE: 185

```
gaagttcagc tgcaagaatc tggcggcgga cttgtgaaac ctggcggctc tctgaagctg      60
tcttgtgccg cctctggctt caccttctcc tcttacgcca tgtcctgggt ccgacagacc     120
cctgagaaga gactggaatg ggtcgccacc atctctaacg gcggaggcta cacctactat     180
cccgactccg tgaagggcag attcaccatc tccagagaca cgccaagaa caccctgtac     240
ctgcagatgt ccagcctgag atctgaggac accgccatgt actactgcgc cagacatatc     300
accaccgtgc ggcccaccaa gtacttcgat tattggggcc agggcaccac actgaccgtg     360
tcctctgcga gcaccaaagg cccgagcgtg tttccgctgg cgccgagcag caaaagcacc     420
```

```
agcggcggca ccgcggcgct gggctgcctg gtgaaagatt attttccgga accggtgacc    480
gtgagctgga acagcggcgc gctgaccagc ggcgtgcata cctttccggc ggtgctgcag    540
agcagcggcc tgtatagcct gagcagcgtg gtgaccgtgc cgagcagcag cctgggcacc    600
cagacctata tttgcaacgt gaaccataaa ccgagcaaca ccaaagtgga taaaaaagtg    660
gaaccgaaaa gctgcgataa aacccatacc tgcccgccgt gcccggcgcc ggaactgctg    720
ggcggcccga cgtgtttcct gtttccgccg aaaccgaaag atacccctgat gattagccgc    780
accccggaag tgacctgcgt ggtggtggat gtgagccatg aagatccgga agtgaaattt    840
aactggtatg tggatggcgt ggaagtgcat aacgcgaaaa ccaaaccgcg cgaagaacag    900
tataacagca cctatcgcgt ggtgagcgtg ctgaccgtgc tgcatcagga ttggctgaac    960
ggcaaagaat ataaatgcaa agtgagcaac aaagcgctgc cggcgccgat tgaaaaaacc   1020
attagcaaag cgaaaggcca gccgcgcgaa ccgcaggtgt ataccctgcc gccgagccgc   1080
gaagaaatga ccaaaaacca ggtgagcctg acctgcctgg tgaaaggctt ttatccgagc   1140
gatattgcgg tggaatggga aagcaacggc cagccggaaa acaactataa aaccaccccg   1200
ccggtgctgg atagcgatgg cagcttttt ctgtatagca aactgaccgt ggataaaagc   1260
cgctggcagc agggcaacgt gtttagctgc agcgtgatgc atgaagcgct gcataaccat   1320
tatcccaga aaagcctgag cctgagcccg ggcaaa                              1356
```

<210> SEQ ID NO 186
<211> LENGTH: 1329
<212> TYPE: DNA
<213> ORGANISM: Artificial Sequence
<220> FEATURE:
<223> OTHER INFORMATION: 10F10 Heavy chain comprising Human IgG1
      constant region

<400> SEQUENCE: 186

```
gaagttcagc tgcaagagtc tggccctggc ctggtcaaac cttctcagtc tctgtccctg     60
acctgctccg tgaccggata ttctatcacc ggcggcttct actggaactg gatcagacag    120
ttccccggca caacctgga atggatgggc tacatcaact acgacggctc ctccgactac    180
tcccctagcc tgaagaaccg gatctccatc accagagaca cctccaagaa ccagttcttc    240
ctgaacctga cagcgtgac caccgaggac accgccacct attattgtgt gcggggcgat    300
tatgactggg gccagggaac aacactgacc gtgtcctctg cgagcaccaa ggcccgagc    360
gtgtttccgc tggcgccgag cagcaaaagc accagcggcg caccgcggc gctgggctgc    420
ctggtgaaag attattttcc ggaaccggtg accgtgagct ggaacagcgg cgcgctgacc    480
agcggcgtgc ataccttcc ggcggtgctg cagagcagcg gcctgtatag cctgagcagc    540
gtggtgaccg tgccgagcag cagcctgggc acccagacct atatttgcaa cgtgaaccat    600
aaaccgagca caccaaagt ggataaaaaa gtggaaccga aaagctgcga taaacccat    660
acctgcccgc cgtgcccggc ccggaactg ctgggcggcc cgagcgtgtt tctgtttccg    720
ccgaaaccga agatacccct gatgattagc cgcaccccgg aagtgacctg cgtggtggtg    780
gatgtgagcc atgaagatcc ggaagtgaaa tttaactggt atgtggatgg cgtggaagtg    840
cataacgcga aaaccaaacc gcgcgaagaa cagtataaca gcacctatcg cgtggtgagc    900
gtgctgaccg tgctgcatca ggattggctg aacggcaaag aatataaatg caaagtgagc    960
aacaaagcgc tgccggcgcc gattgaaaaa accattagca aagcgaaagg ccagccgcgc   1020
gaaccgcagg tgtatacccct gccgccgagc cgcgaagaaa tgaccaaaaa ccaggtgagc   1080
```

-continued

```
ctgacctgcc tggtgaaagg ctttttatccg agcgatattg cggtggaatg ggaaagcaac       1140
ggccagccgg aaaacaacta taaaaccacc ccgccggtgc tggatagcga tggcagcttt       1200
tttctgtata gcaaactgac cgtggataaa agccgctggc agcagggcaa cgtgtttagc       1260
tgcagcgtga tgcatgaagc gctgcataac cattataccc agaaaagcct gagcctgagc       1320
ccgggcaaa                                                                1329
```

<210> SEQ ID NO 187
<211> LENGTH: 1350
<212> TYPE: DNA
<213> ORGANISM: Artificial Sequence
<220> FEATURE:
<223> OTHER INFORMATION: 11F11 Heavy chain comprising Human IgG1 constant region

<400> SEQUENCE: 187

```
gaagttcagc tgcaagaatc tggcggcgga ttggttcagc ctggcggatc tctgagactg        60
tcttgtgcca cctccggctt cacctcctcc gacttctaca tggaatgggt ccgacagcct       120
cctggcaaga gactggaatg gatcgccgcc tccagaaaca aggccaacga ctacaccacc       180
gagtactccg cctctgtgaa gggcagattc atcgtgtctc gggacaccag ccagtccatc       240
ctgtacctgc agatgaatgc cctgagagcc gaggacaccg ccatctacta ctgtgctaga       300
gatgcccacg gcaagccttt tgcttattgg ggccagggca ccctggtcac cgtgtctgct       360
gcgagcacca aaggcccgag cgtgtttccg ctggcgccga gcagcaaaag caccagcggc       420
ggcaccgcgg cgctgggctg cctggtgaaa gattattttc cggaaccggt gaccgtgagc       480
tggaacagcg gcgcgctgac cagcggcgtg cataccttc cggcggtgct gcagagcagc       540
ggcctgtata gcctgagcag cgtggtgacc gtgccgagca gcagcctggg cacccagacc       600
tatatttgca acgtgaacca taaaccgagc aacaccaaag tggataaaaa agtggaaccg       660
aaaagctgcg ataaaaccca tacctgcccc ccgtgcccgg cgccggaact gctgggcggc       720
ccgagcgtgt ttctgtttcc gccgaaaccg aaagatacc tgatgattag ccgcaccccg       780
gaagtgacct gcgtggtggt ggatgtgagc catgaagatc cggaagtgaa atttaactgg       840
tatgtggatg gcgtggaagt gcataacgcg aaaaccaaac gcgcgaaga acagtataac       900 agcacctatc gcgtggtgag cgtgctgacc gtgctgcatc aggattggct gaacggcaaa       960
gaatataaat gcaaagtgag caacaaagcg ctgccggcgc cgattgaaaa aaccattagc       1020 aaaagcgaaag gccagccgcg cgaaccgcag gtgtatacc tgccgccgag ccgcgaagaa       1080
atgaccaaaa accaggtgag cctgacctgc tggtgaaag ctttttatcc gagcgatatt       1140
gcggtggaat gggaaagcaa cggccagccg gaaaacaact ataaaaccac cccgccggtg       1200
ctggatagcg atggcagctt ttttctgtat agcaaactga ccgtggataa agccgctgg       1260 cagcagggca acgtgtttag ctgcagcgtg atgcatgaag cgctgcataa ccattatacc       1320
cagaaaagcc tgagcctgag cccgggcaaa                                        1350
```

<210> SEQ ID NO 188
<211> LENGTH: 1338
<212> TYPE: DNA
<213> ORGANISM: Artificial Sequence
<220> FEATURE:
<223> OTHER INFORMATION: Synthetic: AC8 Heavy chain comprising Human IgG1 constant region

<400> SEQUENCE: 188

```
gaagttcagc tgctcgaatc aggaggggga ctggtccagc caggtggttc cttgcgactg        60
```

```
tcatgcgctg cttccggttt tacttttagt gattactcaa tgagttgggt gagacaagca    120
cctgggaagg gtttggagtg ggtgagcggc ataagttcag gaggctcttc caagtattac    180
gcagattcag taaagggtcg ctttaccatc tcacgggata atagtaagaa cacactttac    240
cttcaaatga actctctgag agctgaggat accgcagttt attattgtgc aaagattttt    300
cataattttg actactgggg ccaggggact cttgttaccg tcagcagcgc gagcaccaaa    360
ggcccgagcg tgtttccgct ggcgccgagc agcaaaagca ccagcggcgg caccgcggcg    420
ctgggctgcc tggtgaaaga ttattttccg aaccggtgac cgtgagctga acagcggc     480 gcgctgacca gcggcgtgca tacctttccg gcggtgctgc agagcagcgg cctgtatagc    540
ctgagcagcg tggtgaccgt gccgagcagc agcctgggca cccagaccta tatttgcaac    600
gtgaaccata aaccgagcaa caccaaagtg ataaaaaag tggaaccgaa aagctgcgat     660
aaaacccata cctgcccgcc gtgcccggcg ccggaactgc tgggcggccc gagcgtgttt    720
ctgtttccgc cgaaaccgaa agataccctg atgattagcc gcaccccgga agtgacctgc    780
gtggtggtgg atgtgagcca tgaagatccg gaagtgaaat ttaactggta tgtggatggc    840
gtggaagtgc ataacgcgaa aaccaaaccg cgcgaagaac agtataacag cacctatcgc    900
gtggtgagcg tgctgaccgt gctgcatcag gattggctga acggcaaaga atataaatgc    960
aaagtgagca caaagcgct gccggcgccg attgaaaaaa ccattagcaa agcgaaaggc    1020
cagccgcgcg aaccgcaggt gtataccctg ccgccgagcc gcgaagaaat gaccaaaaac    1080
caggtgagcc tgacctgcct ggtgaaaggc ttttatccga gcgatattgc ggtgaatgg    1140 gaaagcaacg gccagccgga aaacaactat aaaaccaccc cgccggtgct ggatagcgat    1200
ggcagctttt ttctgtatag caaactgacc gtggataaaa gccgctggca gcagggcaac    1260
gtgtttagct gcagcgtgat gcatgaagcg ctgcataacc attataccca gaaaagcctg    1320
agcctgagcc cgggcaaa                                                 1338

<210> SEQ ID NO 189
<211> LENGTH: 1338
<212> TYPE: DNA
<213> ORGANISM: Artificial Sequence
<220> FEATURE:
<223> OTHER INFORMATION: Synthetic: AE8 Heavy chain comprising Human
      IgG1 constant region

<400> SEQUENCE: 189
gaagtgcaac ttcttgaatc aggtggagga ctcgtacaac ccggaggtag cctgagactt     60
tcatgtgcag cctcagggtt taccttctct aactacgcca tgagctgggt acggcaggca    120
cctggcaaag gactggaatg ggtttcagca atatcctctg gcgtggtaa catctattac    180 gccgattcag tgaagggtcg attcacaatt tctaggata actccaaaaa cacactgtac    240
ctccaaatga actcccttag agccgaagat accgctgtgt actattgtgc tcgaagaccc    300
ctctactttg actattgggg acaagggacc cttgtgaccg tatcatctgc gagcaccaaa    360
ggcccgagcg tgtttccgct ggcgccgagc agcaaaagca ccagcggcgg caccgcggcg    420
ctgggctgcc tggtgaaaga ttattttccg aaccggtgac cgtgagctga acagcggc     480 gcgctgacca gcggcgtgca tacctttccg gcggtgctgc agagcagcgg cctgtatagc    540
ctgagcagcg tggtgaccgt gccgagcagc agcctgggca cccagaccta tatttgcaac    600
gtgaaccata aaccgagcaa caccaaagtg ataaaaaag tggaaccgaa aagctgcgat     660
aaaacccata cctgcccgcc gtgcccggcg ccggaactgc tgggcggccc gagcgtgttt    720
```

```
ctgtttccgc cgaaaccgaa agatacccctg atgattagcc gcaccccgga agtgacctgc    780
gtggtggtgg atgtgagcca tgaagatccg gaagtgaaat ttaactggta tgtggatggc    840
gtggaagtgc ataacgcgaa aaccaaaccg cgcgaagaac agtataacag cacctatcgc    900
gtggtgagcg tgctgaccgt gctgcatcag gattggctga acggcaaaga atataaatgc    960
aaagtgagca caaagcgct gccggcgccg attgaaaaaa ccattagcaa agcgaaaggc    1020
cagccgcgcg aaccgcaggt gtatacccctg ccgccgagcc gcgaagaaat gaccaaaaac    1080
caggtgagcc tgacctgcct ggtgaaaggc ttttatccga gcgatattgc ggtggaatgg    1140
gaaagcaacg gccagccgga aaacaactat aaaaccaccc cgccggtgct ggatagcgat    1200
ggcagctttt ttctgtatag caaactgacc gtggataaaa gccgctggca gcagggcaac    1260
gtgtttagct gcagcgtgat gcatgaagcg ctgcataacc attatacccca gaaaagcctg    1320 agcctgagcc cgggcaaa                                                   1338
```

<210> SEQ ID NO 190
<211> LENGTH: 1338
<212> TYPE: DNA
<213> ORGANISM: Artificial Sequence
<220> FEATURE:
<223> OTHER INFORMATION: Synthetic: AA9 Heavy chain comprising Human
      IgG1 constant region

<400> SEQUENCE: 190

```
gaggttcagc ttctggaaag cggaggggga ttggtccaac ctgggggttc acttcgtttg     60
tcatgcgccg cttccggctt tactttcagt tcatactcta tgagctgggt acggcaggct    120
ccagggaaag gacttgagtg ggtttctgca atatccctg atcaagcaa caagtactac    180 gcagattctg taaagggcg gttcactatc tcacgtgata actcaaagaa cactctttac    240
ctccagatga atagtttgag gcagaagac actgctgttt actattgcgc tcgtcatgcc    300
gccacatttg attattgggg acagggaact ctggttacag tgagtagtgc gagcaccaaa    360
ggcccgagcg tgtttccgct ggcgccgagc agcaaaagca ccagcggcgg caccgcggcg    420
ctgggctgcc tggtgaaaga ttattttccg aaccggtga ccgtgagctg gaacagcggc    480
gcgctgacca gcggcgtgca tacctttccg gcggtgctgc agagcagcgg cctgtatagc    540
ctgagcagcg tggtgaccgt gccgagcagc agcctgggca cccagaccta tatttgcaac    600
gtgaaccata aaccgagcaa caccaaagtg gataaaaaag tggaaccgaa aagctgcgat    660 aaacccata cctgcccgcc gtgcccggc ccggaactgc tgggcggccc gagcgtgttt    720
ctgtttccgc cgaaaccgaa agatacccctg atgattagcc gcaccccgga agtgacctgc    780
gtggtggtgg atgtgagcca tgaagatccg gaagtgaaat ttaactggta tgtggatggc    840
gtggaagtgc ataacgcgaa aaccaaaccg cgcgaagaac agtataacag cacctatcgc    900
gtggtgagcg tgctgaccgt gctgcatcag gattggctga acggcaaaga atataaatgc    960
aaagtgagca caaagcgct gccggcgccg attgaaaaaa ccattagcaa agcgaaaggc    1020
cagccgcgcg aaccgcaggt gtatacccctg ccgccgagcc gcgaagaaat gaccaaaaac    1080
caggtgagcc tgacctgcct ggtgaaaggc ttttatccga gcgatattgc ggtggaatgg    1140
gaaagcaacg gccagccgga aaacaactat aaaaccaccc cgccggtgct ggatagcgat    1200
ggcagctttt ttctgtatag caaactgacc gtggataaaa gccgctggca gcagggcaac    1260
gtgtttagct gcagcgtgat gcatgaagcg ctgcataacc attatacccca gaaaagcctg    1320 agcctgagcc cgggcaaa                                                   1338
```

<210> SEQ ID NO 191
<211> LENGTH: 1371
<212> TYPE: DNA
<213> ORGANISM: Artificial Sequence
<220> FEATURE:
<223> OTHER INFORMATION: Synthetic: DG5 Heavy chain comprising Human
    IgG1 constant region

<400> SEQUENCE: 191

```
gaggtccaac ttctggaatc aggtggtggc ctggttcagc caggaggctc tctccgactc      60
tcctgtgctg cttctggctt cacctttagt aattacgcca tgtcatgggt gcgtcaggca     120
ccaggcaaag gcttgaatg gtctcagtc atctctcctg aagcggtaa tacctattac        180 gcagattctg tcaagggag gtttactatc tcaagagaca tagcaagaa tactttgtac      240 ctgcaaatga atagccttcg agcagaagac acagccgtgt actactgcgc acgagtcacc    300
atcgcctgcc caacaaaacg atgttctac tccaatggga tggatgtatg gggacaagga     360
actctcgtaa ctgtttcatc tgcgagcacc aaaggcccga gcgtgtttcc gctggcgccg    420
agcagcaaaa gcaccagcgg cggcaccgcg gcgctgggct gcctggtgaa agattatttt    480
ccggaaccgg tgaccgtgag ctggaacagc ggcgcgctga ccagcggcgt gcatacctt    540 ccggcggtgc tgcagagcag cggcctgtat agcctgagca gcgtggtgac cgtgccgagc    600
agcagcctgg gcacccagac ctatatttgc aacgtgaacc ataaaccgag caacaccaaa    660
gtggataaaa aagtggaacc gaaaagctgc gataaaaccc atacctgccc gccgtgcccg    720
gcgccggaac tgctgggcgg cccgagcgtg tttctgtttc cgccgaaacc gaaagatacc    780
ctgatgatta gccgcacccc ggaagtgacc tgcgtggtgg tggatgtgag ccatgaagat    840
ccggaagtga aatttaactg gtatgtggat ggcgtggaag tgcataacgc gaaaaccaaa    900
ccgcgcgaag aacagtataa cagcacctat cgcgtggtga gcgtgctgac cgtgctgcat    960
caggattggc tgaacggcaa agaatataaa tgcaaagtga gcaacaaagc gctgccggcg   1020
ccgattgaaa aaaccattag caaagcgaaa ggccagccgc gcgaaccgca ggtgtatacc   1080
ctgccgccga gccgcgaaga atgaccaaa aaccaggtga gcctgacctg cctggtgaaa   1140
ggcttttatc cgagcgatat tgcggtggaa tgggaaagca cggccagcc ggaaaacaac    1200 tataaaacca cccgccggt gctggatagc gatggcagct ttttctgta tagcaaactg     1260 accgtggata aagccgctg gcagcagggc aacgtgttta gctgcagcgt gatgcatgaa    1320
gcgctgcata accattatac ccagaaaagc ctgagcctga gcccgggcaa a           1371
```

<210> SEQ ID NO 192
<211> LENGTH: 1338
<212> TYPE: DNA
<213> ORGANISM: Artificial Sequence
<220> FEATURE:
<223> OTHER INFORMATION: Synthetic: AD2 Heavy chain comprising Human
    IgG1 constant region

<400> SEQUENCE: 192

```
gaggtacaac ttcttgagag cggcggcggt ctcgtacagc ctgggggctc cttgcggttg     60
tcttgtgccg cttcaggttt cacattctct aactacgcca tgagctgggt caggcaagcc   120
cccggcaaag gtttggagtg gtcagtgct attagtcatt ctgggtcctc aaaatactac    180
gcagactcag tgaaaggacg atttaccata agtcgggata tagcaaaaa cacactttat    240 ctccaaatga atagtttgcg ggccgaagac actgctgtct attactgtgc caggtccgga    300
```

| | |
|---|---|
| aataatttcg attattgggg tcagggaaca ctggtcaccg tcagctccgc gagcaccaaa | 360 |
| ggcccgagcg tgtttccgct ggcgccgagc agcaaaagca ccagcggcgg caccgcggcg | 420 |
| ctgggctgcc tggtgaaaga ttattttccg aaccggtga ccgtgagctg aacagcggc | 480 |
| gcgctgacca gcggcgtgca tacctttccg gcggtgctgc agagcagcgg cctgtatagc | 540 |
| ctgagcagcg tggtgaccgt gccgagcagc agcctgggca cccagaccta tatttgcaac | 600 |
| gtgaaccata aaccgagcaa caccaaagtg gataaaaaag tggaaccgaa aagctgcgat | 660 |
| aaaacccata cctgcccgcc gtgcccggcg ccggaactgc tgggcggccc gagcgtgttt | 720 |
| ctgtttccgc cgaaaccgaa agatacccctg atgattagcc gcaccccgga agtgacctgc | 780 |
| gtggtggtgg atgtgagcca tgaagatccg gaagtgaaat taactggta tgtggatggc | 840 |
| gtggaagtgc ataacgcgaa aaccaaaccg cgcgaagaac agtataacag cacctatcgc | 900 |
| gtggtgagcg tgctgaccgt gctgcatcag gattggctga acggcaaaga atataaatgc | 960 |
| aaagtgagca caaagcgct gccggcgccg attgaaaaaa ccattagcaa agcgaaaggc | 1020 |
| cagccgcgcg aaccgcaggt gtatacccctg ccgccgagcc gcgaagaaat gaccaaaaac | 1080 |
| caggtgagcc tgacctgcct ggtgaaaggc ttttatccga gcgatattgc ggtggaatgg | 1140 |
| gaaagcaacg gccagccgga aaacaactat aaaaccaccc cgccggtgct ggatagcgat | 1200 |
| ggcagctttt tcctgtatag caaactgacc gtggataaaa gccgctggca gcagggcaac | 1260 |
| gtgtttagct gcagcgtgat gcatgaagcg ctgcataacc attatcccca gaaaagcctg | 1320 |
| agcctgagcc cgggcaaa | 1338 |

<210> SEQ ID NO 193
<211> LENGTH: 1338
<212> TYPE: DNA
<213> ORGANISM: Artificial Sequence
<220> FEATURE:
<223> OTHER INFORMATION: Synthetic: AD7 Heavy chain comprising Human IgG1 constant region

<400> SEQUENCE: 193

| | |
|---|---|
| gaagttcaac tgcttgaaag cggggggcgga ttggtccagc caggagggtc cttgcggctg | 60 |
| agctgcgctg cctccggttt tacctttagt ggttatgcta tgtcatgggt tcgtcaggcc | 120 |
| ccaggtaaag gtttggagtg ggtgagtgcc atctcaccca acggaggtaa taaatattat | 180 |
| gccgactcag tcaaggggcg attcactatc tctaggggaca tagcaaaaa cacactctac | 240 |
| cttcaaatga acagtcttcg agctgaagac acagcagtgt actattgcgc aaggaggccc | 300 |
| gtctatttcg attactgggg gcaggggaca ctcgtgacag tttctagtgc gagcaccaaa | 360 |
| ggcccgagcg tgtttccgct ggcgccgagc agcaaaagca ccagcggcgg caccgcggcg | 420 |
| ctgggctgcc tggtgaaaga ttattttccg aaccggtga ccgtgagctg aacagcggc | 480 |
| gcgctgacca gcggcgtgca tacctttccg gcggtgctgc agagcagcgg cctgtatagc | 540 |
| ctgagcagcg tggtgaccgt gccgagcagc agcctgggca cccagaccta tatttgcaac | 600 |
| gtgaaccata aaccgagcaa caccaaagtg gataaaaaag tggaaccgaa aagctgcgat | 660 |
| aaaacccata cctgcccgcc gtgcccggcg ccggaactgc tgggcggccc gagcgtgttt | 720 |
| ctgtttccgc cgaaaccgaa agatacccctg atgattagcc gcaccccgga agtgacctgc | 780 |
| gtggtggtgg atgtgagcca tgaagatccg gaagtgaaat taactggta tgtggatggc | 840 |
| gtggaagtgc ataacgcgaa aaccaaaccg cgcgaagaac agtataacag cacctatcgc | 900 |
| gtggtgagcg tgctgaccgt gctgcatcag gattggctga acggcaaaga atataaatgc | 960 |

```
aaagtgagca acaaagcgct gccggcgccg attgaaaaaa ccattagcaa agcgaaaggc    1020
cagccgcgcg aaccgcaggt gtataccctg ccgccgagcc gcgaagaaat gaccaaaaac    1080
caggtgagcc tgacctgcct ggtgaaaggc ttttatccga gcgatattgc ggtggaatgg    1140
gaaagcaacg gccagccgga aaacaactat aaaaccaccc cgccggtgct ggatagcgat    1200
ggcagctttt ttctgtatag caaactgacc gtggataaaa gccgctggca gcagggcaac    1260
gtgtttagct gcagcgtgat gcatgaagcg ctgcataacc attatcccca gaaaagcctg    1320
agcctgagcc cgggcaaa                                                  1338

<210> SEQ ID NO 194
<211> LENGTH: 1371
<212> TYPE: DNA
<213> ORGANISM: Artificial Sequence
<220> FEATURE:
<223> OTHER INFORMATION: Synthetic: DG11 Heavy chain comprising Human
      IgG1 constant region

<400> SEQUENCE: 194
gaggtgcagc ttctggagtc tggcggaggg ctggttcaac tggtgggtc tcttcgtctc      60 tcttgtgcag cttctggctt cactttctcc gactatgcca tgagctgggt caggcaggca    120
cctggcaaag gtctggagtg gtctccgtg atttctcctg gctcagggag caagtattac     180
gcagactcag tgaaaggaag attcaccata tcccgagata cagtaaaaaa tactctctat    240
ttgcagatga acagtctcag agccgaagat acagcagtct actattgcgc taaagttact    300
atatcttgcg ctcgaatgag gtgctcctac gcagatggta tggacgtatg ggggcagggt    360
accctggtta ccgttagctc cgcgagcacc aaaggcccga gcgtgtttcc gctggcgccg    420
agcagcaaaa gcaccagcgg cggcaccgcg gcgctgggct gcctggtgaa agattatttt    480
ccggaaccgg tgaccgtgag ctggaacagc ggcgcgctga ccagcggcgt gcatacctt     540 ccggcggtgc tgcagagcag cggcctgtat agcctgagca gcgtggtgac cgtgccgagc    600
agcagcctgg gcacccagac ctatatttgc aacgtgaacc ataaaccgag caacaccaaa    660
gtggataaaa aagtggaacc gaaaagctgc gataaaaccc atacctgccc gccgtgcccg    720
gcgccggaac tgctgggcgg cccgagcgtg tttctgtttc cgccgaaacc gaaagatacc    780
ctgatgatta gccgcacccc ggaagtgacc tgcgtggtgg tggatgtgag ccatgaagat    840
ccggaagtga aatttaactg gtatgtggat ggcgtggaag tgcataacgc gaaaaccaaa    900
ccgcgcgaag aacagtataa cagcacctat cgcgtggtga gcgtgctgac cgtgctgcat    960
caggattggc tgaacggcaa agaatataaa tgcaaagtga gcaacaaagc gctgccggcg    1020
ccgattgaaa aaaccattag caaagcgaaa ggccagccgc gcgaaccgca ggtgtatacc    1080
ctgccgccga gccgcgaaga atgaccaaa accaggtgaa gcctgacctg cctggtgaaa    1140
ggcttttatc cgagcgatat tgcggtggaa tgggaaagca acggccagcc ggaaaacaac    1200
tataaaacca cccgccggt gctggatagc gatggcagct ttttctgta tagcaaactg    1260 accgtggata aaagccgctg gcagcagggc aacgtgttta gctgcagcgt gatgcatgaa    1320
gcgctgcata accattatac ccagaaaagc ctgagcctga gcccgggcaa a             1371

<210> SEQ ID NO 195
<211> LENGTH: 1371
<212> TYPE: DNA
<213> ORGANISM: Artificial Sequence
<220> FEATURE:
<223> OTHER INFORMATION: Synthetic: DG8 Heavy chain comprising Human
      IgG1 constant region
```

<400> SEQUENCE: 195

```
gaagtacaat tgcttgaaag tggggggggc ttggtacagc ctggcggctc ccttcggctt      60
tcttgtgctg cttcaggatt taccttcagt gaccacgcca tgtcctgggt ccgtcaagct     120
ccaggtaaag ggctcgaatg ggtatctgta attagccatg gtaacggttc taagtattac     180
gccgatagtg taaagggacg atttaccatt agtagagata attctaagaa tactctttat     240
ctccaaatga actctttgag ggccgaggac acagccgtgt actactgcgc ccgtgttgcc     300
tctcggtgtc gacgggacg atgcagttat tcagacggca tggacgtttg gggacaaggg      360
actttggtca ctgtgagttc tgcgagcacc aaaggcccga gcgtgtttcc gctggcgccg     420
agcagcaaaa gcaccagcgg cggcaccgcg gcgctgggct gcctggtgaa agattatttt     480
ccggaaccgg tgaccgtgag ctggaacagc ggcgcgctga ccagcggcgt gcataccttt     540
ccggcggtgc tgcagagcag cggcctgtat agcctgagca gcgtggtgac cgtgccgagc     600
agcagcctgg gcacccagac ctatatttgc aacgtgaacc ataaaccgag caacaccaaa     660
gtggataaaa aagtggaacc gaaaagctgc gataaacccc atacctgccc gccgtgcccg     720
gcgccggaac tgctgggcgg cccgagcgtg tttctgtttc cgccgaaacc gaaagatacc     780
ctgatgatta gccgcacccc ggaagtgacc tgcgtggtgg tggatgtgag ccatgaagat     840
ccggaagtga aatttaactg gtatgtggat ggcgtggaag tgcataacgc gaaaaccaaa     900
ccgcgcgaag aacagtataa cagcacctat cgcgtggtga gcgtgctgac cgtgctgcat     960
caggattggc tgaacggcaa agaatataaa tgcaaagtga gcaacaaagc gctgccggcg    1020
ccgattgaaa aaaccattag caaagcgaaa ggccagccgc gcgaaccgca ggtgtatacc    1080
ctgccgccga gccgcgaaga aatgaccaaa aaccaggtga gcctgacctg cctggtgaaa    1140
ggcttttatc cgagcgatat tgcggtggaa tgggaaagca acggccagcc ggaaaacaac    1200
tataaaacca ccccgccggt gctggatagc gatggcagct tttttctgta tagcaaactg    1260
accgtggata aaagccgctg gcagcagggc aacgtgttta gctgcagcgt gatgcatgaa    1320
gcgctgcata accattatac ccagaaaagc ctgagcctga gcccgggcaa a             1371
```

<210> SEQ ID NO 196
<211> LENGTH: 1371
<212> TYPE: DNA
<213> ORGANISM: Artificial Sequence
<220> FEATURE:
<223> OTHER INFORMATION: Synthetic: DA9 Heavy chain comprising Human
      IgG1 constant region

<400> SEQUENCE: 196

```
gaggttcagc tcctggagtc cggtggtggc ctggttcagc ccggagggtc cttgcgtttg      60
tcttgcgctg caagcgggtt cactttctcc aactatgcta tgtcttgggt caggcaagcc     120
cctggaaagg gactcgagtg ggtcagtgta atttccccat ctgattccaa cacatattat     180
gcagacagcg ttaaaggacg gttcaccatt tcccgtgata ttcaaaaaa taccttgtac      240
ttgcaaatga atagtcttcg tgctgaggat accgcagttt actactgcgc ccgagttacc     300
ctgagttgca gggctagccg atgctcttac agcaatggta tggatgtatg gggtcaaggt     360
acattggtca cagtctcctc cgcgagcacc aaaggcccga gcgtgtttcc gctggcgccg     420
agcagcaaaa gcaccagcgg cggcaccgcg gcgctgggct gcctggtgaa agattatttt     480
ccggaaccgg tgaccgtgag ctggaacagc ggcgcgctga ccagcggcgt gcataccttt     540
ccggcggtgc tgcagagcag cggcctgtat agcctgagca gcgtggtgac cgtgccgagc     600
```

```
agcagcctgg gcacccagac ctatatttgc aacgtgaacc ataaaccgag caacaccaaa    660
gtggataaaa aagtggaacc gaaaagctgc gataaaaccc atacctgccc gccgtgcccg    720
gcgccggaac tgctgggcgg cccgagcgtg tttctgtttc cgccgaaacc gaaagatacc    780
ctgatgatta gccgcacccc ggaagtgacc tgcgtggtgg tggatgtgag ccatgaagat    840
ccggaagtga aatttaactg gtatgtggat ggcgtggaag tgcataacgc gaaaaccaaa    900
ccgcgcgaag aacagtataa cagcacctat cgcgtggtga gcgtgctgac cgtgctgcat    960
caggattggc tgaacggcaa agaatataaa tgcaaagtga gcaacaaagc gctgccggcg   1020
ccgattgaaa aaaccattag caaagcgaaa ggccagccgc gcgaaccgca ggtgtatacc   1080
ctgccgccga gccgcgaaga aatgaccaaa aaccaggtga gcctgacctg cctggtgaaa   1140 ggctttatc cgagcgatat tgcggtgaa tgggaaagca acggccagcc ggaaaacaac   1200
tataaaacca ccccgccggt gctggatagc gatggcagct ttttctgta tagcaaactg   1260 accgtggata aaagccgctg gcagcagggc aacgtgttta gctgcagcgt gatgcatgaa   1320
gcgctgcata accattatac ccagaaaagc ctgagcctga gcccgggcaa a           1371
```

<210> SEQ ID NO 197
<211> LENGTH: 654
<212> TYPE: DNA
<213> ORGANISM: Artificial Sequence
<220> FEATURE:
<223> OTHER INFORMATION: Synthetic: 1E4 Light chain comprisng mouse
      kappa constant region

<400> SEQUENCE: 197

```
gatatcgtga tgacccagtc tcctctgagc ctgcctgtgt ctctgggcga tcaggcctcc     60
atctcctgca gatcttctca gtccctggtg cactccaacg gcaacaccta cctgcactgg    120
tatctgcaga agcccggcca gtctccaaag ctgctgatct acaaggtgtc caaccggttc    180
tctggcgtgc ccgacagatt ttctggctct ggatctggca ccgacttcac cctgaagatc    240
tccagagtgg aagccgagga cctgggcgtg tacttctgta gccagtctac ccacgtgcca    300
agaacctttg gcggaggcac caagctggaa atcaaggcgg atgcggcgcc gaccgtgagc    360
atttttccgc cgagcagcga acagctgacc agcggcggcg cgagcgtggt gtgctttctg    420
aacaactttt atccgaaaga tattaacgtg aaatggaaaa ttgatggcag cgaacgccag    480
aacggcgtgc tgaacagctg gaccgatcag gatagcaaag atagcaccta tagcatgagc    540
agcaccctga ccctgaccaa agatgaatat gaacgccata acagctatac ctgcgaagcg    600
acccataaaa ccagcaccag cccgattgtg aaaagcttta accgcaacga atgc          654
```

<210> SEQ ID NO 198
<211> LENGTH: 654
<212> TYPE: DNA
<213> ORGANISM: Artificial Sequence
<220> FEATURE:
<223> OTHER INFORMATION: Synthetic: 9B11 Light chain comprisng mouse
      kappa constant region

<400> SEQUENCE: 198

```
gatatcgtga tgacccagtc tcctctgagc ctgcctgtgt ctctgggcga tcaggcctcc     60
atctcctgca gatcttctca gtccctggtg cactccaacg gcaacaccta cctgcactgg    120
tatctgcaga agcccggcca gtctccaaag ctgctgatct acaaggtgtc caaccggttc    180
tctggcgtgc ccgacagatt ttctggctct ggatctggca ccgacttcac cctgaagatc    240
```

```
tccagagtgg aagccgagga cctgggcgtg tacttctgta gccagtctac ccacgtgcca    300
ctgacctttg gcgctggcac aaagctggaa cagaaggcgg atgcggcgcc gaccgtgagc    360 attttttccgc cgagcagcga acagctgacc agcggcggcg cgagcgtggt gtgctttctg    420
aacaactttt atccgaaaga tattaacgtg aaatggaaaa ttgatggcag cgaacgccag    480
aacggcgtgc tgaacagctg gaccgatcag gatagcaaag atagcaccta tagcatgagc    540
agcaccctga ccctgaccaa agatgaatat gaacgccata cagctatac ctgcgaagcg     600 acccataaaa ccagcaccag cccgattgtg aaaagcttta accgcaacga atgc          654
```

<210> SEQ ID NO 199
<211> LENGTH: 639
<212> TYPE: DNA
<213> ORGANISM: Artificial Sequence
<220> FEATURE:
<223> OTHER INFORMATION: Synthetic: 3A9 Light chain comprisng mouse
      kappa constant region

<400> SEQUENCE: 199

```
gatatcgtga tgacccagtc tcctaagttc atgtccacct ccgtgggcga cagagtgtcc     60
atcacatgca aggcctctca gaacgtgggc accaccgttg cctggtatca gcagaaacct    120
ggccagtctc caaagctgct gatctactcc gcctctaaca gatacacagg cgtgcccgac    180
agattcaccg gctctggctc tggcaccgat ttcaccctga ccatctccaa catgcagtcc    240
gaggacctgg ccgactactt ctgccagcag tacagcaact accctctgac ctttggcgct    300
ggcaccaagc tggaactgag agcggatgcg gcgccgaccg tgagcatttt tccgccgagc    360
agcgaacagc tgaccagcgg cggcgcgagc gtggtgtgct ttctgaacaa cttttatccg    420
aaagatatta cgtgaaatg gaaaattgat ggcagcgaac gccagaacgg cgtgctgaac    480
agctggaccg atcaggatag caaagatagc acctatagca tgagcagcac cctgaccctg    540
accaaagatg aatatgaacg ccataacagc tataccctgcg aagcgaccca taaaaccagc    600
accagcccga ttgtgaaaag ctttaaccgc aacgaatgc                            639
```

<210> SEQ ID NO 200
<211> LENGTH: 654
<212> TYPE: DNA
<213> ORGANISM: Artificial Sequence
<220> FEATURE:
<223> OTHER INFORMATION: Synthetic: 10F10 Light chain comprisng mouse
      kappa constant region

<400> SEQUENCE: 200

```
gatatcgtga tgacccagtc tcctctgaca ctgtccgtga ccatcggcca gcctgcctcc     60
atttcttgca gtcctctca gtccctgctg gactccgatg gcgagacata cctgaactgg    120
ctgttgcaga ggcctggcca gagtcctaag agactgatct acctggtgtc caagctggat    180
tccggcgtgc ccgatagatt ttccggctct ggctctggca ccgacttcac cctgaagatc    240
tctagagtgg aagccgagga cctgggcgtg tactactgtt ggcagggaac ccactttcct    300
cagacctttg gcggcggaac aaagctggaa atcaaggcgg atgcggcgcc gaccgtgagc    360 attttttccgc cgagcagcga acagctgacc agcggcggcg cgagcgtggt gtgctttctg    420
aacaactttt atccgaaaga tattaacgtg aaatggaaaa ttgatggcag cgaacgccag    480
aacggcgtgc tgaacagctg gaccgatcag gatagcaaag atagcaccta tagcatgagc    540
agcaccctga ccctgaccaa agatgaatat gaacgccata cagctatac ctgcgaagcg     600 acccataaaa ccagcaccag cccgattgtg aaaagcttta accgcaacga atgc          654
```

<210> SEQ ID NO 201
<211> LENGTH: 654
<212> TYPE: DNA
<213> ORGANISM: Artificial Sequence
<220> FEATURE:
<223> OTHER INFORMATION: Synthetic: 11F11 Light chain comprisng mouse
      kappa constant region

<400> SEQUENCE: 201
gatatcgtga tgacccagtc tcctctgaca ctgtccgtga ccatcggcca gcctgcctcc      60
atttcttgca gtcctctca gtccctgctg gactccgatg gcgagacata cctgaactgg     120
ctgttgcaga ggcctggcca gagtcctaag agactgatct acctggtgtc caagctggat     180
tccggcgtgc cgatagatt ttccggctct ggctctggca ccgacttcac cctgaagatc     240
tctagagtgg aagccgagga cctgggcgtg tactactgtt ggcagggaac ccactttcct     300
cagacctttg gcggcggaac aaagctggaa atcaaggcgg atgcggcgcc gaccgtgagc     360 attttccgc cgagcagcga acagctgacc agcggcggcg cgagcgtggt gtgctttctg     420
aacaactttt atccgaaaga tattaacgtg aaatggaaaa ttgatggcag cgaacgccag     480
aacggcgtgc tgaacagctg gaccgatcag gatagcaaag atagcaccta gcatgagc     540 agcaccctga ccctgaccaa agatgaatat gaacgccata cagctatac ctgcgaagcg     600 acccataaaa ccagcaccag cccgattgtg aaaagcttta ccgcaacga atgc           654

<210> SEQ ID NO 202
<211> LENGTH: 651
<212> TYPE: DNA
<213> ORGANISM: Artificial Sequence
<220> FEATURE:
<223> OTHER INFORMATION: AC8 Light chain comprisng mouse kappa constant
      region

<400> SEQUENCE: 202
caaagcgtac ttactcagcc tccaagcgcc agcgggacac ccggtcagag ggtcactatt      60
agttgctctg ggagctcttc aaatataggc tctaataacg tgtactggta tcagcaactg     120
cccggtactg caccaaaact gctcatatac tacgatagcc aacgtcctag cggagtccca     180
gaccgcttca gcggcagtaa atccggcacc tccgccagtt tggccataag cggacttcgc     240
tcagaggacg aagcagacta ctattgcgct tcttgggatg cttcattgag tgcttatgtg     300
ttcggtggcg ggactaagct cactgtcctt ggtgcggatg cggcgccgac cgtgagcatt     360
tttccgccga gcgaacaa gctgaccagc ggcggcgcga gcgtggtgtg ctttctgaac     420 aactttatc cgaaagatat taacgtgaaa tggaaaattg atggcagcga acgccagaac     480
ggcgtgctga acagctggac cgatcaggat agcaaagata gcacctatag catgagcagc     540
accctgaccc tgaccaaaga tgaatatgaa cgccataaca gctatacctg cgaagcgacc     600
cataaaacca gcaccagccc gattgtgaaa agctttaacc gcaacgaatg c             651

<210> SEQ ID NO 203
<211> LENGTH: 651
<212> TYPE: DNA
<213> ORGANISM: Artificial Sequence
<220> FEATURE:
<223> OTHER INFORMATION: AE8 Light chain comprisng mouse kappa constant
      region

<400> SEQUENCE: 203
caaagtgtgc tcacacagcc accaagcgcc agcgggactc ctggtcaacg agttactata      60

```
agctgttcag gaagtagttc taacattggc aataactccg tcaactggta tcaacaactc    120
ccaggcacag cacctaagtt gctgatctac gccaataata accgcccag cggggttcca    180 gaccgcttct ccgggtctaa gagcgggact tctgcatcat tggcaatttc cggccttagg    240
tccgaagacg aggcagatta ttattgtggt agctgggacg catctctcaa tggatacgtt    300
tttggcgggg gcaccaagct tacagttctt ggagcggatg cggcgccgac cgtgagcatt    360
tttccgccga gcagcgaaca gctgaccagc ggcggcgcga gcgtggtgtg ctttctgaac    420
aacttttatc cgaaagatat taacgtgaaa tggaaaattg atggcagcga acgccagaac    480
ggcgtgctga acagctggac cgatcaggat agcaaagata gcacctatag catgagcagc    540
accctgaccc tgaccaaaga tgaatatgaa cgccataaca gctatacctg cgaagcgacc    600
cataaaacca gcaccagccc gattgtgaaa agctttaacc gcaacgaatg c              651
```

<210> SEQ ID NO 204
<211> LENGTH: 651
<212> TYPE: DNA
<213> ORGANISM: Artificial Sequence
<220> FEATURE:
<223> OTHER INFORMATION: AA9 Light chain comprisng mouse kappa constant
      region

<400> SEQUENCE: 204

```
caatctgtgc ttactcaacc ccccagtgca tccggtactc ccggtcaaag ggtcactatc      60
agctgttcag gttcaagctc caatatcggt agtaattatg ttagctggta tcaacagctc    120
cctggaacag ctccaaagct gctcatttat ggggacaaca gcgtccatc tggcgtgcct     180 gacagattta gtggctccaa gtccgggaca tccgcatctt tggcaatcag cggacttcga    240
tccgaggatg aggccgacta ttattgtgga gcctgggacg attcactgag cgggtacgtt    300
tttggtgggg gtactaaact gacagtgctt ggagcggatg cggcgccgac cgtgagcatt    360
tttccgccga gcagcgaaca gctgaccagc ggcggcgcga gcgtggtgtg ctttctgaac    420
aacttttatc cgaaagatat taacgtgaaa tggaaaattg atggcagcga acgccagaac    480
ggcgtgctga acagctggac cgatcaggat agcaaagata gcacctatag catgagcagc    540
accctgaccc tgaccaaaga tgaatatgaa cgccataaca gctatacctg cgaagcgacc    600
cataaaacca gcaccagccc gattgtgaaa agctttaacc gcaacgaatg c              651
```

<210> SEQ ID NO 205
<211> LENGTH: 651
<212> TYPE: DNA
<213> ORGANISM: Artificial Sequence
<220> FEATURE:
<223> OTHER INFORMATION: DG5 Light chain comprisng mouse kappa constant
      region

<400> SEQUENCE: 205

```
cagagtgtgc tcactcaacc tccatccgcc tctggtacac aggtcaacg ggtcactatc      60 tcatgcagcg gctccagctc caacatagga tctaatgctg tcagttggta tcaacagttg    120
cccggaacag cacctaagtt gctgatatac agcaattcca accgccctc tggcgtgccc    180 gaccggtttt caggttccaa gtctggcaca tcagcttctc tcgccattag tgggctccgt    240
tctgaggatg aggcagacta ctactgtgct gcctgggacg catccctgtc cgggtacgtc    300
tttggaggcg gaaccaagtt gaccgtgctg gagcggatg cggcgccgac cgtgagcatt    360
tttccgccga gcagcgaaca gctgaccagc ggcggcgcga gcgtggtgtg ctttctgaac    420
```

```
aactttatc cgaaagatat taacgtgaaa tggaaaattg atggcagcga acgccagaac    480
ggcgtgctga acagctggac cgatcaggat agcaaagata gcacctatag catgagcagc    540
accctgaccc tgaccaaaga tgaatatgaa cgccataaca gctatacctg cgaagcgacc    600
cataaaacca gcaccagccc gattgtgaaa agctttaacc gcaacgaatg c             651
```

<210> SEQ ID NO 206
<211> LENGTH: 651
<212> TYPE: DNA
<213> ORGANISM: Artificial Sequence
<220> FEATURE:
<223> OTHER INFORMATION: AD2 Light chain comprisng mouse kappa constant region

<400> SEQUENCE: 206

```
caaagtgtgc tcactcagcc tccatcagct agtggaactc ccggacaaag ggtaaccatt     60
agctgcactg gatcttcctc caatatcggt aataatagtg taagttggta tcagcaattg    120
cctggaaccg cacccaagtt gctcatctac tctgataaca accgtccatc aggtgtccct    180
gaccgttttt caggttctaa agtgggact tcagcctctc tcgccatctc aggtctgcga    240
agcgaagacg aagcagacta ctattgtggt tcctgggatg ctagcctcag tggctacgtg    300
tttggtggtg gaacaaaact cactgtactt ggtgcgatg cggcgccgac cgtgagcatt    360
tttccgccga gcagcgaaca gctgaccagc ggcggcgcga gcgtggtgtg ctttctgaac    420 aactttatc cgaaagatat taacgtgaaa tggaaaattg atggcagcga acgccagaac    480
ggcgtgctga acagctggac cgatcaggat agcaaagata gcacctatag catgagcagc    540
accctgaccc tgaccaaaga tgaatatgaa cgccataaca gctatacctg cgaagcgacc    600
cataaaacca gcaccagccc gattgtgaaa agctttaacc gcaacgaatg c             651
```

<210> SEQ ID NO 207
<211> LENGTH: 651
<212> TYPE: DNA
<213> ORGANISM: Artificial Sequence
<220> FEATURE:
<223> OTHER INFORMATION: AD7 Light chain comprisng mouse kappa constant region

<400> SEQUENCE: 207

```
caatctgtct tgactcaacc tcctagtgct tcaggtactc ctgggcagcg tgtaactatt     60
tcttgtactg ggagcagttc caacatcggg agcaatgccg tgaactggta tcagcagttg    120
ccaggtacag ctcccaaact tctcatttac agcaacaacc atcgcccatc cggggtgccc    180
gataggttct ctggctctaa agtggaaca agcgcaagcc tggcaatctc cggcttgcgt    240
tcagaggatg aagccgacta ctactgcggc gcatgggact cctctctcaa tggatatgtg    300
tttggaggcg gcactaaact taccgtattg ggagcggatg cggcgccgac cgtgagcatt    360
tttccgccga gcagcgaaca gctgaccagc ggcggcgcga gcgtggtgtg ctttctgaac    420 aactttatc cgaaagatat taacgtgaaa tggaaaattg atggcagcga acgccagaac    480
ggcgtgctga acagctggac cgatcaggat agcaaagata gcacctatag catgagcagc    540
accctgaccc tgaccaaaga tgaatatgaa cgccataaca gctatacctg cgaagcgacc    600
cataaaacca gcaccagccc gattgtgaaa agctttaacc gcaacgaatg c             651
```

<210> SEQ ID NO 208
<211> LENGTH: 651
<212> TYPE: DNA
<213> ORGANISM: Artificial Sequence

```
<220> FEATURE:
<223> OTHER INFORMATION: DG11 Light chain comprisng mouse kappa constant
      region

<400> SEQUENCE: 208
cagtctgtac tgactcaacc acccagtgcc agtggtaccc cagggcaacg tgtaactatt       60
agttgcactg gaagttcctc taacatagga agcaactcag tgagttggta ccagcaactt      120
ccagggacag ctcctaaact tttgatatac gcaaattcta accgacctc tggagtccct       180 gataggttta gcgggagcaa gtcaggaacc agcgcatccc ttgctataag cggacttcgg      240
agcgaagacg aggccgatta ctattgcgct gcctgggatg cctctttgtc tgcctacgtg      300
tttggtggag ggactaagct caccgtactt ggggcggatg cggcgccgac cgtgagcatt      360
tttccgccga gcagcgaaca gctgaccagc ggcggcgcga gcgtggtgtg ctttctgaac      420 aactttatc cgaaagatat taacgtgaaa tggaaaattg atggcagcga acgccagaac       480
ggcgtgctga acagctggac cgatcaggat agcaaagata gcacctatag catgagcagc      540
accctgaccc tgaccaaaga tgaatatgaa cgccataaca gctataccctg cgaagcgacc    600 cataaaacca gcaccagccc gattgtgaaa agctttaacc gcaacgaatg c              651

<210> SEQ ID NO 209
<211> LENGTH: 651
<212> TYPE: DNA
<213> ORGANISM: Artificial Sequence
<220> FEATURE:
<223> OTHER INFORMATION: DG8 Light chain comprisng mouse kappa constant
      region

<400> SEQUENCE: 209
cagtctgttc tgacccaacc accttcagca agcgggactc ctggccaacg ggtgacaata      60
agttgctcag ggtcttcctc aaatatagga agcaacagcg taagctggta tcagcagttg     120
ccaggcaccg cacccaaact gctcatttat gccaacaaca atcgaccatc tggtgtgcca     180
gatcggttta gcgggtctaa gtcaggcact agtgccagtc tggccatttc cggcctccgg     240
tctgaagacg aagccgacta ctattgcggg catgggata gctcattgtc cgcatacgtg      300
tttggcggcg ggaccaagtt gaccgttctg ggggcggatg cggcgccgac cgtgagcatt    360
tttccgccga gcagcgaaca gctgaccagc ggcggcgcga gcgtggtgtg ctttctgaac    420 aactttatc cgaaagatat taacgtgaaa tggaaaattg atggcagcga acgccagaac     480
ggcgtgctga acagctggac cgatcaggat agcaaagata gcacctatag catgagcagc    540
accctgaccc tgaccaaaga tgaatatgaa cgccataaca gctataccctg cgaagcgacc  600 cataaaacca gcaccagccc gattgtgaaa agctttaacc gcaacgaatg c              651

<210> SEQ ID NO 210
<211> LENGTH: 651
<212> TYPE: DNA
<213> ORGANISM: Artificial Sequence
<220> FEATURE:
<223> OTHER INFORMATION: DA9 Light chain comprisng mouse kappa constant
      region

<400> SEQUENCE: 210
caaagtgtct tgactcaacc tcccagtgcc tctgggaccc ctgggcaaag agtcaccatt      60
agctgttctg gttccccttc taatatagga aacaattctg taagttggta tcagcagctc    120
ccaggcacag ctcccaaact gcttatctac gctaactcac accggcccag tggagtcccc   180
gaccgtttct ccggtagcaa atccggtacc tccgcctcac ttgctatttc aggacttcgc    240
```

```
agcgaggacg aggccgacta ttattgtggg tcttgggatg cctcactgaa tggatatgtt    300
ttcggtggcg gcaccaagct caccgttttg ggcgcggatg cggcgccgac cgtgagcatt    360
tttccgccga gcagcgaaca gctgaccagc ggcggcgcga gcgtggtgtg ctttctgaac    420 aactttatc  cgaaagatat taacgtgaaa tggaaaattg atggcagcga acgccagaac    480
ggcgtgctga acagctggac cgatcaggat agcaaagata gcacctatag catgagcagc    540
accctgaccc tgaccaaaga tgaatatgaa cgccataaca gctatacctg cgaagcgacc    600
cataaaacca gcaccagccc gattgtgaaa agctttaacc gcaacgaatg c             651
```

<210> SEQ ID NO 211
<211> LENGTH: 657
<212> TYPE: DNA
<213> ORGANISM: Artificial Sequence
<220> FEATURE:
<223> OTHER INFORMATION: 1E4 Light chain comprisng human kappa constant
      region

<400> SEQUENCE: 211

```
gatatcgtga tgacccagtc tcctctgagc ctgcctgtgt ctctgggcga tcaggcctcc    60
atctcctgca gatcttctca gtccctggtg cactccaacg gcaacaccta cctgcactgg    120
tatctgcaga agcccggcca gtctccaaag ctgctgatct acaaggtgtc caaccggttc    180
tctggcgtgc ccgacagatt ttctggctct ggatctggca ccgacttcac cctgaagatc    240
tccagagtgg aagccgagga cctgggcgtg tacttctgta gccagtctac ccacgtgcca    300
agaacctttg gcgaggcac  caagctggaa atcaagcgca ccgtggcggc gccgagcgtg    360
tttatttttc cgccgagcga tgaacagctg aaaagcggca ccgcgagcgt ggtgtgcctg    420
ctgaacaact ttatccgcg  cgaagcgaaa gtgcagtgga agtggataa  cgcgctgcag    480 agcggcaaca gccaggaaag cgtgaccgaa caggatagca agatagcac  ctatagcctg    540 agcagcaccc tgaccctgag caaagcggat tatgaaaaac ataaagtgta tgcgtgcgaa    600
gtgacccatc agggcctgag cagcccggtg accaaaagct taaccgcgg  cgaatgc      657
```

<210> SEQ ID NO 212
<211> LENGTH: 657
<212> TYPE: DNA
<213> ORGANISM: Artificial Sequence
<220> FEATURE:
<223> OTHER INFORMATION: 9B11 Light chain comprisng human kappa constant
      region

<400> SEQUENCE: 212

```
gatatcgtga tgacccagtc tcctctgagc ctgcctgtgt ctctgggcga tcaggcctcc    60
atctcctgca gatcttctca gtccctggtg cactccaacg gcaacaccta cctgcactgg    120
tatctgcaga agcccggcca gtctccaaag ctgctgatct acaaggtgtc caaccggttc    180
tctggcgtgc ccgacagatt ttctggctct ggatctggca ccgacttcac cctgaagatc    240
tccagagtgg aagccgagga cctgggcgtg tacttctgta gccagtctac ccacgtgcca    300
ctgacctttg gcgctggcac aaagctggaa cagaagcgca ccgtggcggc gccgagcgtg    360
tttatttttc cgccgagcga tgaacagctg aaaagcggca ccgcgagcgt ggtgtgcctg    420
ctgaacaact ttatccgcg  cgaagcgaaa gtgcagtgga agtggataa  cgcgctgcag    480 agcggcaaca gccaggaaag cgtgaccgaa caggatagca agatagcac  ctatagcctg    540 agcagcaccc tgaccctgag caaagcggat tatgaaaaac ataaagtgta tgcgtgcgaa    600
```

```
gtgacccatc agggcctgag cagcccggtg accaaaagct ttaaccgcgg cgaatgc      657

<210> SEQ ID NO 213
<211> LENGTH: 642
<212> TYPE: DNA
<213> ORGANISM: Artificial Sequence
<220> FEATURE:
<223> OTHER INFORMATION: 3A9 Light chain comprisng human kappa constant
      region

<400> SEQUENCE: 213
gatatcgtga tgacccagtc tcctaagttc atgtccacct ccgtgggcga cagagtgtcc      60
atcacatgca aggcctctca gaacgtgggc accaccgttg cctggtatca gcagaaacct     120
ggccagtctc caaagctgct gatctactcc gcctctaaca gatacacagg cgtgcccgac     180
agattcaccg gctctggctc tggcaccgat ttcacccctg acatctccaa catgcagtcc     240
gaggacctgg ccgactactt ctgccagcag tacagcaact accctctgac ctttggcgct     300
ggcaccaagc tggaactgag acgcaccgtg gcggcgccga gcgtgtttat ttttccgccg     360
agcgatgaac agctgaaaag cggcaccgcg agcgtggtgt gcctgctgaa caacttttat     420
ccgcgcgaag cgaaagtgca gtggaaagtg ataacgcgc tgcagagcgg caacagccag     480
gaaagcgtga ccgaacagga tagcaaagat agcacctata gcctgagcag caccctgacc     540
ctgagcaaag cggattatga aaaacataaa gtgtatgcgt gcgaagtgac ccatcagggc     600
ctgagcagcc cggtgaccaa aagctttaac cgcggcgaat gc                       642

<210> SEQ ID NO 214
<211> LENGTH: 657
<212> TYPE: DNA
<213> ORGANISM: Artificial Sequence
<220> FEATURE:
<223> OTHER INFORMATION: 10F10 Light chain comprisng human kappa
      constant region

<400> SEQUENCE: 214
gatatcgtga tgacccagtc tcctctgaca ctgtccgtga ccatcggcca gcctgcctcc      60
atttcttgca gtcctctca gtccctgctg gactccgatg gcgagacata cctgaactgg     120
ctgttgcaga ggcctggcca gagtcctaag agactgatct acctggtgtc caagctggat     180
tccggcgtgc ccgatagatt ttccggctct ggctctggca ccgacttcac cctgaagatc     240
tctagagtgg aagccgagga cctgggcgtg tactactgtt ggcagggaac ccactttcct     300
cagacctttg gcggcggaac aaagctggaa atcaagcgca ccgtggcggc gccgagcgtg     360 tttattttc cgccgagcga tgaacagctg aaaagcggca ccgcgagcgt ggtgtgcctg     420
ctgaacaact tttatccgcg cgaagcgaaa gtgcagtgga agtggataa cgcgctgcag     480 agcggcaaca gccaggaaag cgtgaccgaa caggatagca agatagcac ctatagcctg     540 agcagcaccc tgaccctgag caaagcggat tatgaaaaac ataaagtgta tgcgtgcgaa     600
gtgacccatc agggcctgag cagcccggtg accaaaagct ttaaccgcgg cgaatgc      657

<210> SEQ ID NO 215
<211> LENGTH: 660
<212> TYPE: DNA
<213> ORGANISM: Artificial Sequence
<220> FEATURE:
<223> OTHER INFORMATION: 11F11 Light chain comprisng human kappa
      constant region

<400> SEQUENCE: 215
```

```
gatatcgtga tgacccagtc tccttcctct ctggctgtgt ccgtgggcga aaagtgacc      60 atgtcctgca agtcctctca gtccctgctg tactcctcca accagaagaa ctacctggcc    120
tggtatcagc agaagcccgg ccagtctcca aagctgctga tctactgggc ctccaccaga    180
gaatctggcg tgccagatag attcaccggc tctggctctg gcaccgactt cacccctgaca   240 atctcttccg tgaaggccga ggacctggcc gtgtactact gccagcagta ctacagctac    300
ccctggacct ttggcggagg caccaagctg gaaatcaagc gcaccgtggc ggcgccagc     360 gtgtttattt ttccgccgag cgatgaacag ctgaaaagcg gcaccgcgag cgtggtgtgc    420
ctgctgaaca ctttttatcc gcgcgaagcg aaagtgcagt ggaaagtgga taacgcgctg    480
cagagcggca acagccagga aagcgtgacc gaacaggata gcaaagatag cacctatagc    540
ctgagcagca ccctgacccT gagcaaagcg gattatgaaa aacataaagt gtatgcgtgc    600
gaagtgaccc atcagggcct gagcagcccg gtgaccaaaa gctttaaccg cggcgaatgc    660
```

<210> SEQ ID NO 216  
<211> LENGTH: 654  
<212> TYPE: DNA  
<213> ORGANISM: Artificial Sequence  
<220> FEATURE:  
<223> OTHER INFORMATION: Synthetic: AC8 Light chain comprisng human kappa constant region

<400> SEQUENCE: 216

```
caaagcgtac ttactcagcc tccaagcgcc agcgggacac ccggtcagag ggtcactatt      60
agttgctctg ggagctcttc aaatataggc tctaataacg tgtactggta tcagcaactg    120
cccggtactg caccaaaact gctcatatac tacgatagcc aacgtcctag cggagtccca    180
gaccgcttca gcggcagtaa atccggcacc tccgccagtt tggccataag cggacttcgc    240
tcagaggacg aagcagacta ctattgcgct tcttgggatg cttcattgag tgcttatgtg    300
ttcggtggcg ggactaagct cactgtcctt ggtcgcaccg tggcggcgcc gagcgtgttt    360
atttttccgc cgagcgatga acagctgaaa agcggcaccg cgagcgtggt gtgcctgctg    420
aacaactttt atccgcgcga agcgaaagtg cagtggaaag tggataacgc gctgcagagc    480
ggcaacagcc aggaaagcgt gaccgaacag gatagcaaag atagcaccta tagcctgagc    540
agcaccctga ccctgagcaa agcggattat gaaaaacata agtgtatgc gtgcgaagtg    600 acccatcagg gcctgagcag cccggtgacc aaaagcttta ccgcggcga atgc           654
```

<210> SEQ ID NO 217  
<211> LENGTH: 654  
<212> TYPE: DNA  
<213> ORGANISM: Artificial Sequence  
<220> FEATURE:  
<223> OTHER INFORMATION: Synthetic: AE8 Light chain comprisng human kappa constant region

<400> SEQUENCE: 217

```
caaagtgtgc tcacacagcc accaagcgcc agcgggactc ctggtcaacg agttactata      60
agctgttcag gaagtagttc taacattggc aataactccg tcaactggta tcaacaactc    120
ccaggcacag cacctaagtt gctgatctac gccaataata accgcccag cggggttcca    180 gaccgcttct ccgggtctaa gagcgggact tctgcatcat tggcaatttc cggccttagg    240
tccgaagacg aggcagatta ttattgtggt agctgggacg catctctcaa tggatacgtt    300
tttggcgggg gcaccaagct tacagttctt ggacgcaccg tggcggcgcc gagcgtgttt    360
atttttccgc cgagcgatga acagctgaaa agcggcaccg cgagcgtggt gtgcctgctg    420
```

```
aacaacttttt atccgcgcga agcgaaagtg cagtggaaag tggataacgc gctgcagagc    480
ggcaacagcc aggaaagcgt gaccgaacag gatagcaaag atagcaccta tagcctgagc    540
agcaccctga ccctgagcaa agcggattat gaaaaacata agtgtatgc gtgcgaagtg     600 acccatcagg gcctgagcag cccggtgacc aaaagcttta ccgcggcga atgc           654
```

<210> SEQ ID NO 218
<211> LENGTH: 654
<212> TYPE: DNA
<213> ORGANISM: Artificial Sequence
<220> FEATURE:
<223> OTHER INFORMATION: Synthetic: AA9 Light chain comprisng human
      kappa constant region

<400> SEQUENCE: 218

```
caatctgtgc ttactcaacc ccccagtgca tccggtactc ccggtcaaag ggtcactatc     60
agctgttcag gttcaagctc caatatcggt agtaattatg ttagctggta tcaacagctc    120
cctggaacag ctccaaagct gctcatttat ggggacaaca agcgtccatc tggcgtgcct    180
gacagattta gtggctccaa gtccgggaca tccgcatctt tggcaatcag cggacttcga    240
tccgaggatg aggccgacta ttattgtgga gcctgggacg attcactgag cgggtacgtt    300
tttggtgggg gtactaaact gacagtgctt ggacgcaccg tggcggcgcc gagcgtgttt    360 attttccgc cgagcgatga acagctgaaa agcggcaccg cgagcgtggt gtgcctgctg     420 aacaacttttt atccgcgcga agcgaaagtg cagtggaaag tggataacgc gctgcagagc   480
ggcaacagcc aggaaagcgt gaccgaacag gatagcaaag atagcaccta tagcctgagc    540
agcaccctga ccctgagcaa agcggattat gaaaaacata agtgtatgc gtgcgaagtg     600 acccatcagg gcctgagcag cccggtgacc aaaagcttta ccgcggcga atgc           654
```

<210> SEQ ID NO 219
<211> LENGTH: 654
<212> TYPE: DNA
<213> ORGANISM: Artificial Sequence
<220> FEATURE:
<223> OTHER INFORMATION: Synthetic: DG5 Light chain comprisng human
      kappa constant region

<400> SEQUENCE: 219

```
cagagtgtgc tcactcaacc tccatccgcc tctggtacac aggtcaacg ggtcactatc      60 tcatgcagcg gctccagctc caacatagga tctaatgctg tcagttggta tcaacagttg    120
cccggaacag cacctaagtt gctgatatac agcaattcca accgcccctc tggcgtgccc    180
gaccggtttt caggttccaa gtctggcaca tcagcttctc tcgccattag tgggctccgt    240
tctgaggatg aggcagacta ctactgtgct gcctgggacg catccctgtc cgggtacgtc    300
tttggaggcg gaaccaagtt gaccgtgctg gacgcaccg tggcggcgcc gagcgtgttt     360 attttccgc cgagcgatga acagctgaaa agcggcaccg cgagcgtggt gtgcctgctg     420 aacaacttttt atccgcgcga agcgaaagtg cagtggaaag tggataacgc gctgcagagc   480
ggcaacagcc aggaaagcgt gaccgaacag gatagcaaag atagcaccta tagcctgagc    540
agcaccctga ccctgagcaa agcggattat gaaaaacata agtgtatgc gtgcgaagtg     600 acccatcagg gcctgagcag cccggtgacc aaaagcttta ccgcggcga atgc           654
```

<210> SEQ ID NO 220
<211> LENGTH: 654
<212> TYPE: DNA

<213> ORGANISM: Artificial Sequence
<220> FEATURE:
<223> OTHER INFORMATION: Synthetic: AD2 Light chain comprisng human
      kappa constant region

<400> SEQUENCE: 220

| | | | | | |
|---|---|---|---|---|---|
| caaagtgtgc | tcactcagcc | tccatcagct | agtggaactc | ccggacaaag | ggtaaccatt | 60 |
| agctgcactg | gatcttcctc | caatatcggt | aataatagtg | taagttggta | tcagcaattg | 120 |
| cctggaaccg | cacccaagtt | gctcatctac | tctgataaca | accgtccatc | aggtgtccct | 180 |
| gaccgttttt | caggttctaa | aagtgggact | tcagcctctc | tcgccatctc | aggtctgcga | 240 |
| agcgaagacg | aagcagacta | ctattgtggt | tcctgggatg | ctagcctcag | tggctacgtg | 300 |
| tttggtggtg | gaacaaaact | cactgtactt | ggtcgcaccg | tggcggcgcc | gagcgtgttt | 360 |
| attttccgc | cgagcgatga | acagctgaaa | agcggcaccg | cgagcgtggt | gtgcctgctg | 420 |
| aacaactttt | atccgcgcga | agcgaaagtg | cagtggaaag | tggataacgc | gctgcagagc | 480 |
| ggcaacagcc | aggaaagcgt | gaccgaacag | gatagcaaag | atagcaccta | tagcctgagc | 540 |
| agcaccctga | ccctgagcaa | agcggattat | gaaaaacata | aagtgtatgc | gtgcgaagtg | 600 |
| acccatcagg | gcctgagcag | cccggtgacc | aaaagcttta | accgcggcga | atgc | 654 |

<210> SEQ ID NO 221
<211> LENGTH: 654
<212> TYPE: DNA
<213> ORGANISM: Artificial Sequence
<220> FEATURE:
<223> OTHER INFORMATION: Synthetic: AD7 Light chain comprisng human
      kappa constant region

<400> SEQUENCE: 221

| | | | | | |
|---|---|---|---|---|---|
| caatctgtct | tgactcaacc | tcctagtgct | tcaggtactc | ctgggcagcg | tgtaactatt | 60 |
| tcttgtactg | ggagcagttc | caacatcggg | agcaatgccg | tgaactggta | tcagcagttg | 120 |
| ccaggtacag | ctcccaaact | tctcatttac | agcaacaacc | atcgcccatc | cggggtgccc | 180 |
| gataggttct | ctggctctaa | aagtggaaca | agcgcaagcc | tggcaatctc | cggcttgcgt | 240 |
| tcagaggatg | aagccgacta | ctactgcggc | gcatgggact | cctctctcaa | tggatatgtg | 300 |
| tttggaggcg | gcactaaact | taccgtattg | ggacgcaccg | tggcggcgcc | gagcgtgttt | 360 |
| attttccgc | cgagcgatga | acagctgaaa | agcggcaccg | cgagcgtggt | gtgcctgctg | 420 |
| aacaactttt | atccgcgcga | agcgaaagtg | cagtggaaag | tggataacgc | gctgcagagc | 480 |
| ggcaacagcc | aggaaagcgt | gaccgaacag | gatagcaaag | atagcaccta | tagcctgagc | 540 |
| agcaccctga | ccctgagcaa | agcggattat | gaaaaacata | aagtgtatgc | gtgcgaagtg | 600 |
| acccatcagg | gcctgagcag | cccggtgacc | aaaagcttta | accgcggcga | atgc | 654 |

<210> SEQ ID NO 222
<211> LENGTH: 654
<212> TYPE: DNA
<213> ORGANISM: Artificial Sequence
<220> FEATURE:
<223> OTHER INFORMATION: Synthetic: DG11 Light chain comprisng human
      kappa constant region

<400> SEQUENCE: 222

| | | | | | |
|---|---|---|---|---|---|
| cagtctgtac | tgactcaacc | acccagtgcc | agtggtaccc | cagggcaacg | tgtaactatt | 60 |
| agttgcactg | gaagttcctc | taacatagga | agcaactcag | tgagttggta | ccagcaactt | 120 |
| ccagggacag | ctcctaaact | tttgatatac | gcaaattcta | accgaccctc | tggagtccct | 180 |

```
gataggttta gcgggagcaa gtcaggaacc agcgcatccc ttgctataag cggacttcgg    240
agcgaagacg aggccgatta ctattgcgct gcctgggatg cctctttgtc tgcctacgtg    300
tttggtggag ggactaagct caccgtactt gggcgcaccg tggcggcgcc gagcgtgttt    360 attttccgc cgagcgatga acagctgaaa agcggcaccg cgagcgtggt gtgcctgctg     420
aacaactttt atccgcgcga agcgaaagtg cagtggaaag tggataacgc gctgcagagc    480
ggcaacagcc aggaaagcgt gaccgaacag gatagcaaag atagcaccta tagcctgagc    540
agcaccctga ccctgagcaa agcggattat gaaaaacata agtgtatgc gtgcgaagtg     600 acccatcagg gcctgagcag cccggtgacc aaaagcttta ccgcggcga atgc           654
```

```
<210> SEQ ID NO 223
<211> LENGTH: 654
<212> TYPE: DNA
<213> ORGANISM: Artificial Sequence
<220> FEATURE:
<223> OTHER INFORMATION: Synthetic: DG8 Light chain comprisng human
      kappa constant region

<400> SEQUENCE: 223
cagtctgttc tgacccaacc accttcagca agcgggactc ctggccaacg ggtgacaata    60
agttgctcag ggtcttcctc aaatatagga agcaacagcg taagctggta tcagcagttg    120
ccaggcaccg cacccaaact gctcatttat gccaacaaca atcgaccatc tggtgtgcca    180
gatcggttta gcgggtctaa gtcaggcact agtgccagtc tggccatttc cggcctccgg    240
tctgaagacg aagccgacta ctattgcggg gcatgggata gctcattgtc cgcatacgtg    300
tttggcggcg ggaccaagtt gaccgttctg gggcgcaccg tggcggcgcc gagcgtgttt    360 attttccgc cgagcgatga acagctgaaa agcggcaccg cgagcgtggt gtgcctgctg     420
aacaactttt atccgcgcga agcgaaagtg cagtggaaag tggataacgc gctgcagagc    480
ggcaacagcc aggaaagcgt gaccgaacag gatagcaaag atagcaccta tagcctgagc    540
agcaccctga ccctgagcaa agcggattat gaaaaacata agtgtatgc gtgcgaagtg     600 acccatcagg gcctgagcag cccggtgacc aaaagcttta ccgcggcga atgc           654
```

```
<210> SEQ ID NO 224
<211> LENGTH: 654
<212> TYPE: DNA
<213> ORGANISM: Artificial Sequence
<220> FEATURE:
<223> OTHER INFORMATION: Synthetic: DA9 Light chain comprisng human
      kappa constant region

<400> SEQUENCE: 224
caaagtgtct tgactcaacc tcccagtgcc tctgggaccc ctgggcaaag agtcaccatt    60
agctgttctg gttccccttc taatatagga aacaattctg taagttggta tcagcagctc    120
ccaggcacag ctcccaaact gcttatctac gctaactcac accggcccag tggagtcccc    180
gaccgtttct ccggtagcaa atccggtacc tccgcctcac ttgctatttc aggacttcgc    240
agcgaggacg aggccgacta ttattgtggg tcttgggatg cctcactgaa tggatatgtt    300
ttcggtggcg gcaccaagct caccgttttg ggccgcaccg tggcggcgcc gagcgtgttt    360 attttccgc cgagcgatga acagctgaaa agcggcaccg cgagcgtggt gtgcctgctg     420
aacaactttt atccgcgcga agcgaaagtg cagtggaaag tggataacgc gctgcagagc    480
ggcaacagcc aggaaagcgt gaccgaacag gatagcaaag atagcaccta tagcctgagc    540
agcaccctga ccctgagcaa agcggattat gaaaaacata agtgtatgc gtgcgaagtg     600
```

```
acccatcagg gcctgagcag cccggtgacc aaaagcttta accgcggcga atgc         654

<210> SEQ ID NO 225
<211> LENGTH: 140
<212> TYPE: PRT
<213> ORGANISM: Homo sapiens
<220> FEATURE:
<221> NAME/KEY: misc_feature
<223> OTHER INFORMATION: Homo sapiens alpha-synuclein

<400> SEQUENCE: 225

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```